US008937159B2

(12) United States Patent
Harding et al.

(10) Patent No.: US 8,937,159 B2
(45) Date of Patent: Jan. 20, 2015

(54) ANTI-HER2 ANTIBODIES AND THEIR USES

(75) Inventors: Fiona A. Harding, Santa Clara, CA (US); Yoshiko Akamatsu, Palo Alto, CA (US); Robert B. Dubridge, Belmont, CA (US); David B. Powers, Fairfax, CA (US)

(73) Assignee: AbbVie Biotherapeutics Inc., Redwood City, CA (US)

(*) Notice: Subject to any disclaimer, the term of this patent is extended or adjusted under 35 U.S.C. 154(b) by 702 days.

(21) Appl. No.: 12/969,375

(22) Filed: Dec. 15, 2010

(65) Prior Publication Data

US 2011/0177095 A1 Jul. 21, 2011

Related U.S. Application Data

(60) Provisional application No. 61/287,155, filed on Dec. 16, 2009.

(51) Int. Cl.
*C07K 16/00* (2006.01)

(52) U.S. Cl.
USPC .................................... 530/387.1; 424/130.1

(58) Field of Classification Search
None
See application file for complete search history.

(56) References Cited

U.S. PATENT DOCUMENTS

| | | | |
|---|---|---|---|
| 5,821,047 | A | 10/1998 | Garrard et al. |
| 5,821,337 | A | 10/1998 | Carter et al. |
| 5,834,598 | A | 11/1998 | Lowman et al. |
| 6,040,136 | A | 3/2000 | Bass et al. |
| 6,407,213 | B1 | 6/2002 | Carter et al. |
| 7,435,797 | B2 | 10/2008 | Lowman et al. |
| 7,560,111 | B2 | 7/2009 | Kao et al. |
| 7,799,899 | B2 | 9/2010 | Ackerly et al. |
| 2003/0229212 | A1 | 12/2003 | Fahrner et al. |
| 2005/0079574 | A1 | 4/2005 | Bond |
| 2005/0119455 | A1 | 6/2005 | Fuh et al. |
| 2005/0260711 | A1 | 11/2005 | Datta et al. |
| 2006/0013819 | A1 | 1/2006 | Kelsey |
| 2006/0073152 | A1 | 4/2006 | Dennis |
| 2006/0088523 | A1 | 4/2006 | Andya et al. |
| 2006/0118574 | A1 | 6/2006 | Anderson et al. |
| 2006/0153885 | A1 | 7/2006 | Korb et al. |
| 2006/0177448 | A1 | 8/2006 | Carey et al. |
| 2006/0188509 | A1 | 8/2006 | Derynck et al. |
| 2006/0204505 | A1 | 9/2006 | Sliwkowski et al. |
| 2006/0212956 | A1 | 9/2006 | Crocker et al. |
| 2006/0270003 | A1 | 11/2006 | Arnott et al. |
| 2007/0020261 | A1 | 1/2007 | Sliwkowski et al. |
| 2007/0161089 | A1 | 7/2007 | Yang et al. |
| 2007/0202552 | A1 | 8/2007 | Sidhu et al. |
| 2007/0218069 | A1 | 9/2007 | Gordon et al. |
| 2007/0237764 | A1 | 10/2007 | Birtalan et al. |
| 2007/0292936 | A1 | 12/2007 | Barthelemy et al. |
| 2008/0038717 | A1 | 2/2008 | Garrard et al. |
| 2008/0050377 | A1 | 2/2008 | Ackerly et al. |
| 2008/0069820 | A1 | 3/2008 | Fuh et al. |
| 2008/0112961 | A1 | 5/2008 | Stavenhagen et al. |
| 2008/0213268 | A1 | 9/2008 | Watts et al. |
| 2008/0248037 | A1 | 10/2008 | Li et al. |
| 2008/0317753 | A1 | 12/2008 | Amler et al. |
| 2009/0023602 | A1 | 1/2009 | Fellouse et al. |
| 2009/0053786 | A1 | 2/2009 | Kao et al. |
| 2009/0081211 | A1 | 3/2009 | Campagne |
| 2009/0081223 | A1 | 3/2009 | Allison et al. |
| 2009/0123376 | A1 | 5/2009 | Dennis |
| 2009/0148402 | A1 | 6/2009 | Brunetta et al. |
| 2009/0175865 | A1 | 7/2009 | Eigenbrot et al. |
| 2009/0187007 | A1 | 7/2009 | Lowman et al. |
| 2009/0202546 | A1 | 8/2009 | Harris et al. |

FOREIGN PATENT DOCUMENTS

| | | | |
|---|---|---|---|
| EP | 1308455 | B9 | 6/2006 |
| JP | 2002-119294 | | 4/2002 |
| JP | 2004-121261 | | 4/2004 |
| JP | 2006-104205 | | 4/2006 |
| WO | 92/22653 | A1 | 12/1992 |
| WO | 03/066662 | A2 | 8/2003 |
| WO | 03/068801 | A2 | 8/2003 |
| WO | 03/074679 | A2 | 9/2003 |
| WO | 03/087131 | A2 | 10/2003 |
| WO | 03/102157 | A3 | 12/2003 |
| WO | 2004/065416 | A2 | 8/2004 |
| WO | 2005/092925 | A2 | 10/2005 |
| WO | 2006/041641 | A2 | 4/2006 |
| WO | 2007/064919 | A2 | 6/2007 |
| WO | 2007/094842 | A2 | 8/2007 |
| WO | 2007/097812 | A2 | 8/2007 |
| WO | 2007/145862 | A2 | 12/2007 |
| WO | 2008/109440 | A2 | 9/2008 |

OTHER PUBLICATIONS

Berezov et al., "Disabling ErbB receptors with rationally designed exocyclic mimetics of antibodies: Structure-function analysis," J. Med. Chem., 44, 2565-2574 (2001).

Bostrom et al., "Variants of the antibody herceptin that interact with Her2 and VEGF at the antigen binding site," Science, 323, 1610-1614 (2009).

Eigenbrot et al., "X-ray structures of the antigen-binding domains from three variants of humanized anti-p185$^{HER2}$ antibody 4D5 and comparison with molecular modeling," J. Mol. Biol., 229, 969-995 (1993).

Finkle et al., "HER2-Targeted therapy reduces incidence and progression of midlife mammary tumors in female murine mammary tumor virus huHER2-Transgenic mice," Clin. Cancer Res., 10, 2499-2511 (2004).

(Continued)

*Primary Examiner* — Laura B Goddard
*Assistant Examiner* — Meera Natarajan
(74) *Attorney, Agent, or Firm* — Dechert LLP

(57) ABSTRACT

The present disclosure relates to antibodies directed to HER2 and uses of such antibodies, for example to treat diseases associated with the activity and/or overproduction of HER2.

16 Claims, 110 Drawing Sheets

(56) References Cited

OTHER PUBLICATIONS

Figure 26C:
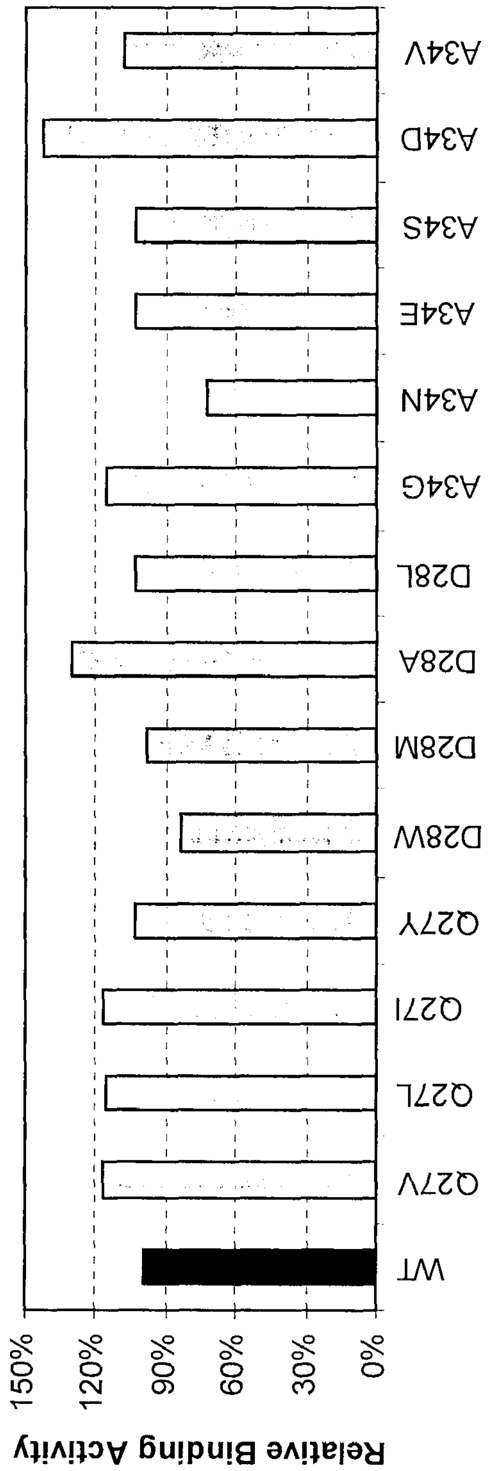
Figure 26D:
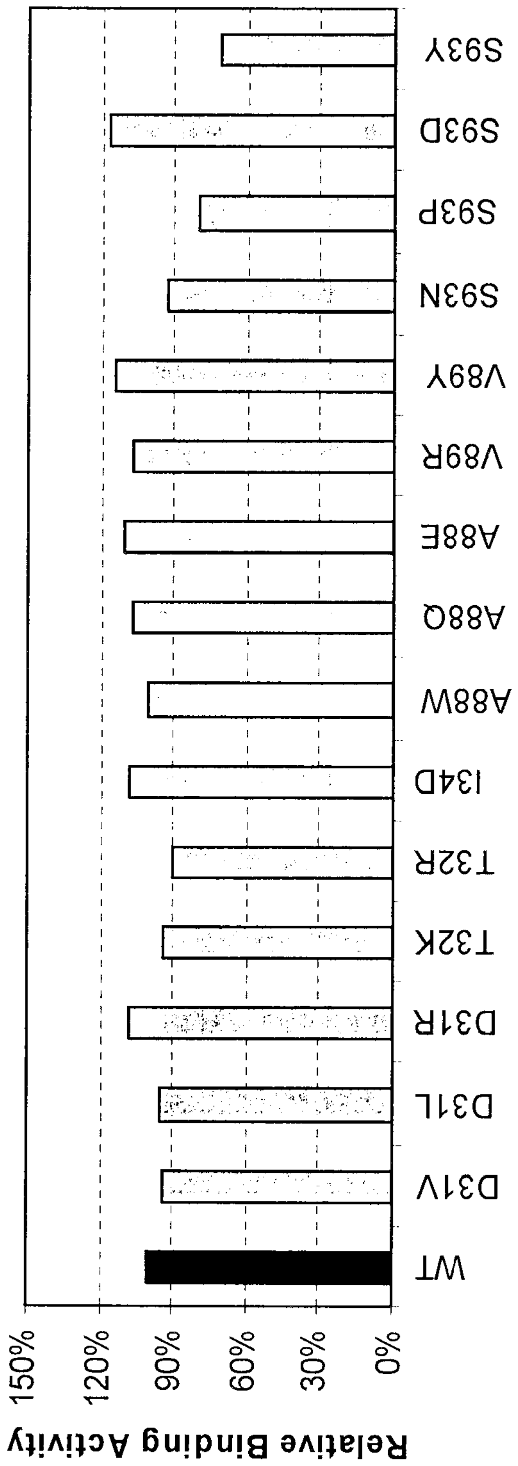
Figure 26E:
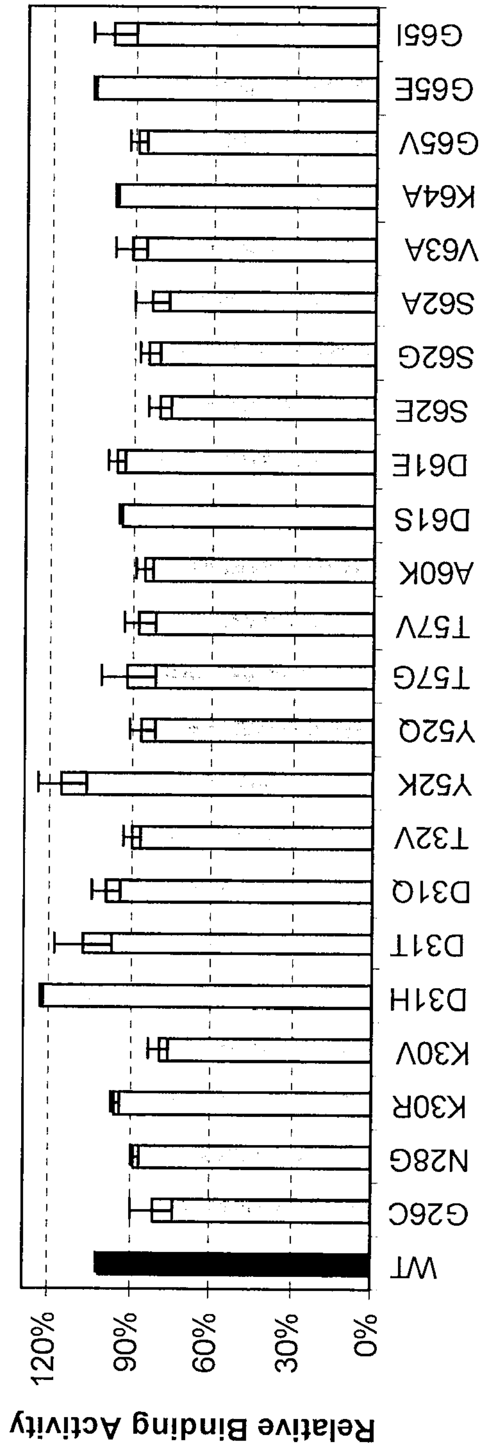
Figure 26F:
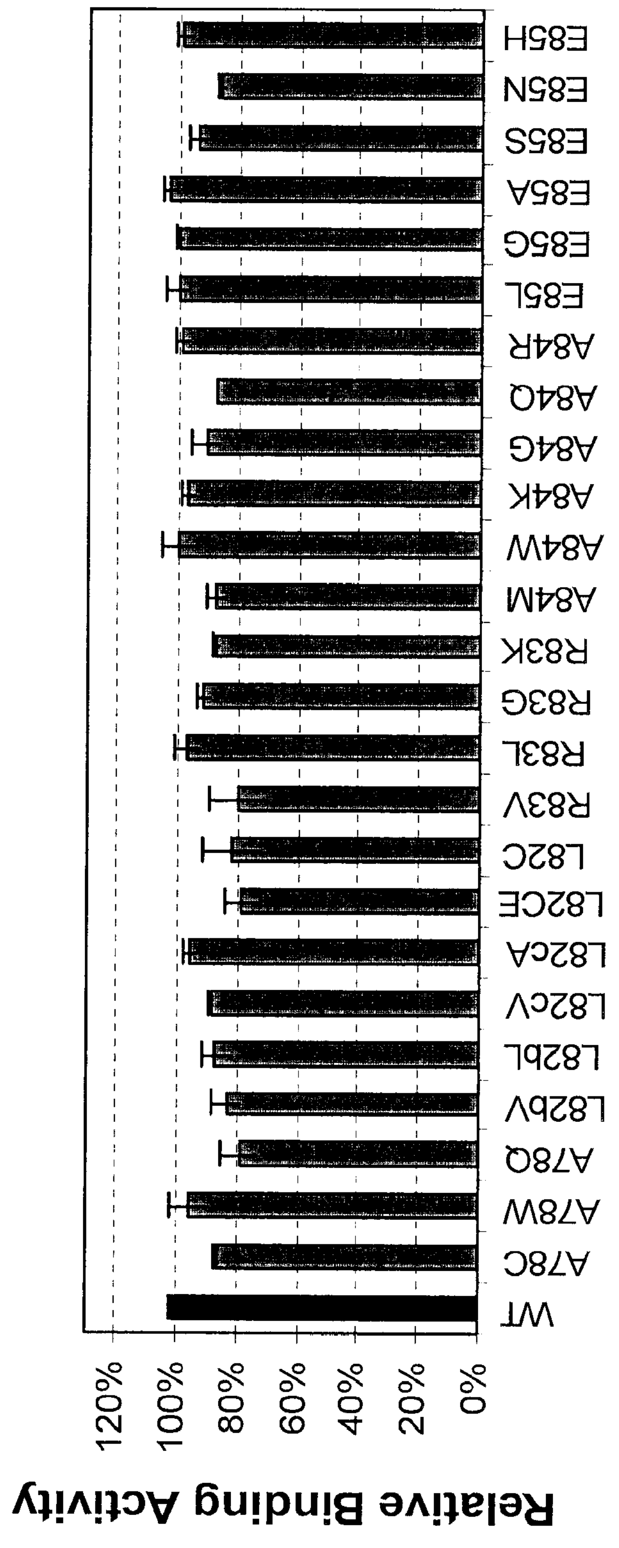
Figure 26G:
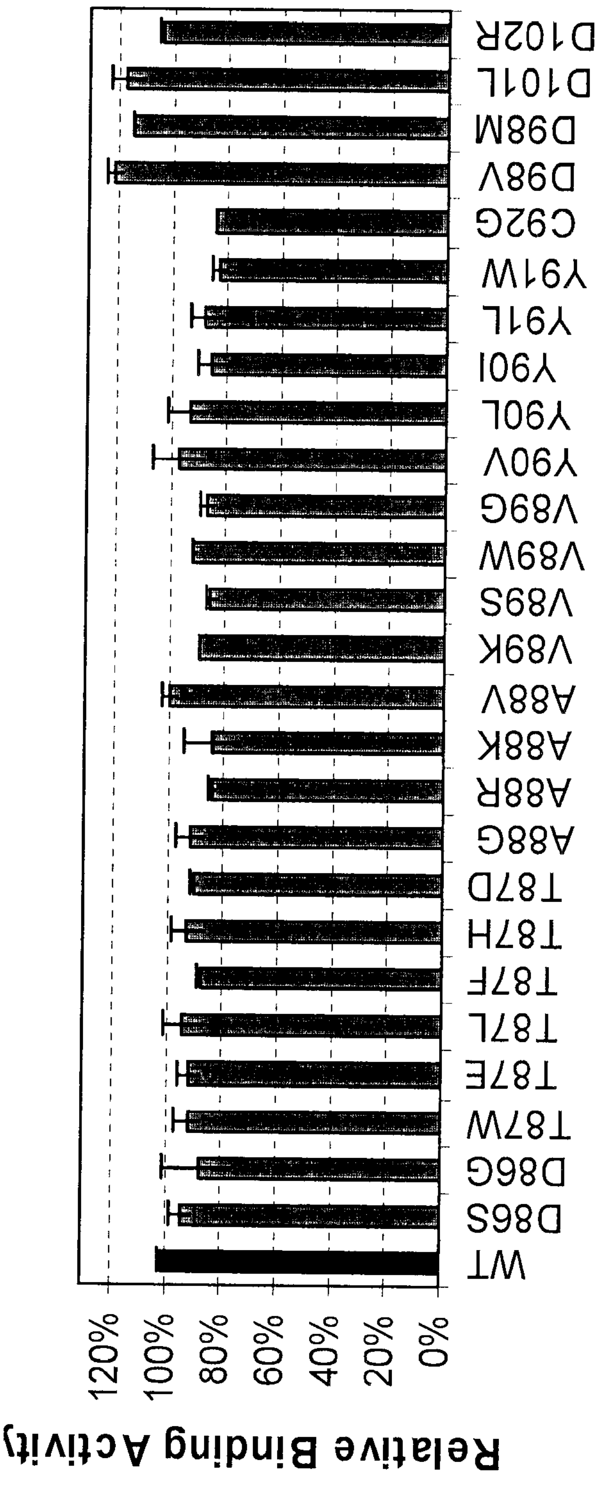
Figure 27A:
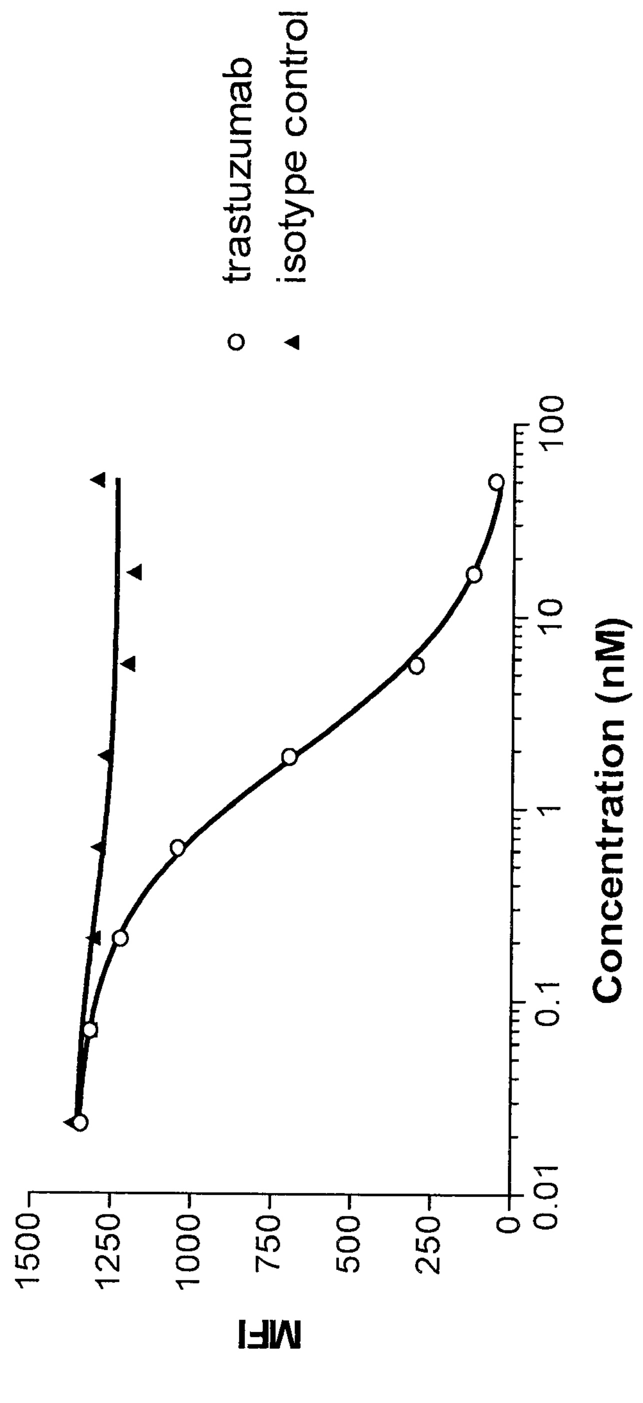
Figure 27B:
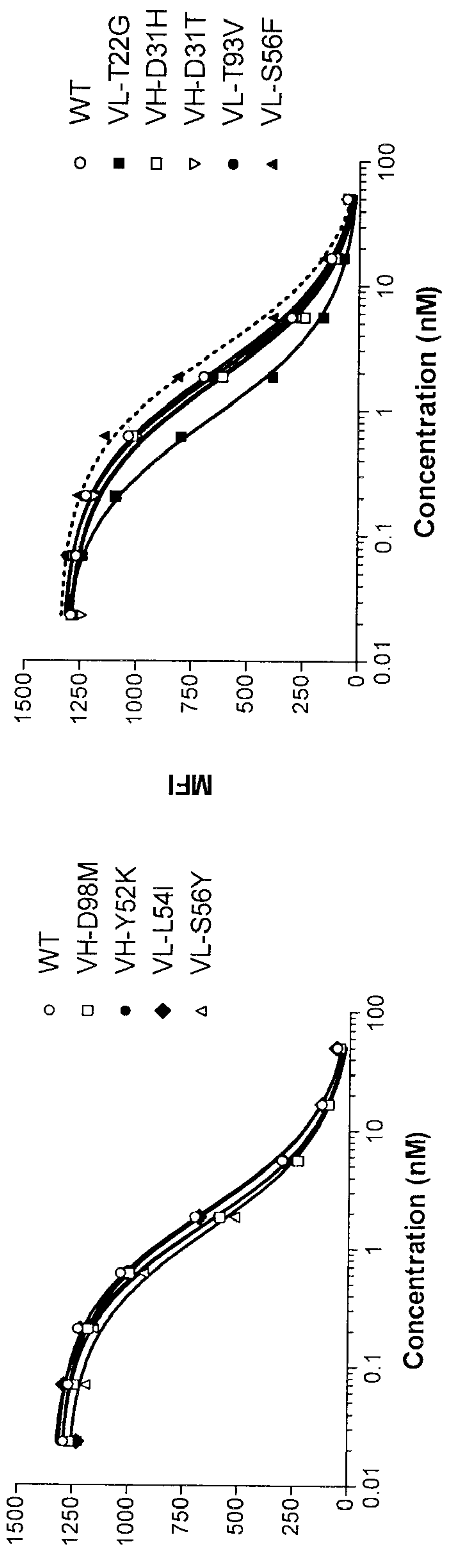
Figure 27C:
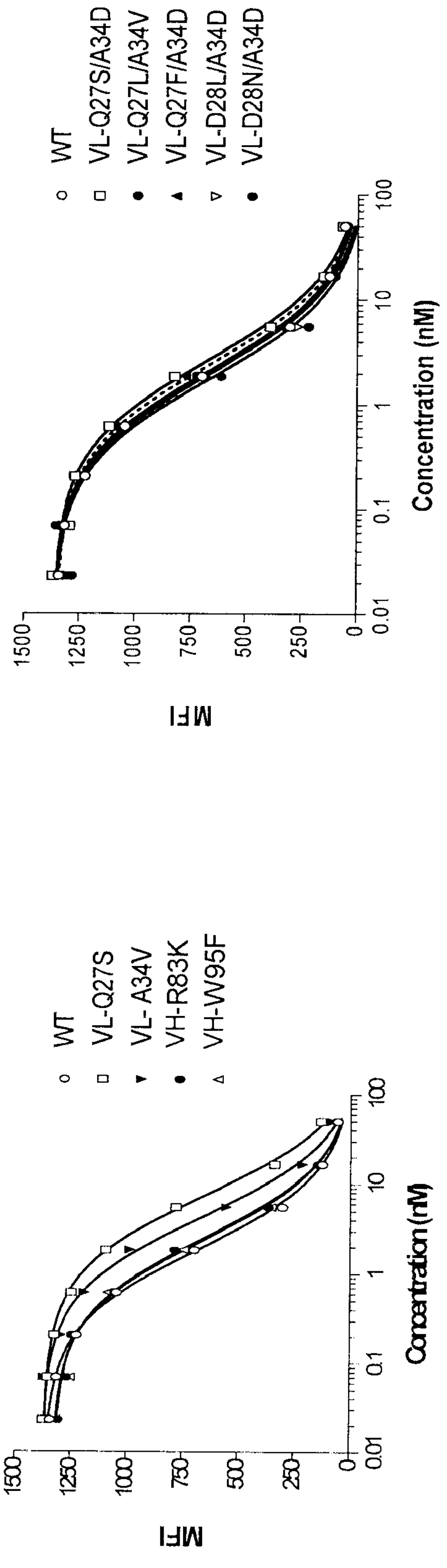
Figure 27D:
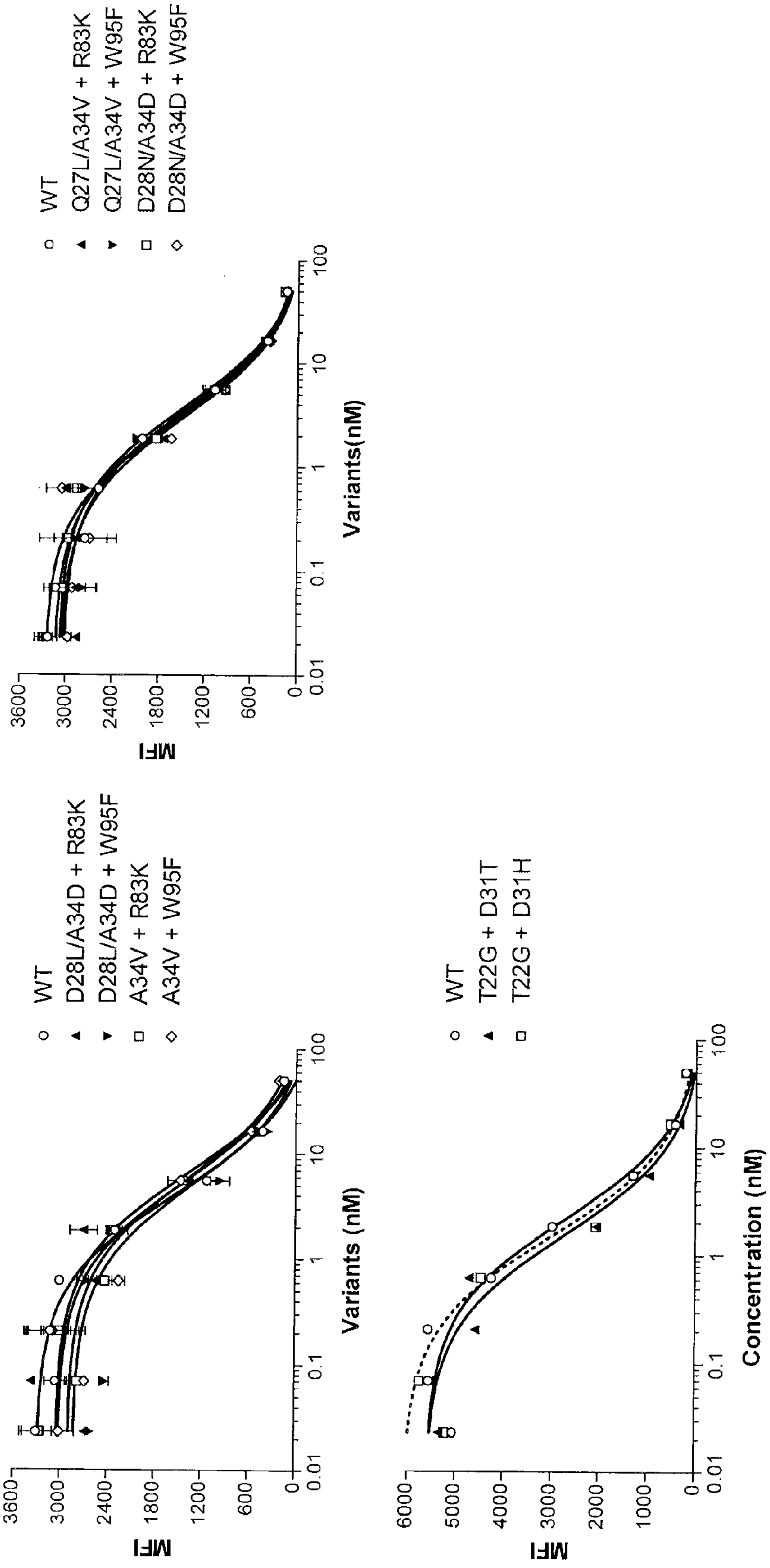
Figure 27E:
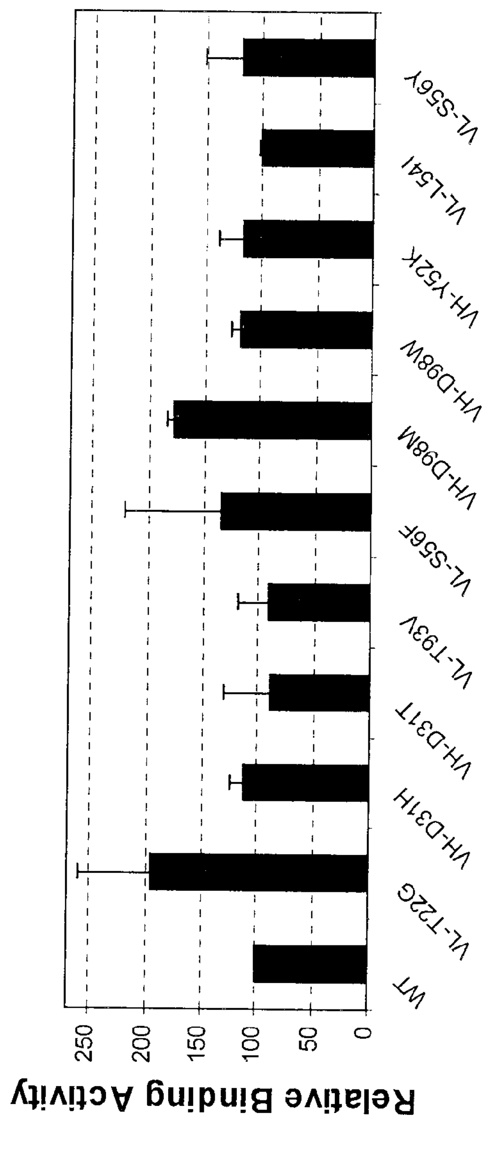
Figure 27F:
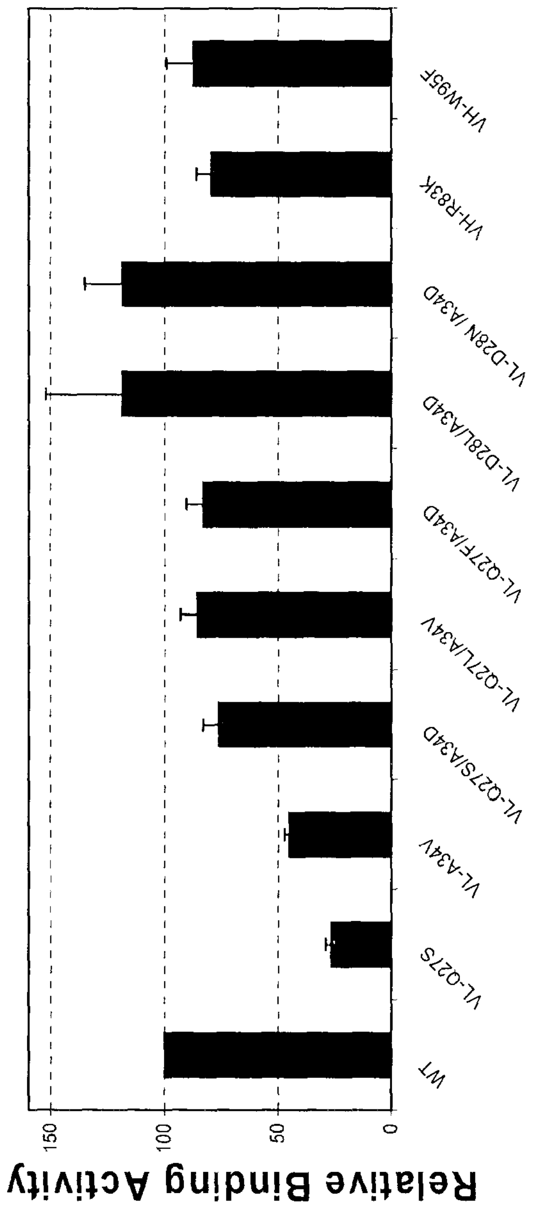
Figure 27G:
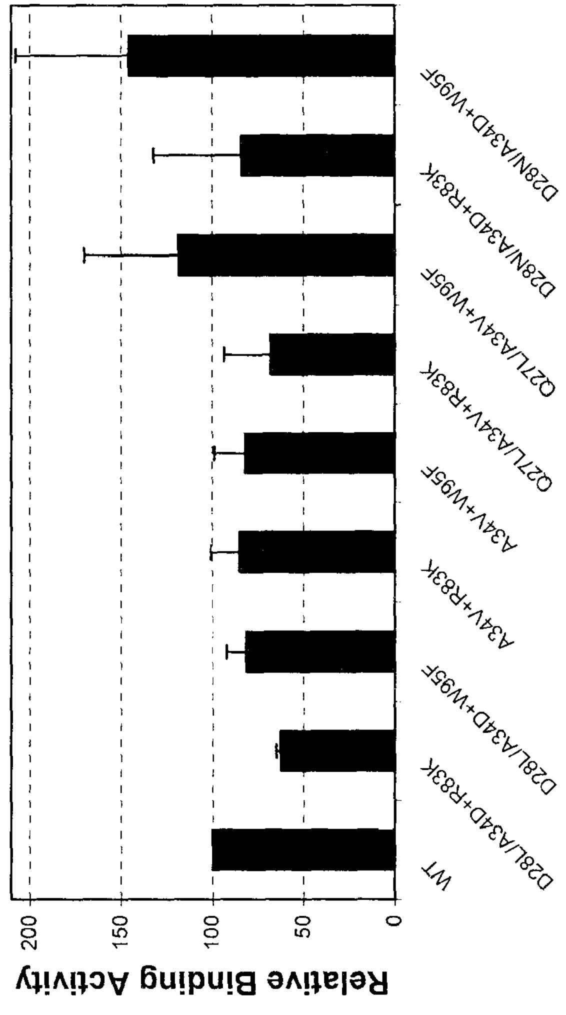
Figure 29:
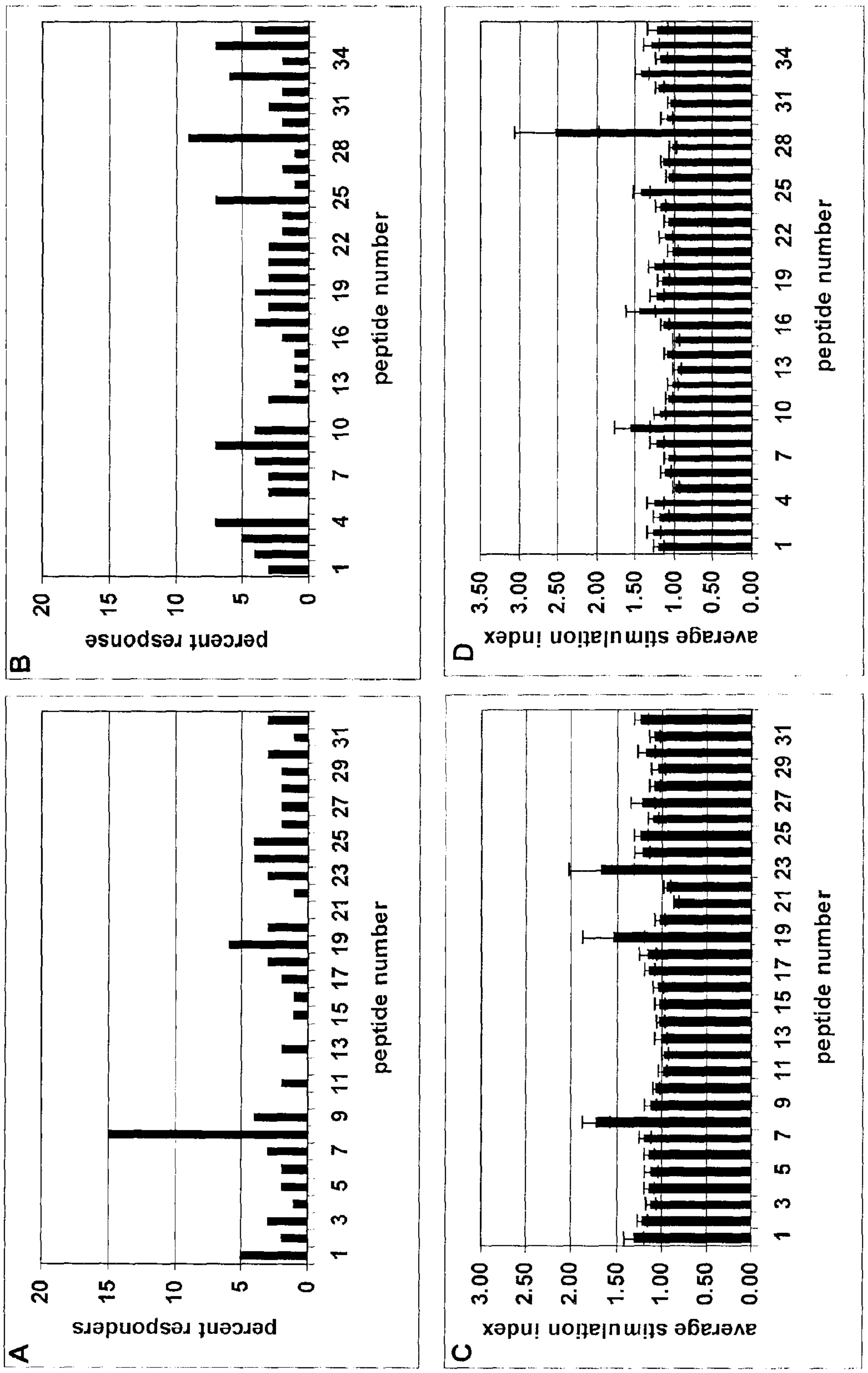
Figure 31A:
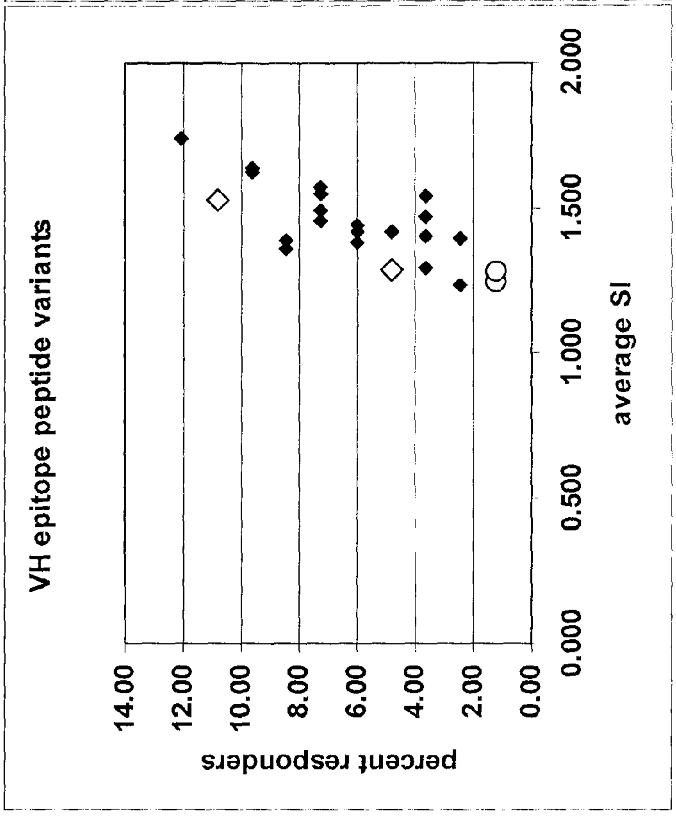
Figure 31B:
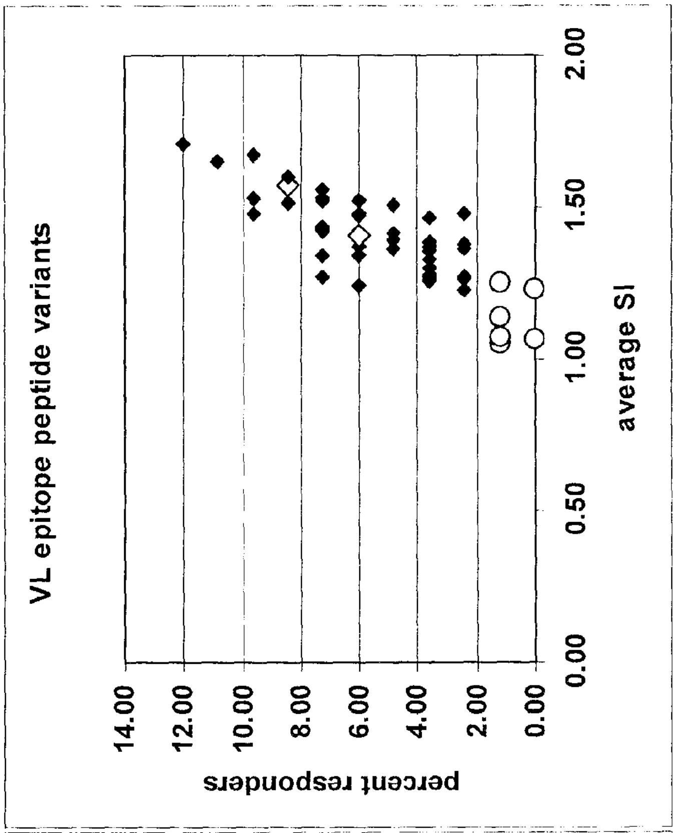
Figure 33A:
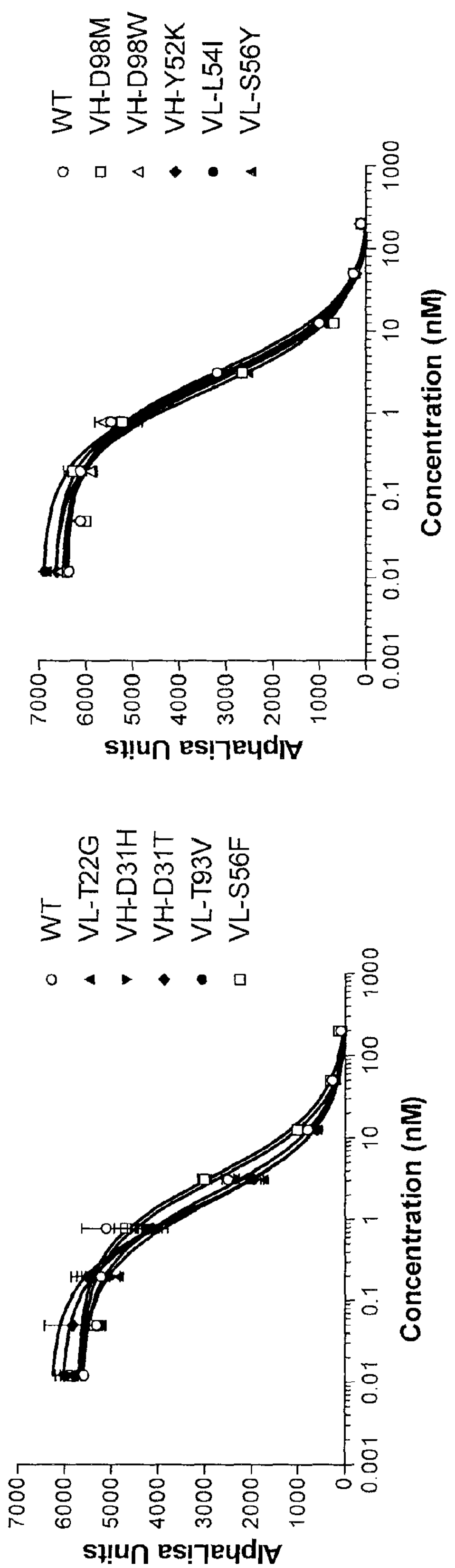
Figure 33B:
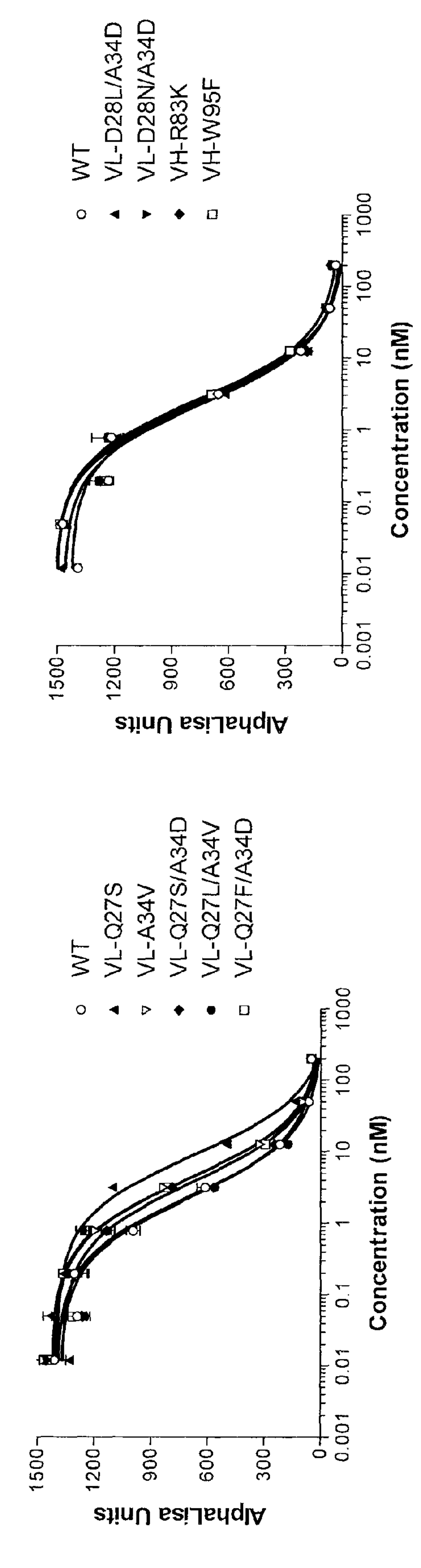
Figure 33C:
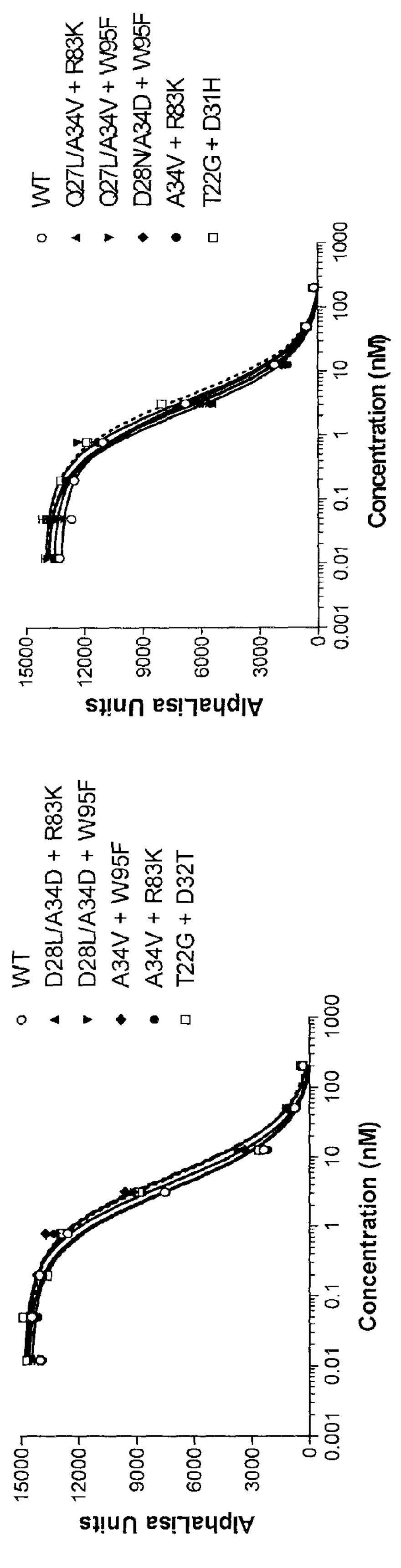
Figure 33D:
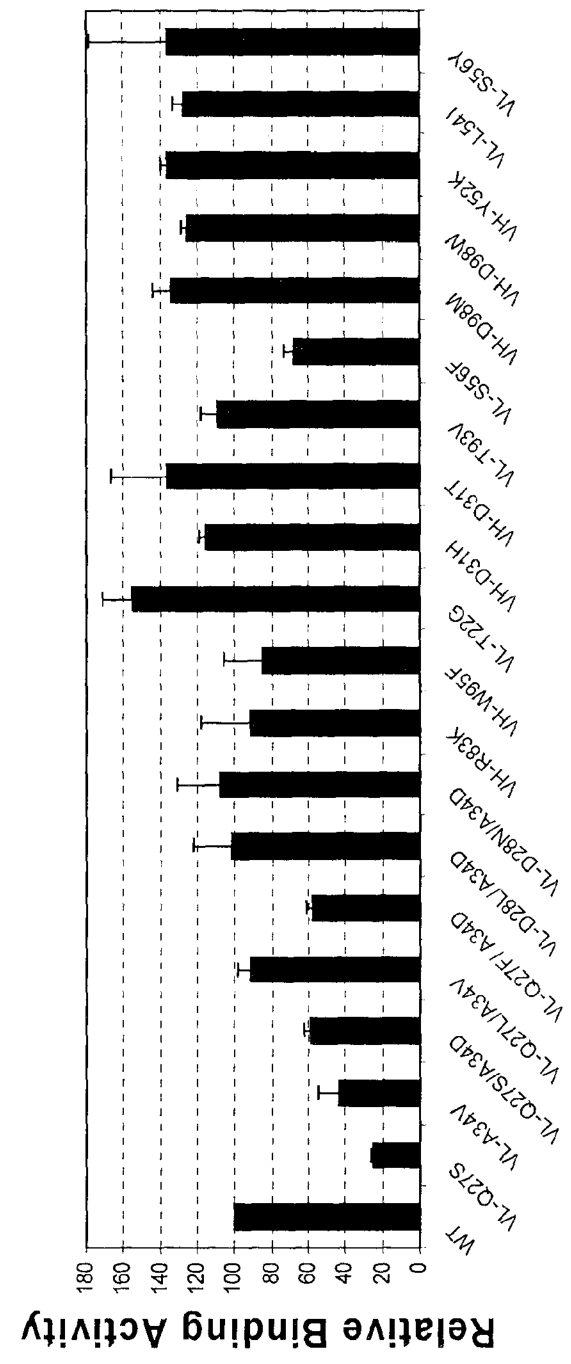
Figure 33E:
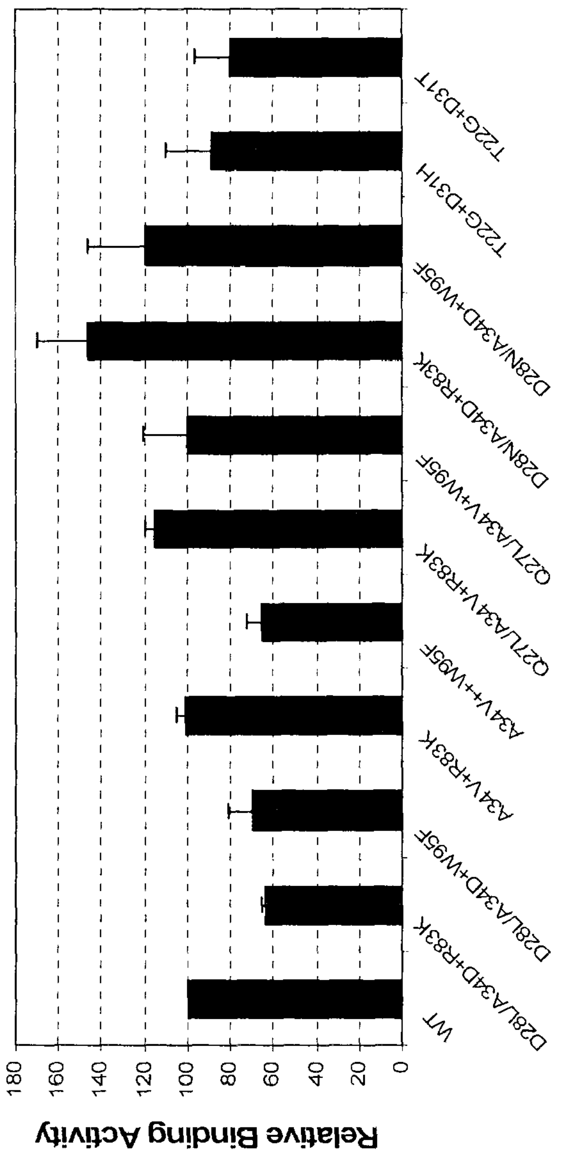

Gerstner et al., "Sequence plasticity in the Antigen-binding site of a Therapeutic Anti-HER2 antibody," J. Mol. Biol. 321, 851-862 (2002).
International Search report dated May 23, 2011, corresponding to International Application No. PCT/US2010/060533.
Jung et al., "Improving in vivo folding and stability of a single-chain Fv antibody fragment by loop grafting," Protein Engineering, 10, 959-966 (1997).
Kelley et al., "Thermodynamic Analysis of an Antibody Functional Epitope," Biochemistry, 32, 6828-6835 (1993).
Kelley, et al., "Antigen Binding Thermodynamics and Antiproliferative Effects of Chimeric and Humanized anti-p185$^{HER2}$ Antibody Fab Fragments," Biochemistry, 31, 5434-5441 (1992).
Li et al., "The protein-protein interface evolution acts in a similar way to antibody affinity maturation," J. Biol. Chem., 285, 3865-3871 (2010).
Nahta et al., "Herceptin: Mechanisms of action and resistance," Cancer Letters, 232, 123-128 (2006).
Pack et al., "Simultaneous suppression of epidermal growth factor receptor and c-erbB-2 reverses aneuploidy and malignant phenotype of a human ovarian carcinoma cell line," Cancer Res., 64, 789-794 (2004).
Schier et al., "Isolation of picomolar affinity anti-c-erbB-2 single-chain Fv by molecular evaluation of the complementarity determining regions in the center of the antibody binding site," J. Mol. Biol., 263, 551-67 (1996).
Sidhu, et al., "Phage-displayed antibody libraries of synthetic heavy chain complementarity determining regions," J. Mol. Biol. 338, 299-310 (2004).
Simon et al., "Patterns of HER-2.neu amplification and over-expression in primary and metastatic breast cancer," J. National Cancer Institute, 93, 1141 (2001).
Tagliabue et al., "Selection of monoclonal antibodies which induce internalization and phosphorylation of p185.sup.HER2 and growth inhibition of cells with HER2/neu gene amplification," Int. J. Cancer, 47, 933-937 (1991).
Vajdos et al., "Comprehensive functional maps of the antigen-binding site of an anti-ErbB2 antibody obtained with shotgun scanning mutagenesis," J. Mol. Biol., 320, 415-428 (2002).
Wang et al., "Structural analysis of the epitopes on erbB2 interacted with inhibitory or non-inhibitory monoclonal antibodies," Mol. Immunol., 40, 963-969 (2003).
Watier, et al., "Structure-function relationships of the variable domains of monoclonal antibodies approved for cancer treatment," Critical Reviews in Oncology/Hematology 64, 210-225 (2007).
Weiner et al., "The rollercoaster ride to anti-cancer antibodies," Nature Biotechnology, 21, 510-511 (2003).
Worn et al., "Different Equilibrium Stability Behavior of ScFv fragments: Identification, classification, and improvement by protein engineering," Biochemistry, 38, 8739-8750 (1999).
Yazaki, et al., "Humanization of the anti-CEA T84.66 antibody based on crystal structure data," Protein Eng Des Sel., 17, 481-489 (2004).

| SEQ ID NO: | ANTIBODY CHAIN | CDR NO. | RESIDUE | POSITION IN CDR | KABAT NO. |
|---|---|---|---|---|---|
| 3 | Heavy | 1 | G | 1 | 26 |
| | | | F | 2 | 27 |
| | | | N | 3 | 28 |
| | | | I | 4 | 29 |
| | | | K | 5 | 30 |
| | | | D | 6 | 31 |
| | | | T | 7 | 32 |
| | | | Y | 8 | 33 |
| | | | I | 9 | 34 |
| | | | H | 10 | 35 |
| 4 | Heavy | 2 | R | 1 | 50 |
| | | | I | 2 | 51 |
| | | | Y | 3 | 52 |
| | | | P | 4 | 52a |
| | | | T | 5 | 53 |
| | | | N | 6 | 54 |
| | | | G | 7 | 55 |
| | | | Y | 8 | 56 |
| | | | T | 9 | 57 |
| | | | R | 10 | 58 |
| | | | Y | 11 | 59 |
| | | | A | 12 | 60 |
| | | | D | 13 | 61 |
| | | | S | 14 | 62 |
| | | | V | 15 | 63 |
| | | | K | 16 | 64 |
| | | | G | 17 | 65 |
| 5 | Heavy | 3 | W | 1 | 95 |
| | | | G | 2 | 96 |
| | | | G | 3 | 97 |
| | | | D | 4 | 98 |
| | | | G | 5 | 99 |
| | | | F | 6 | 100 |
| | | | Y | 7 | 100a |
| | | | A | 8 | 100b |
| | | | M | 9 | 100c |
| | | | D | 10 | 101 |
| | | | Y | 11 | 102 |

FIG. 1

| SEQ ID NO: | ANTIBODY CHAIN | CDR NO. | RESIDUE | POSITION IN CDR | KABAT NO. |
|---|---|---|---|---|---|
| 6 | Light | 1 | R | 1 | 24 |
| | | | A | 2 | 25 |
| | | | S | 3 | 26 |
| | | | Q | 4 | 27 |
| | | | D | 5 | 28 |
| | | | V | 6 | 29 |
| | | | N | 7 | 30 |
| | | | T | 8 | 31 |
| | | | A | 9 | 32 |
| | | | V | 10 | 33 |
| | | | A | 11 | 34 |
| 7 | Light | 2 | S | 1 | 50 |
| | | | A | 2 | 51 |
| | | | S | 3 | 52 |
| | | | F | 4 | 53 |
| | | | L | 5 | 54 |
| | | | Y | 6 | 55 |
| | | | S | 7 | 56 |
| 8 | Light | 3 | Q | 1 | 89 |
| | | | Q | 2 | 90 |
| | | | H | 3 | 91 |
| | | | Y | 4 | 92 |
| | | | T | 5 | 93 |
| | | | T | 6 | 94 |
| | | | P | 7 | 95 |
| | | | P | 8 | 96 |
| | | | T | 9 | 97 |

FIG. 2

| WT | KABAT NO / POSITION IN CDR | HEAVY CHAIN SUBSTITUTIONS | SEQ ID NO: |
|---|---|---|---|
| | | **CDR-H1** | |
| D | 31/6 | L, R,V | 86-88 |
| T | 32/7 | K, R | 89-90 |
| I | 34/9 | D | 91 |
| | | **CDR-H2** | |
| T | 53/5 | L, R | 92-93 |
| K | 64/16 | R, S | 94-95 |

FIG. 3

| WT | KABAT NO/ POSITION IN CDR | LIGHT CHAIN SUBSTITUTIONS | SEQ ID NO: |
|---|---|---|---|
| | | **CDR-L1** | |
| Q | 27/4 | L, V, I, Y | 96-99 |
| D | 28/5 | L, A, M, W | 100-103 |
| A | 34/11 | V, G, D, S, E | 104-108 |

FIG. 4

| WT | KABAT NO/ POSITION IN CDR | HEAVY CHAIN SUBSTITUTIONS | SEQ ID NO: |
|---|---|---|---|
| | | **CDR-H1** | |
| N | 28/3 | S, W | 109-110 |
| K | 30/5 | W, A | 111-112 |
| D | 31/6 | W, A, G, S | 113-116 |
| | | **CDR-H2** | |
| Y | 52/3 | R, S | 117-118 |
| T | 53/5 | S, K, G | 119-121 |
| N | 54/6 | S | 122 |
| T | 57/9 | S | 123 |
| S | 62/14 | R | 124 |
| K | 64/16 | Q | 125 |
| | | **CDR-H3** | |
| W | 95/1 | Y, F | 126-127 |
| G | 97/3 | R, T | 128-129 |
| D | 98/4 | G, T, A, R,Q, E, S, Y, F, L, P, H | 130-141 |
| A | 100b/8 | V, S, E | 142-144 |
| M | 100c/9 | F | 145 |
| Y | 102/11 | G, S, K, H | 146-149 |

FIG. 5

| WT | KABAT NO / POSITION IN CDR | LIGHT CHAIN SUBSTITUTIONS | SEQ ID NO: |
|---|---|---|---|
| | | **CDR-L1** | |
| R | 24/3 | K | 150 |
| A | 25/4 | S | 151 |
| Q | 27/6 | R, S, F, K | 152-155 |
| D | 28/7 | G, N, R, P, S | 156-160 |
| V | 29/8 | I | 161 |
| T | 31/10 | S | 162 |
| A | 34/13 | N | 163 |
| | | **CDR-L2** | |
| A | 51/2 | G | 164 |
| F | 53/4 | W, Y | 165-166 |
| L | 54/5 | S | 167 |
| Y | 55/6 | L, A | 168-169 |
| | | **CDR-L3** | |
| H | 91/3 | W, Y | 170-171 |
| T | 93/5 | S, A | 172-173 |
| T | 94/6 | S | 174 |
| P | 96/8 | S | 175 |

FIG. 6

| WT | KABAT NO / POSITION IN CDR | HEAVY CHAIN SUBSTITUTIONS | SEQ ID NO: |
|---|---|---|---|
| | | **CDR-H1** | |
| G | 26/1 | C | 176 |
| N | 28/3 | G | 177 |
| K | 30/5 | R, V | 178-179 |
| D | 31/6 | H, Q, T | 180-182 |
| T | 32/7 | V | 183 |
| | | **CDR-H2** | |
| Y | 52/3 | K, Q | 184-185 |
| T | 57/9 | G, V | 186-187 |
| A | 60/12 | K | 188 |
| D | 61/13 | S, E | 189-190 |
| S | 62/14 | E, G, A | 191-193 |
| V | 63/15 | A | 194 |
| K | 64/16 | A | 195 |
| G | 65/17 | V, E, I | 196-198 |
| | | **CDR-H3** | |
| D | 98/4 | V, M | 199-200 |
| D | 101/10 | L | 201 |
| Y | 102/11 | R | 202 |

FIG. 7

| WT | KABAT NO / POSITION IN CDR | LIGHT CHAIN SUBSTITUTIONS | SEQ ID NO: |
|---|---|---|---|
| | | **CDR-L1** | |
| R | 24/3 | H, E, C, V | 203-206 |
| A | 25/4 | C, G, P | 207-209 |
| V | 29/8 | A, S | 210-211 |
| | | **CDR-L2** | |
| A | 51/2 | S | 212 |
| S | 52/3 | W, M, Q, H, G, R | 213-218 |
| L | 54/5 | I, G, V | 219-221 |
| S | 56/7 | A, P, G, H, Y, F, N, M | 222-229 |
| | | **CDR-L3** | |
| Y | 92/4 | M | 230 |
| T | 93/5 | L, M, G, V | 231-234 |
| P | 96/8 | G | 235 |
| T | 97/9 | D | 236 |

FIG. 8

| WT | KABAT NO. | HEAVY CHAIN MUTATIONS | SEQ ID NO: |
|---|---|---|---|
| | | **Framework 3** | |
| A | 88 | Q, W, E | 237-239 |
| V | 89 | R, Y | 240-241 |
| S | 93 | N, P, Y, D | 242-245 |

FIG. 9

| WT | KABAT NO. | HEAVY CHAIN MUTATIONS | SEQ ID NO: |
|---|---|---|---|
| | | **Framework 3** | |
| A | 78 | C, W, Q | 246-248 |
| S | 82b | V, L | 249-250 |
| L | 82c | V, A, E, G | 251-254 |
| R | 83 | V, L, G, K | 255-258 |
| A | 84 | M, W, K, G, Q, R | 259-264 |
| E | 85 | L, G, A, S, N, H | 265-270 |
| D | 86 | S, G | 271-272 |
| T | 87 | W, E, L, F, H, D | 273-278 |
| A | 88 | G, R, K, V | 279-282 |
| V | 89 | K, S, W, G | 283-286 |
| Y | 90 | V, L, I | 287-289 |
| Y | 91 | L, W | 290-291 |
| C | 92 | G | 292 |

FIG. 10

| WT | KABAT NO . | LIGHT CHAIN MUTATIONS | SEQ ID NO: |
|---|---|---|---|
| | | **Framework 1** | |
| T | 22 | G, S | 293-294 |
| C | 23 | A, N | 295-296 |
| | | **Framework 2** | |
| W | 35 | H, F | 297-298 |
| | | **Framework 3** | |
| R | 66 | K | 299 |

FIG. 11

| WT | KABAT NO . | HEAVY CHAIN MUTATIONS | SEQ ID NO: |
|---|---|---|---|
| | | **Framework 3** | |
| A | 78 | V | 300 |
| A | 88 | C | 301 |
| Y | 91 | F | 302 |
| S | 93 | V, A, L, Q, T | 303-307 |

FIG. 12

| HEAVY CHAIN COMBINATION MUTATIONS | SEQ ID NO: |
|---|---|
| S93N + W95Y | 308 & 126 |
| S93D + W95Y | 309 & 126 |
| S93A + W95Y | 310 & 126 |
| S93V + W95Y | 311 & 126 |
| S93L + W95Y | 312 & 126 |
| S93N + W95F | 313 & 127 |
| S93D + W95F | 314 & 127 |
| S93A + W95F | 315 & 127 |
| S93V + W95F | 316 & 127 |
| S93L + W95F | 317 & 127 |

FIG. 13

| LIGHT CHAIN COMBINATION MUTATIONS | SEQ ID NO: |
|---|---|
| Q27S + A34G | 318 |
| Q27K + A34G | 319 |
| Q27V + A34G | 320 |
| Q27L + A34G | 321 |
| Q27F + A34G | 322 |
| Q27I + A34G | 323 |
| Q27Y + A34G | 324 |
| Q27R + A34G | 325 |
| Q27S + A34D | 326 |
| Q27K + A34D | 327 |
| Q27V + A34D | 328 |
| Q27L + A34D | 329 |
| Q27F + A34D | 330 |
| Q27I + A34D | 331 |
| Q27Y + A34D | 332 |
| Q27R + A34D | 333 |
| Q27S + A34V | 334 |
| Q27K + A34V | 335 |
| Q27V + A34V | 336 |
| Q27L + A34V | 337 |
| Q27F + A34V | 338 |
| Q27I + A34V | 339 |
| Q27Y + A34V | 340 |
| Q27R + A34V | 341 |
| D28G + A34G | 342 |
| D28A + A34G | 343 |
| D28N + A34G | 344 |
| D28L + A34G | 345 |
| D28G + A34D | 346 |
| D28A + A34D | 347 |
| D28N + A34D | 348 |
| D28L + A34D | 349 |
| D28G + A34V | 350 |
| D28A + A34V | 351 |
| D28N + A34V | 352 |
| D28L + A34V | 353 |

FIG. 14

| KNOWN HEAVY CHAIN MUTATIONS | | | | | | | | | | | | | |
|---|---|---|---|---|---|---|---|---|---|---|---|---|---|
| CDR-VH1 | | | | | | | | | | | | | |
| SEQ ID NO: | 1 | 2 | 3 | 4 | | | 5 | 6 | 7 | 8 | 9 | 10 | Continued |
| | 26 | 27 | 28 | 29 | 29a | 29b | 30 | 31 | 32 | 33 | 34 | 35 | |
| 3 | G | F | N | I | – | – | K | D | T | Y | I | H | |
| 3 | | | | | | | | | | | | | |
| 3 | | | | | | | | | | | | | |
| 3 | | | | | | | | | | | | | |
| 3 | | | | | | | | | | | | | |
| 3 | | | | | | | | | | | | | |
| 3 | | | | | | | | | | | | | |

FIG. 15.1

KNOWN HEAVY CHAIN MUTATIONS

CDR-VH2

Continued from previous table

| SEQ ID NO: | 1 | 2 | 3 | 4 | | | 5 | | | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|---|
| | 50 | 51 | 52 | 52a | 52b | 52c | 53 | 53a | 53b | 54 | 55 | 56 | 57 | 58 | 59 | 60 | 61 | 62 | 63 | 64 | 65 |
| 4 | R | I | Y | P | – | – | T | – | – | N | G | Y | T | R | Y | A | D | S | V | K | G |
| 4 | | | | | | | | | | | | | | | | | | | | | |
| 4 | | | | | | | | | | | | | | | | | | | | | |
| 354 | | | | | | | | | | | | | | | | D | P | K | F | Q | - |
| 355 | | | | | | | | | | | | | | | | D | P | K | F | Q | D |
| 4 | | | | | | | | | | | | | | | | | | | | | |
| 4 | | | | | | | | | | | | | | | | | | | | | |

Continued

FIG. 15.2

KNOWN HEAVY CHAIN MUTATIONS

CDR-VH3

Continued from previous table

| SEQ ID NO: | 1 | 2 | 3 | 4 | 5 | | | | 6 | 7 | 8 | 9 | | 10 | 11 |
|---|---|---|---|---|---|---|---|---|---|---|---|---|---|---|---|
| | 95 | 96 | 97 | 98 | 99 | 99a | 99b | 99c | 100 | 100a | 100b | 100c | 100d | 101 | 102 |
| 5 | W | G | G | D | G | – | – | – | F | Y | A | M | – | D | Y |
| 356 | | | | K | | | | | | | | | | | |
| 357 | | | | | | | | | | | | | | | V |
| 5 | | | | | | | | | | | | | | | |
| 5 | | | | | | | | | | | | | | | |
| 358 | | | | | | | | | P | | | | | | K |
| 359 | | | | | | | | | P | | | | | | L |

FIG. 15.3

KNOWN LIGHT CHAIN MUTATIONS

CDR-VL1

| SEQ ID NO: | 1 | 2 | 3 | 4 | | | | | | 5 | 6 | 7 | | | | | 8 | 9 | 10 | 11 |
|---|---|---|---|---|---|---|---|---|---|---|---|---|---|---|---|---|---|---|---|---|
| | 24 | 25 | 26 | 27 | 27a | 27b | 27c | 27d | 27e | 28 | 29 | 30 | 30a | 30b | 30c | 30d | 31 | 32 | 33 | 34 |
| 6 | R | A | S | Q | – | – | – | – | – | D | V | N | – | – | – | – | T | A | V | A |
| 360 | | | | | | | | | | | | D | | | | | | | | |
| 361 | | | | K | | | | | | | | | | | | | | | | |
| 362 | | | | | | | | | | K | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 363 | | | | | | | | | | | | S | | | | | | | | |
| 6 | | | | | | | | | | | | | | | | | | | | |
| 6 | | | | | | | | | | | | | | | | | | | | |
| 363 | | | | | | | | | | | | S | | | | | | | | |
| 364 | K | | | | | | | | | | | | | | | | | | | |
| 364 | K | | | | | | | | | | | | | | | | | | | |
| 364 | K | | | | | | | | | | | | | | | | | | | |
| 6 | | | | | | | | | | | | | | | | | | | | |
| 6 | | | | | | | | | | | | | | | | | | | | |
| 363 | | | | | | | | | | | | S | | | | | | | | |

Continued

FIG. 16.1

| KNOWN LIGHT CHAIN MUTATIONS | | | | | | | | | | | | | | | | | | | | |
|---|---|---|---|---|---|---|---|---|---|---|---|---|---|---|---|---|---|---|---|---|
| | CDR-VH2 | | | | | | | | CDR-VH3 | | | | | | | | | | | |
| Continued from previous table | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| | 7 | S | A | S | F | L | Y | S | Q | Q | H | Y | T | – | – | T | P | P | T | 8 |
| | 7 | | | | | | | | | | | | | | | | | | | 8 |
| | 7 | | | | | | | | | | | | | | | | | | | 8 |
| | 7 | | | | | | | | | | | | | | | | | | | 8 |
| | 365 | | | K | | | | | | | | | | | | | | | | 8 |
| | 366 | | | | | | | K | | | | | | | | | | | | 8 |
| | 7 | | | | | | | | | | A | | | | | | | | | 370 |
| | 7 | | | | | | | | | | | A | | | | | | | | 371 |
| | 7 | | | | | | | | | | S | | | | | | | | | 372 |
| | 367 | | | | | | E | | | | | | | | | | | | | 8 |
| | 7 | | | | | | | | | | Y | | | | | | | | L | 373 |
| | 7 | | | | | | | | | | | | | | | | | | | 8 |
| | 7 | | | | | | | | | | | | | | | | | | | 8 |
| | 368 | | | | | R | | T | | | | | | | | | | | | 8 |
| | 7 | | | | | | | | | | | | | | | | | | | 8 |
| | 368 | | | | | R | | T | | | | | | | | | | | | 8 |
| | 369 | | | | W | | W | | | | | | | | | | | | | 8 |
| | 7 | | | | | | | | | | F | W | | | | | | | | 374 |

FIG. 16.2

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SEQ ID NO: | |
| | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | | |
| 3 | G | F | N | I | – | – | K | D | T | Y | I | H | R | I | Y | P | – | – | T | – | – | N | G | Y | T | R | Y | A | D | S | V | K | G | 4 | Continued |
| 375 | | | Y | | | | S | S | S | | | | S | | | | | | Y | | | S | | | | | | | | | | | | 382 | |
| 375 | | | Y | | | | S | S | S | | | | S | | | | | | Y | | | S | | | | | | | | | | | | 382 | |
| 376 | | | S | | | | S | S | S | | | | S | | | | | | Y | | | S | | | | | | | | | | | | 382 | |
| 377 | | | S | | | | S | Y | S | | | | S | | | | | | Y | | | S | | | | | | | | | | | | 382 | |
| 376 | | | S | | | | S | S | S | | | | S | | | | | | Y | | | S | | | | | | | | | | | | 382 | |
| 378 | | | S | | | | Y | S | S | | | | S | | | | | | Y | | | S | | | | | | | | | | | | 382 | |
| 377 | | | S | | | | S | Y | S | | | | S | | | | | | S | | | S | | | | | | | | | | | | 383 | |
| 376 | | | S | | | | S | S | S | | | | S | | | | | | Y | | | S | | | | | | | | | | | | 382 | |
| 379 | | | S | | | | Y | Y | S | | | | S | | | | | | S | | | S | | | | | | | | | | | | 383 | |
| 379 | | | S | | | | Y | Y | S | | | | S | | | | | | S | | | S | | | | | | | | | | | | 383 | |
| 378 | | | S | | | | Y | S | S | | | | S | | | | | | Y | | | S | | | | | | | | | | | | 382 | |
| 377 | | | S | | | | S | Y | S | | | | S | | | | | | Y | | | S | | | | | | | | | | | | 382 | |
| 380 | | | S | | | | Y | Y | S | | | | S | | | | | | S | | | S | | | | | | | | | | | | 383 | |
| 380 | | | S | | | | Y | Y | S | | | | S | | | | | | S | | | S | | | | | | | | | | | | 383 | |
| 376 | | | S | | | | S | S | S | | | | S | | | | | | Y | | | S | | | | | | | | | | | | 382 | |
| 377 | | | S | | | | S | Y | S | | | | S | | | | | | Y | | | S | | | | | | | | | | | | 382 | |
| 381 | | | Y | | | | Y | S | S | | | | S | | | | | | Y | | | S | | | | | | | | | | | | 382 | |
| 376 | | | S | | | | S | S | S | | | | S | | | | | | Y | | | S | | | | | | | | | | | | 382 | |
| 376 | | | S | | | | S | S | S | | | | S | | | | | | Y | | | S | | | | | | | | | | | | 382 | |

FIG. 17-1.1

Continued from previous table

HEAVY CHAIN MUTATIONS IN HER2 BINDING PHAGE LIBRARIES

CDR-VH3

| SEQ ID NO: | 1<br>95 | 2<br>96 | 3<br>97 | 4<br>98 | 5<br>99 | 99a | 99b | 99c | 6<br>100 | 7<br>100a | 8<br>100b | 9<br>100c | 100d | 100e | 100f | 100g | 100h | 100i | 100j | 100k | 100l | 100m | 10<br>101 | 11<br>102 |
|---|---|---|---|---|---|---|---|---|---|---|---|---|---|---|---|---|---|---|---|---|---|---|---|---|
| 5 | W | G | G | D | G | – | – | – | F | Y | A | M | – | – | – | – | – | – | – | – | – | – | D | Y |
| 384 | Y | Y | S | Y | A | | | | | – | – | – | | | | | | | | | | | | |
| 385 | Y | Y | S | S | | | | | | – | – | – | | | | | | | | | | | | |
| 385 | Y | Y | S | S | | | | | | – | – | – | | | | | | | | | | | | |
| 385 | Y | Y | S | S | | | | | | – | – | – | | | | | | | | | | | | |
| 386 | Y | Y | S | Y | A | | | | L | – | – | – | | | | | | | | | | | | |
| 387 | | W | S | S | A | | | | | – | – | – | | | | | | | | | | | | |
| 388 | | W | S | S | A | | | | M | – | – | – | | | | | | | | | | | | |
| 389 | | W | S | W | | | | | | – | – | – | | | | | | | | | | | | |
| 390 | | W | S | S | A | | | | | – | – | – | | | | | | | | | | | | |
| 391 | | W | S | S | | | | | | – | – | – | | | | | | | | | | | | |
| 390 | | W | S | S | A | | | | | – | – | – | | | | | | | | | | | | |
| 392 | | W | S | W | A | | | | | – | – | – | | | | | | | | | | | | |
| 393 | | W | S | S | A | | | | | – | – | – | | | | | | | | | | | | |
| 393 | | W | S | S | A | | | | | – | – | – | | | | | | | | | | | | |
| 394 | | W | S | S | A | | | | L | – | – | – | | | | | | | | | | | | |
| 393 | | W | S | S | A | | | | | – | – | – | | | | | | | | | | | | |
| 391 | | W | S | S | | | | | | – | – | – | | | | | | | | | | | | |
| 393 | | W | S | S | A | | | | | – | – | – | | | | | | | | | | | | |
| 394 | | W | S | S | A | | | | L | – | – | – | | | | | | | | | | | | |

FIG. 17-1.2

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| SE Q ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SE Q ID NO: |
| | 26 | 27 | 28 | 29 | 29 a | 29 b | 30 | 31 | 32 | 33 | 34 | 35 | 50 | 51 | 52 | 52 a | 52 b | 52 c | 53 | 53 a | 53 b | 54 | 55 | 56 | 57 | 58 | 59 | 60 | 61 | 62 | 63 | 64 | 65 | |
| 3 | G | F | N | I | – | – | K | D | T | Y | I | H | R | I | Y | P | – | – | T | – | – | N | G | Y | T | R | Y | A | D | S | V | K | G | 4 |
| 395 | | | S | | | | Y | S | S | | | | S | | | | | | Y | | | S | | | | | | | | | | | | 406 |
| 396 | | | S | | | | S | S | S | | | | S | | | | | | Y | | | S | | | | | | | | | | | | 406 |
| 397 | | | Y | | | | S | Y | S | | | | S | | | | | | Y | | | S | | | | | | | | | | | | 406 |
| 398 | | | S | | | | S | Y | S | | | | S | | | | | | Y | | | S | | | | | | | | | | | | 406 |
| 399 | | | S | | | | S | Y | S | S | | | S | | | | | | Y | | | Y | | | | | | | | | | | | 407 |
| 399 | | | S | | | | S | Y | S | S | | | S | | | | | | Y | | | Y | | | | | | | | | | | | 407 |
| 399 | | | S | | | | S | Y | S | S | | | S | | | | | | Y | | | Y | | | | | | | | | | | | 407 |
| 400 | | | S | | | | S | S | S | S | | | Y | | S | | | | S | | | S | | | | | | | | | | | | 408 |
| 401 | | | S | | | | W | W | S | W | | | S | | S | | | | S | | | S | | W | | S | | | | | | | | 409 |
| 401 | | | S | | | | W | W | S | W | | | S | | S | | | | S | | | S | | W | | S | | | | | | | | 409 |
| 401 | | | S | | | | W | W | S | W | | | S | | | | | | S | | | S | | | | S | | | | | | | | 410 |
| 401 | | | S | | | | W | W | S | W | | | S | | S | | | | S | | | S | | W | | S | | | | | | | | 411 |
| 402 | | | S | | | | W | S | S | W | | | S | | S | | | | S | | | S | | W | | S | | | | | | | | 411 |
| 401 | | | S | | | | W | W | S | W | | | S | | S | | | | S | | | S | | W | | S | | | | | | | | 411 |
| 403 | | | S | | | | S | W | S | W | | | S | | W | | | | S | | | S | | W | | S | | | | | | | | 412 |
| 401 | | | S | | | | W | W | S | W | | | S | | S | | | | S | | | S | | W | | S | | | | | | | | 413 |
| 401 | | | S | | | | W | W | S | W | | | S | | S | | | | S | | | S | | W | | S | | | | | | | | 411 |
| 401 | | | S | | | | W | W | S | W | | | W | | S | | | | S | | | S | | W | | S | | | | | | | | 414 |
| 404 | | | W | | | | W | S | S | S | | | W | | S | | | | S | | | S | | S | | W | | | | | | | | 415 |
| 404 | | | W | | | | W | S | S | S | | | W | | S | | | | S | | | S | | S | | W | | | | | | | | 416 |
| 405 | | | S | | | | S | S | S | W | | | W | | W | | | | S | | | S | | W | | S | | | | | | | | 417 |
| 400 | | | S | | | | S | S | S | S | | | W | | S | | | | S | | | W | | S | | W | | | | | | | | 418 |
| 404 | | | W | | | | W | S | S | S | | | W | | S | | | | S | | | S | | S | | W | | | | | | | | 419 |

Continued

FIG. 17-2.1

Continued from previous table

HEAVY CHAIN MUTATIONS IN HER2 BINDING PHAGE LIBRARIES

CDR-VH3

| SEQ ID NO: | 1 | 2 | 3 | 4 | 5 | | | | 6 | 7 | 8 | 9 | | | | | | | | | | | 10 | 11 |
|---|---|---|---|---|---|---|---|---|---|---|---|---|---|---|---|---|---|---|---|---|---|---|---|---|
| | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| 5 | W | G | G | D | G | – | – | – | F | Y | A | M | – | – | – | – | – | – | – | – | – | – | D | Y |
| 420 | | S | S | S | | | | | | – | – | – | | | | | | | | | | | | |
| 421 | | W | S | S | A | | | | M | – | – | – | | | | | | | | | | | | |
| 422 | | W | S | S | A | | | | L | – | – | – | | | | | | | | | | | | |
| 422 | | W | S | S | A | | | | L | – | – | – | | | | | | | | | | | | |
| 423 | F | S | F | S | S | | | | S | S | F | A | M | | | | | | | | | | | |
| 424 | F | S | F | S | S | | | | S | S | F | A | I | | | | | | | | | | | |
| 425 | F | F | F | F | S | | | | S | S | F | F | G | F | | | | | | | | | | |
| 426 | Y | Y | S | S | Y | | | | Y | S | Y | Y | S | F | G | L | | | | | | | | |
| 427 | | W | S | S | A | | | | I | – | – | – | | | | | | | | | | | | |
| 428 | | W | S | S | A | | | | L | – | – | – | | | | | | | | | | | | |
| 428 | | W | S | S | A | | | | L | – | – | – | | | | | | | | | | | | |
| 429 | | W | S | S | | | | | M | – | – | – | | | | | | | | | | | | |
| 422 | | W | S | S | A | | | | L | – | – | – | | | | | | | | | | | | |
| 430 | | W | S | S | A | | | | | – | – | – | | | | | | | | | | | | |
| 422 | | W | S | S | A | | | | L | – | – | – | | | | | | | | | | | | |
| 431 | | S | S | S | A | | | | | – | – | – | | | | | | | | | | | | |
| 432 | | W | S | S | A | | | | M | – | – | – | | | | | | | | | | | | |
| 433 | | S | S | W | | | | | L | – | – | – | | | | | | | | | | | | |
| 434 | S | S | W | S | S | | | | W | S | S | A | L | | | | | | | | | | | |
| 434 | S | S | W | S | S | | | | W | S | S | A | L | | | | | | | | | | | |
| 435 | S | S | S | S | S | | | | W | W | S | A | I | | | | | | | | | | | |
| 436 | S | S | W | S | S | | | | W | S | W | A | L | | | | | | | | | | | |
| 437 | S | S | W | S | S | | | | W | S | S | A | M | | | | | | | | | | | |

FIG. 17-2.2

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SEQ ID NO: |
| | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | |
| 3 | G | F | N | I | – | – | K | D | T | Y | I | H | R | I | Y | P | – | – | T | – | – | N | G | Y | T | R | Y | A | D | S | V | K | G | 4 |
| 438 | | | S | | | | W | S | S | S | | | S | | S | | | | S | | | S | | S | | W | | | | | | | | 456 |
| 439 | | | S | | | | Y | S | Y | Y | | | S | | | | | | S | | | S | | | | S | | | | | | | | 457 |
| 440 | | | Y | | | | S | Y | S | Y | | | S | | | | | | Y | | | S | | | | S | | | | | | | | 458 |
| 441 | | | Y | | | | S | S | S | Y | | | S | | | | | | Y | | | S | | | | S | | | | | | | | 458 |
| 442 | | | S | | | | S | S | S | Y | | | S | | | | | | Y | | | S | | | | S | | | | | | | | 458 |
| 442 | | | S | | | | S | S | S | Y | | | S | | | | | | Y | | | S | | | | S | | | | | | | | 458 |
| 443 | | | S | | | | Y | S | S | Y | | | S | | | | | | Y | | | S | | | | S | | | | | | | | 458 |
| 444 | | | Y | | | | S | S | S | Y | | | S | | | | | | Y | | | S | | | | S | | | | | | | | 458 |
| 445 | | | Y | | | | S | Y | S | S | | | S | | S | | | | Y | | | S | | | | Y | | | | | | | | 459 |
| 446 | | | Y | | | | S | S | S | S | | | Y | | S | | | | S | | | S | | | | Y | | | | | | | | 460 |
| 447 | | | S | | | | Y | Y | S | S | | | S | | | | | | Y | | | S | | S | | Y | | | | | | | | 461 |
| 447 | | | S | | | | Y | Y | S | S | | | S | | | | | | S | | | S | | S | | Y | | | | | | | | 462 |
| 448 | | | Y | | | | S | S | S | S | | | Y | | | | | | S | | | S | | | | | | | | | | | | 463 |
| 449 | | | S | | | | S | Y | S | S | | | S | | | | | | Y | | | Y | | | | | | | | | | | | 464 |
| 450 | | | S | | | | S | Y | S | | | | S | | | | | | S | | | S | | | | | | | | | | | | 465 |
| 451 | | | S | | | | | S | S | | | | S | | | | | | Y | | | S | | | | S | | | | | | | | 466 |
| 452 | | | S | | | | | Y | S | | | | S | | | | | | Y | | | S | | | | S | | | | | | | | 466 |
| 453 | | | S | | | | | S | S | | | | S | | | | | | Y | | | S | | | | S | | | | | | | | 466 |
| 454 | | | Y | | | | | S | S | | | | S | | | | | | Y | | | S | | | | S | | | | | | | | 466 |
| 454 | | | Y | | | | | S | S | | | | S | | | | | | Y | | | S | | | | S | | | | | | | | 466 |
| 455 | | | S | | | | | S | S | | | | S | | | | | | S | | | S | | | | S | | | | | | | | 467 |

Continued

FIG. 17-3.1

Continued from previous table

HEAVY CHAIN MUTATIONS IN HER2 BINDING PHAGE LIBRARIES

CDR-VH3

| SEQ ID NO: | 1 | 2 | 3 | 4 | 5 | | | | 6 | 7 | 8 | 9 | | | | | | | | | | | 10 | 11 |
|---|---|---|---|---|---|---|---|---|---|---|---|---|---|---|---|---|---|---|---|---|---|---|---|---|
| | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| 5 | W | G | G | D | G | – | – | – | F | Y | A | M | – | – | – | – | – | – | – | – | – | – | D | Y |
| 468 | S | S | W | S | S | | | | W | S | S | A | M | | | | | | | | | | | |
| 469 | Y | Y | S | Y | A | | | | L | – | – | – | | | | | | | | | | | | |
| 470 | Y | Y | S | Y | A | | | | | – | – | – | | | | | | | | | | | | |
| 470 | Y | Y | S | Y | A | | | | | – | – | – | | | | | | | | | | | | |
| 471 | Y | Y | S | S | A | | | | | – | – | – | | | | | | | | | | | | |
| 472 | Y | Y | S | Y | A | | | | L | – | – | – | | | | | | | | | | | | |
| 473 | Y | Y | S | Y | A | | | | | – | – | – | | | | | | | | | | | | |
| 474 | Y | Y | S | Y | A | | | | L | – | – | – | | | | | | | | | | | | |
| 475 | S | S | Y | S | Y | | | | Y | | Y | S | Y | A | L | | | | | | | | | |
| 476 | Y | Y | S | S | Y | | | | Y | S | Y | Y | S | Y | A | L | | | | | | | | |
| 477 | Y | Y | S | S | Y | | | | S | S | S | S | S | Y | Y | Y | Y | A | F | | | | | |
| 478 | Y | Y | S | S | S | | | | S | S | Y | S | S | S | Y | Y | Y | Y | A | F | | | | |
| 479 | G | Y | Y | Y | S | | | | Y | | S | G | Y | | | | | | | | | | A | L |
| 480 | G | | | Y | | | | | Y | – | – | – | | | | | | | | | | | G | I |
| 481 | E | Y | Y | Q | | | | | Y | G | P | Y | R | S | T | Y | | | | | | | G | L |
| 482 | Y | Y | S | S | | | | | | – | – | – | | | | | | | | | | | | |
| 483 | Y | Y | | Y | | | | | M | – | – | – | | | | | | | | | | | | |
| 484 | Y | Y | | Y | | | | | L | – | – | – | | | | | | | | | | | | |
| 485 | Y | Y | | Y | | | | | | – | – | – | | | | | | | | | | | | |
| 486 | Y | Y | | S | | | | | | – | – | – | | | | | | | | | | | | |
| 487 | Y | Y | | G | A | | | | | – | – | – | | | | | | | | | | | | |

FIG. 17-3.2

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SEQ ID NO: |
| | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | |
| 3 | G | F | N | I | – | – | K | D | T | Y | I | H | R | I | Y | P | – | – | T | – | – | N | G | Y | T | R | Y | A | D | S | V | K | G | 4 |
| 488 | | | S | | | | | Y | S | | | | S | | | | | | S | | | S | | | | S | | | | | | | | 496 |
| 488 | | | S | | | | | Y | S | | | | S | | | | | | S | | | S | | | | S | | | | | | | | 496 |
| 489 | | | S | | | | | S | S | | | | S | | | | | | Y | | | S | | | | S | | | | | | | | 497 |
| 490 | | | S | | | | | Y | S | | | | S | | | | | | Y | | | S | | | | S | | | | | | | | 497 |
| 491 | | | S | | | | | Y | S | S | | | S | | | | | | S | | | S | | S | | Y | | | | | | | | 498 |
| 492 | | | S | | | | | S | Y | S | | | S | | | | | | Y | | | S | | S | | S | | | | | | | | 499 |
| 493 | | | S | | | | | S | S | S | | | S | | | | | | Y | | | Y | | | | S | | | | | | | | 500 |
| 494 | | | Y | | | | | S | S | S | | | S | | | | | | Y | | | Y | | S | | Y | | | | | | | | 501 |
| 493 | | | S | | | | | S | S | S | | | S | | | | | | Y | | | Y | | | | S | | | | | | | | 502 |
| 495 | | | Y | | | | | S | Y | S | | | S | | | | | | S | | | Y | | | | S | | | | | | | | 503 |
| 494 | | | Y | | | | | S | S | S | | | S | | | | | | Y | | | Y | | S | | Y | | | | | | | | 504 |
| 493 | | | S | | | | | S | S | S | | | S | | | | | | Y | | | Y | | S | | Y | | | | | | | | 504 |
| 495 | | | Y | | | | | S | Y | S | | | S | | | | | | Y | | | Y | | S | | Y | | | | | | | | 504 |
| 493 | | | S | | | | | S | S | S | | | S | | | | | | Y | | | Y | | | | S | | | | | | | | 505 |
| 494 | | | Y | | | | | S | S | S | | | S | | | | | | Y | | | Y | | | | S | | | | | | | | 505 |
| 493 | | | S | | | | | S | S | S | | | S | | | | | | Y | | | Y | | | | S | | | | | | | | 505 |
| 493 | | | S | | | | | S | S | S | | | S | | | | | | S | | | Y | | | | S | | | | | | | | 506 |
| 493 | | | S | | | | | S | S | S | | | S | | | | | | Y | | | Y | | | | S | | | | | | | | 507 |
| 493 | | | S | | | | | S | S | S | | | S | | | | | | Y | | | Y | | | | S | | | | | | | | 507 |

Continued

FIG. 17-4.1

HEAVY CHAIN MUTATIONS IN HER2 BINDING PHAGE LIBRARIES

Continued from previous table

| CDR-VH3 | | | | | | | | | | | | | | | | | | | | | | | | |
|---|---|---|---|---|---|---|---|---|---|---|---|---|---|---|---|---|---|---|---|---|---|---|---|---|
| SEQ ID | 1 | 2 | 3 | 4 | 5 | | | | 6 | 7 | 8 | 9 | | | | | | | | | | | 10 | 11 |
| NO: | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| 5 | W | G | G | D | G | – | – | – | F | Y | A | M | – | – | – | – | – | – | – | – | – | – | D | Y |
| 508 | Y | Y | | R | | | | | A | M | – | – | | | | | | | | | | | | |
| 509 | Y | S | Y | S | | | | | A | L | – | – | | | | | | | | | | | | |
| 510 | Y | R | Y | Y | | | | | A | L | – | – | | | | | | | | | | | | |
| 511 | Y | R | Y | G | | | | | A | M | – | – | | | | | | | | | | | | |
| 512 | Y | Y | | G | Y | | | | Y | G | M | – | | | | | | | | | | | | |
| 513 | Y | S | Y | Y | Y | | | | Y | A | L | – | | | | | | | | | | | | |
| 514 | S | S | Y | Y | Y | | | | Y | G | M | – | | | | | | | | | | | | |
| 515 | S | S | Y | Y | Y | | | | Y | G | F | – | | | | | | | | | | | | |
| 516 | S | S | Y | Y | Y | | | | Y | G | L | – | | | | | | | | | | | | |
| 517 | S | | | Y | S | | | | R | G | I | – | | | | | | | | | | | | |
| 518 | G | Y | S | Y | S | | | | R | G | I | – | | | | | | | | | | | | |
| 519 | G | Y | S | Y | S | | | | R | G | M | – | | | | | | | | | | | | |
| 520 | G | S | S | Y | S | | | | Y | G | M | – | | | | | | | | | | | | |
| 521 | G | S | | Y | | | | | Y | G | M | – | | | | | | | | | | | | |
| 522 | G | S | | Y | | | | | Y | G | I | – | | | | | | | | | | | | |
| 523 | G | R | R | Y | S | | | | R | G | I | – | | | | | | | | | | | | |
| 524 | G | | S | Y | | | | | Y | G | M | – | | | | | | | | | | | | |
| 525 | G | | S | Y | | | | | Y | G | M | – | | | | | | | | | | | | |
| 526 | G | | R | Y | | | | | Y | G | L | – | | | | | | | | | | | | |

FIG. 17-4.2

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | | Continued |
|---|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SEQ ID NO: | |
| | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | | |
| 3 | G | F | N | I | – | – | K | D | T | Y | I | H | R | I | Y | P | – | – | T | – | – | N | G | Y | T | R | Y | A | D | S | V | K | G | 4 | |
| 527 | | | Y | | | | | S | S | S | | | S | | | | | | Y | | | Y | | S | | Y | | | | | | | | 533 | |
| 528 | | | S | | | | | S | S | S | | | S | | | | | | Y | | | Y | | | | S | | | | | | | | 534 | |
| 528 | | | S | | | | | S | S | S | | | S | | | | | | S | | | Y | | S | | Y | | | | | | | | 535 | |
| 529 | | | S | | | | | Y | S | S | | | Y | | | | | | S | | | S | | S | | Y | | | | | | | | 536 | |
| 528 | | | S | | | | | S | S | S | | | S | | S | | | | Y | | | Y | | S | | Y | | | | | | | | 537 | |
| 528 | | | S | | | | | S | S | S | | | S | | S | | | | Y | | | S | | S | | S | | | | | | | | 538 | |
| 528 | | | S | | | | | S | S | S | | | S | | S | | | | Y | | | S | | | | S | | | | | | | | 539 | |
| 530 | | | S | | | | | S | Y | S | | | Y | | S | | | | S | | | S | | | | Y | | | | | | | | 540 | |
| 531 | | | Y | | | | | S | S | | | | S | | | | | | S | | | S | | | | S | | | | | | | | 541 | |
| 527 | | | Y | | | | | S | S | S | | | S | | | | | | S | | | S | | | | S | | | | | | | | 541 | |
| 528 | | | S | | | | | S | S | S | | | S | | S | | | | S | | | S | | | | S | | | | | | | | 542 | |
| 532 | | | Y | | | | | S | Y | S | | | S | | | | | | S | | | S | | | | Y | | | | | | | | 543 | |
| 527 | | | Y | | | | | S | S | S | | | S | | | | | | S | | | S | | | | S | | | | | | | | 544 | |
| 528 | | | S | | | | | S | S | S | | | S | | | | | | S | | | S | | | | S | | | | | | | | 544 | |
| 527 | | | Y | | | | | S | S | S | | | Y | | | | | | S | | | S | | | | S | | | | | | | | 545 | |
| 528 | | | S | | | | | S | S | S | | | S | | | | | | S | | | S | | | | S | | | | | | | | 544 | |
| 527 | | | Y | | | | | S | S | S | | | Y | | | | | | S | | | S | | | | S | | | | | | | | 546 | |
| 528 | | | S | | | | | S | S | S | | | Y | | S | | | | Y | | | S | | | | S | | | | | | | | 547 | |
| 528 | | | S | | | | | S | S | S | | | S | | | | | | S | | | S | | | | S | | | | | | | | 548 | |

FIG. 17-5.1

HEAVY CHAIN MUTATIONS IN HER2 BINDING PHAGE LIBRARIES

Continued from previous table

CDR-VH3

| SEQ ID NO: | 1 | 2 | 3 | 4 | 5 | | | | 6 | 7 | 8 | 9 | | | | | | | | | | | 10 | 11 |
|---|---|---|---|---|---|---|---|---|---|---|---|---|---|---|---|---|---|---|---|---|---|---|---|---|
| | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| 5 | W | G | G | D | G | – | – | – | F | Y | A | M | – | – | – | – | – | – | – | – | – | – | D | Y |
| 549 | G | | R | Y | | | | | R | G | I | – | | | | | | | | | | | | |
| 550 | G | | | Y | | | | | Y | G | I | – | | | | | | | | | | | | |
| 550 | G | | | Y | | | | | Y | G | I | – | | | | | | | | | | | | |
| 551 | Y | Y | Y | S | | | | | G | S | Y | G | M | | | | | | | | | | | |
| 552 | S | Y | S | S | Y | | | | Y | S | S | G | M | | | | | | | | | | | |
| 553 | R | Y | Y | Y | Y | | | | Y | | S | A | F | | | | | | | | | | | |
| 554 | Y | Y | Y | Y | S | | | | Y | | S | G | G | A | I | | | | | | | | | |
| 555 | S | Y | Y | Y | S | | | | Y | | S | G | Y | G | M | | | | | | | | | |
| 556 | S | Y | Y | Y | S | | | | Y | | S | G | Y | G | L | | | | | | | | | |
| 557 | S | Y | Y | Y | S | | | | Y | | Y | G | Y | G | M | | | | | | | | | |
| 558 | S | Y | Y | G | S | | | | Y | | Y | G | Y | G | F | | | | | | | | | |
| 559 | S | D | Y | Y | | | | | Y | | S | G | Y | G | I | | | | | | | | | |
| 560 | S | D | Y | Y | S | | | | Y | | S | G | Y | G | L | | | | | | | | | |
| 561 | G | Y | Y | Y | S | | | | Y | | Y | G | Y | G | M | | | | | | | | | |
| 562 | G | Y | Y | Y | S | | | | Y | | Y | G | S | A | M | | | | | | | | | |
| 563 | G | Y | Y | Y | S | | | | Y | | S | G | Y | G | M | | | | | | | | | |
| 564 | G | Y | Y | Y | S | | | | Y | | S | G | Y | A | L | | | | | | | | | |
| 565 | G | Y | Y | Y | S | | | | Y | | S | G | Y | A | I | | | | | | | | | |
| 566 | G | Y | Y | Y | S | | | | Y | | S | G | Y | A | M | | | | | | | | | |

FIG. 17-5.2

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SEQ ID NO: |
| | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | |
| 3 | G | F | N | I | – | – | K | D | T | Y | I | H | R | I | Y | P | – | – | T | – | – | N | G | Y | T | R | Y | A | D | S | V | K | G | 4 |
| 567 | | | | Y | | | | | S | S | S | | | S | | | | | | S | | | S | | S | | S | | | | | | | 572 |
| 568 | | | | Y | | | | | S | Y | S | | | Y | | S | | | | S | | | S | | | | S | | | | | | | 573 |
| 569 | | | | S | | | | | S | Y | S | | | S | | | | | | S | | | S | | | | S | | | | | | | 574 |
| 570 | | | | Y | | | | | S | Y | | | | S | | S | | | | S | | | S | | | | S | | | | | | | 575 |
| 569 | | | | S | | | | | S | Y | S | | | S | | | | | | S | | | S | | | | S | | | | | | | 574 |
| 567 | | | | Y | | | | | S | S | S | | | S | | | | | | S | | | S | | | | Y | | | | | | | 576 |
| 571 | | | | S | | | | | S | S | S | | | Y | | | | | | S | | | S | | | | S | | | | | | | 577 |
| 567 | | | | Y | | | | | S | S | S | | | S | | | | | | S | | | Y | | | | S | | | | | | | 578 |
| 567 | | | | Y | | | | | S | S | S | | | Y | | | | | | S | | | S | | S | | S | | | | | | | 579 |
| 567 | | | | Y | | | | | S | S | S | | | S | | | | | | S | | | S | | | | Y | | | | | | | 580 |
| 571 | | | | S | | | | | S | S | S | | | S | | | | | | S | | | S | | | | S | | | | | | | 574 |
| 571 | | | | S | | | | | S | S | S | | | S | | | | | | S | | | S | | S | | S | | | | | | | 572 |
| 567 | | | | Y | | | | | S | S | S | | | S | | S | | | | S | | | S | | | | S | | | | | | | 573 |
| 567 | | | | Y | | | | | S | S | S | | | Y | | | | | | S | | | S | | | | S | | | | | | | 577 |
| 568 | | | | Y | | | | | S | Y | S | | | S | | | | | | S | | | S | | | | S | | | | | | | 574 |
| 567 | | | | Y | | | | | S | S | S | | | Y | | S | | | | S | | | S | | | | S | | | | | | | 573 |
| 567 | | | | Y | | | | | S | S | S | | | S | | | | | | S | | | S | | | | S | | | | | | | 574 |
| 567 | | | | Y | | | | | S | S | S | | | Y | | | | | | S | | | S | | | | S | | | | | | | 577 |
| 567 | | | | Y | | | | | S | S | S | | | Y | | | | | | S | | | S | | | | Y | | | | | | | 581 |

Continued

FIG. 17-6.1

HEAVY CHAIN MUTATIONS IN HER2 BINDING PHAGE LIBRARIES

Continued from previous table

| | CDR-VH3 | | | | | | | | | | | | | | | | | | | | | | | |
|---|---|---|---|---|---|---|---|---|---|---|---|---|---|---|---|---|---|---|---|---|---|---|---|---|
| SEQ ID NO: | 1 | 2 | 3 | 4 | 5 | | | | 6 | 7 | 8 | 9 | | | | | | | | | | | 10 | 11 |
| | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| 5 | W | G | G | D | G | – | – | – | F | Y | A | M | – | – | – | – | – | – | – | – | – | – | D | Y |
| 582 | G | Y | Y | Y | S | | | | Y | | S | G | Y | G | I | | | | | | | | | |
| 583 | G | Y | Y | Y | S | | | | Y | | S | G | Y | G | L | | | | | | | | | |
| 584 | G | Y | Y | Y | S | | | | Y | | S | G | Y | G | M | | | | | | | | | |
| 585 | G | Y | Y | Y | S | | | | Y | | G | G | S | G | L | | | | | | | | | |
| 586 | G | Y | Y | Y | S | | | | Y | | G | G | Y | G | M | | | | | | | | | |
| 587 | G | Y | Y | Y | S | | | | Y | | G | G | Y | G | I | | | | | | | | | |
| 588 | G | Y | Y | Y | S | | | | Y | | G | G | Y | G | M | | | | | | | | | |
| 589 | G | Y | Y | Y | S | | | | Y | | G | G | Y | G | M | | | | | | | | | |
| 590 | G | Y | Y | Y | S | | | | Y | | G | G | Y | G | M | | | | | | | | | |
| 591 | G | Y | Y | Y | S | | | | Y | | G | G | Y | G | L | | | | | | | | | |
| 592 | G | Y | Y | Y | S | | | | Y | | G | G | Y | G | M | | | | | | | | | |
| 593 | G | Y | Y | Y | S | | | | Y | | G | G | Y | G | M | | | | | | | | | |
| 594 | G | Y | Y | Y | | | | | Y | | S | G | Y | G | I | | | | | | | | | |
| 595 | G | S | Y | Y | S | | | | Y | | S | G | Y | G | M | | | | | | | | | |
| 596 | G | S | Y | Y | S | | | | Y | | S | G | Y | A | I | | | | | | | | | |
| 597 | G | S | Y | Y | S | | | | Y | | S | G | Y | A | F | | | | | | | | | |
| 598 | G | S | Y | Y | S | | | | Y | | S | G | S | G | I | | | | | | | | | |
| 599 | G | S | Y | Y | | | | | Y | | Y | G | S | A | I | | | | | | | | | |
| 600 | G | S | Y | Y | | | | | Y | | Y | G | S | G | M | | | | | | | | | |

FIG. 17-6.2

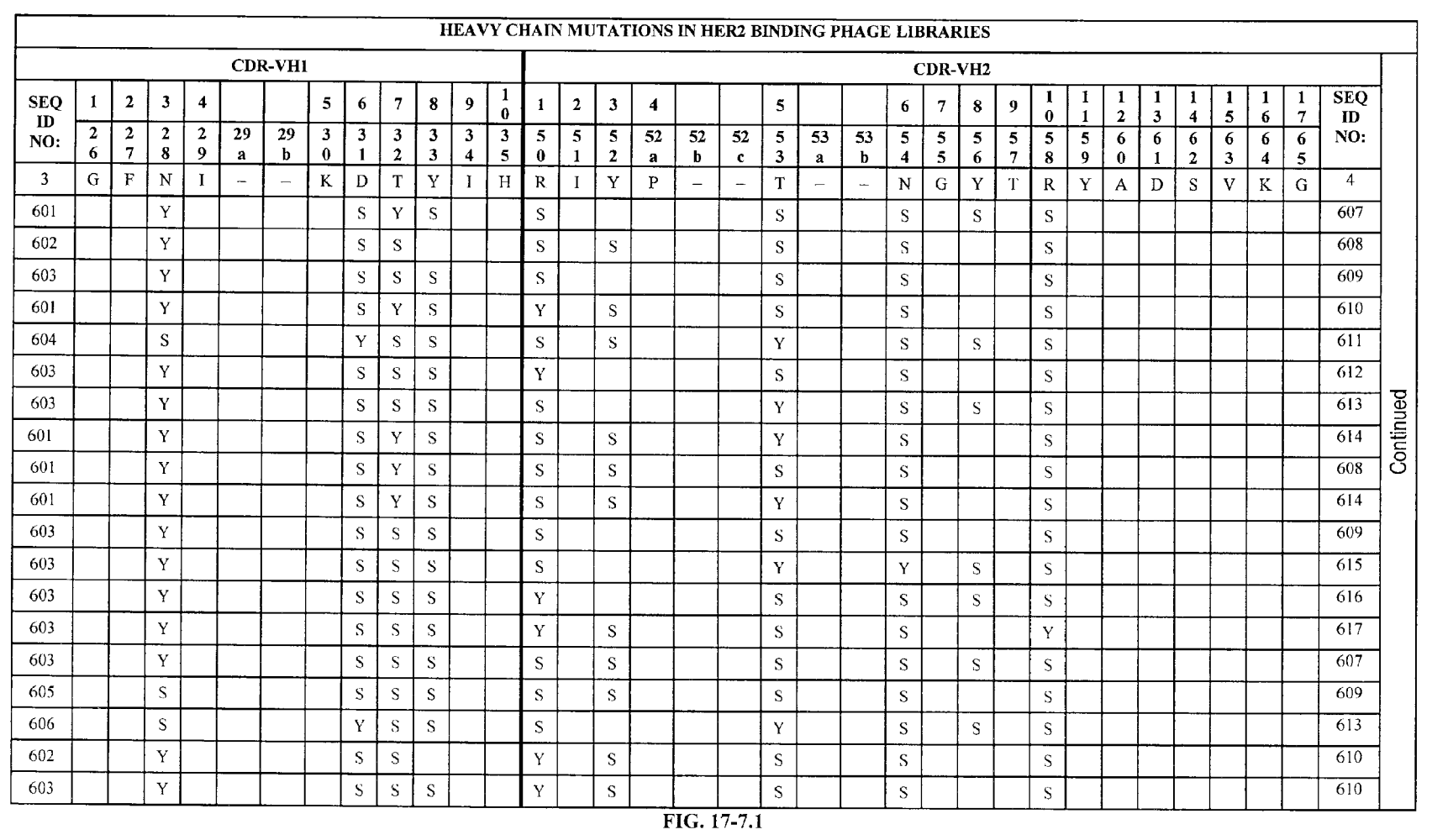

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SEQ ID NO: |
| | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | |
| 3 | G | F | N | I | – | – | K | D | T | Y | I | H | R | I | Y | P | – | – | T | – | – | N | G | Y | T | R | Y | A | D | S | V | K | G | 4 |
| 601 | | | Y | | | | | S | Y | S | | | S | | | | | | S | | | S | | S | | S | | | | | | | | 607 |
| 602 | | | Y | | | | | S | S | | | | S | | S | | | | S | | | S | | | | S | | | | | | | | 608 |
| 603 | | | Y | | | | | S | S | S | | | S | | | | | | S | | | S | | | | S | | | | | | | | 609 |
| 601 | | | Y | | | | | S | Y | S | | | Y | | S | | | | S | | | S | | | | S | | | | | | | | 610 |
| 604 | | | S | | | | | Y | S | S | | | S | | S | | | | Y | | | S | | S | | S | | | | | | | | 611 |
| 603 | | | Y | | | | | S | S | S | | | Y | | | | | | S | | | S | | | | S | | | | | | | | 612 |
| 603 | | | Y | | | | | S | S | S | | | S | | | | | | Y | | | S | | S | | S | | | | | | | | 613 |
| 601 | | | Y | | | | | S | Y | S | | | S | | S | | | | Y | | | S | | | | S | | | | | | | | 614 |
| 601 | | | Y | | | | | S | Y | S | | | S | | S | | | | S | | | S | | | | S | | | | | | | | 608 |
| 601 | | | Y | | | | | S | Y | S | | | S | | S | | | | Y | | | S | | | | S | | | | | | | | 614 |
| 603 | | | Y | | | | | S | S | S | | | S | | | | | | S | | | S | | | | S | | | | | | | | 609 |
| 603 | | | Y | | | | | S | S | S | | | S | | | | | | Y | | | Y | | S | | S | | | | | | | | 615 |
| 603 | | | Y | | | | | S | S | S | | | Y | | | | | | S | | | S | | S | | S | | | | | | | | 616 |
| 603 | | | Y | | | | | S | S | S | | | Y | | S | | | | S | | | S | | | | Y | | | | | | | | 617 |
| 603 | | | Y | | | | | S | S | S | | | S | | S | | | | S | | | S | | S | | S | | | | | | | | 607 |
| 605 | | | S | | | | | S | S | S | | | S | | S | | | | S | | | S | | | | S | | | | | | | | 609 |
| 606 | | | S | | | | | Y | S | S | | | S | | | | | | Y | | | S | | S | | S | | | | | | | | 613 |
| 602 | | | Y | | | | | S | S | | | | Y | | S | | | | S | | | S | | | | S | | | | | | | | 610 |
| 603 | | | Y | | | | | S | S | S | | | Y | | S | | | | S | | | S | | | | S | | | | | | | | 610 |

Continued

FIG. 17-7.1

HEAVY CHAIN MUTATIONS IN HER2 BINDING PHAGE LIBRARIES

Continued from previous table

| CDR-VH3 | | | | | | | | | | | | | | | | | | | | | | | | |
|---|---|---|---|---|---|---|---|---|---|---|---|---|---|---|---|---|---|---|---|---|---|---|---|---|
| SEQ ID NO: | 1 | 2 | 3 | 4 | 5 | | | | 6 | 7 | 8 | 9 | | | | | | | | | | | 10 | 11 |
| | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| 5 | W | G | G | D | G | – | – | – | F | Y | A | M | – | – | – | – | – | – | – | – | – | – | D | Y |
| 618 | G | S | Y | Y | | | | | Y | | S | G | S | G | M | | | | | | | | | |
| 619 | G | S | | Y | S | | | | Y | | G | G | Y | G | L | | | | | | | | | |
| 620 | G | S | Y | S | | | | | Y | | Y | G | Y | G | L | | | | | | | | | |
| 621 | G | R | Y | S | | | | | Y | | G | G | Y | G | M | | | | | | | | | |
| 622 | Y | Y | Y | S | S | | | | G | | Y | Y | Y | Y | A | F | | | | | | | | |
| 623 | Y | S | Y | S | Y | | | | Y | G | Y | Y | G | S | G | M | | | | | | | | |
| 624 | Y | R | S | Y | Y | | | | S | | R | Y | G | Y | G | M | | | | | | | | |
| 625 | Y | | Y | Y | Y | | | | S | | Y | G | G | S | G | L | | | | | | | | |
| 626 | Y | | Y | Y | Y | | | | S | | Y | G | G | S | G | L | | | | | | | | |
| 627 | Y | | Y | S | Y | | | | S | | S | S | G | S | A | L | | | | | | | | |
| 628 | S | Y | Y | Y | | | | | G | | Y | S | G | Y | G | M | | | | | | | | |
| 629 | R | R | S | Y | Y | | | | S | | R | Y | S | Y | G | L | | | | | | | | |
| 630 | R | R | S | Y | Y | | | | S | | S | R | S | Y | A | M | | | | | | | | |
| 631 | Y | Y | Y | G | Y | | | | Y | S | Y | Y | S | G | Y | G | L | | | | | | | |
| 632 | Y | Y | Y | G | Y | | | | Y | S | Y | Y | G | G | S | G | L | | | | | | | |
| 633 | Y | Y | Y | G | Y | | | | Y | S | Y | Y | G | G | S | A | M | | | | | | | |
| 634 | Y | Y | Y | S | | | | | G | S | Y | Y | Y | Y | Y | A | F | | | | | | | |
| 635 | Y | Y | Y | S | Y | | | | Y | S | Y | Y | S | Y | G | G | I | | | | | | | |
| 636 | Y | Y | S | S | Y | | | | Y | S | Y | Y | Y | Y | G | G | M | | | | | | | |

FIG. 17-7.2

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SEQ ID NO: |
| | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | |
| 3 | G | F | N | I | – | – | K | D | T | Y | I | H | R | I | Y | P | – | – | T | – | – | N | G | Y | T | R | Y | A | D | S | V | K | G | 4 |
| 637 | | | Y | | | | | S | S | S | | | S | | S | | | | S | | | S | | | | S | | | | | | | | 645 |
| 638 | | | S | | | | | S | S | S | | | Y | | S | | | | Y | | | S | | | | Y | | | | | | | | 646 |
| 638 | | | S | | | | | S | S | S | | | Y | | S | | | | Y | | | S | | | | Y | | | | | | | | 646 |
| 639 | | | S | | | | | Y | S | S | | | Y | | | | | | Y | | | S | | S | | S | | | | | | | | 647 |
| 640 | | | Y | | | | | Y | S | S | | | S | | S | | | | S | | | Y | | | | S | | | | | | | | 648 |
| 637 | | | Y | | | | | S | S | S | | | S | | S | | | | S | | | Y | | | | S | | | | | | | | 648 |
| 638 | | | S | | | | | S | S | S | | | S | | | | | | Y | | | S | | | | S | | | | | | | | 649 |
| 637 | | | Y | | | | | S | S | S | | | S | | S | | | | Y | | | S | | | | S | | | | | | | | 650 |
| 638 | | | S | | | | | S | S | S | | | Y | | | | | | Y | | | S | | | | Y | | | | | | | | 651 |
| 637 | | | Y | | | | | S | S | S | | | Y | | S | | | | S | | | S | | | | S | | | | | | | | 652 |
| 637 | | | Y | | | | | S | S | S | | | Y | | S | | | | S | | | S | | | | S | | | | | | | | 652 |
| 641 | | | S | | | | | S | S | | | | Y | | S | | | | S | | | Y | | S | | Y | | | | | | | | 653 |
| 642 | | | F | | | | | Y | Y | | | | S | | S | | | | S | | | S | | | | S | | | | | | | | 645 |
| 643 | | | S | | | | | S | S | | | | S | | | | | | Y | | | S | | | | S | | | | | | | | 649 |
| 640 | | | Y | | | | | Y | S | S | | | S | | | | | | Y | | | Y | | S | | Y | | | | | | | | 654 |
| 644 | | | Y | | | | | S | Y | S | | | S | | | | | | Y | | | Y | | | | S | | | | | | | | 655 |
| 640 | | | Y | | | | | Y | S | S | | | S | | | | | | Y | | | Y | | S | | Y | | | | | | | | 656 |
| 639 | | | S | | | | | Y | S | S | | | S | | | | | | Y | | | Y | | S | | Y | | | | | | | | 656 |
| 639 | | | S | | | | | Y | S | S | | | S | | | | | | S | | | Y | | | | S | | | | | | | | 657 |

Continued

FIG. 17-8.1

HEAVY CHAIN MUTATIONS IN HER2 BINDING PHAGE LIBRARIES

Continued from previous table

| CDR-VH3 | | | | | | | | | | | | | | | | | | | | | | | | |
|---|---|---|---|---|---|---|---|---|---|---|---|---|---|---|---|---|---|---|---|---|---|---|---|---|
| SEQ ID NO: | 1 | 2 | 3 | 4 | 5 | | | | 6 | 7 | 8 | 9 | | | | | | | | | | | 10 | 11 |
| | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| 5 | W | G | G | D | G | – | – | – | F | Y | A | M | – | – | – | – | – | – | – | – | – | – | D | Y |
| 658 | Y | S | Y | Y | Y | | | | Y | S | Y | Y | Y | G | S | A | M | | | | | | | |
| 659 | Y | S | Y | Y | Y | | | | Y | S | Y | Y | S | G | Y | G | F | | | | | | | |
| 660 | Y | S | Y | Y | Y | | | | Y | S | Y | Y | S | G | Y | G | F | | | | | | | |
| 661 | Y | S | Y | Y | Y | | | | Y | S | Y | Y | G | G | S | A | F | | | | | | | |
| 662 | Y | S | Y | Y | Y | | | | Y | S | Y | Y | G | G | S | G | M | | | | | | | |
| 663 | Y | S | Y | Y | Y | | | | Y | S | Y | Y | G | G | S | G | L | | | | | | | |
| 664 | Y | S | Y | S | Y | | | | Y | G | Y | Y | Y | G | S | G | L | | | | | | | |
| 665 | Y | S | S | Y | Y | | | | Y | S | Y | Y | S | G | S | G | L | | | | | | | |
| 666 | S | S | Y | Y | Y | | | | Y | S | Y | Y | G | G | S | G | I | | | | | | | |
| 667 | R | S | Y | Y | Y | | | | Y | S | Y | Y | Y | S | R | A | M | | | | | | | |
| 668 | S | Y | S | S | Y | | | | Y | S | Y | Y | S | S | Y | G | G | M | | | | | | |
| 669 | Y | R | Y | Y | Y | | | | S | R | Y | G | Y | R | Y | Y | Y | Y | Y | R | A | L | | |
| 670 | R | Y | S | S | | | | | M | – | – | – | | | | | | | | | | | | |
| 671 | Y | S | H | S | | | | | A | F | – | – | | | | | | | | | | | | |
| 672 | G | Y | S | Y | | | | | H | G | I | – | | | | | | | | | | | | |
| 673 | G | S | S | F | | | | | R | G | F | – | | | | | | | | | | | | |
| 674 | G | S | S | Y | S | | | | W | G | L | – | | | | | | | | | | | | |
| 675 | G | S | R | Y | S | | | | H | G | M | – | | | | | | | | | | | | |
| 676 | G | A | S | Y | | | | | Y | G | M | – | | | | | | | | | | | | |

FIG. 17-8.2

HEAVY CHAIN MUTATIONS IN HER2 BINDING PHAGE LIBRARIES

| | CDR-VH1 | | | | | | | | | | | | CDR-VH2 | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | | | 5 | 6 | 7 | 8 | 9 | 10 | 1 | 2 | 3 | 4 | | | 5 | | | 6 | 7 | 8 | 9 | 10 | 11 | 12 | 13 | 14 | 15 | 16 | 17 | SEQ ID NO: |
| | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | |
| 3 | G | F | N | I | – | – | K | D | T | Y | I | H | R | I | Y | P | – | – | T | – | – | N | G | Y | T | R | Y | A | D | S | V | K | G | 4 |
| 677 | | | Y | | | | | Y | S | S | | | S | | | | | | Y | | | Y | | | | S | | | | | | | | 682 |
| 678 | | | S | | | | | Y | S | S | | | S | | | | | | Y | | | Y | | S | | Y | | | | | | | | 683 |
| 679 | | | S | | | | | Y | S | | | | S | | | | | | S | | | S | | | | S | | | | | | | | 684 |
| 680 | | | S | | | | | Y | S | | | | S | | | | | | S | | | S | | | | S | | | | | | | | 684 |
| 681 | | | Y | | | | | Y | S | | | | S | | | | | | S | | | S | | | | S | | | | | | | | 684 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | A | | | | | | | | | | 685 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | A | | | | | | | | | | 685 |
| 3 | | | | | | | | | | | | | | | | | | | | | | | | W | | I | | | | | | | | 686 |
| 3 | | | | | | | | | | | | | | | | | | | | | | | | W | | I | | | | | | | | 686 |

Continued

FIG. 17-9.1

HEAVY CHAIN MUTATIONS IN HER2 BINDING PHAGE LIBRARIES

Continued from previous table

CDR-VH3

| SEQ ID NO: | 1 | 2 | 3 | 4 | 5 | | | | 6 | 7 | 8 | 9 | | | | | | | | | | | 10 | 11 |
|---|---|---|---|---|---|---|---|---|---|---|---|---|---|---|---|---|---|---|---|---|---|---|---|---|
| | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| 5 | W | G | G | D | G | – | – | – | F | Y | A | M | – | – | – | – | – | – | – | – | – | – | D | Y |
| 687 | G | M | S | Y | | | | | Y | G | M | – | | | | | | | | | | | | |
| 688 | G | | R | Y | N | | | | H | G | L | – | | | | | | | | | | | | |
| 689 | E | Y | Y | Q | | | | | Y | G | P | Y | R | S | T | Y | G | L | | | | | | |
| 690 | S | S | W | S | S | | | | R | G | V | S | Y | S | R | T | A | G | G | M | | | | |
| 691 | E | | Y | Y | S | | | | V | S | G | S | Y | S | Y | S | T | R | G | G | P | | | |
| 692 | | | | | | | | | | F | | | | | | | | | | | | | | |
| 693 | | | | W | | | | | | F | | | | | | | | | | | | | | V |
| 5 | | | | | | | | | | | | | | | | | | | | | | | | |
| 5 | | | | | | | | | | | | | | | | | | | | | | | | |
| 694 | | | | | | | | | | | | | | | | | | | | | | | | Y |
| 694 | | | | | | | | | | | | | | | | | | | | | | | | Y |
| 694 | | | | | | | | | | | | | | | | | | | | | | | | Y |
| 694 | | | | | | | | | | | | | | | | | | | | | | | | Y |
| 694 | | | | | | | | | | | | | | | | | | | | | | | | Y |
| 694 | | | | | | | | | | | | | | | | | | | | | | | | Y |
| 694 | | | | | | | | | | | | | | | | | | | | | | | | Y |
| 694 | | | | | | | | | | | | | | | | | | | | | | | | Y |
| 694 | | | | | | | | | | | | | | | | | | | | | | | | Y |

FIG. 17-9.2

HEAVY CHAIN MUTATIONS IN HER2 BINDING PHAGE LIBRARIES

| | | CDR-VH3 | | | | | | | | | | | | | | | | | | | | | | | |
|---|---|---|---|---|---|---|---|---|---|---|---|---|---|---|---|---|---|---|---|---|---|---|---|---|---|
| | SEQ | 1 | 2 | 3 | 4 | 5 | | | | 6 | 7 | 8 | 9 | | | | | | | | | | | 10 | 11 |
| | ID NO: | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| * | 5 | W | G | G | D | G | – | – | – | F | Y | A | M | – | – | – | – | – | – | – | – | – | – | D | Y |
| | 695 | | | | | | | | | | | | | | | | | | | | | | | | Y |
| | 695 | | | | | | | | | | | | | | | | | | | | | | | | Y |
| | 695 | | | | | | | | | | | | | | | | | | | | | | | | Y |
| | 695 | | | | | | | | | | | | | | | | | | | | | | | | Y |
| | 695 | | | | | | | | | | | | | | | | | | | | | | | | Y |
| | 695 | | | | | | | | | | | | | | | | | | | | | | | | Y |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 696 | | | H | | | | | M | | | | | | | | | | | | | | | | |
| | 697 | | | A | | | | | | N | | | | | | | | | | | | | | | |
| | 698 | | | R | S | | | | Y | | | | | | | | | | | | | | | | |
| | 699 | | | A | S | | | | L | F | | | | | | | | | | | | | | | |
| | 700 | | | R | | | | | L | | | | | | | | | | | | | | | | |
| | 701 | | | S | | | | | | | | | | | | | | | | | | | | | |
| | 702 | | | T | | | | | A | | | | | | | | | | | | | | | | |
| | 703 | | | K | | | | | | | | | | | | | | | | | | | | | |
| | 5 | | | | | | | | | | | | | | | | | | | | | | | | |
| | 5 | | | | | | | | | | | | | | | | | | | | | | | | |
| | 704 | | | L | | | | | H | | | | | | | | | | | | | | | | |
| | 705 | | | H | L | | | | Y | | | | | | | | | | | | | | | | |
| | 5 | | | | | | | | | | | | | | | | | | | | | | | | |
| | 5 | | | | | | | | | | | | | | | | | | | | | | | | |
| | 706 | | | | | | | | P | | | | | | | | | | | | | | | K | |
| | 707 | | | | | | | | P | | | | | | | | | | | | | | | L | |
| | 707 | | | | | | | | P | | | | | | | | | | | | | | | L | |
| | 708 | | | | | | | | P | | | | | | | | | | | | | | | W | |

*CDRs VH1 and VH2 contain no point mutations, additions, or deletions for the corresponding VH3 variants in this TABLE.

FIG. 17-10

HEAVY CHAIN MUTATIONS IN HER2 BINDING PHAGE LIBRARIES

| | CDR-VH3 | | | | | | | | | | | | | | | | | | | | | | | | |
|---|---|---|---|---|---|---|---|---|---|---|---|---|---|---|---|---|---|---|---|---|---|---|---|---|---|
| | SEQ | 1 | 2 | 3 | 4 | 5 | | | | 6 | 7 | 8 | 9 | | | | | | | | | | | 10 | 11 |
| | ID NO: | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| * | 5 | W | G | G | D | G | – | – | – | F | Y | A | M | – | – | – | – | – | – | – | – | – | – | D | Y |
| | 5 | | | | | | | | | | | | | | | | | | | | | | | | |
| | 709 | | | | | | | | | W | | | | | | | | | | | | | | | M |
| | 710 | | | | | | | | | W | | | | | | | | | | | | | | | L |
| | 711 | | | | | | | | | H | | | | | | | | | | | | | | | L |
| | 5 | | | | | | | | | | | | | | | | | | | | | | | | |
| | 712 | | | | | | | | | | | | | | | | | | | | | | | | W |
| | 713 | | | | | | | | | P | | | | | | | | | | | | | | | H |
| | 5 | | | | | | | | | | | | | | | | | | | | | | | | |
| | 5 | | | | | | | | | | | | | | | | | | | | | | | | |
| | 714 | | | | | | | | | P | | | | | | | | | | | | | | | K |
| | 715 | | | | | | | | | P | | | | | | | | | | | | | | | L |
| | 5 | | | | | | | | | | | | | | | | | | | | | | | | |
| | 716 | | | | | | | | | P | | | | | | | | | | | | | | | K |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 717 | | | | | | | | | M | | | | | | | | | | | | | | | A |
| | 5 | | | | | | | | | | | | | | | | | | | | | | | | |
| | 5 | | | | | | | | | | | | | | | | | | | | | | | | |
| | 718 | | | | | | | | | L | | | | | | | | | | | | | | | S |
| | 718 | | | | | | | | | L | | | | | | | | | | | | | | | S |
| | 5 | | | | | | | | | | | | | | | | | | | | | | | | |
| | 5 | | | | | | | | | | | | | | | | | | | | | | | | |
| | 718 | | | | | | | | | L | | | | | | | | | | | | | | | S |
| | 719 | | | | | | | | | L | | | | | | | | | | | | | | | T |
| | 5 | | | | | | | | | | | | | | | | | | | | | | | | |
| | 720 | | | | | | | | | R | | | | | | | | | | | | | | | G |
| | 721 | | | | | | | | | M | | | | | | | | | | | | | | | G |
| | 721 | | | | | | | | | M | | | | | | | | | | | | | | | |
| | 722 | | | | | | | | | R | | | | | | | | | | | | | | | L |
| | 5 | | | | | | | | | | | | | | | | | | | | | | | | |
| | 723 | | | | | | | | | P | | | | | | | | | | | | | | | A |
| | 5 | | | | | | | | | | | | | | | | | | | | | | | | |
| | 724 | | | | | | | | | P | | | | | | | | | | | | | | | V |

*CDRs VH1 and VH2 contain no point mutations, additions, or deletions for the corresponding VH3 variants in this TABLE.

FIG. 17-11

| HEAVY CHAIN MUTATIONS IN HER2 BINDING PHAGE LIBRARIES | | | | | | | | | | | | | | | | | | | | | | | | | |
|---|---|---|---|---|---|---|---|---|---|---|---|---|---|---|---|---|---|---|---|---|---|---|---|---|---|
| | CDR-VH3 | | | | | | | | | | | | | | | | | | | | | | | | |
| | SEQ ID NO: | 1 | 2 | 3 | 4 | 5 | | | | 6 | 7 | 8 | 9 | | | | | | | | | | | 10 | 11 |
| | | 95 | 96 | 97 | 98 | 99 | 99a | 99b | 99c | 100 | 100a | 100b | 100c | 100d | 100e | 100f | 100g | 100h | 100i | 100j | 100k | 100l | 100m | 101 | 102 |
| * | 5 | W | G | G | D | G | – | – | – | F | Y | A | M | – | – | – | – | – | – | – | – | – | – | D | Y |
| | 5 | | | | | | | | | | | | | | | | | | | | | | | | |
| | 725 | | | | | | | | | P | | | | | | | | | | | | | | | K |
| | 5 | | | | | | | | | | | | | | | | | | | | | | | | |
| | 726 | | | | | | | | | P | | | | | | | | | | | | | | | L |
| | 727 | | | | | | | | | L | | | | | | | | | | | | | | | |
| | 726 | | | | | | | | | P | | | | | | | | | | | | | | | L |
| | 728 | | | | W | | | | | | | | | | | | | | | | | | | | |
| | 729 | | | | | | | | | | F | | | | | | | | | | | | | | |
| | 730 | | | | W | | | | | P | | | | | | | | | | | | | | | K |
| | 731 | | | | W | | | | | P | | | | | | | | | | | | | | | L |
| | 5 | | | | | | | | | | | | | | | | | | | | | | | | |
| | 728 | | | | W | | | | | | | | | | | | | | | | | | | | |
| | 5 | | | | | | | | | | | | | | | | | | | | | | | | |
| | 5 | | | | | | | | | | | | | | | | | | | | | | | | |
| | 5 | | | | | | | | | | | | | | | | | | | | | | | | |
| | 732 | | | | | | | | | | | | | | | | | | | | | | | | V |
| | 733 | | | | | | | | | P | | | | | | | | | | | | | | | K |
| | 726 | | | | | | | | | P | | | | | | | | | | | | | | | L |

*CDRs VH1 and VH2 contain no point mutations, additions, or deletions for the corresponding VH3 variants in this TABLE.

FIG. 17-12

LIGHT CHAIN MUTATIONS IN HER2 BINDING PHAGE LIBRARIES

| | CDR-VL2 | | | | | | | | CDR-VL3 | | | | | | | | | | | |
|---|---|---|---|---|---|---|---|---|---|---|---|---|---|---|---|---|---|---|---|---|
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| | 7 | S | A | S | F | L | Y | S | Q | Q | H | Y | T | – | – | T | P | P | T | 8 |
| | 7 | | | | | | | | | | S | | Y | | | S | | S | | 734 |
| | 7 | | | | | | | | | | S | | Y | | | S | | S | | 734 |
| | 7 | | | | | | | | | | S | | Y | | | Y | | S | | 735 |
| | 7 | | | | | | | | | | S | | Y | | | S | | S | | 734 |
| | 7 | | | | | | | | | | S | | Y | | | S | | S | | 734 |
| | 7 | | | | | | | | | | Y | | Y | | | S | | S | | 736 |
| | 7 | | | | | | | | | | S | | Y | | | Y | | S | | 735 |
| * | 7 | | | | | | | | | | S | | Y | | | Y | | S | | 735 |
| | 7 | | | | | | | | | | S | | Y | | | S | | S | | 734 |
| | 7 | | | | | | | | | | S | | Y | | | S | | S | | 734 |
| | 7 | | | | | | | | | | S | | Y | | | Y | | S | | 735 |
| | 7 | | | | | | | | | | Y | | Y | | | S | | S | | 736 |
| | 7 | | | | | | | | | | S | | Y | | | Y | | S | | 735 |
| | 7 | | | | | | | | | | Y | | Y | | | Y | | Y | | 737 |
| | 7 | | | | | | | | | | S | | Y | | | S | | S | | 734 |
| | 7 | | | | | | | | | | Y | | Y | | | Y | | S | | 738 |
| | 7 | | | | | | | | | | S | | Y | | | Y | | S | | 739 |
| | 7 | | | | | | | | | | Y | | Y | | | S | | S | | 736 |
| | 7 | | | | | | | | | | S | | Y | | | S | | S | | 734 |

*CDR VL1 contains no point mutations, additions, or deletions for the corresponding VL2/3 variants in this TABLE.

FIG. 18-1

LIGHT CHAIN MUTATIONS IN HER2 BINDING PHAGE LIBRARIES

| | CDR-VL2 | | | | | | | | CDR-VL3 | | | | | | | | | | | |
|---|---|---|---|---|---|---|---|---|---|---|---|---|---|---|---|---|---|---|---|---|
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| | 7 | S | A | S | F | L | Y | S | Q | Q | H | Y | T | – | – | T | P | P | T | 8 |
| * | 7 | | | | | | | | | | W | S | S | | | S | | S | | 740 |
| | 7 | | | | | | | | | | W | S | S | | | W | | S | | 741 |
| | 7 | | | | | | | | | | W | S | S | | | W | | S | | 741 |
| | 7 | | | | | | | | | | S | | Y | | | S | | S | | 742 |
| | 7 | | | | | | | | | | Y | | Y | | | S | | S | | 743 |
| | 7 | | | | | | | | | | S | | Y | | | Y | | S | | 744 |
| | 7 | | | | | | | | | | S | | Y | | | Y | | S | | 744 |
| | 7 | | | | | | | | | | S | | Y | | | Y | | S | | 744 |
| | 7 | | | | | | | | | | S | | Y | | | Y | | S | | 744 |
| | 7 | | | | | | | | | | S | | Y | | | S | | S | | 742 |
| | 7 | | | | | | | | | | S | S | S | | | S | | S | | 745 |
| | 7 | | | | | | | | | | S | | Y | | | Y | | Y | | 746 |
| | 7 | | | | | | | | | | Y | | Y | | | S | | Y | | 747 |
| | 7 | | | | | | | | | | Y | | Y | | | S | | Y | | 747 |
| | 7 | | | | | | | | | | S | | S | | | S | | S | | 748 |
| | 7 | | | | | | | | | | Y | S | Y | | | Y | | Y | | 749 |
| | 7 | | | | | | | | | | Y | S | S | | | S | | S | | 750 |
| | 7 | | | | | | | | | | S | | Y | | | S | | S | | 742 |

*CDR VL1 contains no point mutations, additions, or deletions for the corresponding VL2/3 variants in this TABLE.

FIG. 18-2

| LIGHT CHAIN MUTATIONS IN HER2 BINDING PHAGE LIBRARIES | | | | | | | | | | | | | | | | | | | | |
|---|---|---|---|---|---|---|---|---|---|---|---|---|---|---|---|---|---|---|---|---|
| | CDR-VL2 | | | | | | | | CDR-VL3 | | | | | | | | | | | |
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| * | 7 | S | A | S | F | L | Y | S | Q | Q | H | Y | T | – | – | T | P | P | T | 8 |
| | 7 | | | | | | | | | | S | S | Y | | | Y | | S | | 751 |
| | 7 | | | | | | | | | | S | S | Y | | | Y | | S | | 751 |
| | 7 | | | | | | | | | | S | | Y | | | S | | S | | 752 |
| | 7 | | | | | | | | | | S | | Y | | | Y | | S | | 753 |
| | 7 | | | | | | | | | | S | | Y | | | S | | S | | 752 |
| | 7 | | | | | | | | | | S | | Y | | | Y | | S | | 753 |
| | 7 | | | | | | | | | | | | Y | | | Y | | Y | | 754 |
| | 7 | | | | | | | | | | | | Y | | | S | | S | | 755 |
| | 7 | | | | | | | | | | S | | Y | | | Y | | Y | | 756 |
| | 7 | | | | | | | | | | X | X | X | | | X | | X | | 757 |
| | 7 | | | | | | | | | | | | | | | | | | | 8 |
| | 7 | | | | | | | | | | | S | Y | | | Y | | Y | | 758 |
| | 7 | | | | | | | | | | | S | Y | | | Y | | S | | 759 |
| | 7 | | | | | | | | | | | S | Y | | | Y | | Y | | 758 |
| | 7 | | | | | | | | | | S | S | Y | | | S | | S | | 760 |
| | 7 | | | | | | | | | | | S | Y | | | Y | | Y | | 757 |
| | 7 | | | | | | | | | | | S | Y | | | Y | | S | | 758 |
| | 7 | | | | | | | | | | | S | Y | | | Y | | Y | | 757 |
| | 7 | | | | | | | | | | | S | Y | | | Y | | Y | | 757 |

*CDR VL1 contains no point mutations, additions, or deletions for the corresponding VL2/3 variants in this TABLE.

FIG. 18-3

| LIGHT CHAIN MUTATIONS IN HER2 BINDING PHAGE LIBRARIES | | | | | | | | | | | | | | | | | | | | |
|---|---|---|---|---|---|---|---|---|---|---|---|---|---|---|---|---|---|---|---|---|
| | CDR-VL2 | | | | | | | | CDR-VL3 | | | | | | | | | | | |
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| | 7 | S | A | S | F | L | Y | S | Q | Q | H | Y | T | – | – | T | P | P | T | 8 |
| * | 7 | | | | | | | | | | | S | Y | | | Y | | Y | | 761 |
| | 7 | | | | | | | | | | | S | Y | | | Y | | Y | | 761 |
| | 7 | | | | | | | | | | | S | Y | | | Y | | Y | | 761 |
| | 7 | | | | | | | | | | | S | Y | | | Y | | Y | | 761 |
| | 7 | | | | | | | | | | | S | Y | | | Y | | S | | 762 |
| | 7 | | | | | | | | | | | S | Y | | | Y | | S | | 762 |
| | 7 | | | | | | | | | | | S | Y | | | Y | | Y | | 761 |
| | 7 | | | | | | | | | | | S | Y | | | Y | | Y | | 761 |
| | 7 | | | | | | | | | | S | S | Y | | | S | | S | | 763 |
| | 7 | | | | | | | | | | S | S | Y | | | Y | | Y | | 764 |
| | 7 | | | | | | | | | | S | | Y | | | Y | | S | | 765 |
| | 7 | | | | | | | | | | S | S | Y | | | Y | | Y | | 764 |
| | 7 | | | | | | | | | | S | F | S | | | S | | Y | | 766 |
| | 7 | | | | | | | | | | S | | S | | | S | | Y | | 767 |
| | 7 | | | | | | | | | | S | | S | | | Y | | S | | 768 |
| | 7 | | | | | | | | | | S | F | S | | | Y | | Y | | 769 |
| | 7 | | | | | | | | | | S | | S | | | S | | Y | | 767 |
| | 7 | | | | | | | | | | S | | S | | | S | | S | | 770 |
| | 7 | | | | | | | | | | S | | S | | | Y | | S | | 768 |

*CDR VL1 contains no point mutations, additions, or deletions for the corresponding VL2/3 variants in this TABLE.

FIG. 18-4

LIGHT CHAIN MUTATIONS IN HER2 BINDING PHAGE LIBRARIES

| | CDR-VL2 | | | | | | | | CDR-VL3 | | | | | | | | | | | |
|---|---|---|---|---|---|---|---|---|---|---|---|---|---|---|---|---|---|---|---|---|
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| | 7 | S | A | S | F | L | Y | S | Q | Q | H | Y | T | – | – | T | P | P | T | 8 |
| * | 7 | | | | | | | | | | S | | S | | | S | | Y | | 771 |
| | 7 | | | | | | | | | | S | | S | | | S | | S | | 772 |
| | 7 | | | | | | | | | | S | | S | | | S | | S | | 772 |
| | 7 | | | | | | | | | | S | F | S | | | S | | S | | 773 |
| | 7 | | | | | | | | | | S | S | S | | | S | | Y | | 774 |
| | 7 | | | | | | | | | | S | | S | | | S | | Y | | 771 |
| | 7 | | | | | | | | | | S | S | S | | | S | | Y | | 774 |
| | 7 | | | | | | | | | | S | | S | | | S | | S | | 772 |
| | 7 | | | | | | | | | | S | S | S | | | Y | | Y | | 775 |
| | 7 | | | | | | | | | | S | | S | | | Y | | S | | 776 |
| | 7 | | | | | | | | | | S | S | S | | | S | | Y | | 777 |
| | 7 | | | | | | | | | | S | S | S | | | Y | | Y | | 775 |
| | 7 | | | | | | | | | | S | S | S | | | Y | | S | | 778 |
| | 7 | | | | | | | | | | S | | S | | | S | | S | | 772 |
| | 7 | | | | | | | | | | S | S | S | | | S | | Y | | 777 |
| | 7 | | | | | | | | | | S | S | S | | | Y | | S | | 778 |
| | 7 | | | | | | | | | | S | S | Y | | | Y | | S | | 779 |
| | 7 | | | | | | | | | | S | S | F | | | S | | Y | | 780 |
| | 7 | | | | | | | | | | S | S | S | | | Y | | Y | | 775 |

*CDR VL1 contains no point mutations, additions, or deletions for the corresponding VL2/3 variants in this TABLE.

FIG. 18-5

LIGHT CHAIN MUTATIONS IN HER2 BINDING PHAGE LIBRARIES

| | CDR-VL2 | | | | | | | | CDR-VL3 | | | | | | | | | | | |
|---|---|---|---|---|---|---|---|---|---|---|---|---|---|---|---|---|---|---|---|---|
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| | 7 | S | A | S | F | L | Y | S | Q | Q | H | Y | T | – | – | T | P | P | T | 8 |
| * | 7 | | | | | | | | | | S | S | S | | | Y | | S | | 781 |
| | 7 | | | | | | | | | | S | S | S | | | S | | Y | | 782 |
| | 7 | | | | | | | | | | S | | S | | | S | | Y | | 783 |
| | 7 | | | | | | | | | | S | | S | | | S | | S | | 784 |
| | 7 | | | | | | | | | | S | | S | | | S | | S | | 784 |
| | 7 | | | | | | | | | | S | S | S | | | Y | | Y | | 785 |
| | 7 | | | | | | | | | | S | F | S | | | S | | Y | | 786 |
| | 7 | | | | | | | | | | S | | S | | | Y | | S | | 787 |
| | 7 | | | | | | | | | | S | | S | | | S | | Y | | 783 |
| | 7 | | | | | | | | | | | | S | | | S | | Y | | 788 |
| | 7 | | | | | | | | | | S | S | S | | | Y | | S | | 789 |
| | 7 | | | | | | | | | | | | S | | | S | | S | | 790 |
| | 7 | | | | | | | | | | S | S | Y | | | Y | | S | | 791 |
| | 7 | | | | | | | | | | S | S | F | | | Y | | S | | 792 |
| | 7 | | | | | | | | | | S | S | Y | | | S | | Y | | 793 |
| | 7 | | | | | | | | | | S | S | S | | | Y | | S | | 789 |
| | 7 | | | | | | | | | | S | S | S | | | S | | S | | 794 |
| | 7 | | | | | | | | | | | | Y | | | Y | | Y | | 795 |
| | 7 | | | | | | | | | | S | S | Y | | | S | | Y | | 793 |

*CDR VL1 contains no point mutations, additions, or deletions for the corresponding VL2/3 variants in this TABLE.

FIG. 18-6

| LIGHT CHAIN MUTATIONS IN HER2 BINDING PHAGE LIBRARIES | | | | | | | | | | | | | | | | | | | | | |
|---|---|---|---|---|---|---|---|---|---|---|---|---|---|---|---|---|---|---|---|---|---|
| | CDR-VL2 | | | | | | | | CDR-VL3 | | | | | | | | | | | | |
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| | 7 | S | A | S | F | L | Y | S | Q | Q | H | Y | T | – | – | T | P | P | T | 8 |
| * | 7 | | | | | | | | | | S | S | Y | | | S | | Y | | 796 |
| | 7 | | | | | | | | | | S | S | Y | | | S | | Y | | 796 |
| | 7 | | | | | | | | | | | | S | | | S | | Y | | 797 |
| | 7 | | | | | | | | | | | | S | | | Y | | S | | 798 |
| | 7 | | | | | | | | | | S | S | Y | | | Y | | S | | 799 |
| | 7 | | | | | | | | | | S | S | Y | | | S | | Y | | 796 |
| | 7 | | | | | | | | | | S | S | Y | | | S | | Y | | 796 |
| | 7 | | | | | | | | | | S | S | Y | | | S | | Y | | 796 |
| | 7 | | | | | | | | | | S | S | Y | | | S | | Y | | 796 |
| | 7 | | | | | | | | | | S | S | Y | | | Y | | S | | 799 |
| | 7 | | | | | | | | | | S | S | S | | | S | | Y | | 800 |
| | 7 | | | | | | | | | | S | S | Y | | | S | | Y | | 796 |
| | 7 | | | | | | | | | | S | S | Y | | | S | | Y | | 796 |
| | 7 | | | | | | | | | | S | S | S | | | S | | Y | | 800 |
| | 7 | | | | | | | | | | | | S | | | S | | Y | | 797 |
| | 7 | | | | | | | | | | S | S | S | | | S | | Y | | 800 |
| | 7 | | | | | | | | | | S | S | Y | | | Y | | Y | | 801 |
| | 7 | | | | | | | | | | S | | Y | | | Y | | Y | | 802 |
| | 7 | | | | | | | | | | | | Y | | | S | | S | | 803 |

*CDR VL1 contains no point mutations, additions, or deletions for the corresponding VL2/3 variants in this TABLE.

FIG. 18-7

LIGHT CHAIN MUTATIONS IN HER2 BINDING PHAGE LIBRARIES

CDR-VL1

| SEQ ID NO: | 1 | 2 | 3 | 4 | | | | | | 5 | 6 | 7 | | | | | 8 | 9 | 10 | 11 |
|---|---|---|---|---|---|---|---|---|---|---|---|---|---|---|---|---|---|---|---|---|
| | 24 | 25 | 26 | 27 | 27a | 27b | 27c | 27d | 27e | 28 | 29 | 30 | 30a | 30b | 30c | 30d | 31 | 32 | 33 | 34 |
| 6 | R | A | S | Q | – | – | – | – | – | D | V | N | – | – | – | – | T | A | V | A |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 804 | | | | | | | | | | | | S | | | | | | | | |
| 804 | | | | | | | | | | | | S | | | | | | | | |
| 805 | | | | | | | | | | | | | | | | | | | Y | |
| 805 | | | | | | | | | | | | | | | | | | | Y | |
| 805 | | | | | | | | | | | | | | | | | | | Y | |
| 805 | | | | | | | | | | | | | | | | | | | Y | |
| 6 | | | | | | | | | | | | | | | | | | | | |
| 6 | | | | | | | | | | | | | | | | | | | | |
| 806 | | | | | | | | | | | | | | | | | | | W | |

Continued

FIG. 18-8.1

| LIGHT CHAIN MUTATIONS IN HER2 BINDING PHAGE LIBRARIES | | | | | | | | | | | | | | | | | | | | |
|---|---|---|---|---|---|---|---|---|---|---|---|---|---|---|---|---|---|---|---|---|
| | CDR-VL2 | | | | | | | | CDR-VL3 | | | | | | | | | | | |
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| Continued from previous table | 7 | S | A | S | F | L | Y | S | Q | Q | H | Y | T | – | – | T | P | P | T | 8 |
| | 7 | | | | | | | | | | | S | Y | | | Y | | Y | | 808 |
| | 7 | | | | | | | | | | | S | Y | | | Y | | Y | | 808 |
| | 7 | | | | | | | | | | | S | Y | | | Y | | Y | | 808 |
| | 7 | | | | | | | | | | S | S | Y | | | Y | | Y | | 809 |
| | 7 | | | | | | | | | | | S | Y | | | Y | | Y | | 808 |
| | 7 | | | | | | | | | | | S | Y | | | Y | | Y | | 808 |
| | 7 | | | | | | | | | | | S | Y | | | Y | | S | | 810 |
| | 7 | | | | | | | | | | | S | S | | | S | | S | | 811 |
| | 7 | | | | | | | | | | | S | S | | | S | | Y | | 812 |
| | 7 | | | | | | | | | | S | | S | | | S | | S | | 813 |
| | 7 | | | | | | | | | | F | W | | | | S | | | | 814 |
| | 7 | | | | | | | | | | F | W | | | | S | | | | 814 |
| | 807 | R | | | | | | | | | | | | | | | | | | 8 |
| | 807 | R | | | | | | | | | | | | | | | | | | 8 |
| | 807 | R | | | | | | | | | | | | | | | | | | 8 |
| | 807 | R | | | | | | | | | | | | | | | | | | 8 |
| | 7 | | | | | | | | | | | | | | | | | | | 8 |
| | 7 | | | | | | | | | | | | | | | | | | | 8 |
| | 807 | R | | | | | | | | | | | | | | | | | | 8 |

FIG. 18-8.2

LIGHT CHAIN MUTATIONS IN HER2 BINDING PHAGE LIBRARIES

CDR-VL1

| SEQ ID NO: | 1 | 2 | 3 | 4 | | | | | | 5 | 6 | 7 | | | | | 8 | 9 | 10 | 11 |
|---|---|---|---|---|---|---|---|---|---|---|---|---|---|---|---|---|---|---|---|---|
| | 24 | 25 | 26 | 27 | 27a | 27b | 27c | 27d | 27e | 28 | 29 | 30 | 30a | 30b | 30c | 30d | 31 | 32 | 33 | 34 |
| 6 | R | A | S | Q | – | – | – | – | – | D | V | N | – | – | – | – | T | A | V | A |
| 6 | | | | | | | | | | | | | | | | | | | | |
| 815 | | | | | | | | | | | | | | | | | | | Y | |
| 816 | | | | | | | | | | | | | | | | | | | W | |
| 816 | | | | | | | | | | | | | | | | | | | W | |
| 815 | | | | | | | | | | | | | | | | | | | Y | |
| 815 | | | | | | | | | | | | | | | | | | | Y | |
| 815 | | | | | | | | | | | | | | | | | | | Y | |
| 6 | | | | | | | | | | | | | | | | | | | | |
| 815 | | | | | | | | | | | | | | | | | | | Y | |
| 817 | | | | | | | | | | | | | | | | | | | F | |
| 818 | | | | | | | | | | | | S | | | | | | | | |
| 818 | | | | | | | | | | | | S | | | | | | | | |
| 818 | | | | | | | | | | | | S | | | | | | | | |
| 818 | | | | | | | | | | | | S | | | | | | | | |
| 818 | | | | | | | | | | | | S | | | | | | | | |
| 818 | | | | | | | | | | | | S | | | | | | | | |
| 818 | | | | | | | | | | | | S | | | | | | | | |
| 818 | | | | | | | | | | | | S | | | | | | | | |
| 818 | | | | | | | | | | | | S | | | | | | | | |

Continued

FIG. 18-9.1

LIGHT CHAIN MUTATIONS IN HER2 BINDING PHAGE LIBRARIES

Continued from previous table

| | CDR-VL2 | | | | | | | CDR-VL3 | | | | | | | | | | | |
|---|---|---|---|---|---|---|---|---|---|---|---|---|---|---|---|---|---|---|---|
| SEQ ID NO: | 1 | 2 | 3 | 4 | 5 | 6 | 7 | 1 | 2 | 3 | 4 | 5 | | | 6 | 7 | 8 | 9 | SEQ ID NO: |
| | 50 | 51 | 52 | 53 | 54 | 55 | 56 | 89 | 90 | 91 | 92 | 93 | 93a | 93b | 94 | 95 | 96 | 97 | |
| 7 | S | A | S | F | L | Y | S | Q | Q | H | Y | T | – | – | T | P | P | T | 8 |
| 7 | | | | | | | | | | | | | | | | | | | 8 |
| 819 | R | | | | | | | | | | | | | | | | | | 8 |
| 819 | R | | | | | | | | | | | | | | | | | | 8 |
| 819 | R | | | | | | | | | | | | | | | | | | 8 |
| 819 | R | | | | | | | | | | | | | | | | | | 8 |
| 819 | R | | | | | | | | | | | | | | | | | | 8 |
| 819 | R | | | | | | | | | | | | | | | | | | 8 |
| 7 | | | | | | | | | | | | | | | | | | | 8 |
| 819 | R | | | | | | | | | | | | | | | | | | 8 |
| 819 | R | | | | | | | | | | | | | | | | | | 8 |
| 7 | | | | | | | | | | F | W | | | | | | | | 820 |
| 7 | | | | | | | | | | F | W | | | | | | | | 820 |
| 7 | | | | | | | | | | F | W | | | | | | | | 820 |
| 7 | | | | | | | | | | F | W | | | | | | | | 820 |
| 7 | | | | | | | | | | Y | W | | | | | | | | 821 |
| 7 | | | | | | | | | | F | W | | | | | | | | 820 |
| 7 | | | | | | | | | | | W | | | | | | | | 822 |
| 7 | | | | | | | | | | F | F | | | | | | | | 823 |
| 7 | | | | | | | | | | F | G | | | | | | | | 824 |

FIG. 18-9.2

LIGHT CHAIN MUTATIONS IN HER2 BINDING PHAGE LIBRARIES

| SEQ ID NO: | CDR-VL1 | | | | | | | | | | | | | | | | | | | |
|---|---|---|---|---|---|---|---|---|---|---|---|---|---|---|---|---|---|---|---|---|
| | 1 | 2 | 3 | 4 | | | | | | 5 | 6 | 7 | | | | | 8 | 9 | 10 | 11 |
| | 24 | 25 | 26 | 27 | 27a | 27b | 27c | 27d | 27e | 28 | 29 | 30 | 30a | 30b | 30c | 30d | 31 | 32 | 33 | 34 |
| 6 | R | A | S | Q | - | - | - | - | - | D | V | N | - | - | - | - | T | A | V | A |
| 825 | | | | | | | | | | | | S | | | | | | | | |
| 825 | | | | | | | | | | | | S | | | | | | | | |
| 825 | | | | | | | | | | | | S | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |

Continued

FIG. 18-10.1

LIGHT CHAIN MUTATIONS IN HER2 BINDING PHAGE LIBRARIES

Continued from previous table

| | CDR-VL2 | | | | | | | CDR-VL3 | | | | | | | | | | | |
|---|---|---|---|---|---|---|---|---|---|---|---|---|---|---|---|---|---|---|---|
| SEQ ID NO: | 1 | 2 | 3 | 4 | 5 | 6 | 7 | 1 | 2 | 3 | 4 | 5 | | | 6 | 7 | 8 | 9 | SEQ ID NO: |
| | 50 | 51 | 52 | 53 | 54 | 55 | 56 | 89 | 90 | 91 | 92 | 93 | 93a | 93b | 94 | 95 | 96 | 97 | |
| 7 | S | A | S | F | L | Y | S | Q | Q | H | Y | T | – | – | T | P | P | T | 8 |
| 7 | | | | | | | | | | F | G | | | | | | | | 830 |
| 7 | | | | | | | | | | I | W | | | | | | | | 831 |
| 7 | | | | | | | | | | F | W | | | | | | | | 832 |
| 826 | | | | V | | | | | | Y | | | | | | | | | 833 |
| 7 | | | | | | | | | | Y | | | | | | | | | 833 |
| 7 | | | | | | | | | | | | | | | | | | | 8 |
| 7 | | | | | | | | | | Y | | | | | | | | | 833 |
| 826 | | | | V | | | | | | F | | | | | | | | | 834 |
| 827 | | | | W | | | | | | F | | | | | | | | | 834 |
| 7 | | | | | | | | | | Y | | | | | | | | | 833 |
| 7 | | | | | | | | | | F | | | | | | | | | 834 |
| 827 | | | | W | | | | | | Y | | | | | | | | | 833 |
| 7 | | | | | | | | | | F | | | | | | | | | 834 |
| 827 | | | | W | | | | | | Y | | | | | | | | | 833 |
| 7 | | | | | | | | | | | | | | | | | | | 8 |
| 828 | | | | L | | | | | | T | | | | | | | | | 835 |
| 827 | | | | W | | | | | | W | | | | | | | | | 836 |
| 829 | | | | W | | W | | | | | | | | | | | | | 8 |

FIG. 18-10.2

LIGHT CHAIN MUTATIONS IN HER2 BINDING PHAGE LIBRARIES

| | CDR-VL2 | | | | | | | | CDR-VL3 | | | | | | | | | | | |
|---|---|---|---|---|---|---|---|---|---|---|---|---|---|---|---|---|---|---|---|---|
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| * | 7 | S | A | S | F | L | Y | S | Q | Q | H | Y | T | – | – | T | P | P | T | 8 |
| | 837 | | | | W | | W | | | | | | | | | | | | | 8 |
| | 837 | | | | W | | W | | | | | | | | | | | | | 8 |
| | 838 | | | | T | | W | | | | | | | | | | | | | 8 |
| | 839 | | | | | | W | | | | | | | | | | | | | 8 |
| | 840 | | | | H | | W | | | | | | | | | | | | | 8 |
| | 841 | | | | V | | W | | | | | | | | | | | | | 8 |
| | 842 | | | | V | | L | | | | | | | | | | | | | 8 |
| | 843 | | | | R | | W | | | | | | | | | | | | | 8 |
| | 844 | | | | Q | | F | | | | | | | | | | | | | 8 |
| | 845 | | | | W | | L | | | | | | | | | | | | | 8 |
| | 846 | | | | T | | | | | | | | | | | | | | | 8 |
| | 837 | | | | W | | W | | | | | | | | | | | | | 8 |
| | 837 | | | | W | | W | | | | | | | | | | | | | 8 |
| | 837 | | | | W | | W | | | | | | | | | | | | | 8 |
| | 837 | | | | W | | W | | | | | | | | | | | | | 8 |
| | 839 | | | | | | W | | | | | | | | | | | | | 8 |
| | 840 | | | | H | | W | | | | | | | | | | | | | 8 |
| | 837 | | | | W | | W | | | | | | | | | | | | | 8 |
| | 847 | | | | W | | V | | | | | | | | | | | | | 8 |

*CDR VL1 contains no point mutations, additions, or deletions for the corresponding VL2/3 variants in this TABLE.

FIG. 18-11

| LIGHT CHAIN MUTATIONS IN HER2 BINDING PHAGE LIBRARIES | | | | | | | | | | | | | | | | | | | | |
|---|---|---|---|---|---|---|---|---|---|---|---|---|---|---|---|---|---|---|---|---|
| | CDR-VL2 | | | | | | | | CDR-VL3 | | | | | | | | | | | |
| | SEQ ID NO: | 1 | 2 | 3 | 4 | 5 | 6 | 7 | 1 | 2 | 3 | 4 | 5 | | | 6 | 7 | 8 | 9 | SEQ ID NO: |
| | | 50 | 51 | 52 | 53 | 54 | 55 | 56 | 89 | 90 | 91 | 92 | 93 | 93a | 93b | 94 | 95 | 96 | 97 | |
| * | 7 | S | A | S | F | L | Y | S | Q | Q | H | Y | T | – | – | T | P | P | T | 8 |
| | 848 | | | | K | | W | | | | | | | | | | | | | 8 |
| | 849 | | | | A | | W | | | | | | | | | | | | | 8 |
| | 850 | | | | R | | V | | | | | | | | | | | | | 8 |
| | 851 | | | | K | | S | | | | | | | | | | | | | 8 |
| | 852 | | | | V | | W | | | | | | | | | | | | | 8 |
| | 837 | | | | W | | W | | | | | | | | | | | | | 8 |
| | 7 | | | | | | | | | | | | | | | | | | | 8 |
| | 837 | | | | W | | W | | | | | | | | | | | | | 8 |
| | 837 | | | | W | | W | | | | | | | | | | | | | 8 |
| | 837 | | | | W | | W | | | | | | | | | | | | | 8 |
| | 837 | | | | W | | W | | | | | | | | | | | | | 8 |
| | 848 | | | | K | | W | | | | | | | | | | | | | 8 |
| | 837 | | | | W | | W | | | | | | | | | | | | | 8 |
| | 853 | | | | R | | A | | | | | | | | | | | | | 8 |
| | 853 | | | | R | | A | | | | | | | | | | | | | 8 |
| | 854 | | | | L | | P | | | | | | | | | | | | | 8 |
| | 855 | | | | M | | G | | | | | | | | | | | | | 8 |

*CDR VL1 contains no point mutations. additions. or deletions for the corresponding VL2/3 variants in this TABLE.

FIG. 18-12

LIGHT CHAIN MUTATIONS IN HER2 BINDING PHAGE LIBRARIES

CDR-VL1

| SEQ ID NO: | 1 | 2 | 3 | 4 | | | | | | 5 | 6 | 7 | | | | | 8 | 9 | 10 | 11 |
|---|---|---|---|---|---|---|---|---|---|---|---|---|---|---|---|---|---|---|---|---|
| | 24 | 25 | 26 | 27 | 27a | 27b | 27c | 27d | 27e | 28 | 29 | 30 | 30a | 30b | 30c | 30d | 31 | 32 | 33 | 34 |
| 6 | R | A | S | Q | – | – | – | – | – | D | V | N | – | – | – | – | T | A | V | A |
| 856 | | | | | S | | | | | | Q | | S | | | | | S | G | |
| 857 | | | | S | | | | | | Q | | S | | | | | G | G | | |
| 858 | | | | R | | | | | | Q | | | | | | | | | | |
| 859 | | | | A | | | | | | Q | | S | | | | | A | G | | |
| 860 | | | | | | | | | | G | | S | | | | | S | G | | |
| 861 | | | | | | | | | | G | | S | | | | | S | | | |
| 862 | | | | | | | | | | R | | | | | | | S | | | |
| 863 | | | | | | | | | | G | | S | | | | | S | | | |
| 864 | | | | N | | | | | | P | | S | | | | | Q | | | |
| 865 | | | | S | | | | | | S | | K | | | | | A | S | | |
| 866 | | | | F | | | | | | | | | | | | | A | C | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 867 | | | | | | | | | | | | S | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |

Continued

FIG. 18-13.1

LIGHT CHAIN MUTATIONS IN HER2 BINDING PHAGE LIBRARIES

Continued from previous table

| | CDR-VL2 | | | | | | | CDR-VL3 | | | | | | | | | | | |
|---|---|---|---|---|---|---|---|---|---|---|---|---|---|---|---|---|---|---|---|
| SEQ ID NO: | 1 | 2 | 3 | 4 | 5 | 6 | 7 | 1 | 2 | 3 | 4 | 5 | | | 6 | 7 | 8 | 9 | SEQ ID NO: |
| | 50 | 51 | 52 | 53 | 54 | 55 | 56 | 89 | 90 | 91 | 92 | 93 | 93a | 93b | 94 | 95 | 96 | 97 | |
| 7 | S | A | S | F | L | Y | S | Q | Q | H | Y | T | – | – | T | P | P | T | 8 |
| 7 | | | | | | | | | | | W | | | | | | | | 868 |
| 7 | | | | | | | | | | | W | | | | | | | | 868 |
| 7 | | | | | | | | | | F | F | | | | | | | | 869 |
| 7 | | | | | | | | | | Y | W | | | | | | | | 870 |
| 7 | | | | | | | | | | | W | | | | | | | | 868 |
| 7 | | | | | | | | | | | W | | | | | | | | 868 |
| 7 | | | | | | | | | | | F | | | | | | | | 871 |
| 7 | | | | | | | | | | | F | | | | | | | | 871 |
| 7 | | | | | | | | | | | W | | | | | | | | 868 |
| 7 | | | | | | | | | | L | P | | | | | | | | 872 |
| 7 | | | | | | | | | | | Q | | | | | | | | 873 |
| 7 | | | | | | | | | | | | | | | | | | | 8 |
| 7 | | | | | | | | | | | | | | | | | | | 8 |
| 7 | | | | | | | | | | | | | | | | | | | 8 |
| 7 | | | | | | | | | | | | | | | | | | | 8 |
| 837 | | | | W | | W | | | | | | | | | | | | | 8 |
| 837 | | | | W | | W | | | | | | | | | | | | | 8 |
| 7 | | | | | | | | | | | | | | | | | | | 8 |
| 7 | | | | | | | | | | F | | | | | | | | | 874 |
| 7 | | | | | | | | | | | | | | | S | | | | 875 |
| 7 | | | | | | | | | | | | | | | | | | | 8 |
| 837 | | | | W | | W | | | | | | | | | | | | | 8 |
| 837 | | | | W | | W | | | | | | | | | | | | | 8 |

FIG. 18-13.2

LIGHT CHAIN MUTATIONS IN BISPECIFIC HER2 BINDING PHAGE LIBRARIES

| | CDR-VL1* | | | | | | | | | | | | | | | CDR-VL2 | | | | | | | CDR-VL3 | | | | | | | | | | |
|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | 5 | 6 | 7 | | | | | 8 | 9 | 10 | 11 | 1 | 2 | 3 | 4 | 5 | 6 | 7 | 1 | 2 | 3 | 4 | 5 | | | 6 | 7 | 8 | 9 |
| | 24 | 25 | 26 | 27 | 28 | 29 | 30 | 30a | 30b | 30c | 30d | 31 | 32 | 33 | 34 | 50 | 51 | 52 | 53 | 54 | 55 | 56 | 89 | 90 | 91 | 92 | 93 | 93a | 93b | 94 | 95 | 96 | 97 |
| 6, 7 and 8 | R | A | S | Q | D | V | N | – | – | – | – | T | A | V | A | S | A | S | F | L | Y | S | Q | Q | H | Y | T | – | – | T | P | P | T |
| 876, 893 and 8 | | | | | | | W | | | | | K | W | | | A | | | S | | | | | | | | | | | | | | |
| 877. 894 and 8 | | | | | | I | K | N | | | | G | S | | | W | | | | | | | | | | | | | | | | | |
| 878, 894 and 8 | | | | | | I | L | G | | | | G | S | | | W | | | | | | | | | | | | | | | | | |
| 879, 894 and 8 | | | | | | I | M | S | | | | G | S | | | W | | | | | | | | | | | | | | | | | |
| 880, 894 and 8 | | | | | | I | R | A | | | | G | S | | | W | | | | | | | | | | | | | | | | | |
| 881, 894 and 8 | | | | | | I | R | G | | | | G | S | | | W | | | | | | | | | | | | | | | | | |
| 882, 895 and 8 | | | | | | | R | Q | | | | G | S | | | W | G | | | | | | | | | | | | | | | | |
| 883, 896 and 8 | | | | | | I | A | A | | | | G | S | | | W | | | Y | | | | | | | | | | | | | | |
| 884, 896 and 8 | | | | | | I | A | G | | | | G | S | | | W | | | Y | | | | | | | | | | | | | | |
| 885, 896 and 8 | | | | | | I | A | H | | | | G | S | | | W | | | Y | | | | | | | | | | | | | | |
| 886, 897 and 8 | | | | | | I | A | K | | | | G | S | | | W | G | | | | | | | | | | | | | | | | |
| 887. 897 and 8 | | | | | | I | G | A | | | | G | S | | | W | G | | | | | | | | | | | | | | | | |
| 888, 897 and 8 | | | | | | I | G | G | | | | G | S | | | W | G | | | | | | | | | | | | | | | | |
| 889, 896 and 8 | | | | | | I | G | L | | | | G | S | | | W | | | Y | | | | | | | | | | | | | | |
| 890. 896 and 8 | | | | | | I | G | M | | | | G | S | | | W | | | Y | | | | | | | | | | | | | | |
| 891, 897 and 8 | | | | | | I | K | H | | | | G | S | | | W | G | | | | | | | | | | | | | | | | |
| 892, 897 and 8 | | | | | | I | L | A | | | | G | S | | | W | G | | | | | | | | | | | | | | | | |

FIG. 19-1

LIGHT CHAIN MUTATIONS IN BISPECIFIC HER2 BINDING PHAGE LIBRARIES

| | CDR-VL1* | | | | | | | | | | | | | | | CDR-VL2 | | | | | | | CDR-VL3 | | | | | | | | | | |
|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | 5 | 6 | 7 | | | | | 8 | 9 | 10 | 11 | 1 | 2 | 3 | 4 | 5 | 6 | 7 | 1 | 2 | 3 | 4 | 5 | | | 6 | 7 | 8 | 9 |
| | 24 | 25 | 26 | 27 | 28 | 29 | 30 | 30a | 30b | 30c | 30d | 31 | 32 | 33 | 34 | 50 | 51 | 52 | 53 | 54 | 55 | 56 | 89 | 90 | 91 | 92 | 93 | 93a | 93b | 94 | 95 | 96 | 97 |
| 6, 7 and 8 | R | A | S | Q | D | V | N | – | – | – | – | T | A | V | A | S | A | S | F | L | Y | S | Q | Q | H | Y | T | – | – | T | P | P | T |
| 898, 897 and 8 | | | | | | I | L | G | | | | G | S | | | W | G | | | | | | | | | | | | | | | | |
| 899, 897 and 8 | | | | | | I | L | I | | | | G | S | | | W | G | | | | | | | | | | | | | | | | |
| 900, 897 and 8 | | | | | | I | L | T | | | | G | S | | | W | G | | | | | | | | | | | | | | | | |
| 901, 897 and 8 | | | | | | I | M | L | | | | G | S | | | W | G | | | | | | | | | | | | | | | | |
| 902, 897 and 8 | | | | | | I | Q | S | | | | G | S | | | W | G | | | | | | | | | | | | | | | | |
| 903, 897 and 8 | | | | | | I | R | I | | | | G | S | | | W | G | | | | | | | | | | | | | | | | |
| 904, 897 and 8 | | | | | | I | R | M | | | | G | S | | | W | G | | | | | | | | | | | | | | | | |
| 905, 896 and 8 | | | | | | I | R | Q | | | | G | S | | | W | | | Y | | | | | | | | | | | | | | |
| 906, 897 and 8 | | | | | | I | R | T | | | | G | S | | | W | G | | | | | | | | | | | | | | | | |
| 907, 897 and 8 | | | | | | I | R | V | | | | G | S | | | W | G | | | | | | | | | | | | | | | | |
| 908, 897 and 8 | | | | | | I | S | M | | | | G | S | | | W | G | | | | | | | | | | | | | | | | |
| 909, 897 and 8 | | | | | | I | S | R | | | | G | S | | | W | G | | | | | | | | | | | | | | | | |
| 910, 897 and 8 | | | | | | I | S | V | | | | G | S | | | W | G | | | | | | | | | | | | | | | | |
| 911, 897 and 8 | | | | | | I | V | S | | | | G | S | | | W | G | | | | | | | | | | | | | | | | |
| 912, 919 and 8 | | | | | | I | W | | | | | H | W | | | A | G | | S | | | | | | | | | | | | | | |
| 913, 920 and 8 | | | | | N | I | A | Q | | | | G | S | | | W | | | | | | | | | | | | | | | | | |
| 914, 897 and 8 | | | | | | I | A | F | | | | G | S | L | | W | G | | | | | | | | | | | | | | | | |
| 915, 921 and 8 | | | | | | I | A | M | | | | G | S | | | W | G | | Y | | | | | | | | | | | | | | |
| 916, 922 and 8 | | | | | | I | A | R | | | | G | S | | | W | G | | M | | | | | | | | | | | | | | |
| 917, 923 and 8 | | | | | | I | A | S | | | | G | S | | | W | G | | L | | | | | | | | | | | | | | |
| 918, 924 and 8 | | | | | | I | A | S | | | | G | S | | | W | G | | S | | | | | | | | | | | | | | |

FIG. 19-2

| LIGHT CHAIN MUTATIONS IN BISPECIFIC HER2 BINDING PHAGE LIBRARIES | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| | CDR-VL1* | | | | | | | | | | | | | | CDR-VL2 | | | | | | | CDR-VL3 | | | | | | | | | | |
| SEQ ID NO: | 1 | 2 | 3 | 4 | 5 | 6 | 7 | | | | | 8 | 9 | 10 | 11 | 1 | 2 | 3 | 4 | 5 | 6 | 7 | 1 | 2 | 3 | 4 | 5 | | | 6 | 7 | 8 | 9 |
| | 24 | 25 | 26 | 27 | 28 | 29 | 30 | 30a | 30b | 30c | 30d | 31 | 32 | 33 | 34 | 50 | 51 | 52 | 53 | 54 | 55 | 56 | 89 | 90 | 91 | 92 | 93 | 93a | 93b | 94 | 95 | 96 | 97 |
| 6, 7 and 8 | R | A | S | Q | D | V | N | – | – | – | – | T | A | V | A | S | A | S | F | L | Y | S | Q | Q | H | Y | T | – | – | T | P | P | T |
| 925, 943 and 8 | | | | | | I | G | S | | | | G | S | | | W | G | | Y | | | | | | | | | | | | | | |
| 926, 943 and 8 | | | | | | I | I | G | | | | G | S | | | W | G | | Y | | | | | | | | | | | | | | |
| 927, 943 and 8 | | | | | | I | K | A | | | | G | S | | | W | G | | Y | | | | | | | | | | | | | | |
| 928, 944 and 8 | | | | | | I | K | F | | | | G | S | | | W | G | | S | | | | | | | | | | | | | | |
| 929, 945 and 8 | | | | | | I | K | L | | | | G | S | | | W | G | | L | | | | | | | | | | | | | | |
| 930, 946 and 8 | | | | | | I | K | L | | | | G | S | | | W | G | | M | | | | | | | | | | | | | | |
| 931, 947 and 8 | | | | | | I | K | S | | | | G | S | | | W | G | | T | | | | | | | | | | | | | | |
| 932, 943 and 8 | | | | | | I | K | V | | | | G | S | | | W | G | | Y | | | | | | | | | | | | | | |
| 933, 947 and 8 | | | | | | I | K | W | | | | G | S | | | W | G | | T | | | | | | | | | | | | | | |
| 934, 943 and 8 | | | | | | I | L | K | | | | G | S | | | W | G | | Y | | | | | | | | | | | | | | |
| 935, 948 and 8 | | | | | | I | L | S | | | | G | S | | | W | G | | W | | | | | | | | | | | | | | |
| 936, 949 and 8 | | | | | | I | Q | R | | | | G | S | | | W | G | | C | | | | | | | | | | | | | | |
| 937, 943 and 8 | | | | | | I | Q | S | | | | G | S | | | W | G | | Y | | | | | | | | | | | | | | |
| 938, 943 and 8 | | | | | | I | Q | T | | | | G | S | | | W | G | | Y | | | | | | | | | | | | | | |
| 939, 944 and 8 | | | | | | I | R | E | | | | G | S | | | W | G | | S | | | | | | | | | | | | | | |
| 940, 943 and 8 | | | | | | I | R | F | | | | G | S | | | W | G | | Y | | | | | | | | | | | | | | |
| 941, 943 and 8 | | | | | | I | R | G | | | | G | S | | | W | G | | Y | | | | | | | | | | | | | | |
| 942, 943 and 8 | | | | | | I | R | L | | | | G | S | | | W | G | | Y | | | | | | | | | | | | | | |

FIG. 19-3

| LIGHT CHAIN MUTATIONS IN BISPECIFIC HER2 BINDING PHAGE LIBRARIES | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| | CDR-VL1* | | | | | | | | | | | | | | | CDR-VL2 | | | | | | | CDR-VL3 | | | | | | | | | | |
| SEQ ID NO: | 1 | 2 | 3 | 4 | 5 | 6 | 7 | | | | | 8 | 9 | 10 | 11 | 1 | 2 | 3 | 4 | 5 | 6 | 7 | 1 | 2 | 3 | 4 | 5 | | | 6 | 7 | 8 | 9 |
| | 24 | 25 | 26 | 27 | 28 | 29 | 30 | 30a | 30b | 30c | 30d | 31 | 32 | 33 | 34 | 50 | 51 | 52 | 53 | 54 | 55 | 56 | 89 | 90 | 91 | 92 | 93 | 93a | 93b | 94 | 95 | 96 | 97 |
| **6, 7 and 8** | **R** | **A** | **S** | **Q** | **D** | **V** | **N** | **–** | **–** | **–** | **–** | **T** | **A** | **V** | **A** | **S** | **A** | **S** | **F** | **L** | **Y** | **S** | **Q** | **Q** | **H** | **Y** | **T** | **–** | **–** | **T** | **P** | **P** | **T** |
| 950, 963 and 8 | | | | | | I | R | M | | | | G | S | | | W | G | | S | | | | | | | | | | | | | | |
| 951, 964 and 8 | | | | | | I | R | R | | | | G | S | | | W | G | | Y | | | | | | | | | | | | | | |
| 951, 965 and 8 | | | | | | I | R | R | | | | G | S | | | W | G | | A | | | | | | | | | | | | | | |
| 952, 964 and 8 | | | | | | I | R | S | | | | G | S | | | W | G | | Y | | | | | | | | | | | | | | |
| 952, 966 and 8 | | | | | | I | R | S | | | | G | S | | | W | G | | T | | | | | | | | | | | | | | |
| 952, 967 and 8 | | | | | | I | R | S | | | | G | S | | | W | G | | N | | | | | | | | | | | | | | |
| 952, 968 and 8 | | | | | | I | R | S | | | | G | S | | | W | G | | E | | | | | | | | | | | | | | |
| 952, 963 and 8 | | | | | | I | R | S | | | | G | S | | | W | G | | S | | | | | | | | | | | | | | |
| 953, 964 and 8 | | | | | | I | R | V | | | | G | S | | | W | G | | Y | | | | | | | | | | | | | | |
| 954, 964 and 8 | | | | | | I | S | S | | | | G | S | | | W | G | | Y | | | | | | | | | | | | | | |
| 955, 969 and 8 | | | | | | I | T | M | | | | G | S | | | W | G | | L | | | | | | | | | | | | | | |
| 956, 964 and 8 | | | | | | I | Y | M | | | | G | S | | | W | G | | Y | | | | | | | | | | | | | | |
| 957, 964 and 8 | | | | | | I | A | T | | | | G | S | L | | W | G | | Y | | | | | | | | | | | | | | |
| 958, 964 and 8 | | | | | | I | K | S | | | | G | S | L | | W | G | | Y | | | | | | | | | | | | | | |
| 959, 970 and 972 | | | | | | I | R | G | | | | G | S | | | G | G | | Y | | | | | | Y | | | | | | | | |
| 960, 964 and 8 | | | | | G | I | R | T | | | | G | S | | | W | G | | Y | | | | | | | | | | | | | | |
| 961, 964 and 8 | | | | | N | I | A | M | | | | G | S | | | W | G | | Y | | | | | | | | | | | | | | |
| 962, 971 and 8 | | | | | N | I | R | S | | | | G | S | | | W | G | | V | | | | | | | | | | | | | | |

FIG. 19-4

LIGHT CHAIN MUTATIONS IN BISPECIFIC HER2 BINDING PHAGE LIBRARIES

| | CDR-VL1* | | | | | | | | | | | | | | | CDR-VL2 | | | | | | | CDR-VL3 | | | | | | | | | | |
|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | 5 | 6 | 7 | | | | | 8 | 9 | 10 | 11 | 1 | 2 | 3 | 4 | 5 | 6 | 7 | 1 | 2 | 3 | 4 | 5 | | | 6 | 7 | 8 | 9 |
| | 24 | 25 | 26 | 27 | 28 | 29 | 30 | 30a | 30b | 30c | 30d | 31 | 32 | 33 | 34 | 50 | 51 | 52 | 53 | 54 | 55 | 56 | 89 | 90 | 91 | 92 | 93 | 93a | 93b | 94 | 95 | 96 | 97 |
| 6, 7 and 8 | R | A | S | Q | D | V | N | – | – | – | – | T | A | V | A | S | A | S | F | L | Y | S | Q | Q | H | Y | T | – | – | T | P | P | T |
| 973, 964 and 8 | | | | | N | I | R | T | | | | G | S | | | W | G | | Y | | | | | | | | | | | | | | |
| 974, 964 and 990 | | | | | | I | R | A | | | | G | S | | | W | G | | Y | | | | | | | F | N | | | A | | | |
| 975, 964 and 8 | | | | | N | I | Y | A | | | | G | S | L | | W | G | | Y | | | | | | | | | | | | | | |
| 976, 964 and 8 | | | | | N | I | Y | S | | | | G | S | L | | W | G | | Y | | | | | | | | | | | | | | |
| 977, 964 and 8 | | | | | | I | P | R | S | I | S | G | Y | | | W | G | | Y | | | | | | | | | | | | | | |
| 978, 986 and 8 | | | | | N | I | R | N | G | | | G | G | L | | | | | | H | | | | | | | | | | | | | |
| 979, 987 and 991 | | | | | N | | S | | | | | K | H | | | W | G | | Y | S | | | | | S | | S | | | G | | | |
| 980, 988 and 992 | | | | | Q | | S | K | | | | Y | D | | | W | G | | S | S | | | | | S | G | F | R | | S | | | |
| 981, 964 and 8 | | | | | | I | P | R | S | I | S | G | Y | | | W | G | | Y | | | | | | | | | | | | | | |
| 982, 989 and 8 | | | | | | I | G | L | | | | G | S | | | W | | | Y | | | | | | | | | | | | | | |
| 983, 964 and 8 | | | | | | I | R | S | | | | G | S | | | W | G | | Y | | | | | | | | | | | | | | |
| 984, 964 and 993 | | | | | N | | S | | | | | K | H | | | W | G | | Y | | | | | | S | | S | | | | | | |
| 985, 7 and 8 | | | | | N | I | R | N | G | | | G | G | | | | | | | | | | | | | | | | | | | | |

*CDR positions 27a-27e contain no mutations and are not shown.

FIG. 19-5

| KNOWN HEAVY CHAIN MUTATIONS | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| | CDR-VH1 | | | | | | | | | | | | CDR-VH2 | | | | | | | | | | | | | | | | | | | | | |
| SEQ ID NO: | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | SEQ ID NO: |
| 3 | G | F | N | I | – | – | K | D | T | Y | I | H | R | I | Y | P | – | – | T | – | – | N | G | Y | T | R | Y | A | D | S | V | K | G | 4 |
| 3 | | | | | | | | | | | | | | | | | | | | | | | | | | | | | | | | | | 4 |
| 994 | | | | | | | A | | | | | | | | | | | | | | | | | | | | | | | | | | | 4 |
| 995 | | | | | | | | A | | | | | | | | | | | | | | | | | | | | | | | | | | 4 |
| 996 | | | | | | | | | A | | | | | | | | | | | | | | | | | | | | | | | | | 4 |
| 997 | | | | | | | | | | A | | | | | | | | | | | | | | | | | | | | | | | | 4 |
| 3 | | | | | | | | | | | | | A | | | | | | | | | | | | | | | | | | | | | 998 |
| 3 | | | | | | | | | | | | | | | A | | | | | | | | | | | | | | | | | | | 999 |
| 3 | | | | | | | | | | | | | | | | | | | A | | | | | | | | | | | | | | | 1000 |
| 3 | | | | | | | | | | | | | | | | | | | | | | A | | | | | | | | | | | | 1001 |
| 3 | | | | | | | | | | | | | | | | | | | | | | | | A | | | | | | | | | | 1002 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |
| 3 | | | | | | | | | | | | | | | | | | | | | | | | | | | | | | | | | | 4 |

Continued

FIG. 20-1.1

Continued from previous table

| KNOWN HEAVY CHAIN MUTATIONS | | | | | | | | | | | | | | | |
|---|---|---|---|---|---|---|---|---|---|---|---|---|---|---|---|
| CDR-VH3 | | | | | | | | | | | | | | | |
| SEQ ID NO: | 95 | 96 | 97 | 98 | 99 | 99a | 99b | 99c | 100 | 100a | 100b | 100c | 100d | 101 | 102 |
| 5 | W | G | G | D | G | – | – | – | F | Y | A | M | – | D | Y |
| 1003 | | | | | | | | | | | | | | | V |
| 5 | | | | | | | | | | | | | | | |
| 5 | | | | | | | | | | | | | | | |
| 5 | | | | | | | | | | | | | | | |
| 5 | | | | | | | | | | | | | | | |
| 5 | | | | | | | | | | | | | | | |
| 5 | | | | | | | | | | | | | | | |
| 5 | | | | | | | | | | | | | | | |
| 5 | | | | | | | | | | | | | | | |
| 5 | | | | | | | | | | | | | | | |
| 1004 | A | | | | | | | | | | | | | | |
| 1005 | | | | A | | | | | | | | | | | |
| 1006 | | | | | A | | | | | | | | | | |
| 1007 | | | | | | | | | A | | | | | | |
| 1008 | | | | | | | | | | A | | | | | |
| 1009 | | | | | | | | | | F | | | | | |

FIG. 20-1.2

KNOWN HEAVY CHAIN MUTATIONS

| | CDR-VH1 | | | | | | | | | | | | CDR-VH2 | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| SEQ ID NO: | 26 | 27 | 28 | 29 | 29a | 29b | 30 | 31 | 32 | 33 | 34 | 35 | 50 | 51 | 52 | 52a | 52b | 52c | 53 | 53a | 53b | 54 | 55 | 56 | 57 | 58 | 59 | 60 | 61 | 62 | 63 | 64 | 65 | SEQ ID NO: |
| 3 | G | F | N | I | – | – | K | D | T | Y | I | H | R | I | Y | P | – | – | T | – | – | N | G | Y | T | R | Y | A | D | S | V | K | G | 4 |
| 1010 | | | | | | | | | | | M | | | | D | | | | A | | | | | N | S | K | | V | P | K | F | Q | | 1029 |
| 1010 | | | | | | | | | | | M | | | | D | | | | A | | | | | N | S | K | | | | | | | | 1030 |
| 1011 | | | T | F | | | S | | Y | W | M | N | Q | | R | N | K | P | Y | | | | Y | E | | Y | | S | | | | | | 1031 |
| 1012 | | | T | F | | | S | | Y | W | M | N | Q | | R | N | K | P | Y | | | | Y | E | | Y | | | | | | | | 1032 |
| 1013 | | | | | | | G | K | S | S | | | W | | S | | | | Y | | | E | | A | | A | | | | | | | | 1033 |
| 1014 | | | | | | | D | N | | A | | | V | | S | | | | H | | | D | | T | | Y | | | | | | | | 1034 |
| 1015 | | | | | | | A | | S | A | | | L | | D | | | | S | | | S | | | | D | | | | | | | | 1035 |
| 1016 | | | T | | | | G | N | S | W | | | V | | A | | | | | | | Y | | | | N | | | | | | | | 1036 |
| 1017 | | | | | | | A | | S | A | | | Y | | A | | | | Y | | | D | | | | Y | | | | | | | | 1037 |
| 1018 | | | T | | | | T | E | S | G | | | V | | | | | | H | | | D | | K | | Y | | | | | | | | 1038 |
| 1019 | | | | | | | T | A | Y | G | | | V | | T | | | | Y | | | D | | D | | T | | | | | | | | 1039 |
| 1020 | | | T | | | | G | G | S | W | | | V | | S | | | | D | | | Y | | | | D | | | | | | | | 1040 |
| 1021 | | | T | | | | G | G | S | W | | | V | | | | | | | | | Y | | | | D | | | | | | | | 1041 |
| 1022 | | | S | | | | A | G | Y | D | | | L | | A | | | | Y | | | A | | | | N | | | | | | | | 1042 |
| 1023 | | | S | L | | | T | N | Y | G | V | | V | | W | S | | | G | | | – | | N | | D | | N | T | P | F | T | S | 1043 |
| 1024 | | Y | T | F | | | T | S | Y | N | M | | A | | | | | | G | | | | | D | | S | | N | Q | K | F | | | 1044 |
| 1025 | | | T | F | | | T | | F | | M | N | F | | R | D | | | K | A | K | G | Y | T | | E | | N | P | | | | | 1045 |
| 1026 | | Y | T | F | | | T | N | Y | G | M | N | W | | N | T | | | Y | | | T | | E | P | T | | | A | D | F | | R | 1046 |
| 1027 | | | T | F | | | T | | Y | T | M | D | D | V | N | | | | N | | | S | | G | S | I | | N | Q | R | F | | | 1047 |
| 1028 | | G | S | V | S | S | G | | Y | | W | T | H | | | Y | | | S | | | – | | N | | N | | N | P | | L | | S | 1048 |

Continued

FIG. 20-2.1

Continued from previous table

| KNOWN HEAVY CHAIN MUTATIONS | | | | | | | | | | | | | | | |
|---|---|---|---|---|---|---|---|---|---|---|---|---|---|---|---|
| CDR-VH3 | | | | | | | | | | | | | | | |
| SEQ ID NO: | 95 | 96 | 97 | 98 | 99 | 99a | 99b | 99c | 100 | 100a | 100b | 100c | 100d | 101 | 102 |
| **5** | **W** | **G** | **G** | **D** | **G** | – | – | – | **F** | **Y** | **A** | **M** | – | **D** | **Y** |
| 1049 | F | | Y | Y | V | | | | S | D | Y | A | M | A | |
| 1049 | F | | Y | Y | V | | | | S | D | Y | A | M | A | |
| 1050 | S | Y | – | – | – | | | | – | | G | | | | |
| 1050 | S | Y | – | – | – | | | | – | | G | | | | |
| 1051 | T | S | W | S | K | | | | P | | | | | | |
| 1052 | | | W | E | T | | | | D | G | | | | | |
| 1053 | S | R | A | G | Y | | | | T | | | | | | |
| 1054 | | | A | K | | | | | T | W | | | | | |
| 1055 | | | W | T | T | | | | N | G | | | | | |
| 1056 | | W | Y | S | W | | | | N | W | | | | | |
| 1057 | | | W | E | A | | | | N | W | | | | | |
| 1058 | | | S | G | Y | | | | T | W | | | | | |
| 1059 | | | A | G | | | | | T | W | | | | | |
| 1060 | A | A | A | W | A | | | | S | | | | | | |
| 1061 | A | L | T | Y | Y | | | | D | | E | F | – | A | |
| 1062 | S | T | Y | Y | | | | G | D | W | Y | F | | N | V |
| 1063 | E | | H | T | – | | | | A | A | P | F | | | |
| 1064 | Y | P | H | Y | Y | G | S | S | H | W | Y | F | | | V |
| 1065 | N | L | | P | – | | | | S | F | Y | F | | | |
| 1066 | D | R | V | T | – | | | | – | G | | F | | | I |

FIG. 20-2.2

| KNOWN LIGHT CHAIN MUTATIONS | | | | | | | | | | | | | | | | | | | | |
|---|---|---|---|---|---|---|---|---|---|---|---|---|---|---|---|---|---|---|---|---|
| | CDR-VL1 | | | | | | | | | | | | | | | | | | | |
| SEQ ID NO: | 24 | 25 | 26 | 27 | 27a | 27b | 27c | 27d | 27e | 28 | 29 | 30 | 30a | 30b | 30c | 30d | 31 | 32 | 33 | 34 |
| 6 | R | A | S | Q | – | – | – | – | – | D | V | N | – | – | – | – | T | A | V | A |
| 6 | | | | | | | | | | | | | | | | | | | | |
| 1067 | | | | | | | | | | N | | | | | | | | | | |
| 1068 | | | | | | | | | | | | A | | | | | | | | |
| 1069 | | | | | | | | | | | | | | | | | A | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 6 | | | | | | | | | | | | | | | | | | | | |
| 1070 | | | | | | | | | | N | | W | | | | | D | W | | |
| 1071 | | | | | | | | | | | I | P | R | S | I | S | G | Y | | |
| 1072 | | | | | | | | | | | I | G | L | | | | G | S | | |
| 1073 | | | | | | | | | | | I | R | S | | | | G | S | | |
| 1074 | | | | | | | | | | | I | W | N | R | | | R | A | L | |
| 1075 | | | | | | | | | | N | | G | | | | | R | P | | |
| 1076 | | | | | | | | | | N | | S | | | | | K | H | | |
| 1077 | | | | | | | | | | N | I | R | N | G | | | G | G | L | |
| 1078 | | | | | | | | | | S | | D | I | F | G | V | G | F | L | H |
| 1079 | | | | | | | | | | S | | D | I | F | G | V | G | F | L | H |
| 1080 | | S | | | S | L | V | H | S | Q | G | | | | | | | Y | L | R |
| 1081 | | | | | S | L | V | H | S | Q | G | | | | | | | Y | L | R |
| 1082 | | | | | | | | | | S | I | G | | | | | | N | I | H |
| 1083 | | | | S | | | | | | S | | – | | | | | S | Y | I | H |
| 1084 | K | | | | | | | | | N | I | D | | | | | K | Y | L | N |
| 1085 | S | | | | | | | | | | I | S | | | | | N | Y | L | N |
| 1086 | K | | | | | | | | | | | S | | | | | I | G | | |
| 1087 | Q | | | | | | | | | | I | S | | | | | N | Y | L | N |

Continued

FIG. 21.1

Continued from previous table

| KNOWN LIGHT CHAIN MUTATIONS | | | | | | | | | | | | | | | | | | | |
|---|---|---|---|---|---|---|---|---|---|---|---|---|---|---|---|---|---|---|---|
| | CDR-VL2 | | | | | | | CDR-VL3 | | | | | | | | | | | |
| SEQ ID NO: | 50 | 51 | 52 | 53 | 54 | 55 | 56 | 89 | 90 | 91 | 92 | 93 | 93a | 93b | 94 | 95 | 96 | 97 | SEQ ID NO: |
| **7** | **S** | **A** | **S** | **F** | **L** | **Y** | **S** | **Q** | **Q** | **H** | **Y** | **T** | **–** | **–** | **T** | **P** | **P** | **T** | **8** |
| 1088 | | | | | | E | | | | | | | | | | | | | 8 |
| 7 | | | | | | | | | | | | | | | | | | | 8 |
| 7 | | | | | | | | | | | | | | | | | | | 8 |
| 7 | | | | | | | | | | | | | | | | | | | 8 |
| 7 | | | | | | | | | | | | | | | | | | | 8 |
| 1089 | A | | | | | | | | | | | | | | | | | | 8 |
| 1090 | | | A | | | | | | | | | | | | | | | | 8 |
| 1091 | | | | N | | | | | | | | | | | | | | | 8 |
| 7 | | | | | | | | | | A | | | | | | | | | 1110 |
| 7 | | | | | | | | | | F | | | | | | | | | 1111 |
| 7 | | | | | | | | | | | A | | | | | | | | 1112 |
| 7 | | | | | | | | | | | F | | | | | | | | 1113 |
| 7 | | | | | | | | | | | | A | | | | | | | 1114 |
| 7 | | | | | | | | | | | | | | | A | | | | 1115 |
| 1092 | P | | | S | | | | | | G | W | Y | I | | A | | | | 1116 |
| 1093 | W | G | | Y | | | | | | | | | | | | | | | 8 |
| 1094 | W | | | Y | | | | | | | | | | | | | | | 8 |
| 1095 | W | G | | Y | | | | | | | | | | | | | | | 8 |
| 1096 | E | G | | | | | | | | G | G | S | Y | S | S | | | | 1117 |
| 1097 | G | G | | | | | | | | Y | G | S | F | G | | | | | 1118 |
| 1098 | | G | | Y | | | | | | S | | S | | | G | | | | 1119 |
| 1099 | | | | F | | | | | | | | | | | | | | | 8 |
| 1100 | R | | | N | | E | | | | T | N | E | | | D | | Y | | 1120 |
| 1101 | R | | | N | | E | | | | T | N | E | | | D | | Y | | 1121 |
| 1102 | K | V | | N | R | F | | S | | S | T | H | | | V | | W | | 1122 |
| 1103 | K | V | | N | R | F | | | | S | T | H | | | V | | W | | 1123 |
| 1104 | Y | | | E | S | I | | | | N | N | N | | | W | | T | | 1124 |
| 1105 | A | T | | N | | A | | | | W | T | S | | | N | | | | 1125 |
| 1106 | N | T | N | N | | Q | T | L | | | I | S | | | R | | R | | 1126 |
| 1107 | F | T | | S | | H | | | | Y | S | | | | V | | W | | 1127 |
| 1108 | | A | | Y | R | | T | | | Y | | I | | | Y | | Y | | 1128 |
| 1109 | D | A | | N | | E | T | | H | F | D | H | | | L | | L | A | 1129 |

FIG. 21.2

HEAVY CHAIN MUTATIONS INCLUDING FRAMEWORK

| SEQ ID NO: | 71 | 72 | 73 | 74 | 75 | 76 | 77 | 78 | 79 | 80 | 81 | 82 | 82 a | 82 b | 82 c | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|
| 1130 | A | D | T | S | K | N | T | A | Y | L | Q | M | N | S | L | R | A | E | D | T | A | V | Y | Y | C | S | R |
| 1131 | R | | | | | | | | | | | | | | | | | | | | | | | | | | |
| 1132 | | | | | | | | | | | | | | T | | | | | | | | | | | | | |
| 1133 | | | | | | | | | | | | | | | | | | | | | C | | | | | | |
| 1134 | R | | N | | | | | L | | | | | | | | | | | | | | | | | | | |
| 1135 | | | | | | | | | | | | | | | | | | | | | | | | | | A | |
| 1136 | | | | | | | | | | | | | | | | | | | | | | T | | | | | |
| 1137 | R | | D | | | | | L | | | | | | | | | | | | | | | | | | A | |
| 1138 | A | | D | | | | | L | | | | | | | | | | | | | | | | | | A | |
| 1139 | A | | T | | | | | L | | | | | | | | | | | | | | | | | | S | |
| 1140 | R | | D | | | | | L | | | | | | | | | | | | | | | | | | A | |
| 1141 | | | | | | | | | | | | | | | | | | | | | | | | | | A | K |
| 1142 | | | | | | | | | | | | | | | | | | | | | | | | | | A | R |
| 1143 | | | | | | | | | | | | | | | | | | | | | | | | | | T | S |
| 1144 | | | | | | | | | | | | | | | | | | | | | | | | | | G | L |
| 1145 | | | | | | | | | | | | | | | | | | | | | | | | | | G | V |
| 1146 | | | | | | | | | | | | | | | | | | | | | | | | | | R | T |
| 1147 | | | | | | | | | | | | | | | | | | | | | | | | | | S | T |

FIG. 22-1

| HEAVY CHAIN MUTATIONS INCLUDING FRAMEWORK | | | | | | | | | | | | | | | | | | | | | | | | | | | |
|---|---|---|---|---|---|---|---|---|---|---|---|---|---|---|---|---|---|---|---|---|---|---|---|---|---|---|---|
| SEQ ID NO: | 71 | 72 | 73 | 74 | 75 | 76 | 77 | 78 | 79 | 80 | 81 | 82 | 82 a | 82 b | 82 c | 83 | 84 | 85 | 86 | 87 | 88 | 89 | 90 | 91 | 92 | 93 | 94 |
| **1130** | **A** | **D** | **T** | **S** | **K** | **N** | **T** | **A** | **Y** | **L** | **Q** | **M** | **N** | **S** | **L** | **R** | **A** | **E** | **D** | **T** | **A** | **V** | **Y** | **Y** | **C** | **S** | **R** |
| 1148 | | | | | | | | | | | | | | | | | | | | | | | | | | T | S |
| 1149 | | | | | | | | | | | | | | | | | | | | | | | | | | G | P |
| 1150 | | | | | | | | | | | | | | | | | | | | | | | | | | S | T |
| 1151 | | | | | | | | | | | | | | | | | | | | | | | | | | V | T |
| 1152 | | | | | | | | | | | | | | | | | | | | | | | | | | G | T |
| 1153 | | | | | | | | | | | | | | | | | | | | | | | | | | L | S |
| 1154 | | | | | | | | | | | | | | | | | | | | | | | | | | S | A |
| 1155 | | | | | | | | | | | | | | | | | | | | | | | | | | M | K |
| 1156 | | | | | | | | | | | | | | | | | | | | | | | | | | T | S |
| 1157 | | | | | | | | | | | | | | | | | | | | | | | | | | G | S |
| 1158 | | | | | | | | | | | | | | | | | | | | | | | | | | I | R |
| 1159 | | | | | | | | | | | | | | | | | | | | | | | | | | R | S |
| 1160 | | | | | | | | | | | | | | | | | | | | | | | | | | G | G |
| 1161 | | | | | | | | | | | | | | | | | | | | | | | | | | G | F |
| 1162 | | | | | | | | | | | | | | | | | | | | | | | | Y | | R | T |
| 1163 | | | | | | | | | | | | | | | | | | | | | | | | Y | | S | M |
| 1164 | | | | | | | | | | | | | | | | | | | | | | | | S | | G | A |

FIG. 22-2

HEAVY CHAIN MUTATIONS INCLUDING FRAMEWORK

| SEQ ID NO: | 71 | 72 | 73 | 74 | 75 | 76 | 77 | 78 | 79 | 80 | 81 | 82 | 82 a | 82 b | 82 c | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|
| **1130** | **A** | **D** | **T** | **S** | **K** | **N** | **T** | **A** | **Y** | **L** | **Q** | **M** | **N** | **S** | **L** | **R** | **A** | **E** | **D** | **T** | **A** | **V** | **Y** | **Y** | **C** | **S** | **R** |
| 1165 | | | | | | | | | | | | | | | | | | | | | | | | Y | | R | S |
| 1166 | | | | | | | | | | | | | | | | | | | | | | | | F | | T | T |
| 1167 | | | | | | | | | | | | | | | | | | | | | | | | N | | T | T |
| 1168 | | | | | | | | | | | | | | | | | | | | | | | | Y | | G | M |
| 1169 | | | | | | | | | | | | | | | | | | | | | | | | Y | | G | T |
| 1170 | | | | | | | | | | | | | | | | | | | | | | | | Y | | R | P |
| 1171 | | | | | | | | | | | | | | | | | | | | | | | | Y | | R | T |
| 1172 | | | | | | | | | | | | | | | | | | | | | | | | Y | | T | T |
| 1173 | | | | | | | | | | | | | | | | | | | | | | | | Y | | R | M |
| 1174 | | | | | | | | | | | | | | | | | | | | | | | | R | | I | T |
| 1175 | | | | | | | | | | | | | | | | | | | | | | | | Y | | G | S |
| 1176 | | | | | | | | | | | | | | | | | | | | | | | | V | | R | A |
| 1177 | | | | | | | | | | | | | | | | | | | | | | | | Y | | G | M |
| 1178 | | | | | | | | | | | | | | | | | | | | | | | | H | | V | T |
| 1179 | | | | | | | | | | | | | | | | | | | | | | | | Y | | T | R |
| 1180 | | | | | | | | | | | | | | | | | | | | | | | | Y | | Q | T |
| 1181 | | | | | | | | | | | | | | | | | | | | | | | | Y | | K | T |

FIG. 22-3

HEAVY CHAIN MUTATIONS INCLUDING FRAMEWORK

| SEQ ID NO: | 71 | 72 | 73 | 74 | 75 | 76 | 77 | 78 | 79 | 80 | 81 | 82 | 82 a | 82 b | 82 c | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|
| 1130 | A | D | T | S | K | N | T | A | Y | L | Q | M | N | S | L | R | A | E | D | T | A | V | Y | Y | C | S | R |
| 1182 | | | | | | | | | | | | | | | | | | | | | | | | Y | | R | A |
| 1183 | | | | | | | | | | | | | | | | | | | | | | | | Y | | S | M |
| 1184 | | | | | | | | | | | | | | | | | | | | | | | | Y | | V | S |
| 1185 | | | | | | | | | | | | | | | | | | | | | | | | R | | G | M |
| 1186 | | | | | | | | | | | | | | | | | | | | | | | | K | | R | T |
| 1187 | | | | | | | | | | | | | | | | | | | | | | | | Y | | K | T |
| 1188 | | | | | | | | | | | | | | | | | | | | | | | | Y | | R | T |
| 1189 | | | | | | | | | | | | | | | | | | | | | | | | Y | | R | S |
| 1190 | | | | | | | | | | | | | | | | | | | | | | | | F | | S | T |
| 1191 | | | | | | | | | | | | | | | | | | | | | | | | Y | | G | T |
| 1192 | | | | | | | | | | | | | | | | | | | | | | | | Y | | S | T |
| 1193 | | | | | | | | | | | | | | | | | | | | | | | | S | | R | T |
| 1194 | | | | | | | | | | | | | | | | | | | | | | | | H | | I | T |
| 1195 | | | | | | | | | | | | | | | | | | | | | | | | Y | | R | A |
| 1196 | | | | | | | | | | | | | | | | | | | | | | | | S | | R | M |
| 1197 | | | | | | | | | | | | | | | | | | | | | | | | F | | R | T |
| 1198 | | | | | | | | | | | | | | | | | | | | | | | | Y | | T | T |

FIG. 22-4

| HEAVY CHAIN MUTATIONS INCLUDING FRAMEWORK | | | | | | | | | | | | | | | | | | | | | | | | | | | |
|---|---|---|---|---|---|---|---|---|---|---|---|---|---|---|---|---|---|---|---|---|---|---|---|---|---|---|---|
| **SEQ ID NO:** | **71** | **72** | **73** | **74** | **75** | **76** | **77** | **78** | **79** | **80** | **81** | **82** | **82 a** | **82 b** | **82 c** | **83** | **84** | **85** | **86** | **87** | **88** | **89** | **90** | **91** | **92** | **93** | **94** |
| **1130** | **A** | **D** | **T** | **S** | **K** | **N** | **T** | **A** | **Y** | **L** | **Q** | **M** | **N** | **S** | **L** | **R** | **A** | **E** | **D** | **T** | **A** | **V** | **Y** | **Y** | **C** | **S** | **R** |
| 1199 | | | | | | | | | | | | | | | | | | | | | | | | Y | | S | I |
| 1200 | | | | | | | | | | | | | | | | | | | | | | | | Y | | A | T |
| 1201 | | | | | | | | | | | | | | | | | | | | | | | | Y | | V | T |
| 1202 | | | | | | | | | | | | | | | | | | | | | | | | Y | | R | V |
| 1203 | | | | | | | | | | | | | | | | | | | | | | | | Y | | K | T |
| 1204 | | | | | | | | | | | | | | | | | | | | | | | | Y | | G | R |
| 1205 | | | | | | | | | | | | | | | | | | | | | | | | F | | R | A |
| 1206 | | | | | | | | | | | | | | | | | | | | | | | | Y | | K | M |
| 1207 | | | | | | | | | | | | | | | | | | | | | | | | S | | K | T |
| 1208 | | | | | | | | | | | | | | | | | | | | | | | | S | | R | S |
| 1209 | | | | | | | | | | | | | | | | | | | | | | | | H | | R | I |
| 1210 | | | | | | | | | | | | | | | | | | | | | | | | Q | | S | T |
| 1211 | | | N | T | Q | | M | | | | | | | | | | | | | | | | | | | | |
| 1212 | | | | | S | | | | | | | V | S | R | | T | S | | | | | | | | | | |
| 1213 | R | D | N | | | | | L | | | | | | | | | | | | | | | | | | | |
| 1214 | | | | | | | | | | | | | | | | P | | | | | | | | | | | |
| 1215 | V | | R | | S | R | I | V | | M | E | L | R | | | T | F | | | | | | | | | A | |

FIG. 22-5

| HEAVY CHAIN MUTATIONS INCLUDING FRAMEWORK | | | | | | | | | | | | | | | | | | | | | | | | | | | |
|---|---|---|---|---|---|---|---|---|---|---|---|---|---|---|---|---|---|---|---|---|---|---|---|---|---|---|---|
| SEQ ID NO: | 71 | 72 | 73 | 74 | 75 | 76 | 77 | 78 | 79 | 80 | 81 | 82 | 82 a | 82 b | 82 c | 83 | 84 | 85 | 86 | 87 | 88 | 89 | 90 | 91 | 92 | 93 | 94 |
| 1130 | A | D | T | S | K | N | T | A | Y | L | Q | M | N | S | L | R | A | E | D | T | A | V | Y | Y | C | S | R |
| 1216 | V | | R | | | | | L | | | | | | | | | | | | | | | | | | A | |
| 1217 | V | | | | | | | | | | | | | | | | | | | | | | | | | | |
| 1218 | | | R | | | | | | | | | | | | | | | | | | | | | | | | |
| 1219 | V | | R | | | | | | | | | | | | | | | | | | | | | | | | |
| 1220 | V | | R | | | | | | | | | | | | | | | | | | | | | | | | |
| 1221 | V | | R | | | | | | | | | | | | | | | | | | | | | | | | |
| 1222 | V | | R | | | | | V | | | | | | | | | | | | | | | | | | | |
| 1223 | V | | R | | | | | | | | | | | | | | | | | | | | | | | | |
| 1224 | V | | R | | | | | | | | | | | | | | | | | | | | | | | | |

FIG. 22-6

| | LIGHT CHAIN MUTATIONS INCLUDING FRAMEWORK | | | | | | | | | | | | | | | | | | | | | |
|---|---|---|---|---|---|---|---|---|---|---|---|---|---|---|---|---|---|---|---|---|---|---|
| SEQ ID NO: | 22 | 23 | 24 | 25 | 26 | 27 | 28 | 29 | 30 | 31 | 32 | 33 | 34 | 35 | 36 | 37 | 38 | 39 | 40 | 41 | 42 | 43 |
| 1225 | T | C | R | A | S | Q | D | V | N | T | A | V | A | W | Y | Q | Q | K | P | G | K | A |
| 1226 | N | | K | | | | | | | | | | | | | | | | | | | |
| 1225 | | | | | | | | | | | | | | | | | | | | | | |
| 1227 | | | | | | S | Q | | S | S | G | | | | | | | | | | | |
| 1228 | | | | | | R | Q | | N | T | A | | | | | | | | | | | |
| 1229 | | | | | | A | Q | | S | A | G | | | | | | | | | | | |
| 1230 | | | | | | Q | G | | S | S | G | | | | | | | | | | | |
| 1231 | | | | | | Q | G | | S | S | A | | | | | | | | | | | |
| 1232 | | | | | | Q | R | | N | S | A | | | | | | | | | | | |
| 1233 | | | | | | Q | G | | S | S | A | | | | | | | | | | | |
| 1234 | | | | | | N | P | | S | Q | A | | | | | | | | | | | |
| 1235 | | | | | | S | Q | | S | K | A | | | | | | | | | | | |
| 1236 | | | | | | F | | | N | A | C | | | | | | | | | | | |
| 1225 | | | | | | | | | | | | | | | | | | | | | | |
| 1237 | | | | | | | S | | S | S | | | | | | | | | | | | |
| 1225 | | | | | | | | | | | | | | | | | | | | | | |
| 1225 | | | | | | | | | | | | | | | | | | | | | | |
| 1238 | | | | | | | | | | S | Y | L | A | | | | | | | | | |
| 1239 | | | | | | | N | | D | K | Y | | | | | | | | | | | |
| 1225 | | | | | | | | | | | | | | | | | | | | | | |

Continued

FIG. 23-1.1

Continued from previous table

| | LIGHT CHAIN MUTATIONS INCLUDING FRAMEWORK | | | | | | | | | | | | | | | | | | | | | | |
|---|---|---|---|---|---|---|---|---|---|---|---|---|---|---|---|---|---|---|---|---|---|---|---|
| SEQ ID NO: | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
| 1240 | P | K | L | L | I | Y | S | A | S | F | L | Y | S | G | V | P | S | R | F | S | G | S | R |
| 1240 | | | | | | | | | | | | | | | | | | | | | | | |
| 1241 | | | | | | | | | | | | | | | | | | | | | | | G |
| 1242 | | | | | | | | | | | | | | | | | | | | | | | R |
| 1243 | | | | | | | | | | | | | | | | | | | | | | | R |
| 1244 | | | | | | | | | | | | | | | | | | | | | | | R |
| 1245 | | | | | | | | | | | | | | | | | | | | | | | A |
| 1246 | | | | | | | | | | | | | | | | | | | | | | | N |
| 1247 | | | | | | | | | | | | | | | | | | | | | | | R |
| 1248 | | | | | | | | | | | | | | | | | | | | | | | M |
| 1249 | | | | | | | | | | | | | | | | | | | | | | | T |
| 1250 | | | | | | | | | | | | | | | | | | | | | | | S |
| 1251 | | | | | | | | | | | | | | | | | | | | | | | V |
| 1252 | | | | | | | | | | | | | | | | | | | | | | | G |
| 1253 | | | | | | | | | | S | | | | | | | | | | | | | G |
| 1254 | | | | | | | | | | | | E | | | | | | | | | | | G |
| 1255 | | | | | | | | | | | | E | | | | | | | | | | | R |
| 1256 | | | | | | | A | | | S | | | | | | | | | | | | | G |
| 1240 | | | | | | | | | | | | | | | | | | | | | | | |
| 1257 | | | | | | | N | T | N | N | | Q | T | | | | | | | | | | |

FIG. 23-1.2

LIGHT CHAIN MUTATIONS INCLUDING FRAMEWORK

| SEQ ID NO: | 22 | 23 | 24 | 25 | 26 | 27 | 28 | 29 | 30 | 31 | 32 | 33 | 34 | 35 | 36 | 37 | 38 | 39 | 40 | 41 | 42 | 43 |
|---|---|---|---|---|---|---|---|---|---|---|---|---|---|---|---|---|---|---|---|---|---|---|
| 1225 | T | C | R | A | S | Q | D | V | N | T | A | V | A | W | Y | Q | Q | K | P | G | K | A |
| 1258 | | | | | | | N | | D | K | Y | | | | | | | | | | | |
| 1259 | | | | | | | | | | | | | | | | | | | L | | E | S |
| 1260 | | | | | | | | | | | | | | | | | | | | | | C |
| 1261 | | | | | | | | | S | | | | | | | | | | | | | |
| 1261 | | | | | | | | | S | | | | | | | | | | | | | |
| 1261 | | | | | | | | | S | | | | | | | | | | | | | |
| 1261 | | | | | | | | | S | | | | | | | | | | | | | |
| 1261 | | | | | | | | | S | | | | | | | | | | | | | |
| 1261 | | | | | | | | | S | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |

Continued

FIG. 23-2.1

Continued from previous table

| | LIGHT CHAIN MUTATIONS INCLUDING FRAMEWORK | | | | | | | | | | | | | | | | | | | | | | |
|---|---|---|---|---|---|---|---|---|---|---|---|---|---|---|---|---|---|---|---|---|---|---|---|
| SEQ ID NO: | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
| 1240 | P | K | L | L | I | Y | S | A | S | F | L | Y | S | G | V | P | S | R | F | S | G | S | R |
| 1262 | | | | | | | N | T | N | N | | Q | T | | | | | | | | | | |
| 1240 | | | | | | | | | | | | | | | | | | | | | | | |
| 1240 | | | | | | | | | | | | | | | | | | | | | | | |
| 1240 | | | | | | | | | | | | | | | | | | | | | | | |
| 1240 | | | | | | | | | | | | | | | | | | | | | | | |
| 1240 | | | | | | | | | | | | | | | | | | | | | | | |
| 1240 | | | | | | | | | | | | | | | | | | | | | | | |
| 1240 | | | | | | | | | | | | | | | | | | | | | | | |
| 1240 | | | | | | | | | | | | | | | | | | | | | | | |
| 1263 | | | | | | W | | | | V | | | | | | | | | | | | | |
| 1264 | | | | | | W | | | | F | | | | | | | | | | | | | |
| 1265 | | | | | | L | | | | F | | | | | | | | | | | | | |
| 1266 | | | | | | F | | | | F | | | | | | | | | | | | | |
| 1267 | | | | | | W | | | | V | | | | | | | | | | | | | |
| 1268 | | | | | | S | | | | W | | | | | | | | | | | | | |
| 1269 | | | | | | K | | | | F | | | | | | | | | | | | | |
| 1270 | | | | | | Y | | | | F | | | | | | | | | | | | | |

FIG. 23-2.2

| | LIGHT CHAIN MUTATIONS INCLUDING FRAMEWORK | | | | | | | | | | | | | | | | | | | | | |
|---|---|---|---|---|---|---|---|---|---|---|---|---|---|---|---|---|---|---|---|---|---|---|
| SEQ ID NO: | 22 | 23 | 24 | 25 | 26 | 27 | 28 | 29 | 30 | 31 | 32 | 33 | 34 | 35 | 36 | 37 | 38 | 39 | 40 | 41 | 42 | 43 |
| 1225 | T | C | R | A | S | Q | D | V | N | T | A | V | A | W | Y | Q | Q | K | P | G | K | A |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |

Continued

FIG. 23-3.1

Continued from previous table

| | LIGHT CHAIN MUTATIONS INCLUDING FRAMEWORK | | | | | | | | | | | | | | | | | | | | | | |
|---|---|---|---|---|---|---|---|---|---|---|---|---|---|---|---|---|---|---|---|---|---|---|---|
| SEQ ID NO: | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
| 1240 | P | K | L | L | I | Y | S | A | S | F | L | Y | S | G | V | P | S | R | F | S | G | S | R |
| 1271 | | | | | | V | | | | W | | | | | | | | | | | | | |
| 1272 | | | | | | V | | | | F | | | | | | | | | | | | | |
| 1273 | | | | | | F | | | | W | | | | | | | | | | | | | |
| 1274 | | | | | | L | | | | V | | | | | | | | | | | | | |
| 1275 | | | | | | L | | | | L | | | | | | | | | | | | | |
| 1276 | | | | | | W | | | | W | | | | | | | | | | | | | |
| 1277 | | | | | | D | | | | W | | W | | | | | | | | | | | |
| 1278 | | | | | | V | | | | T | | W | | | | | | | | | | | |
| 1279 | | | | | | Y | | | | F | | W | | | | | | | | | | | |
| 1280 | | | | | | F | | | | H | | W | | | | | | | | | | | |
| 1281 | | | | | | V | | | | V | | W | | | | | | | | | | | |
| 1282 | | | | | | A | | | | V | | L | | | | | | | | | | | |
| 1283 | | | | | | W | | | | R | | W | | | | | | | | | | | |
| 1284 | | | | | | W | | | | Q | | F | | | | | | | | | | | |
| 1285 | | | | | | V | | | | W | | L | | | | | | | | | | | |
| 1286 | | | | | | W | | | | T | | Y | | | | | | | | | | | |
| 1287 | | | | | | D | | | | W | | W | | | | | | | | | | | |
| 1288 | | | | | | Y | | | | F | | W | | | | | | | | | | | |

FIG. 23-3.2

| | LIGHT CHAIN MUTATIONS INCLUDING FRAMEWORK | | | | | | | | | | | | | | | | | | | | | |
|---|---|---|---|---|---|---|---|---|---|---|---|---|---|---|---|---|---|---|---|---|---|---|
| SEQ ID NO: | 22 | 23 | 24 | 25 | 26 | 27 | 28 | 29 | 30 | 31 | 32 | 33 | 34 | 35 | 36 | 37 | 38 | 39 | 40 | 41 | 42 | 43 |
| 1225 | T | C | R | A | S | Q | D | V | N | T | A | V | A | W | Y | Q | Q | K | P | G | K | A |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1225 | | | | | | | | | | | | | | | | | | | | | | |
| 1289 | | | | | | | | | N | | | | | | | | | | | | | |
| 1289 | | | | | | | | | N | | | | | | | | | | | | | |
| 1289 | | | | | | | | | N | | | | | | | | | | | | | |
| 1289 | | | | | | | | | N | | | | | | | | | | | | | |
| 1289 | | | | | | | | | N | | | | | | | | | | | | | |
| 1290 | | | K | | | | | | | | | | | | | | | | | | H | S |
| 1225 | | | | | | | | | | | | | | | | | | | | | | |
| 1291 | | | K | | | | | | S | I | G | | | | | | | R | | | Q | S |
| 1292 | | | K | | | | | | S | I | G | | | | | | | R | | | | |

Continued

FIG. 23-4.1

Continued from previous table

| | LIGHT CHAIN MUTATIONS INCLUDING FRAMEWORK | | | | | | | | | | | | | | | | | | | | | | |
|---|---|---|---|---|---|---|---|---|---|---|---|---|---|---|---|---|---|---|---|---|---|---|---|
| SEQ ID NO: | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 |
| 1240 | P | K | L | L | I | Y | S | A | S | F | L | Y | S | G | V | P | S | R | F | S | G | S | R |
| 1293 | | | | | | F | | | | M | | W | | | | | | | | | | | |
| 1294 | | | | | | E | | | | W | | W | | | | | | | | | | | |
| 1295 | | | | | | R | | | | W | | V | | | | | | | | | | | |
| 1296 | | | | | | T | | | | K | | W | | | | | | | | | | | |
| 1297 | | | | | | R | | | | A | | W | | | | | | | | | | | |
| 1298 | | | | | | T | | | | R | | V | | | | | | | | | | | |
| 1299 | | | | | | V | | | | K | | S | | | | | | | | | | | |
| 1300 | | | | | | S | | | | V | | W | | | | | | | | | | | |
| 1301 | | | | | | Y | | | | W | | W | | | | | | | | | | | |
| 1302 | | | | | | F | | | | W | | W | | | | | | | | | | | |
| 1303 | | | | | | V | | | | A | | H | | | | | | | | | | | |
| 1304 | | | | | | W | | | | P | | H | | | | | | | | | | | |
| 1305 | | | | | | L | | | | G | | H | | | | | | | | | | | |
| 1306 | | | | | | | | | | | R | E | T | | | | D | | | T | | N | |
| 1307 | | | | | | | W | | | G | | | | | | | | | | | | | |
| 1308 | | | | | | | | | | Y | R | | T | | | | D | | | T | | | G |
| 1309 | | | | | | | | | | Y | R | | T | | | | | | | | | | G |

FIG. 23-4.2

FIG. 24-1

LiVL

| SEQ ID NO: | CDR-L1 | | | | | | | | | | | CDR-L3 | | | | | | | | | SEQ ID NO: |
|---|---|---|---|---|---|---|---|---|---|---|---|---|---|---|---|---|---|---|---|---|---|
| | R 24 1 | A 25 2 | S 26 3 | Q 27 4 | D 28 5 | V 29 6 | N 30 7 | T 31 8 | A 32 9 | V 33 10 | A 34 11 | Q 89 1 | Q 90 2 | H 91 3 | Y 92 4 | T 93 5 | T 94 6 | P 95 7 | P 96 8 | T 97 9 | |
| 6 | | | | | | | | | | | | | | | | | | | | | 8 |
| 1310 | | | | | P | | | | | | | | | | | | | | | | 8 |
| 1311 | | | | | M | | | | | | | | | | | | | | | | 8 |
| 1312 | | | | | R | | | | | | | | | | | | | | | | 8 |
| 6 | | | | | | | | | | | | | | | | N | | | | | 1313 |
| 6 | | | | | | | | | | | | | | | | Y | | | | | 1314 |

FIG. 24-2

LiVH

| SEQ ID NO: | CDR-H2 | | | | | | | | | | | | | | | | | | CDR-H3 | | | | | | | | | | | SEQ ID NO: |
|---|---|---|---|---|---|---|---|---|---|---|---|---|---|---|---|---|---|---|---|---|---|---|---|---|---|---|---|---|---|---|
| | R 50 1 | I 51 2 | Y 52 3 | P 52a 4 | T 53 5 | N 54 6 | G 55 7 | Y 56 8 | T 57 9 | R 58 10 | Y 59 11 | A 60 12 | D 61 13 | S 62 14 | V 63 15 | K 64 16 | G 65 17 | W 95 1 | G 96 2 | G 97 3 | D 98 4 | G 99 5 | F 100 6 | Y 100a 7 | A 100b 8 | M 100c 9 | D 101 10 | Y 102 11 | |
| 4 | | | | | | | | | | | | | | | | | | | | | | | | | | | | | 5 |
| 1315 | | | | | | T | | | | | | | | | | | | | | | | | | | | | | | |
| 1316 | | | | | | K | | | | | | | | | | | | | | | | | | | | | | | |
| 1317 | | | | | | P | | | | | | | | | | | | | | | | | | | | | | | |
| 1318 | | | | | | M | | | | | | | | | | | | | | | | | | | | | | | |
| 1319 | | | | | | | | I | | | | | | | | | | | | | | | | | | | | | |
| 1320 | | | | | | | | | | T | | | | | | | | | | | | | | | | | | | |
| 1321 | | | | | | | | | | K | | | | | | | | | | | | | | | | | | | |
| 1322 | | | | | | | | | | I | | | | | | | | | | | | | | | | | | | |
| 4 | | | | | | | | | | | | | | | | | | | | | T | | | | | | | | 1323 |
| 4 | | | | | | | | | | | | | | | | | | | | | Y | | | | | | | | 1324 |
| 4 | | | | | | | | | | | | | | | | | | | | | M | | | | | | | | 1325 |
| 4 | | | | | | | | | | | | | | | | | | | | | K | | | | | | | | 1326 |

4D5 (Trastuzumab) VH (SEQ ID NO:1)

| FR1 | | | | | | | | | | | | | | | | | | | | | | | | | CDR1 | | | | |
|---|---|---|---|---|---|---|---|---|---|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| E | V | Q | L | V | E | S | G | G | G | L | V | Q | P | G | G | S | L | R | L | S | C | A | A | S | G | F | N | I | K |

| CDR1 | | | | | FR2 | | | | | | | | | | | | | | CDR2 | | | | | | | | | | |
|---|---|---|---|---|---|---|---|---|---|---|---|---|---|---|---|---|---|---|---|---|---|---|---|---|---|---|---|---|---|
| 31 | 32 | 33 | 34 | 35 | 36 | 37 | 38 | 39 | 40 | 41 | 42 | 43 | 44 | 45 | 46 | 47 | 48 | 49 | 50 | 51 | 52 | 52a | 53 | 54 | 55 | 56 | 57 | 58 | 59 |
| D | T | Y | I | H | W | V | R | Q | A | P | G | K | G | L | E | W | V | A | R | I | Y | P | T | N | G | Y | T | R | Y |

| CDR2 | | | | | | FR3 | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| 60 | 61 | 62 | 63 | 64 | 65 | 66 | 67 | 68 | 69 | 70 | 71 | 82 | 73 | 74 | 75 | 76 | 77 | 78 | 79 | 80 | 81 | 82 | 82a | 82b | 82c | 83 | 84 | 85 | 86 |
| A | D | S | V | K | G | R | F | T | I | S | A | D | T | S | K | N | T | A | Y | L | Q | M | N | S | L | R | A | E | D |

| FR3 | | | | | | | | CDR3 | | | | | | | | | | | | | FR4 | | | | | | | | | | |
|---|---|---|---|---|---|---|---|---|---|---|---|---|---|---|---|---|---|---|---|---|---|---|---|---|---|---|---|---|---|---|
| 87 | 88 | 89 | 90 | 91 | 92 | 93 | 94 | 95 | 96 | 97 | 98 | 99 | 100 | 100a | 100b | 100c | 101 | 102 | 103 | 104 | 105 | 106 | 107 | 108 | 109 | 110 | 111 | 112 | 113 |
| T | A | V | Y | Y | C | S | R | W | G | G | D | G | F | Y | A | M | D | Y | W | G | Q | G | T | L | V | T | V | S | S |

4D5 (Trastuzumab) VL (SEQ ID NO:2)

| FR1 | | | | | | | | | | | | | | | | | | | | | | | CDR1 | | | | | | |
|---|---|---|---|---|---|---|---|---|---|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| D | I | Q | M | T | Q | S | P | S | S | L | S | A | S | V | G | D | R | V | T | I | T | C | R | A | S | Q | D | V | N |

| CDR1 | | | | FR2 | | | | | | | | | | | | | | | CDR2 | | | | | | | FR3 | | | |
|---|---|---|---|---|---|---|---|---|---|---|---|---|---|---|---|---|---|---|---|---|---|---|---|---|---|---|---|---|---|
| 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
| T | A | V | A | W | Y | Q | Q | K | P | G | K | A | P | K | L | L | I | Y | S | A | S | F | L | Y | S | G | V | P | S |

| FR3 | | | | | | | | | | | | | | | | | | | | | | | | | | | | CDR3 | |
|---|---|---|---|---|---|---|---|---|---|---|---|---|---|---|---|---|---|---|---|---|---|---|---|---|---|---|---|---|---|
| 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |
| R | F | S | G | S | R | S | G | T | D | F | T | L | T | I | S | S | L | Q | P | E | D | F | A | T | Y | Y | C | Q | Q |

| CDR3 | | | | | | | FR4 | | | | | | | | | |
|---|---|---|---|---|---|---|---|---|---|---|---|---|---|---|---|---|
| 91 | 92 | 93 | 94 | 95 | 96 | 97 | 98 | 99 | 100 | 101 | 102 | 103 | 104 | 105 | 106 | 107 |
| H | Y | T | T | P | P | T | F | G | Q | G | T | K | L | E | I | K |

FIG. 25A

| ANTIBODY CHAIN | CDR NO. | SEQUENCE | SEQ ID NO. |
|---|---|---|---|
| Heavy | 1 | GFNIKDTYIH | 3 |
| Heavy | 2 | RIYPTNGYTRYADSVKG | 4 |
| Heavy | 3 | WGGDGFYAMDY | 5 |
| Light | 1 | RASQDVNTAVA | 6 |
| Light | 2 | SASFLYS | 7 |
| Light | 3 | QQHYTTPPT | 8 |

FIG. 25B

| ANTIBODY CHAIN | FW NO. | SEQUENCE | SEQ ID NO. |
|---|---|---|---|
| Heavy | 1 | EVQLVESGGGLVQPGGSLRLSCAAS | 77 |
| Heavy | 2 | WVRQAPGKGLEWVA | 78 |
| Heavy | 3 | RFTISADTSKNTAYLQMNSLRAEDTAVYYCSR | 79 |
| Heavy | 4 | WGQGTLVTVSS | 80 |
| Light | 1 | DIQMTQSPSSLSASVGDRVTITC | 81 |
| Light | 2 | WYQQKPGKAPKLLIY | 82 |
| Light | 3 | GVPSRFSGSRSGTDFTLTISSLQPEDFATYYC | 83 |
| Light | 4 | FGQGTKLEIK | 84 |

FIG. 25C

| SEQ ID NO: | WILD TYPE RESIDUE | SUBSTITUTION | KABAT NO. / POSITION IN REGION | ACTIVITY RELATIVE TO WILD-TYPE TRASTUZUMAB |
|---|---|---|---|---|
| | | CDR-H1 | | |
| 176 | G | C | 26/1 | 82 |
| 177 | N | G | 28/3 | 88 |
| 178 | K | R | 30/5 | 96 |
| 179 | K | V | 30/5 | 80 |
| 180 | D | H | 31/6 | 123 |
| 182 | D | T | 31/6 | 108 |
| 181 | D | Q | 31/6 | 100 |
| 88 | D | V | 31/6 | 94 |
| 86 | D | L | 31/6 | 95 |
| 87 | D | R | 31/6 | 108 |
| 183 | T | V | 32/7 | 90 |
| 89 | T | K | 32/7 | 94 |
| 90 | T | R | 32/7 | 90 |
| 91 | I | D | 34/9 | 108 |
| | | CDR-H2 | | |
| 184 | Y | K | 52/3 | 116 |
| 185 | Y | Q | 52/3 | 86 |
| 93 | T | R | 53/5 | 125 |
| 92 | T | L | 53/5 | 86 |
| 186 | T | G | 57/9 | 92 |
| 187 | T | V | 57/9 | 87 |
| 188 | A | K | 60/12 | 86 |
| 189 | D | S | 61/13 | 94 |
| 190 | D | E | 61/13 | 96 |
| 191 | S | E | 62/14 | 80 |
| 192 | S | G | 62/14 | 84 |
| 193 | S | A | 32/14 | 84 |
| 194 | V | A | 63/15 | 91 |
| 195 | K | A | 64/16 | 97 |
| 196 | G | V | 65/17 | 89 |
| 197 | G | E | 65/17 | 105 |
| 198 | G | I | 65/17 | 98 |
| 94 | K | R | 64/16 | 104 |
| 95 | K | S | 64/16 | 119 |
| | | FR-H3 | | |
| 246 | A | C | 78/13 | 87 |
| 247 | A | W | 78/13 | 96 |
| 248 | A | Q | 78/13 | 79 |
| 249 | S | V | 82b/19 | 84 |
| 250 | S | L | 82b/19 | 87 |
| 251 | L | V | 82c/20 | 89 |
| 252 | L | A | 82c/20 | 96 |
| 253 | L | E | 82c/20 | 79 |
| 254 | L | G | 82c/20 | 82 |
| 255 | R | V | 83/21 | 80 |
| 256 | R | L | 83/21 | 97 |
| 257 | R | G | 83/21 | 91 |
| 258 | R | K | 83/21 | 88 |
| | | Continued | | |

FIG. 26A-1

| SEQ ID NO: | WILD TYPE RESIDUE | SUBSTITUTION | KABAT NO. / POSITION IN REGION | ACTIVITY RELATIVE TO WILD-TYPE TRASTUZUMAB |
|---|---|---|---|---|
| Continued from Previous Table | | | | |
| 259 | A | M | 84/22 | 88 |
| 260 | A | W | 84/22 | 100 |
| 261 | A | K | 84/22 | 97 |
| 262 | A | G | 84/22 | 91 |
| 263 | A | Q | 84/22 | 88 |
| 264 | A | R | 84/22 | 99 |
| 265 | E | L | 85/23 | 101 |
| 266 | E | G | 85/23 | 100 |
| 267 | E | A | 85/23 | 104 |
| 268 | E | S | 85/23 | 94 |
| 269 | E | N | 85/23 | 87 |
| 270 | E | H | 85/23 | 99 |
| 271 | D | S | 86/24 | 95 |
| 272 | D | G | 86/24 | 88 |
| 273 | T | W | 87/25 | 92 |
| 274 | T | E | 87/25 | 92 |
| 275 | T | L | 87/25 | 94 |
| 276 | T | F | 87/25 | 88 |
| 277 | T | H | 87/25 | 93 |
| 278 | T | D | 87/25 | 90 |
| 279 | A | G | 88/26 | 91 |
| 280 | A | R | 88/26 | 84 |
| 281 | A | K | 88/26 | 84 |
| 282 | A | V | 88/26 | 99 |
| 238 | A | W | 88/26 | 101 |
| 237 | A | Q | 88/26 | 107 |
| 239 | A | E | 88/26 | 110 |
| 240 | V | R | 89/27 | 107 |
| 241 | V | Y | 89/27 | 115 |
| 283 | V | K | 89/27 | 89 |
| 284 | V | S | 89/27 | 84 |
| 285 | V | W | 89/27 | 91 |
| 286 | V | G | 89/27 | 86 |
| 287 | Y | V | 90/28 | 97 |
| 288 | Y | L | 90/28 | 93 |
| 289 | Y | I | 90/28 | 85 |
| 290 | Y | L | 91/29 | 87 |
| 291 | Y | W | 91/29 | 83 |
| 292 | C | G | 92/30 | 84 |
| 242 | S | N | 93/31 | 93 |
| 243 | S | P | 93/31 | 80 |
| 245 | S | D | 93/31 | 117 |
| 244 | S | Y | 93/31 | 71 |
| **CDR-H3** | | | | |
| 199 | D | V | 98/4 | 121 |
| 200 | D | M | 98/4 | 114 |
| 728 | D | W | 98/4 | 125 |
| 201 | D | L | 101/10 | 116 |
| 202 | D | R | 102/11 | 104 |

FIG. 26A-2

| SEQ ID NO: | WILD TYPE RESIDUE | SUBSTITUTION | KABAT NO. / POSITION IN REGION | ACTIVITY RELATIVE TO WILD-TYPE TRASTUZUMAB |
|---|---|---|---|---|
| FR-L1 | | | | |
| 293 | T | G | 22/22 | 135 |
| 294 | T | S | 22/22 | 128 |
| 295 | C | A | 23/23 | 112 |
| 296 | C | N | 23/23 | 75 |
| CDR-L1 | | | | |
| 203 | R | H | 24/1 | 123 |
| 204 | R | E | 24/1 | 108 |
| 205 | R | C | 24/1 | 121 |
| 206 | R | V | 24/1 | 110 |
| 207 | A | C | 25/2 | 113 |
| 208 | A | G | 25/2 | 126 |
| 209 | A | P | 25/2 | 110 |
| 97 | Q | V | 27/4 | 117 |
| 96 | Q | L | 27/4 | 95 |
| 98 | Q | I | 27/4 | 108 |
| 99 | Q | Y | 27/4 | 94 |
| 103 | D | W | 28/5 | 83 |
| 102 | D | M | 28/5 | 98 |
| 101 | D | A | 28/5 | 130 |
| 100 | D | L | 28/5 | 103 |
| 210 | V | A | 29/6 | 121 |
| 211 | V | S | 29/6 | 130 |
| 105 | A | G | 34/11 | 116 |
| 162 | A | N | 34/11 | 72 |
| 108 | A | E | 34/11 | 103 |
| 107 | A | S | 34/11 | 103 |
| 106 | A | D | 34/11 | 143 |
| 104 | A | V | 34/11 | 108 |
| FR-L2 | | | | |
| 297 | W | H | 35/1 | 103 |
| 298 | W | F | 35/1 | 109 |
| Continued | | | | |

FIG. 26B-1

| SEQ ID NO: | WILD TYPE RESIDUE | SUBSTITUTION | KABAT NO. / POSITION IN REGION | ACTIVITY RELATIVE TO WILD-TYPE TRASTUZUMAB |
|---|---|---|---|---|
| **CDR-L2** | | | | |
| 212 | A | S | 51/2 | 143 |
| 213 | S | W | 52/3 | 128 |
| 214 | S | M | 52/3 | 126 |
| 215 | S | Q | 52/3 | 118 |
| 216 | S | H | 52/3 | 129 |
| 217 | S | G | 52/3 | 136 |
| 218 | S | R | 52/3 | 142 |
| 219 | L | I | 54/5 | 125 |
| 220 | L | G | 54/5 | 135 |
| 221 | L | V | 54/5 | 152 |
| 222 | S | A | 56/7 | 135 |
| 223 | S | P | 56/7 | 136 |
| 224 | S | G | 56/7 | 128 |
| 225 | S | H | 56/7 | 128 |
| 226 | S | Y | 56/7 | 142 |
| 227 | S | F | 56/7 | 136 |
| 228 | S | N | 56/7 | 132 |
| 229 | S | M | 56/7 | 110 |
| **FR-L3** | | | | |
| 299 | R | K | 66/10 | 110 |
| **CDR-L3** | | | | |
| 230 | Y | M | 92/4 | 112 |
| 231 | T | L | 93/5 | 120 |
| 232 | T | M | 93/5 | 130 |
| 233 | T | G | 93/5 | 105 |
| 234 | T | V | 93/5 | 139 |
| 235 | P | G | 96/8 | 130 |
| 236 | T | D | 97/9 | 109 |

FIG. 26B-2

| | trastuzumab | isotype control |
|---|---|---|
| EC50 | 1.898 | 0.2805 |

| TRASTUZUMAB $V_L$ PEPTIDES TESTED | | |
|---|---|---|
| **SEQ ID NO.** | **PEPTIDE NO.** | **Peptide Sequence** |
| 9 | 1 | DIQMTQSPSSLSASV |
| 10 | 2 | MTQSPSSLSASVGDR |
| 11 | 3 | SPSSLSASVGDRVTI |
| 12 | 4 | SLSASVGDRVTITCR |
| 13 | 5 | ASVGDRVTITCRASQ |
| 14 | 6 | GDRVTITCRASQDVN |
| 15 | 7 | VTITCRASQDVNTAV |
| **16** | **8** | **TCRASQDVNTAVAWY** |
| 17 | 9 | ASQDVNTAVAWYQQK |
| 18 | 10 | DVNTAVAWYQQKPGK |
| 19 | 11 | TAVAWYQQKPGKAPK |
| 20 | 12 | AWYQQKPGKAPKLLI |
| 21 | 13 | QQKPGKAPKLLIYSA |
| 22 | 14 | PGKAPKLLIYSASFL |
| 23 | 15 | APKLLIYSASFLYSG |
| 24 | 16 | LLIYSASFLYSGVPS |
| 25 | 17 | YSASFLYSGVPSRFS |
| 26 | 18 | SFLYSGVPSRFSGSR |
| **27** | **19** | **YSGVPSRFSGSRSGT** |
| 28 | 20 | VPSRFSGSRSGTDFT |
| 29 | 21 | RFSGSRSGTDFTLTI |
| 30 | 22 | GSRSGTDFTLTISSL |
| **31** | **23** | **SGTDFTLTISSLQPE** |
| 32 | 24 | DFTLTISSLQPEDFA |
| 33 | 25 | LTISSLQPEDFATYY |
| 34 | 26 | SSLQPEDFATYYCQQ |
| 35 | 27 | QPEDFATYYCQQHYT |
| 36 | 28 | DFATYYCQQHYTTPP |
| 37 | 29 | TYYCQQHYTTPPTFG |
| 38 | 30 | CQQHYTTPPTFGQGT |
| 39 | 31 | HYTTPPTFGQGTKVE |
| 40 | 32 | TPPTFGQGTKVEIKR |

FIG. 28A

| TRASTUZUMAB $V_H$ PEPTIDES TESTED | | |
|---|---|---|
| SEQ ID NO: | PEPTIDE NO. | Peptide Sequence |
| 41 | 1 | EVQLVESGGGLVQPG |
| 42 | 2 | LVESGGGLVQPGGSL |
| 43 | 3 | SGGGLVQPGGSLRLS |
| 44 | 4 | GLVQPGGSLRLSCAA |
| 45 | 5 | QPGGSLRLSCAASGF |
| 46 | 6 | GSLRLSCAASGFNIK |
| 47 | 7 | RLSCAASGFNIKDTY |
| 48 | 8 | CAASGFNIKDTYIHW |
| **49** | **9** | **SGFNIKDTYIHWVRQ** |
| 50 | 10 | NIKDTYIHWVRQAPG |
| 51 | 11 | DTYIHWVRQAPGKGL |
| 52 | 12 | IHWVRQAPGKGLEWV |
| 53 | 13 | VRQAPGKGLEWVARI |
| 54 | 14 | APGKGLEWVARIYPT |
| 55 | 15 | KGLEWVARIYPTNGY |
| 56 | 16 | EWVARIYPTNGYTRY |
| 57 | 17 | ARIYPTNGYTRYADS |
| 58 | 18 | YPTNGYTRYADSVKG |
| 59 | 19 | NGYTRYADSVKGRFT |
| 60 | 20 | TRYADSVKGRFTISA |
| 61 | 21 | ADSVKGRFTISADTS |
| 62 | 22 | VKGRFTISADTSKNT |
| 63 | 23 | RFTISADTSKNTAYL |
| 64 | 24 | ISADTSKNTAYLQMN |
| 65 | 25 | DTSKNTAYLQMNSLR |
| 66 | 26 | KNTAYLQMNSLRAED |
| 67 | 27 | AYLQMNSLRAEDTAV |
| 68 | 28 | QMNSLRAEDTAVYYC |
| **69** | **29** | **SLRAEDTAVYYCSRW** |
| 70 | 30 | AEDTAVYYCSRWGGD |
| 71 | 31 | TAVYYCSRWGGDGFY |
| 72 | 32 | YYCSRWGGDGFYAMD |
| 73 | 33 | SRWGGDGFYAMDYWG |
| 74 | 34 | GGDGFYAMDYWGQGT |
| 75 | 35 | GFYAMDYWGQGTLVT |
| 76 | 36 | AMDYWGQGTLVTVSS |

FIG. 28B

| TRASTUZUMAB HEAVY CHAIN EPITOPE PEPTIDES TESTED | | | | | | | | | | | | | | | | | |
|---|---|---|---|---|---|---|---|---|---|---|---|---|---|---|---|---|---|
| | SEQ ID NO: | $V_H$ peptide #29 (AA 82b – 95) | | | | | | | | | | | | | | | |
| 1 | 1327 | S | L | R | A | E | D | T | A | V | Y | Y | C | S | R | W | control |
| 2 | 1328 | S | L | R | A | E | D | T | A | V | Y | Y | C | N | R | W | |
| 3 | 1329 | S | L | R | A | E | D | T | A | V | Y | Y | C | D | R | W | |
| 4 | 1330 | S | L | R | A | E | D | T | A | V | Y | Y | C | A | R | W | |
| 5 | 1331 | S | L | R | A | E | D | T | A | V | Y | Y | C | V | R | W | |
| 6 | 1332 | S | L | R | A | E | D | T | A | V | Y | Y | C | L | R | W | |
| 7 | 1333 | S | L | R | A | E | D | T | A | V | Y | Y | C | S | R | Y | |
| 8 | 1334 | S | L | R | A | E | D | T | A | V | Y | Y | C | N | R | Y | |
| 9 | 1335 | S | L | R | A | E | D | T | A | V | Y | Y | C | D | R | Y | |
| 10 | 1336 | S | L | R | A | E | D | T | A | V | Y | Y | C | A | R | Y | |
| 11 | 1337 | S | L | R | A | E | D | T | A | V | Y | Y | C | V | R | Y | |
| 12 | 1338 | S | L | R | A | E | D | T | A | V | Y | Y | C | L | R | Y | |
| 13 | 1339 | S | L | R | A | E | D | T | A | V | Y | Y | C | S | R | F | |
| 14 | 1340 | S | L | R | A | E | D | T | A | V | Y | Y | C | N | R | F | |
| 15 | 1341 | S | L | R | A | E | D | T | A | V | Y | Y | C | D | R | F | |
| 16 | 1342 | S | L | R | A | E | D | T | A | V | Y | Y | C | A | R | F | |
| 17 | 1343 | S | L | R | A | E | D | T | A | V | Y | Y | C | V | R | F | |
| 18 | 1344 | S | L | R | A | E | D | T | A | V | Y | Y | C | L | R | F | |
| 19 | 1345 | S | G | R | A | E | D | T | A | V | Y | Y | C | S | R | W | |
| 20 | 1346 | S | L | R | A | E | D | R | A | V | Y | Y | C | S | R | W | |
| 21 | 1347 | V | L | R | A | E | D | T | A | V | Y | Y | C | S | R | W | |
| 22 | 1348 | S | L | K | A | E | D | T | A | V | Y | Y | C | S | R | W | |
| 23 | 1349 | S | L | R | A | E | D | T | A | V | Y | Y | C | S | R | W | control |

FIG. 30A

| TRASTUZUMAB LIGHT CHAIN EPITOPE PEPTIDES TESTED | | | | | | | | | | | | | | | | | |
|---|---|---|---|---|---|---|---|---|---|---|---|---|---|---|---|---|---|
| | SEQ ID NO: | $V_L$ peptide #8 (AA T22-Y36) | | | | | | | | | | | | | | | |
| 1 | 1350 | T | C | R | A | S | Q | D | V | N | T | A | V | A | W | Y | control |
| 2 | 1351 | T | C | R | A | S | Q | G | V | N | T | A | V | A | W | Y | |
| 3 | 1352 | T | C | R | A | S | Q | A | V | N | T | A | V | A | W | Y | |
| 4 | 1353 | T | C | R | A | S | Q | N | V | N | T | A | V | A | W | Y | |
| 5 | 1354 | T | C | R | A | S | Q | L | V | N | T | A | V | A | W | Y | |
| 6 | 1355 | T | C | R | A | S | S | D | V | N | T | A | V | A | W | Y | |
| 7 | 1356 | T | C | R | A | S | K | D | V | N | T | A | V | A | W | Y | |
| 8 | 1357 | T | C | R | A | S | V | D | V | N | T | A | V | A | W | Y | |
| 9 | 1358 | T | C | R | A | S | L | D | V | N | T | A | V | A | W | Y | |
| 10 | 1359 | T | C | R | A | S | F | D | V | N | T | A | V | A | W | Y | |
| 11 | 1360 | T | C | R | A | S | I | D | V | N | T | A | V | A | W | Y | |
| 12 | 1361 | T | C | R | A | S | Y | D | V | N | T | A | V | A | W | Y | |
| 13 | 1362 | T | C | R | A | S | R | D | V | N | T | A | V | A | W | Y | |
| 14 | 1363 | T | C | R | A | S | Q | D | V | N | T | A | V | G | W | Y | |
| 15 | 1364 | T | C | R | A | S | Q | G | V | N | T | A | V | G | W | Y | |
| 16 | 1365 | T | C | R | A | S | Q | A | V | N | T | A | V | G | W | Y | |
| 17 | 1366 | T | C | R | A | S | Q | N | V | N | T | A | V | G | W | Y | |
| 18 | 1367 | T | C | R | A | S | Q | L | V | N | T | A | V | G | W | Y | |
| 19 | 1368 | T | C | R | A | S | S | D | V | N | T | A | V | G | W | Y | |
| 20 | 1369 | T | C | R | A | S | K | D | V | N | T | A | V | G | W | Y | |
| 21 | 1370 | T | C | R | A | S | V | D | V | N | T | A | V | G | W | Y | |
| 22 | 1371 | T | C | R | A | S | L | D | V | N | T | A | V | G | W | Y | |
| 23 | 1372 | T | C | R | A | S | F | D | V | N | T | A | V | G | W | Y | |
| 24 | 1373 | T | C | R | A | S | I | D | V | N | T | A | V | G | W | Y | |
| 25 | 1374 | T | C | R | A | S | Y | D | V | N | T | A | V | G | W | Y | |
| 26 | 1375 | T | C | R | A | S | R | D | V | N | T | A | V | G | W | Y | |
| | 1376 | T | C | R | A | S | Q | D | V | N | T | A | V | A | W | Y | control |

FIG. 30B

| TRASTUZUMAB LIGHT CHAIN EPITOPE PEPTIDES TESTED | | | | | | | | | | | | | | | | | |
|---|---|---|---|---|---|---|---|---|---|---|---|---|---|---|---|---|---|
| | SEQ ID NO: | $V_L$ peptide #8 (AA T22-Y36) | | | | | | | | | | | | | | | |
| | 1377 | T | C | R | A | S | Q | D | V | N | T | A | V | A | W | Y | control |
| 27 | 1378 | T | C | R | A | S | Q | D | V | N | T | A | V | D | W | Y | |
| 28 | 1379 | T | C | R | A | S | Q | G | V | N | T | A | V | D | W | Y | |
| 29 | 1380 | T | C | R | A | S | Q | A | V | N | T | A | V | D | W | Y | |
| 30 | 1381 | T | C | R | A | S | Q | N | V | N | T | A | V | D | W | Y | |
| 31 | 1382 | T | C | R | A | S | Q | L | V | N | T | A | V | D | W | Y | |
| 32 | 1383 | T | C | R | A | S | S | D | V | N | T | A | V | D | W | Y | |
| 33 | 1384 | T | C | R | A | S | K | D | V | N | T | A | V | D | W | Y | |
| 34 | 1385 | T | C | R | A | S | V | D | V | N | T | A | V | D | W | Y | |
| 35 | 1386 | T | C | R | A | S | L | D | V | N | T | A | V | D | W | Y | |
| 36 | 1387 | T | C | R | A | S | F | D | V | N | T | A | V | D | W | Y | |
| 37 | 1388 | T | C | R | A | S | I | D | V | N | T | A | V | D | W | Y | |
| 38 | 1389 | T | C | R | A | S | Y | D | V | N | T | A | V | D | W | Y | |
| 39 | 1390 | T | C | R | A | S | R | D | V | N | T | A | V | D | W | Y | |
| 40 | 1391 | T | C | R | A | S | Q | D | V | N | T | A | V | V | W | Y | |
| 41 | 1392 | T | C | R | A | S | Q | G | V | N | T | A | V | V | W | Y | |
| 42 | 1393 | T | C | R | A | S | Q | A | V | N | T | A | V | V | W | Y | |
| 43 | 1394 | T | C | R | A | S | Q | N | V | N | T | A | V | V | W | Y | |
| 44 | 1395 | T | C | R | A | S | Q | L | V | N | T | A | V | V | W | Y | |
| 45 | 1396 | T | C | R | A | S | S | D | V | N | T | A | V | V | W | Y | |
| 46 | 1397 | T | C | R | A | S | K | D | V | N | T | A | V | V | W | Y | |
| 47 | 1398 | T | C | R | A | S | V | D | V | N | T | A | V | V | W | Y | |
| 48 | 1399 | T | C | R | A | S | L | D | V | N | T | A | V | V | W | Y | |
| 49 | 1400 | T | C | R | A | S | F | D | V | N | T | A | V | V | W | Y | |
| 50 | 1401 | T | C | R | A | S | I | D | V | N | T | A | V | V | W | Y | |
| 51 | 1402 | T | C | R | A | S | Y | D | V | N | T | A | V | V | W | Y | |
| 52 | 1403 | T | C | R | A | S | R | D | V | N | T | A | V | V | W | Y | |
| | 1404 | T | C | R | A | S | Q | D | V | N | T | A | V | A | W | Y | control |

FIG. 30C

| VH DEIMMUNIZED EPITOPE VARIANTS | | | | | | | | | | | | | | | | | |
|---|---|---|---|---|---|---|---|---|---|---|---|---|---|---|---|---|---|
| | S | L | R | A | E | D | T | A | V | Y | Y | C | S | R | W | | |
| SEQ ID NO: | 81 | 82 | 83 | 84 | 85 | 86 | 87 | 88 | 89 | 90 | 91 | 92 | 93 | 94 | 95 | AVERAGE SI | PERCENT RESPONDERS |
| 1405 | | | K | | | | | | | | | | | | | 1.28 | 1.20 |
| 1406 | | | | | | | | | | | | | | | F | 1.25 | 1.20 |

| VL DEIMMUNIZED EPITOPE VARIANTS | | | | | | | | | | | | | | | | | |
|---|---|---|---|---|---|---|---|---|---|---|---|---|---|---|---|---|---|
| | T | C | R | A | S | Q | D | V | N | T | A | V | A | W | Y | | |
| SEQ ID NO: | 22 | 23 | 24 | 25 | 26 | 27 | 28 | 29 | 30 | 31 | 32 | 33 | 34 | 35 | 36 | AVERAGE SI | PERCENT RESPONDERS |
| 1408 | | | | | | S | | | | | | | | | | 1.13 | 1.20 |
| 1409 | | | | | | | N | | | | | | D | | | 1.06 | 1.20 |
| 1410 | | | | | | S | | | | | | | D | | | 1.07 | 0.00 |
| 1411 | | | | | | L | | | | | | | V | | | 1.24 | 0.00 |
| 1412 | | | | | | | L | | | | | | D | | | 1.14 | 1.20 |
| 1413 | | | | | | F | | | | | | | D | | | 1.25 | 1.20 |
| 1414 | | | | | | | | | | | | | V | | | 1.08 | 1.20 |

FIG. 32

| VH (SEQ ID NO:) | VL (SEQ ID NO:) | $k_{on}$ (E+05 1/Ms) | $k_{off}$ (E-04 1/s) | $K_D$ (nM) | Activity relative to wild-type |
|---|---|---|---|---|---|
| WT | WT | 1.00 | 0.63 | 0.62 | **100** |
| D31H (180) | WT | 0.95 | 0.66 | 0.69 | **90** |
| D31T (182) | WT | 0.91 | 0.68 | 0.75 | **83** |
| Y52K (184) | WT | 0.87 | 0.61 | 0.70 | **89** |
| WT | T22G (293) | 0.97 | 0.54 | 0.55 | **113** |
| R83K (258) | WT | 0.98 | 0.61 | 0.63 | **98** |
| W95F (127) | WT | 0.93 | 2.06 | 2.21 | 28 |
| WT | A34V (104) | 1.02 | 0.42 | 0.41 | **151** |
| WT | Q27L + A34V (337) | 1.00 | 0.58 | 0.57 | **109** |
| WT | D28L + A34D (349) | 0.97 | 1.95 | 2.02 | 31 |
| WT | D28N + A34D (348) | 0.99 | 1.28 | 1.30 | 48 |
| D31T (182) | T22G (293) | 1.06 | 0.53 | 0.50 | **124** |
| D31H (180) | T22G (293) | 1.09 | 0.45 | 0.41 | **151** |
| R83K (258) | A34V (104) | 1.16 | 0.85 | 0.73 | **85** |
| W95F (127) | A34V (104) | 1.01 | 1.96 | 1.93 | 32 |
| R83K (258) | Q27L + A34V (337) | 1.06 | 0.87 | 0.82 | **76** |
| W95F (127) | Q27L + A34V (337) | 1.03 | 2.05 | 1.99 | 31 |
| R83K (258) | D28L + A34D (349) | 1.16 | 2.35 | 2.02 | 31 |
| W95F (127) | D28L + A34D (349) | 0.98 | 4.71 | 4.77 | 13 |
| R83K (258) | D28N + A34D (348) | 1.06 | 1.24 | 0.82 | **76** |
| W95F (127) | D28N + A34D (348) | 1.10 | 1.63 | 1.47 | 42 |

FIG. 34

SEQUENCE LISTING

```
<160> NUMBER OF SEQ ID NOS: 1414

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
```

50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Leu Glu Ile Lys
100 105

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Gly Phe Asn Ile Lys Asp Thr Tyr Ile His
1 5 10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Arg Ile Tyr Pro Thr Asn Gly Tyr Thr Arg Tyr Ala Asp Ser Val Lys
1 5 10 15

Gly

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Trp Gly Gly Asp Gly Phe Tyr Ala Met Asp Tyr
1 5 10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Arg Ala Ser Gln Asp Val Asn Thr Ala Val Ala
1 5 10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Ser Ala Ser Phe Leu Tyr Ser
1 5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Gln Gln His Tyr Thr Thr Pro Pro Thr
1 5

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Asp Ile Gln Met Thr Gln Ser Pro Ser Ser Leu Ser Ala Ser Val
1 5 10 15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Met Thr Gln Ser Pro Ser Ser Leu Ser Ala Ser Val Gly Asp Arg
1 5 10 15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Ser Pro Ser Ser Leu Ser Ala Ser Val Gly Asp Arg Val Thr Ile
1 5 10 15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Ser Leu Ser Ala Ser Val Gly Asp Arg Val Thr Ile Thr Cys Arg
1 5 10 15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Ala Ser Val Gly Asp Arg Val Thr Ile Thr Cys Arg Ala Ser Gln
1 5 10 15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Gly Asp Arg Val Thr Ile Thr Cys Arg Ala Ser Gln Asp Val Asn
1 5 10 15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Val Thr Ile Thr Cys Arg Ala Ser Gln Asp Val Asn Thr Ala Val
1 5 10 15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Thr Cys Arg Ala Ser Gln Asp Val Asn Thr Ala Val Ala Trp Tyr
1 5 10 15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Ala Ser Gln Asp Val Asn Thr Ala Val Ala Trp Tyr Gln Gln Lys
1 5 10 15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Asp Val Asn Thr Ala Val Ala Trp Tyr Gln Gln Lys Pro Gly Lys
1 5 10 15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Thr Ala Val Ala Trp Tyr Gln Gln Lys Pro Gly Lys Ala Pro Lys
1 5 10 15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Ala Trp Tyr Gln Gln Lys Pro Gly Lys Ala Pro Lys Leu Leu Ile
1 5 10 15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Gln Gln Lys Pro Gly Lys Ala Pro Lys Leu Leu Ile Tyr Ser Ala
1 5 10 15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Pro Gly Lys Ala Pro Lys Leu Leu Ile Tyr Ser Ala Ser Phe Leu
1 5 10 15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Ala Pro Lys Leu Leu Ile Tyr Ser Ala Ser Phe Leu Tyr Ser Gly
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 24

Leu Leu Ile Tyr Ser Ala Ser Phe Leu Tyr Ser Gly Val Pro Ser
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Tyr Ser Ala Ser Phe Leu Tyr Ser Gly Val Pro Ser Arg Phe Ser
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Ser Phe Leu Tyr Ser Gly Val Pro Ser Arg Phe Ser Gly Ser Arg
1 5 10 15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Tyr Ser Gly Val Pro Ser Arg Phe Ser Gly Ser Arg Ser Gly Thr
1 5 10 15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Val Pro Ser Arg Phe Ser Gly Ser Arg Ser Gly Thr Asp Phe Thr
1 5 10 15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Arg Phe Ser Gly Ser Arg Ser Gly Thr Asp Phe Thr Leu Thr Ile
1 5 10 15

<210> SEQ ID NO 30
<211> LENGTH: 15
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 30

Gly Ser Arg Ser Gly Thr Asp Phe Thr Leu Thr Ile Ser Ser Leu
1 5 10 15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Ser Gly Thr Asp Phe Thr Leu Thr Ile Ser Ser Leu Gln Pro Glu
1 5 10 15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Asp Phe Thr Leu Thr Ile Ser Ser Leu Gln Pro Glu Asp Phe Ala
1 5 10 15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Leu Thr Ile Ser Ser Leu Gln Pro Glu Asp Phe Ala Thr Tyr Tyr
1 5 10 15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Ser Ser Leu Gln Pro Glu Asp Phe Ala Thr Tyr Tyr Cys Gln Gln
1 5 10 15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Gln Pro Glu Asp Phe Ala Thr Tyr Tyr Cys Gln Gln His Tyr Thr
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

```
Asp Phe Ala Thr Tyr Tyr Cys Gln Gln His Tyr Thr Thr Pro Pro
1               5                   10                  15
```

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

```
Thr Tyr Tyr Cys Gln Gln His Tyr Thr Thr Pro Pro Thr Phe Gly
1               5                   10                  15
```

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

```
Cys Gln Gln His Tyr Thr Thr Pro Pro Thr Phe Gly Gln Gly Thr
1               5                   10                  15
```

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

```
His Tyr Thr Thr Pro Pro Thr Phe Gly Gln Gly Thr Lys Val Glu
1               5                   10                  15
```

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

```
Thr Pro Pro Thr Phe Gly Gln Gly Thr Lys Val Glu Ile Lys Arg
1               5                   10                  15
```

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Glu Val Gln Leu Val Glu Ser Gly Gly Gly Leu Val Gln Pro Gly
1 5 10 15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Leu Val Glu Ser Gly Gly Gly Leu Val Gln Pro Gly Gly Ser Leu
1 5 10 15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Ser Gly Gly Gly Leu Val Gln Pro Gly Gly Ser Leu Arg Leu Ser
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Gly Leu Val Gln Pro Gly Gly Ser Leu Arg Leu Ser Cys Ala Ala
1 5 10 15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Gln Pro Gly Gly Ser Leu Arg Leu Ser Cys Ala Ala Ser Gly Phe
1 5 10 15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Gly Ser Leu Arg Leu Ser Cys Ala Ala Ser Gly Phe Asn Ile Lys
1 5 10 15

<210> SEQ ID NO 47
<211> LENGTH: 15

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Arg Leu Ser Cys Ala Ala Ser Gly Phe Asn Ile Lys Asp Thr Tyr
1 5 10 15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Cys Ala Ala Ser Gly Phe Asn Ile Lys Asp Thr Tyr Ile His Trp
1 5 10 15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Ser Gly Phe Asn Ile Lys Asp Thr Tyr Ile His Trp Val Arg Gln
1 5 10 15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Asn Ile Lys Asp Thr Tyr Ile His Trp Val Arg Gln Ala Pro Gly
1 5 10 15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Asp Thr Tyr Ile His Trp Val Arg Gln Ala Pro Gly Lys Gly Leu
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Ile His Trp Val Arg Gln Ala Pro Gly Lys Gly Leu Glu Trp Val

-continued

```
1               5                   10                  15


<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Arg Gln Ala Pro Gly Lys Gly Leu Glu Trp Val Ala Arg Ile
1               5                   10                  15


<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Pro Gly Lys Gly Leu Glu Trp Val Ala Arg Ile Tyr Pro Thr
1               5                   10                  15


<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Gly Leu Glu Trp Val Ala Arg Ile Tyr Pro Thr Asn Gly Tyr
1               5                   10                  15


<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Trp Val Ala Arg Ile Tyr Pro Thr Asn Gly Tyr Thr Arg Tyr
1               5                   10                  15


<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Arg Ile Tyr Pro Thr Asn Gly Tyr Thr Arg Tyr Ala Asp Ser
1               5                   10                  15


<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 58

Tyr Pro Thr Asn Gly Tyr Thr Arg Tyr Ala Asp Ser Val Lys Gly
1 5 10 15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Asn Gly Tyr Thr Arg Tyr Ala Asp Ser Val Lys Gly Arg Phe Thr
1 5 10 15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Thr Arg Tyr Ala Asp Ser Val Lys Gly Arg Phe Thr Ile Ser Ala
1 5 10 15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Ala Asp Ser Val Lys Gly Arg Phe Thr Ile Ser Ala Asp Thr Ser
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Val Lys Gly Arg Phe Thr Ile Ser Ala Asp Thr Ser Lys Asn Thr
1 5 10 15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Arg Phe Thr Ile Ser Ala Asp Thr Ser Lys Asn Thr Ala Tyr Leu
1 5 10 15

<210> SEQ ID NO 64

<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Ile Ser Ala Asp Thr Ser Lys Asn Thr Ala Tyr Leu Gln Met Asn
1 5 10 15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Asp Thr Ser Lys Asn Thr Ala Tyr Leu Gln Met Asn Ser Leu Arg
1 5 10 15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Lys Asn Thr Ala Tyr Leu Gln Met Asn Ser Leu Arg Ala Glu Asp
1 5 10 15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Ala Tyr Leu Gln Met Asn Ser Leu Arg Ala Glu Asp Thr Ala Val
1 5 10 15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Gln Met Asn Ser Leu Arg Ala Glu Asp Thr Ala Val Tyr Tyr Cys
1 5 10 15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Ser Leu Arg Ala Glu Asp Thr Ala Val Tyr Tyr Cys Ser Arg Trp
1 5 10 15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Ala Glu Asp Thr Ala Val Tyr Tyr Cys Ser Arg Trp Gly Gly Asp
1 5 10 15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Thr Ala Val Tyr Tyr Cys Ser Arg Trp Gly Gly Asp Gly Phe Tyr
1 5 10 15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Tyr Tyr Cys Ser Arg Trp Gly Gly Asp Gly Phe Tyr Ala Met Asp
1 5 10 15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Ser Arg Trp Gly Gly Asp Gly Phe Tyr Ala Met Asp Tyr Trp Gly
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Gly Gly Asp Gly Phe Tyr Ala Met Asp Tyr Trp Gly Gln Gly Thr
1 5 10 15

<210> SEQ ID NO 75
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 75

Gly Phe Tyr Ala Met Asp Tyr Trp Gly Gln Gly Thr Leu Val Thr
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Met Asp Tyr Trp Gly Gln Gly Thr Leu Val Thr Val Ser Ser
1               5                   10                  15

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp Val Arg Gln Ala Pro Gly Lys Gly Leu Glu Trp Val Ala
1               5                   10

<210> SEQ ID NO 79
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Trp Gly Gln Gly Thr Leu Val Thr Val Ser Ser
1 5 10

<210> SEQ ID NO 81
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Trp Tyr Gln Gln Lys Pro Gly Lys Ala Pro Lys Leu Leu Ile Tyr
1 5 10 15

<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Gly Val Pro Ser Arg Phe Ser Gly Ser Arg Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Phe Gly Gln Gly Thr Lys Leu Glu Ile Lys
1 5 10

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Gly Gly Gly Gly Ser Gly Gly Gly Gly Ser Gly Gly Gly Gly Ser 1 5 10 15

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gly Phe Asn Ile Lys Leu Thr Tyr Ile His
1 5 10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Gly Phe Asn Ile Lys Arg Thr Tyr Ile His
1 5 10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gly Phe Asn Ile Lys Val Thr Tyr Ile His
1 5 10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Gly Phe Asn Ile Lys Asp Lys Tyr Ile His
1 5 10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Gly Phe Asn Ile Lys Asp Arg Tyr Ile His
1 5 10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Gly Phe Asn Ile Lys Asp Thr Tyr Asp His
1 5 10

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Arg Ile Tyr Pro Leu Asn Gly Tyr Thr Arg Tyr Ala Asp Ser Val Lys
1 5 10 15

Gly

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Arg Ile Tyr Pro Arg Asn Gly Tyr Thr Arg Tyr Ala Asp Ser Val Lys
1 5 10 15

Gly

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Arg Ile Tyr Pro Thr Asn Gly Tyr Thr Arg Tyr Ala Asp Ser Val Arg
1 5 10 15

Gly

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Arg Ile Tyr Pro Thr Asn Gly Tyr Thr Arg Tyr Ala Asp Ser Val Ser
1 5 10 15

Gly

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Arg Ala Ser Leu Asp Val Asn Thr Ala Val Ala
1 5 10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Arg Ala Ser Val Asp Val Asn Thr Ala Val Ala
1 5 10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Arg Ala Ser Ile Asp Val Asn Thr Ala Val Ala
1 5 10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Arg Ala Ser Tyr Asp Val Asn Thr Ala Val Ala
1 5 10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Arg Ala Ser Gln Leu Val Asn Thr Ala Val Ala
1 5 10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Arg Ala Ser Gln Ala Val Asn Thr Ala Val Ala
1 5 10

<210> SEQ ID NO 102
<211> LENGTH: 11

<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Arg Ala Ser Gln Met Val Asn Thr Ala Val Ala
1 5 10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Arg Ala Ser Gln Trp Val Asn Thr Ala Val Ala
1 5 10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Arg Ala Ser Gln Asp Val Asn Thr Ala Val Val
1 5 10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Arg Ala Ser Gln Asp Val Asn Thr Ala Val Gly
1 5 10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Arg Ala Ser Gln Asp Val Asn Thr Ala Val Asp
1 5 10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Arg Ala Ser Gln Asp Val Asn Thr Ala Val Ser 1 5 10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Arg Ala Ser Gln Asp Val Asn Thr Ala Val Glu
1 5 10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Gly Phe Ser Ile Lys Asp Thr Tyr Ile His
1 5 10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gly Phe Trp Ile Lys Asp Thr Tyr Ile His
1 5 10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Gly Phe Asn Ile Trp Asp Thr Tyr Ile His
1 5 10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Gly Phe Asn Ile Ala Asp Thr Tyr Ile His
1 5 10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Gly Phe Asn Ile Lys Trp Thr Tyr Ile His
1 5 10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Gly Phe Asn Ile Lys Ala Thr Tyr Ile His
1 5 10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Gly Phe Asn Ile Lys Gly Thr Tyr Ile His
1 5 10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Gly Phe Asn Ile Lys Ser Thr Tyr Ile His
1 5 10

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Arg Ile Arg Pro Thr Asn Gly Tyr Thr Arg Tyr Ala Asp Ser Val Lys
1 5 10 15

Gly

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Arg Ile Ser Pro Thr Asn Gly Tyr Thr Arg Tyr Ala Asp Ser Val Lys
1 5 10 15

Gly

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Arg Ile Tyr Pro Ser Asn Gly Tyr Thr Arg Tyr Ala Asp Ser Val Lys
1 5 10 15

Gly

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Arg Ile Tyr Pro Lys Asn Gly Tyr Thr Arg Tyr Ala Asp Ser Val Lys
1 5 10 15

Gly

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Arg Ile Tyr Pro Gly Asn Gly Tyr Thr Arg Tyr Ala Asp Ser Val Lys
1 5 10 15

Gly

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Arg Ile Tyr Pro Thr Ser Gly Tyr Thr Arg Tyr Ala Asp Ser Val Lys
1 5 10 15

Gly

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Arg Ile Tyr Pro Thr Asn Gly Tyr Ser Arg Tyr Ala Asp Ser Val Lys
1 5 10 15

Gly

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Arg Ile Tyr Pro Thr Asn Gly Tyr Thr Arg Tyr Ala Asp Arg Val Lys
1 5 10 15

Gly

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Arg Ile Tyr Pro Thr Asn Gly Tyr Thr Arg Tyr Ala Asp Ser Val Gln
1 5 10 15

Gly

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Tyr Gly Gly Asp Gly Phe Tyr Ala Met Asp Tyr
1 5 10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Phe Gly Gly Asp Gly Phe Tyr Ala Met Asp Tyr
1 5 10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Trp Gly Arg Asp Gly Phe Tyr Ala Met Asp Tyr
1 5 10

<210> SEQ ID NO 129

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Trp Gly Thr Asp Gly Phe Tyr Ala Met Asp Tyr
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Trp Gly Gly Gly Gly Phe Tyr Ala Met Asp Tyr
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Trp Gly Gly Thr Gly Phe Tyr Ala Met Asp Tyr
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Trp Gly Gly Ala Gly Phe Tyr Ala Met Asp Tyr
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Gly Gly Arg Gly Phe Tyr Ala Met Asp Tyr
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Gly Gly Gln Gly Phe Tyr Ala Met Asp Tyr
1 5 10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

Trp Gly Gly Glu Gly Phe Tyr Ala Met Asp Tyr
1 5 10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

Trp Gly Gly Ser Gly Phe Tyr Ala Met Asp Tyr
1 5 10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Trp Gly Gly Tyr Gly Phe Tyr Ala Met Asp Tyr
1 5 10

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Trp Gly Gly Phe Gly Phe Tyr Ala Met Asp Tyr
1 5 10

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Trp Gly Gly Leu Gly Phe Tyr Ala Met Asp Tyr
1 5 10

<210> SEQ ID NO 140
<211> LENGTH: 11
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 140

Trp Gly Gly Pro Gly Phe Tyr Ala Met Asp Tyr
1 5 10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Trp Gly Gly His Gly Phe Tyr Ala Met Asp Tyr
1 5 10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Trp Gly Gly Asp Gly Phe Tyr Val Met Asp Tyr
1 5 10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Trp Gly Gly Asp Gly Phe Tyr Ser Met Asp Tyr
1 5 10

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 144

Trp Gly Gly Asp Gly Phe Tyr Glu Met Asp Tyr
1 5 10

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Trp Gly Gly Asp Gly Phe Tyr Ala Phe Asp Tyr
1 5 10

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 146

Trp Gly Gly Asp Gly Phe Tyr Ala Met Asp Gly
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Trp Gly Gly Asp Gly Phe Tyr Ala Met Asp Ser
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Trp Gly Gly Asp Gly Phe Tyr Ala Met Asp Lys
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Trp Gly Gly Asp Gly Phe Tyr Ala Met Asp His
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Lys Ala Ser Gln Asp Val Asn Thr Ala Val Ala
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Arg Ser Ser Gln Asp Val Asn Thr Ala Val Ala
1 5 10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Arg Ala Ser Arg Asp Val Asn Thr Ala Val Ala
1 5 10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Arg Ala Ser Ser Asp Val Asn Thr Ala Val Ala
1 5 10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Arg Ala Ser Phe Asp Val Asn Thr Ala Val Ala
1 5 10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Arg Ala Ser Lys Asp Val Asn Thr Ala Val Ala
1 5 10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Arg Ala Ser Gln Gly Val Asn Thr Ala Val Ala
1 5 10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Arg Ala Ser Gln Asn Val Asn Thr Ala Val Ala
1 5 10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Arg Ala Ser Gln Arg Val Asn Thr Ala Val Ala
1 5 10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Arg Ala Ser Gln Pro Val Asn Thr Ala Val Ala
1 5 10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Arg Ala Ser Gln Ser Val Asn Thr Ala Val Ala
1 5 10

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Arg Ala Ser Gln Asp Ile Asn Thr Ala Val Ala
1 5 10

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Arg Ala Ser Gln Asp Val Asn Ser Ala Val Ala
1 5 10

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 163

Arg Ala Ser Gln Asp Val Asn Thr Ala Val Asn
1 5 10

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 164

Ser Gly Ser Phe Leu Tyr Ser
1 5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 165

Ser Ala Ser Trp Leu Tyr Ser
1 5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 166

Ser Ala Ser Tyr Leu Tyr Ser
1 5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 167

Ser Ala Ser Phe Ser Tyr Ser
1 5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
peptide -continued

<400> SEQUENCE: 168

Ser Ala Ser Phe Leu Leu Ser
1 5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Ser Ala Ser Phe Leu Ala Ser
1 5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Gln Gln Trp Tyr Thr Thr Pro Pro Thr
1 5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Gln Gln Tyr Tyr Thr Thr Pro Pro Thr
1 5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Gln Gln His Tyr Ser Thr Pro Pro Thr
1 5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Gln Gln His Tyr Ala Thr Pro Pro Thr
1 5

<210> SEQ ID NO 174
<211> LENGTH: 9
<212> TYPE: PRT

-continued

<213> ORGANISM: Artificial Sequence
<220> FEATURE:
<223> OTHER INFORMATION: Description of Artificial Sequence: Synthetic
peptide

<400> SEQUENCE: 174

Gln Gln His Tyr Thr Ser Pro Pro Thr
1 5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 175

Gln Gln His Tyr Thr Thr Pro Ser Thr
1 5

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 176

Cys Phe Asn Ile Lys Asp Thr Tyr Ile His
1 5 10

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 177

Gly Phe Gly Ile Lys Asp Thr Tyr Ile His
1 5 10

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 178

Gly Phe Asn Ile Arg Asp Thr Tyr Ile His
1 5 10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

Gly Phe Asn Ile Val Asp Thr Tyr Ile His
1 5 10

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Phe Asn Ile Lys His Thr Tyr Ile His
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Phe Asn Ile Lys Gln Thr Tyr Ile His
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Phe Asn Ile Lys Thr Thr Tyr Ile His
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Phe Asn Ile Lys Asp Val Tyr Ile His
1               5                   10

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ile Lys Pro Thr Asn Gly Tyr Thr Arg Tyr Ala Asp Ser Val Lys
1               5                   10                  15

Gly

<210> SEQ ID NO 185
<211> LENGTH: 17
<212> TYPE: PRT
<213> ORGANISM: Artificial Sequence
<220> FEATURE:

<223> OTHER INFORMATION: Description of Artificial Sequence: Synthetic peptide

<400> SEQUENCE: 185

Arg Ile Gln Pro Thr Asn Gly Tyr Thr Arg Tyr Ala Asp Ser Val Lys
1 5 10 15

Gly

<210> SEQ ID NO 186
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Arg Ile Tyr Pro Thr Asn Gly Tyr Gly Arg Tyr Ala Asp Ser Val Lys
1 5 10 15

Gly

<210> SEQ ID NO 187
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Arg Ile Tyr Pro Thr Asn Gly Tyr Val Arg Tyr Ala Asp Ser Val Lys
1 5 10 15

Gly

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Arg Ile Tyr Pro Thr Asn Gly Tyr Thr Arg Tyr Lys Asp Ser Val Lys
1 5 10 15

Gly

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Arg Ile Tyr Pro Thr Asn Gly Tyr Thr Arg Tyr Ala Ser Ser Val Lys
1 5 10 15

Gly

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Arg Ile Tyr Pro Thr Asn Gly Tyr Thr Arg Tyr Ala Glu Ser Val Lys
1 5 10 15

Gly

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Arg Ile Tyr Pro Thr Asn Gly Tyr Thr Arg Tyr Ala Asp Glu Val Lys
1 5 10 15

Gly

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Arg Ile Tyr Pro Thr Asn Gly Tyr Thr Arg Tyr Ala Asp Gly Val Lys
1 5 10 15

Gly

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Arg Ile Tyr Pro Thr Asn Gly Tyr Thr Arg Tyr Ala Asp Ala Val Lys
1 5 10 15

Gly

<210> SEQ ID NO 194
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Arg Ile Tyr Pro Thr Asn Gly Tyr Thr Arg Tyr Ala Asp Ser Ala Lys
1 5 10 15

Gly

<210> SEQ ID NO 195
<211> LENGTH: 17
<212> TYPE: PRT

<213> ORGANISM: Artificial Sequence
<220> FEATURE:
<223> OTHER INFORMATION: Description of Artificial Sequence: Synthetic peptide

<400> SEQUENCE: 195

Arg Ile Tyr Pro Thr Asn Gly Tyr Thr Arg Tyr Ala Asp Ser Val Ala
1 5 10 15

Gly

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Arg Ile Tyr Pro Thr Asn Gly Tyr Thr Arg Tyr Ala Asp Ser Val Lys
1 5 10 15

Val

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Arg Ile Tyr Pro Thr Asn Gly Tyr Thr Arg Tyr Ala Asp Ser Val Lys
1 5 10 15

Glu

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Arg Ile Tyr Pro Thr Asn Gly Tyr Thr Arg Tyr Ala Asp Ser Val Lys
1 5 10 15

Ile

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Trp Gly Gly Val Gly Phe Tyr Ala Met Asp Tyr
1 5 10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Trp Gly Gly Met Gly Phe Tyr Ala Met Asp Tyr
1 5 10

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Trp Gly Gly Asp Gly Phe Tyr Ala Met Leu Tyr
1 5 10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Trp Gly Gly Asp Gly Phe Tyr Ala Met Asp Arg
1 5 10

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

His Ala Ser Gln Asp Val Asn Thr Ala Val Ala
1 5 10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Glu Ala Ser Gln Asp Val Asn Thr Ala Val Ala
1 5 10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Cys Ala Ser Gln Asp Val Asn Thr Ala Val Ala
1 5 10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Val Ala Ser Gln Asp Val Asn Thr Ala Val Ala
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Arg Cys Ser Gln Asp Val Asn Thr Ala Val Ala
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Arg Gly Ser Gln Asp Val Asn Thr Ala Val Ala
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Arg Pro Ser Gln Asp Val Asn Thr Ala Val Ala
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Arg Ala Ser Gln Asp Ala Asn Thr Ala Val Ala
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 211

Arg Ala Ser Gln Asp Ser Asn Thr Ala Val Ala
1 5 10

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 212

Ser Ser Ser Phe Leu Tyr Ser
1 5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Ser Ala Trp Phe Leu Tyr Ser
1 5

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Ser Ala Met Phe Leu Tyr Ser
1 5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Ser Ala Gln Phe Leu Tyr Ser
1 5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Ser Ala His Phe Leu Tyr Ser
1 5

<210> SEQ ID NO 217
<211> LENGTH: 7
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 217

Ser Ala Gly Phe Leu Tyr Ser
1               5

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Ala Arg Phe Leu Tyr Ser
1               5

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Ala Ser Phe Ile Tyr Ser
1               5

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Ala Ser Phe Gly Tyr Ser
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ser Ala Ser Phe Val Tyr Ser
1               5

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Ala Ser Phe Leu Tyr Ala
1               5

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Ser Ala Ser Phe Leu Tyr Pro
1 5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Ser Ala Ser Phe Leu Tyr Gly
1 5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Ser Ala Ser Phe Leu Tyr His
1 5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Ser Ala Ser Phe Leu Tyr Tyr
1 5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Ser Ala Ser Phe Leu Tyr Phe
1 5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Ser Ala Ser Phe Leu Tyr Asn
1 5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Ser Ala Ser Phe Leu Tyr Met
1 5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Gln Gln His Met Thr Thr Pro Pro Thr
1 5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

Gln Gln His Tyr Leu Thr Pro Pro Thr
1 5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Gln Gln His Tyr Met Thr Pro Pro Thr
1 5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Gln Gln His Tyr Gly Thr Pro Pro Thr
1 5

<210> SEQ ID NO 234
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gln Gln His Tyr Val Thr Pro Pro Thr
1               5


<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gln Gln His Tyr Thr Thr Pro Gly Thr
1               5


<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gln Gln His Tyr Thr Thr Pro Pro Asp
1               5


<210> SEQ ID NO 237
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Arg Phe Thr Ile Ser Ala Asp Thr Ser Lys Asn Thr Ala Tyr Leu Gln
1               5                   10                  15

Met Asn Ser Leu Arg Ala Glu Asp Thr Gln Val Tyr Tyr Cys Ser Arg
            20                  25                  30


<210> SEQ ID NO 238
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Arg Phe Thr Ile Ser Ala Asp Thr Ser Lys Asn Thr Ala Tyr Leu Gln
1               5                   10                  15

Met Asn Ser Leu Arg Ala Glu Asp Thr Trp Val Tyr Tyr Cys Ser Arg
            20                  25                  30


<210> SEQ ID NO 239
<211> LENGTH: 32
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 239

Arg Phe Thr Ile Ser Ala Asp Thr Ser Lys Asn Thr Ala Tyr Leu Gln
1 5 10 15

Met Asn Ser Leu Arg Ala Glu Asp Thr Glu Val Tyr Tyr Cys Ser Arg
20 25 30

<210> SEQ ID NO 240
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 240

Arg Phe Thr Ile Ser Ala Asp Thr Ser Lys Asn Thr Ala Tyr Leu Gln
1 5 10 15

Met Asn Ser Leu Arg Ala Glu Asp Thr Ala Arg Tyr Tyr Cys Ser Arg
20 25 30

<210> SEQ ID NO 241
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 241

Arg Phe Thr Ile Ser Ala Asp Thr Ser Lys Asn Thr Ala Tyr Leu Gln
1 5 10 15

Met Asn Ser Leu Arg Ala Glu Asp Thr Ala Tyr Tyr Tyr Cys Ser Arg
20 25 30

<210> SEQ ID NO 242
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Asn Arg
20 25 30

<210> SEQ ID NO 243
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 243

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Pro Arg
20 25 30

<210> SEQ ID NO 244
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 244

```
Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Tyr Arg
            20                  25                  30
```

<210> SEQ ID NO 245
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 245

```
Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Asp Arg
            20                  25                  30
```

<210> SEQ ID NO 246
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 246

```
Arg Phe Thr Ile Ser Ala Asp Thr Ser Lys Asn Thr Cys Tyr Leu Gln
1               5                   10                  15

Met Asn Ser Leu Arg Ala Glu Asp Thr Ala Val Tyr Tyr Cys Ser Arg
            20                  25                  30
```

<210> SEQ ID NO 247
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 247

```
Arg Phe Thr Ile Ser Ala Asp Thr Ser Lys Asn Thr Trp Tyr Leu Gln
1               5                   10                  15

Met Asn Ser Leu Arg Ala Glu Asp Thr Ala Val Tyr Tyr Cys Ser Arg
            20                  25                  30
```

<210> SEQ ID NO 248
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 248

-continued

Arg Phe Thr Ile Ser Ala Asp Thr Ser Lys Asn Thr Gln Tyr Leu Gln
1 5 10 15

Met Asn Ser Leu Arg Ala Glu Asp Thr Ala Val Tyr Tyr Cys Ser Arg
20 25 30

<210> SEQ ID NO 249
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 249

Arg Phe Thr Ile Ser Ala Asp Thr Ser Lys Asn Thr Ala Tyr Leu Gln
1 5 10 15

Met Asn Val Leu Arg Ala Glu Asp Thr Ala Val Tyr Tyr Cys Ser Arg
20 25 30

<210> SEQ ID NO 250
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

Arg Phe Thr Ile Ser Ala Asp Thr Ser Lys Asn Thr Ala Tyr Leu Gln
1 5 10 15

Met Asn Leu Leu Arg Ala Glu Asp Thr Ala Val Tyr Tyr Cys Ser Arg
20 25 30

<210> SEQ ID NO 251
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 251

Arg Phe Thr Ile Ser Ala Asp Thr Ser Lys Asn Thr Ala Tyr Leu Gln
1 5 10 15

Met Asn Ser Val Arg Ala Glu Asp Thr Ala Val Tyr Tyr Cys Ser Arg
20 25 30

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 252

Arg Phe Thr Ile Ser Ala Asp Thr Ser Lys Asn Thr Ala Tyr Leu Gln
1 5 10 15

Met Asn Ser Ala Arg Ala Glu Asp Thr Ala Val Tyr Tyr Cys Ser Arg
20 25 30

<210> SEQ ID NO 253
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 253

Arg Phe Thr Ile Ser Ala Asp Thr Ser Lys Asn Thr Ala Tyr Leu Gln
1 5 10 15

Met Asn Ser Glu Arg Ala Glu Asp Thr Ala Val Tyr Tyr Cys Ser Arg
20 25 30

<210> SEQ ID NO 254
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 254

Arg Phe Thr Ile Ser Ala Asp Thr Ser Lys Asn Thr Ala Tyr Leu Gln
1 5 10 15

Met Asn Ser Gly Arg Ala Glu Asp Thr Ala Val Tyr Tyr Cys Ser Arg
20 25 30

<210> SEQ ID NO 255
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 255

Arg Phe Thr Ile Ser Ala Asp Thr Ser Lys Asn Thr Ala Tyr Leu Gln
1 5 10 15

Met Asn Ser Leu Val Ala Glu Asp Thr Ala Val Tyr Tyr Cys Ser Arg
20 25 30

<210> SEQ ID NO 256
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 256

Arg Phe Thr Ile Ser Ala Asp Thr Ser Lys Asn Thr Ala Tyr Leu Gln
1 5 10 15

Met Asn Ser Leu Leu Ala Glu Asp Thr Ala Val Tyr Tyr Cys Ser Arg
20 25 30

<210> SEQ ID NO 257
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 257

Arg Phe Thr Ile Ser Ala Asp Thr Ser Lys Asn Thr Ala Tyr Leu Gln
1 5 10 15

Met Asn Ser Leu Gly Ala Glu Asp Thr Ala Val Tyr Tyr Cys Ser Arg
20 25 30

<210> SEQ ID NO 258
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 258

Arg Phe Thr Ile Ser Ala Asp Thr Ser Lys Asn Thr Ala Tyr Leu Gln
1 5 10 15

Met Asn Ser Leu Lys Ala Glu Asp Thr Ala Val Tyr Tyr Cys Ser Arg
20 25 30

<210> SEQ ID NO 259
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 259

Arg Phe Thr Ile Ser Ala Asp Thr Ser Lys Asn Thr Ala Tyr Leu Gln
1 5 10 15

Met Asn Ser Leu Arg Met Glu Asp Thr Ala Val Tyr Tyr Cys Ser Arg
20 25 30

<210> SEQ ID NO 260
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 260

Arg Phe Thr Ile Ser Ala Asp Thr Ser Lys Asn Thr Ala Tyr Leu Gln
1 5 10 15

Met Asn Ser Leu Arg Trp Glu Asp Thr Ala Val Tyr Tyr Cys Ser Arg
20 25 30

<210> SEQ ID NO 261
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 261

Arg Phe Thr Ile Ser Ala Asp Thr Ser Lys Asn Thr Ala Tyr Leu Gln
1 5 10 15

Met Asn Ser Leu Arg Lys Glu Asp Thr Ala Val Tyr Tyr Cys Ser Arg
20 25 30

<210> SEQ ID NO 262
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 262

```
Arg Phe Thr Ile Ser Ala Asp Thr Ser Lys Asn Thr Ala Tyr Leu Gln
1               5                   10                  15

Met Asn Ser Leu Arg Gly Glu Asp Thr Ala Val Tyr Tyr Cys Ser Arg
            20                  25                  30


<210> SEQ ID NO 263
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Arg Phe Thr Ile Ser Ala Asp Thr Ser Lys Asn Thr Ala Tyr Leu Gln
1               5                   10                  15

Met Asn Ser Leu Arg Gln Glu Asp Thr Ala Val Tyr Tyr Cys Ser Arg
            20                  25                  30


<210> SEQ ID NO 264
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Arg Phe Thr Ile Ser Ala Asp Thr Ser Lys Asn Thr Ala Tyr Leu Gln
1               5                   10                  15

Met Asn Ser Leu Arg Arg Glu Asp Thr Ala Val Tyr Tyr Cys Ser Arg
            20                  25                  30


<210> SEQ ID NO 265
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Arg Phe Thr Ile Ser Ala Asp Thr Ser Lys Asn Thr Ala Tyr Leu Gln
1               5                   10                  15

Met Asn Ser Leu Arg Ala Leu Asp Thr Ala Val Tyr Tyr Cys Ser Arg
            20                  25                  30


<210> SEQ ID NO 266
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Arg Phe Thr Ile Ser Ala Asp Thr Ser Lys Asn Thr Ala Tyr Leu Gln
1               5                   10                  15

Met Asn Ser Leu Arg Ala Gly Asp Thr Ala Val Tyr Tyr Cys Ser Arg
            20                  25                  30


<210> SEQ ID NO 267
<211> LENGTH: 32
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 267

```
Arg Phe Thr Ile Ser Ala Asp Thr Ser Lys Asn Thr Ala Tyr Leu Gln
1               5                   10                  15

Met Asn Ser Leu Arg Ala Ala Asp Thr Ala Val Tyr Tyr Cys Ser Arg
            20                  25                  30
```

<210> SEQ ID NO 268
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

```
Arg Phe Thr Ile Ser Ala Asp Thr Ser Lys Asn Thr Ala Tyr Leu Gln
1               5                   10                  15

Met Asn Ser Leu Arg Ala Ser Asp Thr Ala Val Tyr Tyr Cys Ser Arg
            20                  25                  30
```

<210> SEQ ID NO 269
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

```
Arg Phe Thr Ile Ser Ala Asp Thr Ser Lys Asn Thr Ala Tyr Leu Gln
1               5                   10                  15

Met Asn Ser Leu Arg Ala Asn Asp Thr Ala Val Tyr Tyr Cys Ser Arg
            20                  25                  30
```

<210> SEQ ID NO 270
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

```
Arg Phe Thr Ile Ser Ala Asp Thr Ser Lys Asn Thr Ala Tyr Leu Gln
1               5                   10                  15

Met Asn Ser Leu Arg Ala His Asp Thr Ala Val Tyr Tyr Cys Ser Arg
            20                  25                  30
```

<210> SEQ ID NO 271
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

```
Arg Phe Thr Ile Ser Ala Asp Thr Ser Lys Asn Thr Ala Tyr Leu Gln
1               5                   10                  15

Met Asn Ser Leu Arg Ala Glu Ser Thr Ala Val Tyr Tyr Cys Ser Arg
```

20 25 30

<210> SEQ ID NO 272
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 272

Arg Phe Thr Ile Ser Ala Asp Thr Ser Lys Asn Thr Ala Tyr Leu Gln
1 5 10 15

Met Asn Ser Leu Arg Ala Glu Gly Thr Ala Val Tyr Tyr Cys Ser Arg
20 25 30

<210> SEQ ID NO 273
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 273

Arg Phe Thr Ile Ser Ala Asp Thr Ser Lys Asn Thr Ala Tyr Leu Gln
1 5 10 15

Met Asn Ser Leu Arg Ala Glu Asp Trp Ala Val Tyr Tyr Cys Ser Arg
20 25 30

<210> SEQ ID NO 274
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 274

Arg Phe Thr Ile Ser Ala Asp Thr Ser Lys Asn Thr Ala Tyr Leu Gln
1 5 10 15

Met Asn Ser Leu Arg Ala Glu Asp Glu Ala Val Tyr Tyr Cys Ser Arg
20 25 30

<210> SEQ ID NO 275
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 275

Arg Phe Thr Ile Ser Ala Asp Thr Ser Lys Asn Thr Ala Tyr Leu Gln
1 5 10 15

Met Asn Ser Leu Arg Ala Glu Asp Leu Ala Val Tyr Tyr Cys Ser Arg
20 25 30

<210> SEQ ID NO 276
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 276

Arg Phe Thr Ile Ser Ala Asp Thr Ser Lys Asn Thr Ala Tyr Leu Gln
1               5                   10                  15

Met Asn Ser Leu Arg Ala Glu Asp Phe Ala Val Tyr Tyr Cys Ser Arg
            20                  25                  30

<210> SEQ ID NO 277
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Arg Phe Thr Ile Ser Ala Asp Thr Ser Lys Asn Thr Ala Tyr Leu Gln
1               5                   10                  15

Met Asn Ser Leu Arg Ala Glu Asp His Ala Val Tyr Tyr Cys Ser Arg
            20                  25                  30

<210> SEQ ID NO 278
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Arg Phe Thr Ile Ser Ala Asp Thr Ser Lys Asn Thr Ala Tyr Leu Gln
1               5                   10                  15

Met Asn Ser Leu Arg Ala Glu Asp Asp Ala Val Tyr Tyr Cys Ser Arg
            20                  25                  30

<210> SEQ ID NO 279
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Arg Phe Thr Ile Ser Ala Asp Thr Ser Lys Asn Thr Ala Tyr Leu Gln
1               5                   10                  15

Met Asn Ser Leu Arg Ala Glu Asp Thr Gly Val Tyr Tyr Cys Ser Arg
            20                  25                  30

<210> SEQ ID NO 280
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Arg Phe Thr Ile Ser Ala Asp Thr Ser Lys Asn Thr Ala Tyr Leu Gln
1               5                   10                  15

Met Asn Ser Leu Arg Ala Glu Asp Thr Arg Val Tyr Tyr Cys Ser Arg
            20                  25                  30

<210> SEQ ID NO 281
<211> LENGTH: 32

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 281

Arg Phe Thr Ile Ser Ala Asp Thr Ser Lys Asn Thr Ala Tyr Leu Gln
1 5 10 15

Met Asn Ser Leu Arg Ala Glu Asp Thr Lys Val Tyr Tyr Cys Ser Arg
20 25 30

<210> SEQ ID NO 282
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 282

Arg Phe Thr Ile Ser Ala Asp Thr Ser Lys Asn Thr Ala Tyr Leu Gln
1 5 10 15

Met Asn Ser Leu Arg Ala Glu Asp Thr Val Val Tyr Tyr Cys Ser Arg
20 25 30

<210> SEQ ID NO 283
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 283

Arg Phe Thr Ile Ser Ala Asp Thr Ser Lys Asn Thr Ala Tyr Leu Gln
1 5 10 15

Met Asn Ser Leu Arg Ala Glu Asp Thr Ala Lys Tyr Tyr Cys Ser Arg
20 25 30

<210> SEQ ID NO 284
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 284

Arg Phe Thr Ile Ser Ala Asp Thr Ser Lys Asn Thr Ala Tyr Leu Gln
1 5 10 15

Met Asn Ser Leu Arg Ala Glu Asp Thr Ala Ser Tyr Tyr Cys Ser Arg
20 25 30

<210> SEQ ID NO 285
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 285

Arg Phe Thr Ile Ser Ala Asp Thr Ser Lys Asn Thr Ala Tyr Leu Gln
1 5 10 15

```
Met Asn Ser Leu Arg Ala Glu Asp Thr Ala Trp Tyr Tyr Cys Ser Arg
            20                  25                  30


<210> SEQ ID NO 286
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Gly Tyr Tyr Cys Ser Arg
            20                  25                  30


<210> SEQ ID NO 287
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Val Tyr Cys Ser Arg
            20                  25                  30


<210> SEQ ID NO 288
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Leu Tyr Cys Ser Arg
            20                  25                  30


<210> SEQ ID NO 289
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Ile Tyr Cys Ser Arg
            20                  25                  30


<210> SEQ ID NO 290
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 290

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Leu Cys Ser Arg
20 25 30

<210> SEQ ID NO 291
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 291

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Trp Cys Ser Arg
20 25 30

<210> SEQ ID NO 292
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 292

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Gly Ser Arg
20 25 30

<210> SEQ ID NO 293
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 293

Asp Ile Gln Met Thr Gln Ser Pro Ser Ser Leu Ser Ala Ser Val Gly
1 5 10 15

Asp Arg Val Thr Ile Gly Cys
20

<210> SEQ ID NO 294
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 294

Asp Ile Gln Met Thr Gln Ser Pro Ser Ser Leu Ser Ala Ser Val Gly
1 5 10 15

Asp Arg Val Thr Ile Ser Cys
20

<210> SEQ ID NO 295

<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 295

Asp Ile Gln Met Thr Gln Ser Pro Ser Ser Leu Ser Ala Ser Val Gly
1 5 10 15

Asp Arg Val Thr Ile Thr Ala
20

<210> SEQ ID NO 296
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Asp Ile Gln Met Thr Gln Ser Pro Ser Ser Leu Ser Ala Ser Val Gly
1 5 10 15

Asp Arg Val Thr Ile Thr Asn
20

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

His Tyr Gln Gln Lys Pro Gly Lys Ala Pro Lys Leu Leu Ile Tyr
1 5 10 15

<210> SEQ ID NO 298
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Phe Tyr Gln Gln Lys Pro Gly Lys Ala Pro Lys Leu Leu Ile Tyr
1 5 10 15

<210> SEQ ID NO 299
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 299

Gly Val Pro Ser Arg Phe Ser Gly Ser Lys Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 300

<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 300

Arg Phe Thr Ile Ser Ala Asp Thr Ser Lys Asn Thr Val Tyr Leu Gln
1 5 10 15

Met Asn Ser Leu Arg Ala Glu Asp Thr Ala Val Tyr Tyr Cys Ser Arg
20 25 30

<210> SEQ ID NO 301
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 301

Arg Phe Thr Ile Ser Ala Asp Thr Ser Lys Asn Thr Ala Tyr Leu Gln
1 5 10 15

Met Asn Ser Leu Arg Ala Glu Asp Thr Cys Val Tyr Tyr Cys Ser Arg
20 25 30

<210> SEQ ID NO 302
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 302

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Phe Cys Ser Arg
20 25 30

<210> SEQ ID NO 303
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 303

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Val Arg
20 25 30

<210> SEQ ID NO 304
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 304

Arg Phe Thr Ile Ser Ala Asp Thr Ser Lys Asn Thr Ala Tyr Leu Gln
1 5 10 15

```
Met Asn Ser Leu Arg Ala Glu Asp Thr Ala Val Tyr Tyr Cys Ala Arg
            20                  25                  30


<210> SEQ ID NO 305
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Leu Arg
            20                  25                  30


<210> SEQ ID NO 306
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Gln Arg
            20                  25                  30


<210> SEQ ID NO 307
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Thr Arg
            20                  25                  30


<210> SEQ ID NO 308
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Asn Arg
            20                  25                  30


<210> SEQ ID NO 309
<211> LENGTH: 32
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 309

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Asp Arg
20 25 30

<210> SEQ ID NO 310
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 310

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ala Arg
20 25 30

<210> SEQ ID NO 311
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 311

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Val Arg
20 25 30

<210> SEQ ID NO 312
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 312

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Leu Arg
20 25 30

<210> SEQ ID NO 313
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 313

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Asn Arg
20 25 30

<210> SEQ ID NO 314
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 314

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Asp Arg
20 25 30

<210> SEQ ID NO 315
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 315

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ala Arg
20 25 30

<210> SEQ ID NO 316
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 316

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Val Arg
20 25 30

<210> SEQ ID NO 317
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 317

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Leu Arg
20 25 30

<210> SEQ ID NO 318
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 318

Arg Ala Ser Ser Asp Val Asn Thr Ala Val Gly 1 5 10

<210> SEQ ID NO 319
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 319

Arg Ala Ser Lys Asp Val Asn Thr Ala Val Gly
1 5 10

<210> SEQ ID NO 320
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 320

Arg Ala Ser Val Asp Val Asn Thr Ala Val Gly
1 5 10

<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 321

Arg Ala Ser Leu Asp Val Asn Thr Ala Val Gly
1 5 10

<210> SEQ ID NO 322
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 322

Arg Ala Ser Phe Asp Val Asn Thr Ala Val Gly
1 5 10

<210> SEQ ID NO 323
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 323

Arg Ala Ser Ile Asp Val Asn Thr Ala Val Gly
1 5 10

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Arg Ala Ser Tyr Asp Val Asn Thr Ala Val Gly
1 5 10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Arg Ala Ser Arg Asp Val Asn Thr Ala Val Gly
1 5 10

<210> SEQ ID NO 326
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 326

Arg Ala Ser Ser Asp Val Asn Thr Ala Val Asp
1 5 10

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 327

Arg Ala Ser Lys Asp Val Asn Thr Ala Val Asp
1 5 10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 328

Arg Ala Ser Val Asp Val Asn Thr Ala Val Asp
1 5 10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 329

Arg Ala Ser Leu Asp Val Asn Thr Ala Val Asp
1 5 10

<210> SEQ ID NO 330

-continued

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Arg Ala Ser Phe Asp Val Asn Thr Ala Val Asp
1               5                   10

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Arg Ala Ser Ile Asp Val Asn Thr Ala Val Asp
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Arg Ala Ser Tyr Asp Val Asn Thr Ala Val Asp
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Arg Ala Ser Arg Asp Val Asn Thr Ala Val Asp
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Arg Ala Ser Ser Asp Val Asn Thr Ala Val Val
1               5                   10

<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Arg Ala Ser Lys Asp Val Asn Thr Ala Val Val
1 5 10

<210> SEQ ID NO 336
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 336

Arg Ala Ser Val Asp Val Asn Thr Ala Val Val
1 5 10

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 337

Arg Ala Ser Leu Asp Val Asn Thr Ala Val Val
1 5 10

<210> SEQ ID NO 338
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 338

Arg Ala Ser Phe Asp Val Asn Thr Ala Val Val
1 5 10

<210> SEQ ID NO 339
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

Arg Ala Ser Ile Asp Val Asn Thr Ala Val Val
1 5 10

<210> SEQ ID NO 340
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 340

Arg Ala Ser Tyr Asp Val Asn Thr Ala Val Val
1 5 10

<210> SEQ ID NO 341
<211> LENGTH: 11
<212> TYPE: PRT
<213> ORGANISM: Artificial Sequence
<220> FEATURE:

<223> OTHER INFORMATION: Description of Artificial Sequence: Synthetic peptide

<400> SEQUENCE: 341

Arg Ala Ser Arg Asp Val Asn Thr Ala Val Val
1 5 10

<210> SEQ ID NO 342
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Arg Ala Ser Gln Gly Val Asn Thr Ala Val Gly
1 5 10

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Arg Ala Ser Gln Ala Val Asn Thr Ala Val Gly
1 5 10

<210> SEQ ID NO 344
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Arg Ala Ser Gln Asn Val Asn Thr Ala Val Gly
1 5 10

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Arg Ala Ser Gln Leu Val Asn Thr Ala Val Gly
1 5 10

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Arg Ala Ser Gln Gly Val Asn Thr Ala Val Asp
1 5 10

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 347

Arg Ala Ser Gln Ala Val Asn Thr Ala Val Asp
1 5 10

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

Arg Ala Ser Gln Asn Val Asn Thr Ala Val Asp
1 5 10

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Arg Ala Ser Gln Leu Val Asn Thr Ala Val Asp
1 5 10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Arg Ala Ser Gln Gly Val Asn Thr Ala Val Val
1 5 10

<210> SEQ ID NO 351
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Arg Ala Ser Gln Ala Val Asn Thr Ala Val Val
1 5 10

<210> SEQ ID NO 352
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Arg Ala Ser Gln Asn Val Asn Thr Ala Val Val
1 5 10

<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Arg Ala Ser Gln Leu Val Asn Thr Ala Val Val
1 5 10

<210> SEQ ID NO 354
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

Arg Ile Tyr Pro Thr Asn Gly Tyr Thr Arg Tyr Asp Pro Lys Phe Gln
1 5 10 15

<210> SEQ ID NO 355
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 355

Arg Ile Tyr Pro Thr Asn Gly Tyr Thr Arg Tyr Asp Pro Lys Phe Gln
1 5 10 15

Asp

<210> SEQ ID NO 356
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 356

Trp Gly Gly Lys Gly Phe Tyr Ala Met Asp Tyr
1 5 10

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 357

Trp Gly Gly Asp Gly Phe Tyr Ala Met Asp Val
1 5 10

<210> SEQ ID NO 358
<211> LENGTH: 11

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 358

Trp Gly Gly Asp Gly Pro Tyr Ala Met Asp Lys
1 5 10

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 359

Trp Gly Gly Asp Gly Pro Tyr Ala Met Asp Leu
1 5 10

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 360

Arg Ala Ser Gln Asp Val Asp Thr Ala Val Ala
1 5 10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 361

Arg Ala Ser Lys Asp Val Asn Thr Ala Val Ala
1 5 10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 362

Arg Ala Ser Gln Lys Val Asn Thr Ala Val Ala
1 5 10

<210> SEQ ID NO 363
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 363

Arg Ala Ser Gln Asp Val Ser Thr Ala Val Ala 1 5 10

<210> SEQ ID NO 364
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Lys Ala Ser Gln Asp Val Asn Thr Ala Val Ala
1 5 10

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 365

Ser Ala Lys Phe Leu Tyr Ser
1 5

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 366

Ser Ala Ser Phe Leu Tyr Lys
1 5

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 367

Ser Ala Ser Phe Leu Glu Ser
1 5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 368

Ser Ala Ser Phe Arg Tyr Thr
1 5

<210> SEQ ID NO 369
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 369

Ser Ala Ser Trp Leu Trp Ser
1 5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 370

Gln Gln Ala Tyr Thr Thr Pro Pro Thr
1 5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 371

Gln Gln His Ala Thr Thr Pro Pro Thr
1 5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 372

Gln Gln Ser Tyr Thr Thr Pro Pro Thr
1 5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 373

Gln Gln Tyr Tyr Thr Thr Pro Pro Leu
1 5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 374

Gln Gln Phe Trp Thr Thr Pro Pro Thr
1 5

<210> SEQ ID NO 375

<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gly Phe Tyr Ile Ser Ser Ser Tyr Ile His
1               5                   10

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gly Phe Ser Ile Ser Ser Ser Tyr Ile His
1               5                   10

<210> SEQ ID NO 377
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gly Phe Ser Ile Ser Tyr Ser Tyr Ile His
1               5                   10

<210> SEQ ID NO 378
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gly Phe Ser Ile Tyr Ser Ser Tyr Ile His
1               5                   10

<210> SEQ ID NO 379
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gly Phe Ser Ile Tyr Tyr Ser Tyr Ile His
1               5                   10

<210> SEQ ID NO 380
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gly Phe Ser Ile Tyr Tyr Ser Tyr Ile His
1 5 10

<210> SEQ ID NO 381
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 381

Gly Phe Tyr Ile Tyr Ser Ser Tyr Ile His
1 5 10

<210> SEQ ID NO 382
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 382

Ser Ile Tyr Pro Tyr Ser Gly Tyr Thr Arg Tyr Ala Asp Ser Val Lys
1 5 10 15

Gly

<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 383

Ser Ile Tyr Pro Ser Ser Gly Tyr Thr Arg Tyr Ala Asp Ser Val Lys
1 5 10 15

Gly

<210> SEQ ID NO 384
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 384

Tyr Tyr Ser Tyr Ala Phe Asp Tyr
1 5

<210> SEQ ID NO 385
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 385

Tyr Tyr Ser Ser Gly Phe Asp Tyr
1 5

<210> SEQ ID NO 386

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 386

Tyr Tyr Ser Tyr Ala Leu Asp Tyr
1 5

<210> SEQ ID NO 387
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 387

Trp Trp Ser Ser Ala Phe Asp Tyr
1 5

<210> SEQ ID NO 388
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 388

Trp Trp Ser Ser Ala Met Asp Tyr
1 5

<210> SEQ ID NO 389
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 389

Trp Trp Ser Trp Gly Phe Asp Tyr
1 5

<210> SEQ ID NO 390
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 390

Trp Trp Ser Ser Ala Phe Asp Tyr
1 5

<210> SEQ ID NO 391
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 391

Trp Trp Ser Ser Gly Phe Asp Tyr
1 5

<210> SEQ ID NO 392
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 392

Trp Trp Ser Trp Ala Phe Asp Tyr
1 5

<210> SEQ ID NO 393
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 393

Trp Trp Ser Ser Ala Phe Asp Tyr
1 5

<210> SEQ ID NO 394
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 394

Trp Trp Ser Ser Ala Leu Asp Tyr
1 5

<210> SEQ ID NO 395
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 395

Gly Phe Ser Ile Tyr Ser Ser Tyr Ile His
1 5 10

<210> SEQ ID NO 396
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 396

Gly Phe Ser Ile Ser Ser Ser Tyr Ile His
1 5 10

<210> SEQ ID NO 397
<211> LENGTH: 10
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 397

Gly Phe Tyr Ile Ser Tyr Ser Tyr Ile His
1 5 10

<210> SEQ ID NO 398
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 398

Gly Phe Ser Ile Ser Tyr Ser Tyr Ile His
1 5 10

<210> SEQ ID NO 399
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 399

Gly Phe Ser Ile Ser Tyr Ser Ser Ile His
1 5 10

<210> SEQ ID NO 400
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 400

Gly Phe Ser Ile Ser Ser Ser Ser Ile His
1 5 10

<210> SEQ ID NO 401
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 401

Gly Phe Ser Ile Trp Trp Ser Trp Ile His
1 5 10

<210> SEQ ID NO 402
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 402

Gly Phe Ser Ile Trp Ser Ser Trp Ile His
1 5 10

<210> SEQ ID NO 403
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gly Phe Ser Ile Ser Trp Ser Trp Ile His
1               5                   10

<210> SEQ ID NO 404
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gly Phe Trp Ile Trp Ser Ser Ser Ile His
1               5                   10

<210> SEQ ID NO 405
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gly Phe Ser Ile Ser Ser Ser Trp Ile His
1               5                   10

<210> SEQ ID NO 406
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Ser Ile Tyr Pro Tyr Ser Gly Tyr Thr Arg Tyr Ala Asp Ser Val Lys
1               5                   10                  15

Gly

<210> SEQ ID NO 407
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Ser Ile Tyr Pro Tyr Tyr Gly Tyr Thr Arg Tyr Ala Asp Ser Val Lys
1               5                   10                  15

Gly

<210> SEQ ID NO 408
<211> LENGTH: 17
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 408

Tyr Ile Ser Pro Ser Ser Gly Tyr Thr Arg Tyr Ala Asp Ser Val Lys
1 5 10 15

Gly

<210> SEQ ID NO 409
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 409

Ser Ile Ser Pro Ser Ser Gly Trp Thr Ser Tyr Ala Asp Ser Val Lys
1 5 10 15

Gly

<210> SEQ ID NO 410
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 410

Ser Ile Tyr Pro Ser Ser Gly Tyr Thr Ser Tyr Ala Asp Ser Val Lys
1 5 10 15

Gly

<210> SEQ ID NO 411
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 411

Ser Ile Ser Pro Ser Ser Gly Trp Thr Ser Tyr Ala Asp Ser Val Lys
1 5 10 15

Gly

<210> SEQ ID NO 412
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 412

Ser Ile Trp Pro Ser Ser Gly Trp Thr Ser Tyr Ala Asp Ser Val Lys
1 5 10 15

Gly

<210> SEQ ID NO 413
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 413

Ser Ile Ser Pro Ser Ser Gly Trp Thr Ser Tyr Ala Asp Ser Val Lys
1 5 10 15

Gly

<210> SEQ ID NO 414
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 414

Trp Ile Ser Pro Ser Ser Gly Trp Thr Ser Tyr Ala Asp Ser Val Lys
1 5 10 15

Gly

<210> SEQ ID NO 415
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 415

Trp Ile Ser Pro Ser Ser Gly Ser Thr Trp Tyr Ala Asp Ser Val Lys
1 5 10 15

Gly

<210> SEQ ID NO 416
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 416

Trp Ile Ser Pro Ser Ser Gly Ser Thr Trp Tyr Ala Asp Ser Val Lys
1 5 10 15

Gly

<210> SEQ ID NO 417
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 417

Trp Ile Trp Pro Ser Ser Gly Trp Thr Ser Tyr Ala Asp Ser Val Lys
1 5 10 15

Gly

<210> SEQ ID NO 418
<211> LENGTH: 17
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 418

Trp Ile Ser Pro Ser Trp Gly Ser Thr Trp Tyr Ala Asp Ser Val Lys
1               5                   10                  15

Gly

<210> SEQ ID NO 419
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Trp Ile Ser Pro Ser Ser Gly Ser Thr Trp Tyr Ala Asp Ser Val Lys
1               5                   10                  15

Gly

<210> SEQ ID NO 420
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Trp Ser Ser Ser Gly Phe Asp Tyr
1               5

<210> SEQ ID NO 421
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Trp Trp Ser Ser Ala Met Asp Tyr
1               5

<210> SEQ ID NO 422
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Trp Trp Ser Ser Ala Leu Asp Tyr
1               5

<210> SEQ ID NO 423
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Phe Ser Phe Ser Ser Ser Ser Phe Ala Met Asp Tyr
1 5 10

<210> SEQ ID NO 424
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 424

Phe Ser Phe Ser Ser Ser Ser Phe Ala Ile Asp Tyr
1 5 10

<210> SEQ ID NO 425
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 425

Phe Phe Phe Phe Ser Ser Ser Phe Phe Gly Phe Asp Tyr
1 5 10

<210> SEQ ID NO 426
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 426

Tyr Tyr Ser Ser Tyr Tyr Ser Tyr Tyr Ser Phe Gly Leu Asp Tyr
1 5 10 15

<210> SEQ ID NO 427
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 427

Trp Trp Ser Ser Ala Ile Asp Tyr
1 5

<210> SEQ ID NO 428
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 428

Trp Trp Ser Ser Ala Leu Asp Tyr
1 5

<210> SEQ ID NO 429
<211> LENGTH: 8
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 429

Trp Trp Ser Ser Gly Met Asp Tyr
1               5

<210> SEQ ID NO 430
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 430

Trp Trp Ser Ser Ala Phe Asp Tyr
1               5

<210> SEQ ID NO 431
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 431

Trp Ser Ser Ser Ala Phe Asp Tyr
1               5

<210> SEQ ID NO 432
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 432

Trp Trp Ser Ser Ala Met Asp Tyr
1               5

<210> SEQ ID NO 433
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 433

Trp Ser Ser Trp Gly Leu Asp Tyr
1               5

<210> SEQ ID NO 434
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 434

Ser Ser Trp Ser Ser Trp Ser Ser Ala Leu Asp Tyr
1               5                   10

<210> SEQ ID NO 435
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 435

Ser Ser Ser Ser Ser Trp Trp Ser Ala Ile Asp Tyr
1 5 10

<210> SEQ ID NO 436
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 436

Ser Ser Trp Ser Ser Trp Ser Trp Ala Leu Asp Tyr
1 5 10

<210> SEQ ID NO 437
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 437

Ser Ser Trp Ser Ser Trp Ser Ser Ala Met Asp Tyr
1 5 10

<210> SEQ ID NO 438
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 438

Gly Phe Ser Ile Trp Ser Ser Ser Ile His
1 5 10

<210> SEQ ID NO 439
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 439

Gly Phe Ser Ile Tyr Ser Tyr Tyr Ile His
1 5 10

<210> SEQ ID NO 440
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 440

Gly Phe Tyr Ile Ser Tyr Ser Tyr Ile His
1 5 10

<210> SEQ ID NO 441
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 441

Gly Phe Tyr Ile Ser Ser Ser Tyr Ile His
1 5 10

<210> SEQ ID NO 442
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 442

Gly Phe Ser Ile Ser Ser Ser Tyr Ile His
1 5 10

<210> SEQ ID NO 443
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 443

Gly Phe Ser Ile Tyr Ser Ser Tyr Ile His
1 5 10

<210> SEQ ID NO 444
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 444

Gly Phe Tyr Ile Ser Ser Ser Tyr Ile His
1 5 10

<210> SEQ ID NO 445
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 445

Gly Phe Tyr Ile Ser Tyr Ser Ser Ile His
1 5 10

<210> SEQ ID NO 446
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 446

Gly Phe Tyr Ile Ser Ser Ser Ser Ile His
1 5 10

<210> SEQ ID NO 447
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 447

Gly Phe Ser Ile Tyr Tyr Ser Ser Ile His
1 5 10

<210> SEQ ID NO 448
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 448

Gly Phe Tyr Ile Ser Ser Ser Ser Ile His
1 5 10

<210> SEQ ID NO 449
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 449

Gly Phe Ser Ile Ser Tyr Ser Ser Ile His
1 5 10

<210> SEQ ID NO 450
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 450

Gly Phe Ser Ile Ser Tyr Ser Tyr Ile His
1 5 10

<210> SEQ ID NO 451
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 451

Gly Phe Ser Ile Lys Ser Ser Tyr Ile His 1 5 10

<210> SEQ ID NO 452
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 452

Gly Phe Ser Ile Lys Tyr Ser Tyr Ile His
1 5 10

<210> SEQ ID NO 453
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 453

Gly Phe Ser Ile Lys Ser Ser Tyr Ile His
1 5 10

<210> SEQ ID NO 454
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 454

Gly Phe Tyr Ile Lys Ser Ser Tyr Ile His
1 5 10

<210> SEQ ID NO 455
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 455

Gly Phe Ser Ile Lys Ser Ser Tyr Ile His
1 5 10

<210> SEQ ID NO 456
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 456

Ser Ile Ser Pro Ser Ser Gly Ser Thr Trp Tyr Ala Asp Ser Val Lys
1 5 10 15

Gly

<210> SEQ ID NO 457
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 457

Ser Ile Tyr Pro Ser Ser Gly Tyr Thr Ser Tyr Ala Asp Ser Val Lys
1               5                   10                  15

Gly


<210> SEQ ID NO 458
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Ser Ile Tyr Pro Tyr Ser Gly Tyr Thr Ser Tyr Ala Asp Ser Val Lys
1               5                   10                  15

Gly


<210> SEQ ID NO 459
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Ser Ile Ser Pro Tyr Ser Gly Tyr Thr Tyr Tyr Ala Asp Ser Val Lys
1               5                   10                  15

Gly


<210> SEQ ID NO 460
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Tyr Ile Ser Pro Ser Ser Gly Tyr Thr Tyr Tyr Ala Asp Ser Val Lys
1               5                   10                  15

Gly


<210> SEQ ID NO 461
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Ser Ile Tyr Pro Tyr Ser Gly Ser Thr Tyr Tyr Ala Asp Ser Val Lys
1               5                   10                  15

Gly


<210> SEQ ID NO 462
<211> LENGTH: 17
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 462

Ser Ile Tyr Pro Ser Ser Gly Ser Thr Tyr Tyr Ala Asp Ser Val Lys
1 5 10 15

Gly

<210> SEQ ID NO 463
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 463

Tyr Ile Tyr Pro Ser Ser Gly Tyr Thr Arg Tyr Ala Asp Ser Val Lys
1 5 10 15

Gly

<210> SEQ ID NO 464
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 464

Ser Ile Tyr Pro Tyr Tyr Gly Tyr Thr Arg Tyr Ala Asp Ser Val Lys
1 5 10 15

Gly

<210> SEQ ID NO 465
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 465

Ser Ile Tyr Pro Ser Ser Gly Tyr Thr Arg Tyr Ala Asp Ser Val Lys
1 5 10 15

Gly

<210> SEQ ID NO 466
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 466

Ser Ile Tyr Pro Tyr Ser Gly Tyr Thr Ser Tyr Ala Asp Ser Val Lys
1 5 10 15

Gly

<210> SEQ ID NO 467
<211> LENGTH: 17

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 467

Ser Ile Tyr Pro Ser Ser Gly Tyr Thr Ser Tyr Ala Asp Ser Val Lys
1 5 10 15

Gly

<210> SEQ ID NO 468
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 468

Ser Ser Trp Ser Ser Trp Ser Ser Ala Met Asp Tyr
1 5 10

<210> SEQ ID NO 469
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 469

Tyr Tyr Ser Tyr Ala Leu Asp Tyr
1 5

<210> SEQ ID NO 470
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 470

Tyr Tyr Ser Tyr Ala Phe Asp Tyr
1 5

<210> SEQ ID NO 471
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 471

Tyr Tyr Ser Ser Ala Phe Asp Tyr
1 5

<210> SEQ ID NO 472
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 472

```
Tyr Tyr Ser Tyr Ala Leu Asp Tyr
1               5


<210> SEQ ID NO 473
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Tyr Tyr Ser Tyr Ala Phe Asp Tyr
1               5


<210> SEQ ID NO 474
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Tyr Tyr Ser Tyr Ala Leu Asp Tyr
1               5


<210> SEQ ID NO 475
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Ser Ser Tyr Ser Tyr Tyr Tyr Tyr Ser Tyr Ala Leu Asp Tyr
1               5                   10


<210> SEQ ID NO 476
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Tyr Tyr Ser Ser Tyr Tyr Ser Tyr Tyr Ser Tyr Ala Leu Asp Tyr
1               5                   10                  15


<210> SEQ ID NO 477
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Tyr Tyr Ser Ser Tyr Ser Ser Ser Ser Ser Tyr Tyr Tyr Tyr Ala Phe
1               5                   10                  15

Asp Tyr


<210> SEQ ID NO 478
<211> LENGTH: 19
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 478

Tyr Tyr Ser Ser Ser Ser Ser Tyr Ser Ser Ser Tyr Tyr Tyr Tyr Ala
1 5 10 15

Phe Asp Tyr

<210> SEQ ID NO 479
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 479

Gly Tyr Tyr Tyr Ser Tyr Tyr Ser Gly Tyr Ala Leu
1 5 10

<210> SEQ ID NO 480
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 480

Gly Gly Gly Tyr Gly Tyr Gly Ile
1 5

<210> SEQ ID NO 481
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 481

Glu Tyr Tyr Gln Gly Tyr Gly Pro Tyr Arg Ser Thr Tyr Gly Leu
1 5 10 15

<210> SEQ ID NO 482
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 482

Tyr Tyr Ser Ser Gly Phe Asp Tyr
1 5

<210> SEQ ID NO 483
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 483

```
Tyr Tyr Gly Tyr Gly Met Asp Tyr
1               5


<210> SEQ ID NO 484
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Tyr Tyr Gly Tyr Gly Leu Asp Tyr
1               5


<210> SEQ ID NO 485
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Tyr Tyr Gly Tyr Gly Phe Asp Tyr
1               5


<210> SEQ ID NO 486
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Tyr Tyr Gly Ser Gly Phe Asp Tyr
1               5


<210> SEQ ID NO 487
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Tyr Tyr Gly Gly Ala Phe Asp Tyr
1               5


<210> SEQ ID NO 488
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Gly Phe Ser Ile Lys Tyr Ser Tyr Ile His
1               5                   10


<210> SEQ ID NO 489
<211> LENGTH: 10
<212> TYPE: PRT
<213> ORGANISM: Artificial Sequence
```

<220> FEATURE:
<223> OTHER INFORMATION: Description of Artificial Sequence: Synthetic peptide

<400> SEQUENCE: 489

Gly Phe Ser Ile Lys Ser Ser Tyr Ile His
1 5 10

<210> SEQ ID NO 490
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 490

Gly Phe Ser Ile Lys Tyr Ser Tyr Ile His
1 5 10

<210> SEQ ID NO 491
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 491

Gly Phe Ser Ile Lys Tyr Ser Ser Ile His
1 5 10

<210> SEQ ID NO 492
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 492

Gly Phe Ser Ile Lys Ser Tyr Ser Ile His
1 5 10

<210> SEQ ID NO 493
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 493

Gly Phe Ser Ile Lys Ser Ser Ser Ile His
1 5 10

<210> SEQ ID NO 494
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 494

Gly Phe Tyr Ile Lys Ser Ser Ser Ile His
1 5 10

<210> SEQ ID NO 495
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 495

Gly Phe Tyr Ile Lys Ser Tyr Ser Ile His
1 5 10

<210> SEQ ID NO 496
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 496

Ser Ile Tyr Pro Ser Ser Gly Tyr Thr Ser Tyr Ala Asp Ser Val Lys
1 5 10 15

Gly

<210> SEQ ID NO 497
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 497

Ser Ile Tyr Pro Tyr Ser Gly Tyr Thr Ser Tyr Ala Asp Ser Val Lys
1 5 10 15

Gly

<210> SEQ ID NO 498
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 498

Ser Ile Tyr Pro Ser Ser Gly Ser Thr Tyr Tyr Ala Asp Ser Val Lys
1 5 10 15

Gly

<210> SEQ ID NO 499
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 499

Ser Ile Tyr Pro Tyr Ser Gly Ser Thr Ser Tyr Ala Asp Ser Val Lys
1 5 10 15

Gly

<210> SEQ ID NO 500
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 500

Ser Ile Tyr Pro Tyr Tyr Gly Tyr Thr Ser Tyr Ala Asp Ser Val Lys
1 5 10 15

Gly

<210> SEQ ID NO 501
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 501

Ser Ile Tyr Pro Tyr Tyr Gly Ser Thr Tyr Tyr Ala Asp Ser Val Lys
1 5 10 15

Gly

<210> SEQ ID NO 502
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 502

Ser Ile Tyr Pro Tyr Tyr Gly Tyr Thr Ser Tyr Ala Asp Ser Val Lys
1 5 10 15

Gly

<210> SEQ ID NO 503
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 503

Ser Ile Tyr Pro Ser Tyr Gly Tyr Thr Ser Tyr Ala Asp Ser Val Lys
1 5 10 15

Gly

<210> SEQ ID NO 504
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 504

Ser Ile Tyr Pro Tyr Tyr Gly Ser Thr Tyr Tyr Ala Asp Ser Val Lys
1 5 10 15

Gly

<210> SEQ ID NO 505
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 505

Ser Ile Tyr Pro Tyr Tyr Gly Tyr Thr Ser Tyr Ala Asp Ser Val Lys
1 5 10 15

Gly

<210> SEQ ID NO 506
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 506

Ser Ile Tyr Pro Ser Tyr Gly Tyr Thr Ser Tyr Ala Asp Ser Val Lys
1 5 10 15

Gly

<210> SEQ ID NO 507
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 507

Ser Ile Tyr Pro Tyr Tyr Gly Tyr Thr Ser Tyr Ala Asp Ser Val Lys
1 5 10 15

Gly

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 508

Tyr Tyr Gly Arg Gly Ala Met Asp Tyr
1 5

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 509

Tyr Ser Tyr Ser Gly Ala Leu Asp Tyr
1 5

<210> SEQ ID NO 510
<211> LENGTH: 9

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 510

Tyr Arg Tyr Tyr Gly Ala Leu Asp Tyr
1 5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 511

Tyr Arg Tyr Gly Gly Ala Met Asp Tyr
1 5

<210> SEQ ID NO 512
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 512

Tyr Tyr Gly Gly Tyr Tyr Gly Met Asp Tyr
1 5 10

<210> SEQ ID NO 513
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 513

Tyr Ser Tyr Tyr Tyr Tyr Ala Leu Asp Tyr
1 5 10

<210> SEQ ID NO 514
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 514

Ser Ser Tyr Tyr Tyr Tyr Gly Met Asp Tyr
1 5 10

<210> SEQ ID NO 515
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 515

Ser Ser Tyr Tyr Tyr Tyr Gly Phe Asp Tyr 1 5 10

<210> SEQ ID NO 516
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 516

Ser Ser Tyr Tyr Tyr Tyr Gly Leu Asp Tyr
1 5 10

<210> SEQ ID NO 517
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 517

Ser Gly Gly Tyr Ser Arg Gly Ile Asp Tyr
1 5 10

<210> SEQ ID NO 518
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 518

Gly Tyr Ser Tyr Ser Arg Gly Ile Asp Tyr
1 5 10

<210> SEQ ID NO 519
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 519

Gly Tyr Ser Tyr Ser Arg Gly Met Asp Tyr
1 5 10

<210> SEQ ID NO 520
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 520

Gly Ser Ser Tyr Ser Tyr Gly Met Asp Tyr
1 5 10

<210> SEQ ID NO 521
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 521

Gly Ser Gly Tyr Gly Tyr Gly Met Asp Tyr
1 5 10

<210> SEQ ID NO 522
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 522

Gly Ser Gly Tyr Gly Tyr Gly Ile Asp Tyr
1 5 10

<210> SEQ ID NO 523
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 523

Gly Arg Arg Tyr Ser Arg Gly Ile Asp Tyr
1 5 10

<210> SEQ ID NO 524
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 524

Gly Gly Ser Tyr Gly Tyr Gly Met Asp Tyr
1 5 10

<210> SEQ ID NO 525
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 525

Gly Gly Ser Tyr Gly Tyr Gly Met Asp Tyr
1 5 10

<210> SEQ ID NO 526
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 526

Gly Gly Arg Tyr Gly Tyr Gly Leu Asp Tyr
1 5 10

<210> SEQ ID NO 527

-continued

<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 527

Gly Phe Tyr Ile Lys Ser Ser Ser Ile His
1 5 10

<210> SEQ ID NO 528
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 528

Gly Phe Ser Ile Lys Ser Ser Ser Ile His
1 5 10

<210> SEQ ID NO 529
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 529

Gly Phe Ser Ile Lys Tyr Ser Ser Ile His
1 5 10

<210> SEQ ID NO 530
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 530

Gly Phe Ser Ile Lys Ser Tyr Ser Ile His
1 5 10

<210> SEQ ID NO 531
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 531

Gly Phe Tyr Ile Lys Ser Ser Tyr Ile His
1 5 10

<210> SEQ ID NO 532
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 532

Gly Phe Tyr Ile Lys Ser Tyr Ser Ile His
1 5 10

<210> SEQ ID NO 533
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 533

Ser Ile Tyr Pro Tyr Tyr Gly Ser Thr Tyr Tyr Ala Asp Ser Val Lys
1 5 10 15

Gly

<210> SEQ ID NO 534
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 534

Ser Ile Tyr Pro Tyr Tyr Gly Tyr Thr Ser Tyr Ala Asp Ser Val Lys
1 5 10 15

Gly

<210> SEQ ID NO 535
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 535

Ser Ile Tyr Pro Ser Tyr Gly Ser Thr Tyr Tyr Ala Asp Ser Val Lys
1 5 10 15

Gly

<210> SEQ ID NO 536
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 536

Tyr Ile Tyr Pro Ser Ser Gly Ser Thr Tyr Tyr Ala Asp Ser Val Lys
1 5 10 15

Gly

<210> SEQ ID NO 537
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 537

Ser Ile Ser Pro Tyr Tyr Gly Ser Thr Tyr Tyr Ala Asp Ser Val Lys

-continued 1 5 10 15

Gly

<210> SEQ ID NO 538
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 538

Ser Ile Ser Pro Tyr Ser Gly Ser Thr Ser Tyr Ala Asp Ser Val Lys
1 5 10 15

Gly

<210> SEQ ID NO 539
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 539

Ser Ile Ser Pro Tyr Ser Gly Tyr Thr Ser Tyr Ala Asp Ser Val Lys
1 5 10 15

Gly

<210> SEQ ID NO 540
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 540

Tyr Ile Ser Pro Ser Ser Gly Tyr Thr Tyr Tyr Ala Asp Ser Val Lys
1 5 10 15

Gly

<210> SEQ ID NO 541
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 541

Ser Ile Tyr Pro Ser Ser Gly Tyr Thr Ser Tyr Ala Asp Ser Val Lys
1 5 10 15

Gly

<210> SEQ ID NO 542
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 542

Ser Ile Ser Pro Ser Ser Gly Tyr Thr Ser Tyr Ala Asp Ser Val Lys
1 5 10 15

Gly

<210> SEQ ID NO 543
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 543

Ser Ile Tyr Pro Ser Ser Gly Tyr Thr Tyr Tyr Ala Asp Ser Val Lys
1 5 10 15

Gly

<210> SEQ ID NO 544
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 544

Ser Ile Tyr Pro Ser Ser Gly Tyr Thr Ser Tyr Ala Asp Ser Val Lys
1 5 10 15

Gly

<210> SEQ ID NO 545
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 545

Tyr Ile Tyr Pro Ser Ser Gly Tyr Thr Ser Tyr Ala Asp Ser Val Lys
1 5 10 15

Gly

<210> SEQ ID NO 546
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 546

Tyr Ile Tyr Pro Ser Ser Gly Tyr Thr Ser Tyr Ala Asp Ser Val Lys
1 5 10 15

Gly

<210> SEQ ID NO 547
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 547

Tyr Ile Ser Pro Tyr Ser Gly Tyr Thr Ser Tyr Ala Asp Ser Val Lys
1 5 10 15

Gly

<210> SEQ ID NO 548
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 548

Ser Ile Tyr Pro Ser Ser Gly Tyr Thr Ser Tyr Ala Asp Ser Val Lys
1 5 10 15

Gly

<210> SEQ ID NO 549
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 549

Gly Gly Arg Tyr Gly Arg Gly Ile Asp Tyr
1 5 10

<210> SEQ ID NO 550
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 550

Gly Gly Gly Tyr Gly Tyr Gly Ile Asp Tyr
1 5 10

<210> SEQ ID NO 551
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 551

Tyr Tyr Tyr Ser Gly Gly Ser Tyr Gly Met Asp Tyr
1 5 10

<210> SEQ ID NO 552
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 552

Ser Tyr Ser Ser Tyr Tyr Ser Ser Gly Met Asp Tyr
1 5 10

<210> SEQ ID NO 553
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Arg Tyr Tyr Tyr Tyr Tyr Tyr Ser Ala Phe Asp Tyr
1               5                   10

<210> SEQ ID NO 554
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Tyr Tyr Tyr Tyr Ser Tyr Tyr Ser Gly Gly Ala Ile Asp Tyr
1               5                   10

<210> SEQ ID NO 555
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Ser Tyr Tyr Tyr Ser Tyr Tyr Ser Gly Tyr Gly Met Asp Tyr
1               5                   10

<210> SEQ ID NO 556
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Ser Tyr Tyr Tyr Ser Tyr Tyr Ser Gly Tyr Gly Leu Asp Tyr
1               5                   10

<210> SEQ ID NO 557
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Ser Tyr Tyr Tyr Ser Tyr Tyr Tyr Gly Tyr Gly Met Asp Tyr
1               5                   10

<210> SEQ ID NO 558
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Ser Tyr Tyr Gly Ser Tyr Tyr Tyr Gly Tyr Gly Phe Asp Tyr
1 5 10

<210> SEQ ID NO 559
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 559

Ser Asp Tyr Tyr Gly Tyr Tyr Ser Gly Tyr Gly Ile Asp Tyr
1 5 10

<210> SEQ ID NO 560
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 560

Ser Asp Tyr Tyr Ser Tyr Tyr Ser Gly Tyr Gly Leu Asp Tyr
1 5 10

<210> SEQ ID NO 561
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 561

Gly Tyr Tyr Tyr Ser Tyr Tyr Tyr Gly Tyr Gly Met Asp Tyr
1 5 10

<210> SEQ ID NO 562
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 562

Gly Tyr Tyr Tyr Ser Tyr Tyr Tyr Gly Ser Ala Met Asp Tyr
1 5 10

<210> SEQ ID NO 563
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 563

Gly Tyr Tyr Tyr Ser Tyr Tyr Ser Gly Tyr Gly Met Asp Tyr
1 5 10

<210> SEQ ID NO 564
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 564

Gly Tyr Tyr Tyr Ser Tyr Tyr Ser Gly Tyr Ala Leu Asp Tyr
1               5                   10


<210> SEQ ID NO 565
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Gly Tyr Tyr Tyr Ser Tyr Tyr Ser Gly Tyr Ala Ile Asp Tyr
1               5                   10


<210> SEQ ID NO 566
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Gly Tyr Tyr Tyr Ser Tyr Tyr Ser Gly Tyr Ala Met Asp Tyr
1               5                   10


<210> SEQ ID NO 567
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Gly Phe Asn Tyr Lys Asp Ser Ser Ser His
1               5                   10


<210> SEQ ID NO 568
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gly Phe Asn Tyr Lys Asp Ser Tyr Ser His
1               5                   10


<210> SEQ ID NO 569
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Gly Phe Asn Ser Lys Asp Ser Tyr Ser His
1               5                   10
```

-continued

<210> SEQ ID NO 570
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gly Phe Asn Tyr Lys Asp Ser Tyr Ile His
1               5                   10

<210> SEQ ID NO 571
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Gly Phe Asn Ser Lys Asp Ser Ser Ser His
1               5                   10

<210> SEQ ID NO 572
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Arg Ser Tyr Pro Thr Ser Asn Ser Tyr Ser Arg Ser Ala Asp Ser Val
1               5                   10                  15

Lys Gly

<210> SEQ ID NO 573
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Arg Tyr Tyr Ser Thr Ser Asn Ser Tyr Thr Arg Ser Ala Asp Ser Val
1               5                   10                  15

Lys Gly

<210> SEQ ID NO 574
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Arg Ser Tyr Pro Thr Ser Asn Ser Tyr Thr Arg Ser Ala Asp Ser Val
1               5                   10                  15

Lys Gly

<210> SEQ ID NO 575
<211> LENGTH: 18

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Arg Ser Tyr Ser Thr Ser Asn Ser Tyr Thr Arg Ser Ala Asp Ser Val
1               5                   10                  15

Lys Gly

<210> SEQ ID NO 576
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Arg Ser Tyr Pro Thr Ser Asn Ser Tyr Thr Arg Tyr Ala Asp Ser Val
1               5                   10                  15

Lys Gly

<210> SEQ ID NO 577
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Arg Tyr Tyr Pro Thr Ser Asn Ser Tyr Thr Arg Ser Ala Asp Ser Val
1               5                   10                  15

Lys Gly

<210> SEQ ID NO 578
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Arg Ser Tyr Pro Thr Ser Asn Tyr Tyr Thr Arg Ser Ala Asp Ser Val
1               5                   10                  15

Lys Gly

<210> SEQ ID NO 579
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Arg Tyr Tyr Pro Thr Ser Asn Ser Tyr Ser Arg Ser Ala Asp Ser Val
1               5                   10                  15

Lys Gly

<210> SEQ ID NO 580

<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 580

Arg Ser Tyr Pro Thr Ser Asn Ser Tyr Thr Arg Tyr Ala Asp Ser Val
1 5 10 15

Lys Gly

<210> SEQ ID NO 581
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 581

Arg Tyr Tyr Pro Thr Ser Asn Ser Tyr Thr Arg Tyr Ala Asp Ser Val
1 5 10 15

Lys Gly

<210> SEQ ID NO 582
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 582

Gly Tyr Tyr Tyr Ser Tyr Tyr Ser Gly Tyr Gly Ile Asp Tyr
1 5 10

<210> SEQ ID NO 583
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 583

Gly Tyr Tyr Tyr Ser Tyr Tyr Ser Gly Tyr Gly Leu Asp Tyr
1 5 10

<210> SEQ ID NO 584
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 584

Gly Tyr Tyr Tyr Ser Tyr Tyr Ser Gly Tyr Gly Met Asp Tyr
1 5 10

<210> SEQ ID NO 585
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 585

Gly Tyr Tyr Tyr Ser Tyr Tyr Gly Gly Ser Gly Leu Asp Tyr
1 5 10

<210> SEQ ID NO 586
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 586

Gly Tyr Tyr Tyr Ser Tyr Tyr Gly Gly Tyr Gly Met Asp Tyr
1 5 10

<210> SEQ ID NO 587
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 587

Gly Tyr Tyr Tyr Ser Tyr Tyr Gly Gly Tyr Gly Ile Asp Tyr
1 5 10

<210> SEQ ID NO 588
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 588

Gly Tyr Tyr Tyr Ser Tyr Tyr Gly Gly Tyr Gly Met Asp Tyr
1 5 10

<210> SEQ ID NO 589
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 589

Gly Tyr Tyr Tyr Ser Tyr Tyr Gly Gly Tyr Gly Met Asp Tyr
1 5 10

<210> SEQ ID NO 590
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 590

Gly Tyr Tyr Tyr Ser Tyr Tyr Gly Gly Tyr Gly Met Asp Tyr
1 5 10

<210> SEQ ID NO 591

<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 591

Gly Tyr Tyr Tyr Ser Tyr Tyr Gly Gly Tyr Gly Leu Asp Tyr
1 5 10

<210> SEQ ID NO 592
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 592

Gly Tyr Tyr Tyr Ser Tyr Tyr Gly Gly Tyr Gly Met Asp Tyr
1 5 10

<210> SEQ ID NO 593
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 593

Gly Tyr Tyr Tyr Ser Tyr Tyr Gly Gly Tyr Gly Met Asp Tyr
1 5 10

<210> SEQ ID NO 594
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 594

Gly Tyr Tyr Tyr Gly Tyr Tyr Ser Gly Tyr Gly Ile Asp Tyr
1 5 10

<210> SEQ ID NO 595
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 595

Gly Ser Tyr Tyr Ser Tyr Tyr Ser Gly Tyr Gly Met Asp Tyr
1 5 10

<210> SEQ ID NO 596
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 596

Gly Ser Tyr Tyr Ser Tyr Tyr Ser Gly Tyr Ala Ile Asp Tyr
1 5 10

<210> SEQ ID NO 597
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 597

Gly Ser Tyr Tyr Ser Tyr Tyr Ser Gly Tyr Ala Phe Asp Tyr
1 5 10

<210> SEQ ID NO 598
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 598

Gly Ser Tyr Tyr Ser Tyr Tyr Ser Gly Ser Gly Ile Asp Tyr
1 5 10

<210> SEQ ID NO 599
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 599

Gly Ser Tyr Tyr Gly Tyr Tyr Tyr Gly Ser Ala Ile Asp Tyr
1 5 10

<210> SEQ ID NO 600
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 600

Gly Ser Tyr Tyr Gly Tyr Tyr Tyr Gly Ser Gly Met Asp Tyr
1 5 10

<210> SEQ ID NO 601
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 601

Gly Phe Tyr Ile Lys Ser Tyr Ser Ile His
1 5 10

<210> SEQ ID NO 602
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 602

Gly Phe Tyr Ile Lys Ser Ser Tyr Ile His
1               5                   10


<210> SEQ ID NO 603
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Gly Phe Tyr Ile Lys Ser Ser Ser Ile His
1               5                   10


<210> SEQ ID NO 604
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Gly Phe Ser Ile Lys Tyr Ser Ser Ile His
1               5                   10


<210> SEQ ID NO 605
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Gly Phe Ser Ile Lys Ser Ser Ser Ile His
1               5                   10


<210> SEQ ID NO 606
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Gly Phe Ser Ile Lys Tyr Ser Ser Ile His
1               5                   10


<210> SEQ ID NO 607
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Ser Ile Tyr Pro Ser Ser Gly Ser Thr Ser Tyr Ala Asp Ser Val Lys
1               5                   10                  15

Gly
```

<210> SEQ ID NO 608
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 608

Ser Ile Ser Pro Ser Ser Gly Tyr Thr Ser Tyr Ala Asp Ser Val Lys
1 5 10 15

Gly

<210> SEQ ID NO 609
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 609

Ser Ile Tyr Pro Ser Ser Gly Tyr Thr Ser Tyr Ala Asp Ser Val Lys
1 5 10 15

Gly

<210> SEQ ID NO 610
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 610

Tyr Ile Ser Pro Ser Ser Gly Tyr Thr Ser Tyr Ala Asp Ser Val Lys
1 5 10 15

Gly

<210> SEQ ID NO 611
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 611

Ser Ile Ser Pro Tyr Ser Gly Ser Thr Ser Tyr Ala Asp Ser Val Lys
1 5 10 15

Gly

<210> SEQ ID NO 612
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 612

Tyr Ile Tyr Pro Ser Ser Gly Tyr Thr Ser Tyr Ala Asp Ser Val Lys
1 5 10 15

Gly

<210> SEQ ID NO 613
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 613

Ser Ile Tyr Pro Tyr Ser Gly Ser Thr Ser Tyr Ala Asp Ser Val Lys
1 5 10 15

Gly

<210> SEQ ID NO 614
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 614

Ser Ile Ser Pro Tyr Ser Gly Tyr Thr Ser Tyr Ala Asp Ser Val Lys
1 5 10 15

Gly

<210> SEQ ID NO 615
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 615

Ser Ile Tyr Pro Tyr Tyr Gly Ser Thr Ser Tyr Ala Asp Ser Val Lys
1 5 10 15

Gly

<210> SEQ ID NO 616
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 616

Tyr Ile Tyr Pro Ser Ser Gly Ser Thr Ser Tyr Ala Asp Ser Val Lys
1 5 10 15

Gly

<210> SEQ ID NO 617
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 617

Tyr Ile Ser Pro Ser Ser Gly Tyr Thr Tyr Tyr Ala Asp Ser Val Lys
1 5 10 15

Gly

<210> SEQ ID NO 618
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 618

Gly Ser Tyr Tyr Gly Tyr Tyr Ser Gly Ser Gly Met Asp Tyr
1 5 10

<210> SEQ ID NO 619
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 619

Gly Ser Gly Tyr Ser Tyr Tyr Gly Gly Tyr Gly Leu Asp Tyr
1 5 10

<210> SEQ ID NO 620
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 620

Gly Ser Tyr Ser Gly Tyr Tyr Tyr Gly Tyr Gly Leu Asp Tyr
1 5 10

<210> SEQ ID NO 621
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 621

Gly Arg Tyr Ser Gly Tyr Tyr Gly Gly Tyr Gly Met Asp Tyr
1 5 10

<210> SEQ ID NO 622
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 622

Tyr Tyr Tyr Ser Ser Gly Tyr Tyr Tyr Tyr Tyr Ala Phe Asp Tyr
1 5 10 15

<210> SEQ ID NO 623
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 623

Tyr Ser Tyr Ser Tyr Tyr Gly Tyr Tyr Gly Ser Gly Met Asp Tyr
1               5                   10                  15

<210> SEQ ID NO 624
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Tyr Arg Ser Tyr Tyr Ser Tyr Arg Tyr Gly Tyr Gly Met Asp Tyr
1               5                   10                  15

<210> SEQ ID NO 625
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Tyr Gly Tyr Tyr Tyr Ser Tyr Tyr Gly Gly Ser Gly Leu Asp Tyr
1               5                   10                  15

<210> SEQ ID NO 626
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Tyr Gly Tyr Tyr Tyr Ser Tyr Tyr Gly Gly Ser Gly Leu Asp Tyr
1               5                   10                  15

<210> SEQ ID NO 627
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Tyr Gly Tyr Ser Tyr Ser Tyr Ser Ser Gly Ser Ala Leu Asp Tyr
1               5                   10                  15

<210> SEQ ID NO 628
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Ser Tyr Tyr Tyr Gly Gly Tyr Tyr Ser Gly Tyr Gly Met Asp Tyr
1               5                   10                  15

<210> SEQ ID NO 629
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 629

Arg Arg Ser Tyr Tyr Ser Tyr Arg Tyr Ser Tyr Gly Leu Asp Tyr
1 5 10 15

<210> SEQ ID NO 630
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 630

Arg Arg Ser Tyr Tyr Ser Tyr Ser Arg Ser Tyr Ala Met Asp Tyr
1 5 10 15

<210> SEQ ID NO 631
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 631

Tyr Tyr Tyr Gly Tyr Tyr Ser Tyr Tyr Ser Gly Tyr Gly Leu Asp Tyr
1 5 10 15

<210> SEQ ID NO 632
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 632

Tyr Tyr Tyr Gly Tyr Tyr Ser Tyr Tyr Gly Gly Ser Gly Leu Asp Tyr
1 5 10 15

<210> SEQ ID NO 633
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 633

Tyr Tyr Tyr Gly Tyr Tyr Ser Tyr Tyr Gly Gly Ser Ala Met Asp Tyr
1 5 10 15

<210> SEQ ID NO 634
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 634

Tyr Tyr Tyr Ser Gly Gly Ser Tyr Tyr Tyr Tyr Tyr Ala Phe Asp Tyr
1 5 10 15

<210> SEQ ID NO 635
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 635

Tyr Tyr Tyr Ser Tyr Tyr Ser Tyr Tyr Ser Tyr Gly Gly Ile Asp Tyr
1 5 10 15

<210> SEQ ID NO 636
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 636

Tyr Tyr Ser Ser Tyr Tyr Ser Tyr Tyr Tyr Tyr Gly Gly Met Asp Tyr
1 5 10 15

<210> SEQ ID NO 637
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 637

Gly Phe Tyr Ile Lys Ser Ser Ser Ile His
1 5 10

<210> SEQ ID NO 638
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 638

Gly Phe Ser Ile Lys Ser Ser Ser Ile His
1 5 10

<210> SEQ ID NO 639
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 639

Gly Phe Ser Ile Lys Tyr Ser Ser Ile His
1 5 10

<210> SEQ ID NO 640
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 640

Gly Phe Tyr Ile Lys Tyr Ser Ser Ile His
1 5 10

<210> SEQ ID NO 641
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 641

Gly Phe Ser Ile Lys Ser Ser Tyr Ile His
1 5 10

<210> SEQ ID NO 642
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 642

Gly Phe Phe Ile Lys Tyr Tyr Tyr Ile His
1 5 10

<210> SEQ ID NO 643
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 643

Gly Phe Ser Ile Lys Ser Ser Tyr Ile His
1 5 10

<210> SEQ ID NO 644
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 644

Gly Phe Tyr Ile Lys Ser Tyr Ser Ile His
1 5 10

<210> SEQ ID NO 645
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 645

Ser Ile Ser Pro Ser Ser Gly Tyr Thr Ser Tyr Ala Asp Ser Val Lys
1 5 10 15

Gly

<210> SEQ ID NO 646
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 646

Tyr Ile Ser Pro Tyr Ser Gly Tyr Thr Tyr Tyr Ala Asp Ser Val Lys
1 5 10 15

Gly

<210> SEQ ID NO 647
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 647

Tyr Ile Tyr Pro Tyr Ser Gly Ser Thr Ser Tyr Ala Asp Ser Val Lys
1 5 10 15

Gly

<210> SEQ ID NO 648
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 648

Ser Ile Ser Pro Ser Tyr Gly Tyr Thr Ser Tyr Ala Asp Ser Val Lys
1 5 10 15

Gly

<210> SEQ ID NO 649
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 649

Ser Ile Tyr Pro Tyr Ser Gly Tyr Thr Ser Tyr Ala Asp Ser Val Lys
1 5 10 15

Gly

<210> SEQ ID NO 650
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 650

Ser Ile Ser Pro Tyr Ser Gly Tyr Thr Ser Tyr Ala Asp Ser Val Lys
1 5 10 15

Gly

<210> SEQ ID NO 651
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Tyr Ile Tyr Pro Tyr Ser Gly Tyr Thr Tyr Tyr Ala Asp Ser Val Lys
1               5                   10                  15

Gly

<210> SEQ ID NO 652
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Tyr Ile Ser Pro Ser Ser Gly Tyr Thr Ser Tyr Ala Asp Ser Val Lys
1               5                   10                  15

Gly

<210> SEQ ID NO 653
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Tyr Ile Ser Pro Ser Tyr Gly Ser Thr Tyr Tyr Ala Asp Ser Val Lys
1               5                   10                  15

Gly

<210> SEQ ID NO 654
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Ser Ile Tyr Pro Tyr Tyr Gly Ser Thr Tyr Tyr Ala Asp Ser Val Lys
1               5                   10                  15

Gly

<210> SEQ ID NO 655
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Ser Ile Tyr Pro Tyr Tyr Gly Tyr Thr Ser Tyr Ala Asp Ser Val Lys 1 5 10 15

Gly

<210> SEQ ID NO 656
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 656

Ser Ile Tyr Pro Tyr Tyr Gly Ser Thr Tyr Tyr Ala Asp Ser Val Lys
1 5 10 15

Gly

<210> SEQ ID NO 657
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 657

Ser Ile Tyr Pro Ser Tyr Gly Tyr Thr Ser Tyr Ala Asp Ser Val Lys
1 5 10 15

Gly

<210> SEQ ID NO 658
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 658

Tyr Ser Tyr Tyr Tyr Tyr Ser Tyr Tyr Tyr Gly Ser Ala Met Asp Tyr
1 5 10 15

<210> SEQ ID NO 659
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 659

Tyr Ser Tyr Tyr Tyr Tyr Ser Tyr Tyr Ser Gly Tyr Gly Phe Asp Tyr
1 5 10 15

<210> SEQ ID NO 660
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 660

Tyr Ser Tyr Tyr Tyr Tyr Ser Tyr Tyr Ser Gly Tyr Gly Phe Asp Tyr
1 5 10 15

<210> SEQ ID NO 661
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 661

Tyr Ser Tyr Tyr Tyr Tyr Ser Tyr Tyr Gly Gly Ser Ala Phe Asp Tyr
1 5 10 15

<210> SEQ ID NO 662
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 662

Tyr Ser Tyr Tyr Tyr Tyr Ser Tyr Tyr Gly Gly Ser Gly Met Asp Tyr
1 5 10 15

<210> SEQ ID NO 663
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 663

Tyr Ser Tyr Tyr Tyr Tyr Ser Tyr Tyr Gly Gly Ser Gly Leu Asp Tyr
1 5 10 15

<210> SEQ ID NO 664
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 664

Tyr Ser Tyr Ser Tyr Tyr Gly Tyr Tyr Tyr Gly Ser Gly Leu Asp Tyr
1 5 10 15

<210> SEQ ID NO 665
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 665

Tyr Ser Ser Tyr Tyr Tyr Ser Tyr Tyr Ser Gly Ser Gly Leu Asp Tyr
1 5 10 15

<210> SEQ ID NO 666
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 666

Ser Ser Tyr Tyr Tyr Tyr Ser Tyr Tyr Gly Gly Ser Gly Ile Asp Tyr
1 5 10 15

<210> SEQ ID NO 667
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 667

Arg Ser Tyr Tyr Tyr Tyr Ser Tyr Tyr Tyr Ser Arg Ala Met Asp Tyr
1 5 10 15

<210> SEQ ID NO 668
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 668

Ser Tyr Ser Ser Tyr Tyr Ser Tyr Tyr Ser Ser Tyr Gly Gly Met Asp
1 5 10 15

Tyr

<210> SEQ ID NO 669
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 669

Tyr Arg Tyr Tyr Tyr Ser Arg Tyr Gly Tyr Arg Tyr Tyr Tyr Tyr Tyr
1 5 10 15

Arg Ala Leu Asp Tyr
20

<210> SEQ ID NO 670
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 670

Arg Tyr Ser Ser Gly Met Asp Tyr
1 5

<210> SEQ ID NO 671
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 671

Tyr Ser His Ser Gly Ala Phe Asp Tyr
1 5

<210> SEQ ID NO 672
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Gly Tyr Ser Tyr Gly His Gly Ile Asp Tyr
1               5                   10

<210> SEQ ID NO 673
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Gly Ser Ser Phe Gly Arg Gly Phe Asp Tyr
1               5                   10

<210> SEQ ID NO 674
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Gly Ser Ser Tyr Ser Trp Gly Leu Asp Tyr
1               5                   10

<210> SEQ ID NO 675
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Gly Ser Arg Tyr Ser His Gly Met Asp Tyr
1               5                   10

<210> SEQ ID NO 676
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Gly Ala Ser Tyr Gly Tyr Gly Met Asp Tyr
1               5                   10

<210> SEQ ID NO 677
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Gly Phe Tyr Ile Lys Tyr Ser Ser Ile His
1 5 10

<210> SEQ ID NO 678
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 678

Gly Phe Ser Ile Lys Tyr Ser Ser Ile His
1 5 10

<210> SEQ ID NO 679
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 679

Gly Phe Ser Ile Lys Tyr Ser Tyr Ile His
1 5 10

<210> SEQ ID NO 680
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 680

Gly Phe Ser Ile Lys Tyr Ser Tyr Ile His
1 5 10

<210> SEQ ID NO 681
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 681

Gly Phe Tyr Ile Lys Tyr Ser Tyr Ile His
1 5 10

<210> SEQ ID NO 682
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 682

Ser Ile Tyr Pro Tyr Tyr Gly Tyr Thr Ser Tyr Ala Asp Ser Val Lys
1 5 10 15

Gly

<210> SEQ ID NO 683

<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 683

Ser Ile Tyr Pro Tyr Tyr Gly Ser Thr Tyr Tyr Ala Asp Ser Val Lys
1 5 10 15

Gly

<210> SEQ ID NO 684
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 684

Ser Ile Tyr Pro Ser Ser Gly Tyr Thr Ser Tyr Ala Asp Ser Val Lys
1 5 10 15

Gly

<210> SEQ ID NO 685
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 685

Arg Ile Tyr Pro Thr Asn Gly Ala Thr Arg Tyr Ala Asp Ser Val Lys
1 5 10 15

Gly

<210> SEQ ID NO 686
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 686

Arg Ile Tyr Pro Thr Asn Gly Trp Thr Ile Tyr Ala Asp Ser Val Lys
1 5 10 15

Gly

<210> SEQ ID NO 687
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 687

Gly Met Ser Tyr Gly Tyr Gly Met Asp Tyr
1 5 10

<210> SEQ ID NO 688
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 688

Gly Gly Arg Tyr Asn His Gly Leu Asp Tyr
1 5 10

<210> SEQ ID NO 689
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 689

Glu Tyr Tyr Gln Gly Tyr Gly Pro Tyr Arg Ser Thr Tyr Gly Leu Asp
1 5 10 15

Tyr

<210> SEQ ID NO 690
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 690

Ser Ser Trp Ser Ser Arg Gly Val Ser Tyr Ser Arg Thr Ala Gly Gly
1 5 10 15

Met Asp Tyr

<210> SEQ ID NO 691
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 691

Glu Gly Tyr Tyr Ser Val Ser Gly Ser Tyr Ser Tyr Ser Thr Arg Gly
1 5 10 15

Gly Pro Asp Tyr
20

<210> SEQ ID NO 692
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 692

Trp Gly Gly Asp Gly Phe Phe Ala Met Asp Tyr
1 5 10

<210> SEQ ID NO 693
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 693

Trp Gly Gly Trp Gly Phe Phe Ala Met Asp Val
1 5 10

<210> SEQ ID NO 694
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 694

Trp Gly Gly Asp Gly Phe Tyr Ala Met Asp Tyr
1 5 10

<210> SEQ ID NO 695
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 695

Trp Gly Gly Asp Gly Phe Tyr Ala Met Asp Tyr
1 5 10

<210> SEQ ID NO 696
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 696

Trp Gly His Asp Gly Met Phe Tyr Ala Met Asp Tyr
1 5 10

<210> SEQ ID NO 697
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 697

Trp Gly Ala Asp Gly Asn Tyr Ala Met Asp Tyr
1 5 10

<210> SEQ ID NO 698
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 698

Trp Gly Arg Ser Gly Tyr Phe Tyr Ala Met Asp Tyr
1 5 10

<210> SEQ ID NO 699
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 699

Trp Gly Ala Ser Gly Leu Phe Tyr Ala Met Asp Tyr
1 5 10

<210> SEQ ID NO 700
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 700

Trp Gly Arg Asp Gly Leu Phe Tyr Ala Met Asp Tyr
1 5 10

<210> SEQ ID NO 701
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 701

Trp Gly Ser Asp Gly Phe Tyr Ala Met Asp Tyr
1 5 10

<210> SEQ ID NO 702
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 702

Trp Gly Thr Asp Gly Ala Phe Tyr Ala Met Asp Tyr
1 5 10

<210> SEQ ID NO 703
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 703

Trp Gly Lys Asp Gly Phe Tyr Ala Met Asp Tyr
1 5 10

<210> SEQ ID NO 704
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 704

Trp Gly Leu Asp Gly His Phe Tyr Ala Met Asp Tyr
1 5 10

<210> SEQ ID NO 705
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 705

Trp Gly His Leu Gly Tyr Phe Tyr Ala Met Asp Tyr
1 5 10

<210> SEQ ID NO 706
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 706

Trp Gly Gly Asp Gly Pro Phe Tyr Ala Met Lys Tyr
1 5 10

<210> SEQ ID NO 707
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 707

Trp Gly Gly Asp Gly Pro Phe Tyr Ala Met Leu Tyr
1 5 10

<210> SEQ ID NO 708
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 708

Trp Gly Gly Asp Gly Pro Phe Tyr Ala Met Trp Tyr
1 5 10

<210> SEQ ID NO 709
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 709

Trp Gly Gly Asp Gly Trp Tyr Ala Met Asp Met
1 5 10

<210> SEQ ID NO 710
<211> LENGTH: 11
<212> TYPE: PRT

<213> ORGANISM: Artificial Sequence
<220> FEATURE:
<223> OTHER INFORMATION: Description of Artificial Sequence: Synthetic peptide

<400> SEQUENCE: 710

Trp Gly Gly Asp Gly Trp Tyr Ala Met Asp Leu
1 5 10

<210> SEQ ID NO 711
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 711

Trp Gly Gly Asp Gly His Tyr Ala Met Asp Leu
1 5 10

<210> SEQ ID NO 712
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 712

Trp Gly Gly Asp Gly Phe Tyr Ala Met Asp Trp
1 5 10

<210> SEQ ID NO 713
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 713

Trp Gly Gly Asp Gly Pro Tyr Ala Met Asp His
1 5 10

<210> SEQ ID NO 714
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 714

Trp Gly Gly Asp Gly Pro Tyr Ala Met Asp Lys
1 5 10

<210> SEQ ID NO 715
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 715

Trp Gly Gly Asp Gly Pro Tyr Ala Met Asp Leu
1 5 10

<210> SEQ ID NO 716
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 716

Trp Gly Gly Asp Gly Pro Tyr Ala Met Asp Lys
1 5 10

<210> SEQ ID NO 717
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 717

Trp Gly Gly Asp Gly Met Tyr Ala Met Asp Ala
1 5 10

<210> SEQ ID NO 718
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 718

Trp Gly Gly Asp Gly Leu Tyr Ala Met Asp Ser
1 5 10

<210> SEQ ID NO 719
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 719

Trp Gly Gly Asp Gly Leu Tyr Ala Met Asp Thr
1 5 10

<210> SEQ ID NO 720
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 720

Trp Gly Gly Asp Gly Arg Tyr Ala Met Asp Gly
1 5 10

<210> SEQ ID NO 721
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 721

Trp Gly Gly Asp Gly Met Tyr Ala Met Asp Gly
1 5 10

<210> SEQ ID NO 722
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 722

Trp Gly Gly Asp Gly Arg Tyr Ala Met Asp Leu
1 5 10

<210> SEQ ID NO 723
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 723

Trp Gly Gly Asp Gly Pro Tyr Ala Met Asp Ala
1 5 10

<210> SEQ ID NO 724
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 724

Trp Gly Gly Asp Gly Pro Tyr Ala Met Asp Val
1 5 10

<210> SEQ ID NO 725
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 725

Trp Gly Gly Asp Gly Pro Tyr Ala Met Asp Lys
1 5 10

<210> SEQ ID NO 726
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 726

Trp Gly Gly Asp Gly Pro Tyr Ala Met Asp Leu
1 5 10

<210> SEQ ID NO 727
<211> LENGTH: 11

<212> TYPE: PRT
<213> ORGANISM: Artificial Sequence
<220> FEATURE:
<223> OTHER INFORMATION: Description of Artificial Sequence: Synthetic peptide

<400> SEQUENCE: 727

Trp Gly Gly Asp Gly Leu Tyr Ala Met Asp Tyr
1 5 10

<210> SEQ ID NO 728
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 728

Trp Gly Gly Trp Gly Phe Tyr Ala Met Asp Tyr
1 5 10

<210> SEQ ID NO 729
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 729

Trp Gly Gly Asp Gly Phe Phe Ala Met Asp Tyr
1 5 10

<210> SEQ ID NO 730
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 730

Trp Gly Gly Trp Gly Pro Tyr Ala Met Asp Lys
1 5 10

<210> SEQ ID NO 731
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 731

Trp Gly Gly Trp Gly Pro Tyr Ala Met Asp Leu
1 5 10

<210> SEQ ID NO 732
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 732

Trp Gly Gly Asp Gly Phe Tyr Ala Met Asp Val 1 5 10

<210> SEQ ID NO 733
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 733

Trp Gly Gly Asp Gly Pro Tyr Ala Met Asp Lys
1 5 10

<210> SEQ ID NO 734
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 734

Gln Gln Ser Tyr Tyr Ser Pro Ser Thr
1 5

<210> SEQ ID NO 735
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 735

Gln Gln Ser Tyr Tyr Tyr Pro Ser Thr
1 5

<210> SEQ ID NO 736
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 736

Gln Gln Tyr Tyr Tyr Ser Pro Ser Thr
1 5

<210> SEQ ID NO 737
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 737

Gln Gln Tyr Tyr Tyr Tyr Pro Tyr Thr
1 5

<210> SEQ ID NO 738
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 738

Gln Gln Tyr Tyr Tyr Tyr Pro Ser Thr
1               5

<210> SEQ ID NO 739
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 739

Gln Gln Ser Tyr Tyr Tyr Pro Ser Thr
1               5

<210> SEQ ID NO 740
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 740

Gln Gln Trp Ser Ser Ser Pro Ser Thr
1               5

<210> SEQ ID NO 741
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 741

Gln Gln Trp Ser Ser Trp Pro Ser Thr
1               5

<210> SEQ ID NO 742
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 742

Gln Gln Ser Tyr Tyr Ser Pro Ser Thr
1               5

<210> SEQ ID NO 743
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 743

Gln Gln Tyr Tyr Tyr Ser Pro Ser Thr
1               5

<210> SEQ ID NO 744

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Gln Gln Ser Tyr Tyr Tyr Pro Ser Thr
1               5

<210> SEQ ID NO 745
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Gln Gln Ser Ser Ser Ser Pro Ser Thr
1               5

<210> SEQ ID NO 746
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Gln Gln Ser Tyr Tyr Tyr Pro Tyr Thr
1               5

<210> SEQ ID NO 747
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Gln Gln Tyr Tyr Tyr Ser Pro Tyr Thr
1               5

<210> SEQ ID NO 748
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

Gln Gln Ser Tyr Ser Ser Pro Ser Thr
1               5

<210> SEQ ID NO 749
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

Gln Gln Tyr Ser Tyr Tyr Pro Tyr Thr
1 5

<210> SEQ ID NO 750
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 750

Gln Gln Tyr Ser Ser Ser Pro Ser Thr
1 5

<210> SEQ ID NO 751
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 751

Gln Gln Ser Ser Tyr Tyr Pro Ser Thr
1 5

<210> SEQ ID NO 752
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 752

Gln Gln Ser Tyr Tyr Ser Pro Ser Thr
1 5

<210> SEQ ID NO 753
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 753

Gln Gln Ser Tyr Tyr Tyr Pro Ser Thr
1 5

<210> SEQ ID NO 754
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 754

Gln Gln His Tyr Tyr Tyr Pro Tyr Thr
1 5

<210> SEQ ID NO 755
<211> LENGTH: 9
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 755

Gln Gln His Tyr Tyr Ser Pro Ser Thr
1 5

<210> SEQ ID NO 756
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 756

Gln Gln Ser Tyr Tyr Tyr Pro Tyr Thr
1 5

<210> SEQ ID NO 757
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 757

Gln Gln Xaa Xaa Xaa Xaa Pro Xaa Thr
1 5

<210> SEQ ID NO 758
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 758

Gln Gln His Ser Tyr Tyr Pro Tyr Thr
1 5

<210> SEQ ID NO 759
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 759

Gln Gln His Ser Tyr Tyr Pro Ser Thr
1 5

<210> SEQ ID NO 760
<211> LENGTH: 9
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 760

Gln Gln Ser Ser Tyr Ser Pro Ser Thr
1 5

<210> SEQ ID NO 761
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 761

Gln Gln His Ser Tyr Tyr Pro Tyr Thr
1 5

<210> SEQ ID NO 762
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 762

Gln Gln His Ser Tyr Tyr Pro Ser Thr
1 5

<210> SEQ ID NO 763
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 763

Gln Gln Ser Ser Tyr Ser Pro Ser Thr
1 5

<210> SEQ ID NO 764
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 764

Gln Gln Ser Ser Tyr Tyr Pro Tyr Thr
1 5

<210> SEQ ID NO 765
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 765

Gln Gln Ser Tyr Tyr Tyr Pro Ser Thr
1 5

<210> SEQ ID NO 766

<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 766

Gln Gln Ser Phe Ser Ser Pro Tyr Thr
1               5

<210> SEQ ID NO 767
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 767

Gln Gln Ser Tyr Ser Ser Pro Tyr Thr
1               5

<210> SEQ ID NO 768
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 768

Gln Gln Ser Tyr Ser Tyr Pro Ser Thr
1               5

<210> SEQ ID NO 769
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 769

Gln Gln Ser Phe Ser Tyr Pro Tyr Thr
1               5

<210> SEQ ID NO 770
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 770

Gln Gln Ser Tyr Ser Ser Pro Ser Thr
1               5

<210> SEQ ID NO 771
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 771

Gln Gln Ser Tyr Ser Ser Pro Tyr Thr
1 5

<210> SEQ ID NO 772
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 772

Gln Gln Ser Tyr Ser Ser Pro Ser Thr
1 5

<210> SEQ ID NO 773
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 773

Gln Gln Ser Phe Ser Ser Pro Ser Thr
1 5

<210> SEQ ID NO 774
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 774

Gln Gln Ser Ser Ser Ser Pro Tyr Thr
1 5

<210> SEQ ID NO 775
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 775

Gln Gln Ser Ser Ser Tyr Pro Tyr Thr
1 5

<210> SEQ ID NO 776
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 776

Gln Gln Ser Tyr Ser Tyr Pro Ser Thr
1 5

<210> SEQ ID NO 777
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 777

Gln Gln Ser Ser Ser Ser Pro Tyr Thr
1               5

<210> SEQ ID NO 778
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

Gln Gln Ser Ser Ser Tyr Pro Ser Thr
1               5

<210> SEQ ID NO 779
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 779

Gln Gln Ser Ser Tyr Tyr Pro Ser Thr
1               5

<210> SEQ ID NO 780
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 780

Gln Gln Ser Ser Phe Ser Pro Tyr Thr
1               5

<210> SEQ ID NO 781
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

Gln Gln Ser Ser Ser Tyr Pro Ser Thr
1               5

<210> SEQ ID NO 782
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Gln Gln Ser Ser Ser Ser Pro Tyr Thr
1               5

<210> SEQ ID NO 783
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 783

Gln Gln Ser Tyr Ser Ser Pro Tyr Thr
1 5

<210> SEQ ID NO 784
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 784

Gln Gln Ser Tyr Ser Ser Pro Ser Thr
1 5

<210> SEQ ID NO 785
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 785

Gln Gln Ser Ser Ser Tyr Pro Tyr Thr
1 5

<210> SEQ ID NO 786
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 786

Gln Gln Ser Phe Ser Ser Pro Tyr Thr
1 5

<210> SEQ ID NO 787
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 787

Gln Gln Ser Tyr Ser Tyr Pro Ser Thr
1 5

<210> SEQ ID NO 788
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 788

Gln Gln His Tyr Ser Ser Pro Tyr Thr
1 5

<210> SEQ ID NO 789
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 789

Gln Gln Ser Ser Ser Tyr Pro Ser Thr
1 5

<210> SEQ ID NO 790
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 790

Gln Gln His Tyr Ser Ser Pro Ser Thr
1 5

<210> SEQ ID NO 791
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 791

Gln Gln Ser Ser Tyr Tyr Pro Ser Thr
1 5

<210> SEQ ID NO 792
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 792

Gln Gln Ser Ser Phe Tyr Pro Ser Thr
1 5

<210> SEQ ID NO 793
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 793

Gln Gln Ser Ser Tyr Ser Pro Tyr Thr
1 5

<210> SEQ ID NO 794
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 794

Gln Gln Ser Ser Ser Ser Pro Ser Thr
1 5

<210> SEQ ID NO 795
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 795

Gln Gln His Tyr Tyr Tyr Pro Tyr Thr
1 5

<210> SEQ ID NO 796
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 796

Gln Gln Ser Ser Tyr Ser Pro Tyr Thr
1 5

<210> SEQ ID NO 797
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 797

Gln Gln His Tyr Ser Ser Pro Tyr Thr
1 5

<210> SEQ ID NO 798
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 798

Gln Gln His Tyr Ser Tyr Pro Ser Thr
1 5

<210> SEQ ID NO 799
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 799

Gln Gln Ser Ser Tyr Tyr Pro Ser Thr
1 5

<210> SEQ ID NO 800
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 800

Gln Gln Ser Ser Ser Ser Pro Tyr Thr
1 5

<210> SEQ ID NO 801
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 801

Gln Gln Ser Ser Tyr Tyr Pro Tyr Thr
1 5

<210> SEQ ID NO 802
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 802

Gln Gln Ser Tyr Tyr Tyr Pro Tyr Thr
1 5

<210> SEQ ID NO 803
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 803

Gln Gln His Tyr Tyr Ser Pro Ser Thr
1 5

<210> SEQ ID NO 804
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 804

Arg Ala Ser Gln Asp Val Ser Thr Ala Val Ala
1 5 10

<210> SEQ ID NO 805
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 805

Arg Ala Ser Gln Asp Val Asn Thr Ala Tyr Ala
1 5 10

<210> SEQ ID NO 806
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 806

Arg Ala Ser Gln Asp Val Asn Thr Ala Trp Ala
1 5 10

<210> SEQ ID NO 807
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 807

Arg Ala Ser Phe Leu Tyr Ser
1 5

<210> SEQ ID NO 808
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 808

Gln Gln His Ser Tyr Tyr Pro Tyr Thr
1 5

<210> SEQ ID NO 809
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 809

Gln Gln Ser Ser Tyr Tyr Pro Tyr Thr
1 5

<210> SEQ ID NO 810
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 810

Gln Gln His Ser Tyr Tyr Pro Ser Thr
1 5

<210> SEQ ID NO 811
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 811

Gln Gln His Ser Ser Ser Pro Ser Thr
1 5

<210> SEQ ID NO 812
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 812

Gln Gln His Ser Ser Ser Pro Tyr Thr
1 5

<210> SEQ ID NO 813
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 813

Gln Gln Ser Tyr Ser Ser Pro Ser Thr
1 5

<210> SEQ ID NO 814
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 814

Gln Gln Phe Trp Thr Ser Pro Pro Thr
1 5

<210> SEQ ID NO 815
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 815

Arg Ala Ser Gln Asp Val Asn Thr Ala Tyr Ala
1 5 10

<210> SEQ ID NO 816
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 816

Arg Ala Ser Gln Asp Val Asn Thr Ala Trp Ala
1 5 10

<210> SEQ ID NO 817
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 817

Arg Ala Ser Gln Asp Val Asn Thr Ala Phe Ala
1 5 10

<210> SEQ ID NO 818
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 818

Arg Ala Ser Gln Asp Val Ser Thr Ala Val Ala
1 5 10

<210> SEQ ID NO 819
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 819

Arg Ala Ser Phe Leu Tyr Ser
1 5

<210> SEQ ID NO 820
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 820

Gln Gln Phe Trp Thr Thr Pro Pro Thr
1 5

<210> SEQ ID NO 821
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 821

Gln Gln Tyr Trp Thr Thr Pro Pro Thr
1 5

<210> SEQ ID NO 822
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 822

Gln Gln His Trp Thr Thr Pro Pro Thr
1 5

<210> SEQ ID NO 823
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 823

Gln Gln Phe Phe Thr Thr Pro Pro Thr
1 5

<210> SEQ ID NO 824
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 824

Gln Gln Phe Gly Thr Thr Pro Pro Thr
1 5

<210> SEQ ID NO 825
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 825

Arg Ala Ser Gln Asp Val Ser Thr Ala Val Ala
1 5 10

<210> SEQ ID NO 826
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 826

Ser Ala Ser Val Leu Tyr Ser
1 5

<210> SEQ ID NO 827
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 827

Ser Ala Ser Trp Leu Tyr Ser
1 5

<210> SEQ ID NO 828
<211> LENGTH: 7

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 828

Ser Ala Ser Leu Leu Tyr Ser
1 5

<210> SEQ ID NO 829
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 829

Ser Ala Ser Trp Leu Trp Ser
1 5

<210> SEQ ID NO 830
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 830

Gln Gln Phe Gly Thr Thr Pro Pro Thr
1 5

<210> SEQ ID NO 831
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 831

Gln Gln Ile Trp Thr Thr Pro Pro Thr
1 5

<210> SEQ ID NO 832
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 832

Gln Gln Phe Trp Thr Thr Pro Pro Thr
1 5

<210> SEQ ID NO 833
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 833

Gln Gln Tyr Tyr Thr Thr Pro Pro Thr 1 5

<210> SEQ ID NO 834
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 834

Gln Gln Phe Tyr Thr Thr Pro Pro Thr
1 5

<210> SEQ ID NO 835
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 835

Gln Gln Thr Tyr Thr Thr Pro Pro Thr
1 5

<210> SEQ ID NO 836
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 836

Gln Gln Trp Tyr Thr Thr Pro Pro Thr
1 5

<210> SEQ ID NO 837
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 837

Ser Ala Ser Trp Leu Trp Ser
1 5

<210> SEQ ID NO 838
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 838

Ser Ala Ser Thr Leu Trp Ser
1 5

<210> SEQ ID NO 839
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 839

Ser Ala Ser Phe Leu Trp Ser
1 5

<210> SEQ ID NO 840
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 840

Ser Ala Ser His Leu Trp Ser
1 5

<210> SEQ ID NO 841
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 841

Ser Ala Ser Val Leu Trp Ser
1 5

<210> SEQ ID NO 842
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 842

Ser Ala Ser Val Leu Leu Ser
1 5

<210> SEQ ID NO 843
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 843

Ser Ala Ser Arg Leu Trp Ser
1 5

<210> SEQ ID NO 844
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 844

Ser Ala Ser Gln Leu Phe Ser
1 5

<210> SEQ ID NO 845

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 845

Ser Ala Ser Trp Leu Leu Ser
1 5

<210> SEQ ID NO 846
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 846

Ser Ala Ser Thr Leu Tyr Ser
1 5

<210> SEQ ID NO 847
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 847

Ser Ala Ser Trp Leu Val Ser
1 5

<210> SEQ ID NO 848
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 848

Ser Ala Ser Lys Leu Trp Ser
1 5

<210> SEQ ID NO 849
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 849

Ser Ala Ser Ala Leu Trp Ser
1 5

<210> SEQ ID NO 850
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 850

Ser Ala Ser Arg Leu Val Ser
1 5

<210> SEQ ID NO 851
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 851

Ser Ala Ser Lys Leu Ser Ser
1 5

<210> SEQ ID NO 852
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 852

Ser Ala Ser Val Leu Trp Ser
1 5

<210> SEQ ID NO 853
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 853

Ser Ala Ser Arg Leu Ala Ser
1 5

<210> SEQ ID NO 854
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 854

Ser Ala Ser Leu Leu Pro Ser
1 5

<210> SEQ ID NO 855
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 855

Ser Ala Ser Met Leu Gly Ser
1 5

<210> SEQ ID NO 856
<211> LENGTH: 13
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 856

Arg Ala Ser Gln Ser Asp Gln Asn Ser Thr Ser Gly Ala
1 5 10

<210> SEQ ID NO 857
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 857

Arg Ala Ser Ser Gln Val Ser Gly Gly Val Ala
1 5 10

<210> SEQ ID NO 858
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 858

Arg Ala Ser Arg Gln Val Asn Thr Ala Val Ala
1 5 10

<210> SEQ ID NO 859
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 859

Arg Ala Ser Ala Gln Val Ser Ala Gly Val Ala
1 5 10

<210> SEQ ID NO 860
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 860

Arg Ala Ser Gln Gly Val Ser Ser Gly Val Ala
1 5 10

<210> SEQ ID NO 861
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 861

Arg Ala Ser Gln Gly Val Ser Ser Ala Val Ala
1 5 10

<210> SEQ ID NO 862
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 862

Arg Ala Ser Gln Arg Val Asn Ser Ala Val Ala
1 5 10

<210> SEQ ID NO 863
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 863

Arg Ala Ser Gln Gly Val Ser Ser Ala Val Ala
1 5 10

<210> SEQ ID NO 864
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 864

Arg Ala Ser Asn Pro Val Ser Gln Ala Val Ala
1 5 10

<210> SEQ ID NO 865
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 865

Arg Ala Ser Ser Ser Val Lys Ala Ser Val Ala
1 5 10

<210> SEQ ID NO 866
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 866

Arg Ala Ser Phe Asp Val Asn Ala Cys Val Ala
1 5 10

<210> SEQ ID NO 867
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 867

Arg Ala Ser Gln Asp Val Ser Thr Ala Val Ala
1 5 10

<210> SEQ ID NO 868
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 868

Gln Gln His Trp Thr Thr Pro Pro Thr
1 5

<210> SEQ ID NO 869
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 869

Gln Gln Phe Phe Thr Thr Pro Pro Thr
1 5

<210> SEQ ID NO 870
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 870

Gln Gln Tyr Trp Thr Thr Pro Pro Thr
1 5

<210> SEQ ID NO 871
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 871

Gln Gln His Phe Thr Thr Pro Pro Thr
1 5

<210> SEQ ID NO 872
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 872

Gln Gln Leu Pro Thr Thr Pro Pro Thr
1 5

<210> SEQ ID NO 873
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 873

Gln Gln His Gln Thr Thr Pro Pro Thr
1 5

<210> SEQ ID NO 874
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 874

Gln Gln Phe Tyr Thr Thr Pro Pro Thr
1 5

<210> SEQ ID NO 875
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 875

Gln Gln His Tyr Thr Ser Pro Pro Thr
1 5

<210> SEQ ID NO 876
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 876

Arg Ala Ser Gln Asp Val Trp Lys Trp Val Ala
1 5 10

<210> SEQ ID NO 877
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 877

Arg Ala Ser Gln Asp Ile Lys Asn Gly Ser Val Ala
1 5 10

<210> SEQ ID NO 878
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 878

Arg Ala Ser Gln Asp Ile Leu Gly Gly Ser Val Ala
1 5 10

<210> SEQ ID NO 879
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 879

Arg Ala Ser Gln Asp Ile Met Ser Gly Ser Val Ala
1               5                   10

<210> SEQ ID NO 880
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 880

Arg Ala Ser Gln Asp Ile Arg Ala Gly Ser Val Ala
1               5                   10

<210> SEQ ID NO 881
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 881

Arg Ala Ser Gln Asp Ile Arg Gly Gly Ser Val Ala
1               5                   10

<210> SEQ ID NO 882
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 882

Arg Ala Ser Gln Asp Val Arg Gln Gly Ser Val Ala
1               5                   10

<210> SEQ ID NO 883
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883

Arg Ala Ser Gln Asp Ile Ala Ala Gly Ser Val Ala
1               5                   10

<210> SEQ ID NO 884
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

Arg Ala Ser Gln Asp Ile Ala Gly Gly Ser Val Ala
1 5 10

<210> SEQ ID NO 885
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 885

Arg Ala Ser Gln Asp Ile Ala His Gly Ser Val Ala
1 5 10

<210> SEQ ID NO 886
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 886

Arg Ala Ser Gln Asp Ile Ala Lys Gly Ser Val Ala
1 5 10

<210> SEQ ID NO 887
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 887

Arg Ala Ser Gln Asp Ile Gly Ala Gly Ser Val Ala
1 5 10

<210> SEQ ID NO 888
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 888

Arg Ala Ser Gln Asp Ile Gly Gly Gly Ser Val Ala
1 5 10

<210> SEQ ID NO 889
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 889

Arg Ala Ser Gln Asp Ile Gly Leu Gly Ser Val Ala
1 5 10

<210> SEQ ID NO 890
<211> LENGTH: 12
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 890

Arg Ala Ser Gln Asp Ile Gly Met Gly Ser Val Ala
1 5 10

<210> SEQ ID NO 891
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 891

Arg Ala Ser Gln Asp Ile Lys His Gly Ser Val Ala
1 5 10

<210> SEQ ID NO 892
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 892

Arg Ala Ser Gln Asp Ile Leu Ala Gly Ser Val Ala
1 5 10

<210> SEQ ID NO 893
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 893

Ala Ala Ser Ser Leu Tyr Ser
1 5

<210> SEQ ID NO 894
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 894

Trp Ala Ser Phe Leu Tyr Ser
1 5

<210> SEQ ID NO 895
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 895

Trp Gly Ser Phe Leu Tyr Ser
1 5

<210> SEQ ID NO 896
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 896

Trp Ala Ser Tyr Leu Tyr Ser
1 5

<210> SEQ ID NO 897
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 897

Trp Gly Ser Phe Leu Tyr Ser
1 5

<210> SEQ ID NO 898
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 898

Arg Ala Ser Gln Asp Ile Leu Gly Gly Ser Val Ala
1 5 10

<210> SEQ ID NO 899
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 899

Arg Ala Ser Gln Asp Ile Leu Ile Gly Ser Val Ala
1 5 10

<210> SEQ ID NO 900
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 900

Arg Ala Ser Gln Asp Ile Leu Thr Gly Ser Val Ala
1 5 10

<210> SEQ ID NO 901
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 901

Arg Ala Ser Gln Asp Ile Met Leu Gly Ser Val Ala
1 5 10

<210> SEQ ID NO 902
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 902

Arg Ala Ser Gln Asp Ile Gln Ser Gly Ser Val Ala
1 5 10

<210> SEQ ID NO 903
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 903

Arg Ala Ser Gln Asp Ile Arg Ile Gly Ser Val Ala
1 5 10

<210> SEQ ID NO 904
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 904

Arg Ala Ser Gln Asp Ile Arg Met Gly Ser Val Ala
1 5 10

<210> SEQ ID NO 905
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 905

Arg Ala Ser Gln Asp Ile Arg Gln Gly Ser Val Ala
1 5 10

<210> SEQ ID NO 906
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 906

Arg Ala Ser Gln Asp Ile Arg Thr Gly Ser Val Ala
1 5 10

<210> SEQ ID NO 907
<211> LENGTH: 12

<212> TYPE: PRT
<213> ORGANISM: Artificial Sequence
<220> FEATURE:
<223> OTHER INFORMATION: Description of Artificial Sequence: Synthetic peptide

<400> SEQUENCE: 907

Arg Ala Ser Gln Asp Ile Arg Val Gly Ser Val Ala
1 5 10

<210> SEQ ID NO 908
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 908

Arg Ala Ser Gln Asp Ile Ser Met Gly Ser Val Ala
1 5 10

<210> SEQ ID NO 909
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 909

Arg Ala Ser Gln Asp Ile Ser Arg Gly Ser Val Ala
1 5 10

<210> SEQ ID NO 910
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 910

Arg Ala Ser Gln Asp Ile Ser Val Gly Ser Val Ala
1 5 10

<210> SEQ ID NO 911
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 911

Arg Ala Ser Gln Asp Ile Val Ser Gly Ser Val Ala
1 5 10

<210> SEQ ID NO 912
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 912

Arg Ala Ser Gln Asp Ile Trp His Trp Val Ala 1 5 10

<210> SEQ ID NO 913
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 913

Arg Ala Ser Gln Asn Ile Ala Gln Gly Ser Val Ala
1 5 10

<210> SEQ ID NO 914
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 914

Arg Ala Ser Gln Asp Ile Ala Phe Gly Ser Leu Ala
1 5 10

<210> SEQ ID NO 915
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 915

Arg Ala Ser Gln Asp Ile Ala Met Gly Ser Val Ala
1 5 10

<210> SEQ ID NO 916
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 916

Arg Ala Ser Gln Asp Ile Ala Arg Gly Ser Val Ala
1 5 10

<210> SEQ ID NO 917
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 917

Arg Ala Ser Gln Asp Ile Ala Ser Gly Ser Val Ala
1 5 10

<210> SEQ ID NO 918
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 918

Arg Ala Ser Gln Asp Ile Ala Ser Gly Ser Val Ala
1 5 10

<210> SEQ ID NO 919
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 919

Ala Gly Ser Ser Leu Tyr Ser
1 5

<210> SEQ ID NO 920
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 920

Trp Ala Ser Phe Leu Tyr Ser
1 5

<210> SEQ ID NO 921
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 921

Trp Gly Ser Tyr Leu Tyr Ser
1 5

<210> SEQ ID NO 922
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 922

Trp Gly Ser Met Leu Tyr Ser
1 5

<210> SEQ ID NO 923
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 923

Trp Gly Ser Leu Leu Tyr Ser
1 5

<210> SEQ ID NO 924

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 924

Trp Gly Ser Ser Leu Tyr Ser
1 5

<210> SEQ ID NO 925
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 925

Arg Ala Ser Gln Asp Ile Gly Ser Gly Ser Val Ala
1 5 10

<210> SEQ ID NO 926
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 926

Arg Ala Ser Gln Asp Ile Ile Gly Gly Ser Val Ala
1 5 10

<210> SEQ ID NO 927
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 927

Arg Ala Ser Gln Asp Ile Lys Ala Gly Ser Val Ala
1 5 10

<210> SEQ ID NO 928
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 928

Arg Ala Ser Gln Asp Ile Lys Phe Gly Ser Val Ala
1 5 10

<210> SEQ ID NO 929
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 929

Arg Ala Ser Gln Asp Ile Lys Leu Gly Ser Val Ala
1 5 10

<210> SEQ ID NO 930
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 930

Arg Ala Ser Gln Asp Ile Lys Leu Gly Ser Val Ala
1 5 10

<210> SEQ ID NO 931
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 931

Arg Ala Ser Gln Asp Ile Lys Ser Gly Ser Val Ala
1 5 10

<210> SEQ ID NO 932
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 932

Arg Ala Ser Gln Asp Ile Lys Val Gly Ser Val Ala
1 5 10

<210> SEQ ID NO 933
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 933

Arg Ala Ser Gln Asp Ile Lys Trp Gly Ser Val Ala
1 5 10

<210> SEQ ID NO 934
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 934

Arg Ala Ser Gln Asp Ile Leu Lys Gly Ser Val Ala
1 5 10

<210> SEQ ID NO 935
<211> LENGTH: 12
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 935

Arg Ala Ser Gln Asp Ile Leu Ser Gly Ser Val Ala
1 5 10

<210> SEQ ID NO 936
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 936

Arg Ala Ser Gln Asp Ile Gln Arg Gly Ser Val Ala
1 5 10

<210> SEQ ID NO 937
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 937

Arg Ala Ser Gln Asp Ile Gln Ser Gly Ser Val Ala
1 5 10

<210> SEQ ID NO 938
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 938

Arg Ala Ser Gln Asp Ile Gln Thr Gly Ser Val Ala
1 5 10

<210> SEQ ID NO 939
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 939

Arg Ala Ser Gln Asp Ile Arg Glu Gly Ser Val Ala
1 5 10

<210> SEQ ID NO 940
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 940

Arg Ala Ser Gln Asp Ile Arg Phe Gly Ser Val Ala
1 5 10

<210> SEQ ID NO 941
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 941

Arg Ala Ser Gln Asp Ile Arg Gly Gly Ser Val Ala
1 5 10

<210> SEQ ID NO 942
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 942

Arg Ala Ser Gln Asp Ile Arg Leu Gly Ser Val Ala
1 5 10

<210> SEQ ID NO 943
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 943

Trp Gly Ser Tyr Leu Tyr Ser
1 5

<210> SEQ ID NO 944
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 944

Trp Gly Ser Ser Leu Tyr Ser
1 5

<210> SEQ ID NO 945
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 945

Trp Gly Ser Leu Leu Tyr Ser
1 5

<210> SEQ ID NO 946
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 946

Trp Gly Ser Met Leu Tyr Ser
1               5

<210> SEQ ID NO 947
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 947

Trp Gly Ser Thr Leu Tyr Ser
1               5

<210> SEQ ID NO 948
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 948

Trp Gly Ser Trp Leu Tyr Ser
1               5

<210> SEQ ID NO 949
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 949

Trp Gly Ser Cys Leu Tyr Ser
1               5

<210> SEQ ID NO 950
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 950

Arg Ala Ser Gln Asp Ile Arg Met Gly Ser Val Ala
1               5                   10

<210> SEQ ID NO 951
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 951

Arg Ala Ser Gln Asp Ile Arg Arg Gly Ser Val Ala
1               5                   10

<210> SEQ ID NO 952
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 952

Arg Ala Ser Gln Asp Ile Arg Ser Gly Ser Val Ala
1 5 10

<210> SEQ ID NO 953
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 953

Arg Ala Ser Gln Asp Ile Arg Val Gly Ser Val Ala
1 5 10

<210> SEQ ID NO 954
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 954

Arg Ala Ser Gln Asp Ile Ser Ser Gly Ser Val Ala
1 5 10

<210> SEQ ID NO 955
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 955

Arg Ala Ser Gln Asp Ile Thr Met Gly Ser Val Ala
1 5 10

<210> SEQ ID NO 956
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 956

Arg Ala Ser Gln Asp Ile Tyr Met Gly Ser Val Ala
1 5 10

<210> SEQ ID NO 957
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 957

Arg Ala Ser Gln Asp Ile Ala Thr Gly Ser Leu Ala
1 5 10

<210> SEQ ID NO 958
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 958

Arg Ala Ser Gln Asp Ile Lys Ser Gly Ser Leu Ala
1 5 10

<210> SEQ ID NO 959
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 959

Arg Ala Ser Gln Asp Ile Arg Gly Gly Ser Val Ala
1 5 10

<210> SEQ ID NO 960
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 960

Arg Ala Ser Gln Gly Ile Arg Thr Gly Ser Val Ala
1 5 10

<210> SEQ ID NO 961
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 961

Arg Ala Ser Gln Asn Ile Ala Met Gly Ser Val Ala
1 5 10

<210> SEQ ID NO 962
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 962

Arg Ala Ser Gln Asn Ile Arg Ser Gly Ser Val Ala
1 5 10

<210> SEQ ID NO 963
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 963

Trp Gly Ser Ser Leu Tyr Ser
1 5

<210> SEQ ID NO 964
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 964

Trp Gly Ser Tyr Leu Tyr Ser
1 5

<210> SEQ ID NO 965
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 965

Trp Gly Ser Ala Leu Tyr Ser
1 5

<210> SEQ ID NO 966
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 966

Trp Gly Ser Thr Leu Tyr Ser
1 5

<210> SEQ ID NO 967
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 967

Trp Gly Ser Asn Leu Tyr Ser
1 5

<210> SEQ ID NO 968
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 968

Trp Gly Ser Glu Leu Tyr Ser
1 5

<210> SEQ ID NO 969
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 969

Trp Gly Ser Leu Leu Tyr Ser
1 5

<210> SEQ ID NO 970
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 970

Gly Gly Ser Tyr Leu Tyr Ser
1 5

<210> SEQ ID NO 971
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 971

Trp Gly Ser Val Leu Tyr Ser
1 5

<210> SEQ ID NO 972
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 972

Gln Gln Tyr Tyr Thr Thr Pro Pro Thr
1 5

<210> SEQ ID NO 973
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 973

Arg Ala Ser Gln Asn Ile Arg Thr Gly Ser Val Ala
1 5 10

<210> SEQ ID NO 974
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 974

Arg Ala Ser Gln Asp Ile Arg Ala Gly Ser Val Ala
1 5 10

<210> SEQ ID NO 975
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 975

Arg Ala Ser Gln Asn Ile Tyr Ala Gly Ser Leu Ala
1 5 10

<210> SEQ ID NO 976
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 976

Arg Ala Ser Gln Asn Ile Tyr Ser Gly Ser Leu Ala
1 5 10

<210> SEQ ID NO 977
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 977

Arg Ala Ser Gln Asp Ile Pro Arg Ser Ile Ser Gly Tyr Val Ala
1 5 10 15

<210> SEQ ID NO 978
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 978

Arg Ala Ser Gln Asn Ile Arg Asn Gly Gly Gly Leu Ala
1 5 10

<210> SEQ ID NO 979
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 979

Arg Ala Ser Gln Asn Val Ser Lys His Val Ala
1 5 10

<210> SEQ ID NO 980
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 980

Arg Ala Ser Gln Gln Val Ser Lys Tyr Asp Val Ala
1 5 10

<210> SEQ ID NO 981
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 981

Arg Ala Ser Gln Asp Ile Pro Arg Ser Ile Ser Gly Tyr Val Ala
1 5 10 15

<210> SEQ ID NO 982
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 982

Arg Ala Ser Gln Asp Ile Gly Leu Gly Ser Val Ala
1 5 10

<210> SEQ ID NO 983
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 983

Arg Ala Ser Gln Asp Ile Arg Ser Gly Ser Val Ala
1 5 10

<210> SEQ ID NO 984
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 984

Arg Ala Ser Gln Asn Val Ser Lys His Val Ala
1 5 10

<210> SEQ ID NO 985
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 985

Arg Ala Ser Gln Asn Ile Arg Asn Gly Gly Gly Val Ala
1 5 10

<210> SEQ ID NO 986
<211> LENGTH: 7

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 986

Ser Ala Ser Phe His Tyr Ser
1 5

<210> SEQ ID NO 987
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 987

Trp Gly Ser Tyr Ser Tyr Ser
1 5

<210> SEQ ID NO 988
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 988

Trp Gly Ser Ser Ser Tyr Ser
1 5

<210> SEQ ID NO 989
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 989

Trp Ala Ser Tyr Leu Tyr Ser
1 5

<210> SEQ ID NO 990
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 990

Gln Gln His Phe Asn Ala Pro Pro Thr
1 5

<210> SEQ ID NO 991
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 991

Gln Gln Ser Tyr Ser Gly Pro Pro Thr 1 5

<210> SEQ ID NO 992
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 992

Gln Gln Ser Gly Phe Arg Ser Pro Pro Thr
1 5 10

<210> SEQ ID NO 993
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 993

Gln Gln Ser Tyr Ser Thr Pro Pro Thr
1 5

<210> SEQ ID NO 994
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 994

Gly Phe Asn Ile Ala Asp Thr Tyr Ile His
1 5 10

<210> SEQ ID NO 995
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 995

Gly Phe Asn Ile Lys Ala Thr Tyr Ile His
1 5 10

<210> SEQ ID NO 996
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 996

Gly Phe Asn Ile Lys Asp Ala Tyr Ile His
1 5 10

<210> SEQ ID NO 997
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 997

Gly Phe Asn Ile Lys Asp Thr Ala Ile His
1 5 10

<210> SEQ ID NO 998
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 998

Ala Ile Tyr Pro Thr Asn Gly Tyr Thr Arg Tyr Ala Asp Ser Val Lys
1 5 10 15

Gly

<210> SEQ ID NO 999
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 999

Arg Ile Ala Pro Thr Asn Gly Tyr Thr Arg Tyr Ala Asp Ser Val Lys
1 5 10 15

Gly

<210> SEQ ID NO 1000
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1000

Arg Ile Tyr Pro Ala Asn Gly Tyr Thr Arg Tyr Ala Asp Ser Val Lys
1 5 10 15

Gly

<210> SEQ ID NO 1001
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1001

Arg Ile Tyr Pro Thr Ala Gly Tyr Thr Arg Tyr Ala Asp Ser Val Lys
1 5 10 15

Gly

<210> SEQ ID NO 1002
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1002

Arg Ile Tyr Pro Thr Asn Gly Ala Thr Arg Tyr Ala Asp Ser Val Lys
1 5 10 15

Gly

<210> SEQ ID NO 1003
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1003

Trp Gly Gly Asp Gly Phe Tyr Ala Met Asp Val
1 5 10

<210> SEQ ID NO 1004
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1004

Ala Gly Gly Asp Gly Phe Tyr Ala Met Asp Tyr
1 5 10

<210> SEQ ID NO 1005
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1005

Trp Gly Gly Ala Gly Phe Tyr Ala Met Asp Tyr
1 5 10

<210> SEQ ID NO 1006
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1006

Trp Gly Gly Asp Ala Phe Tyr Ala Met Asp Tyr
1 5 10

<210> SEQ ID NO 1007
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1007

Trp Gly Gly Asp Gly Ala Tyr Ala Met Asp Tyr
1 5 10

<210> SEQ ID NO 1008
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1008

Trp Gly Gly Asp Gly Phe Ala Ala Met Asp Tyr
1               5                   10

<210> SEQ ID NO 1009
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1009

Trp Gly Gly Asp Gly Phe Phe Ala Met Asp Tyr
1               5                   10

<210> SEQ ID NO 1010
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1010

Gly Phe Asn Ile Lys Asp Thr Tyr Met His
1               5                   10

<210> SEQ ID NO 1011
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1011

Gly Phe Thr Phe Ser Asp Tyr Trp Met Asn
1               5                   10

<210> SEQ ID NO 1012
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1012

Gly Phe Thr Phe Ser Asp Tyr Trp Met Asn
1               5                   10

<210> SEQ ID NO 1013
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1013

```
Gly Phe Asn Ile Gly Lys Ser Ser Ile His
1               5                   10


<210> SEQ ID NO 1014
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1014

Gly Phe Asn Ile Asp Asn Thr Ala Ile His
1               5                   10


<210> SEQ ID NO 1015
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1015

Gly Phe Asn Ile Ala Asp Ser Ala Ile His
1               5                   10


<210> SEQ ID NO 1016
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1016

Gly Phe Thr Ile Gly Asn Ser Trp Ile His
1               5                   10


<210> SEQ ID NO 1017
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1017

Gly Phe Asn Ile Ala Asp Ser Ala Ile His
1               5                   10


<210> SEQ ID NO 1018
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1018

Gly Phe Thr Ile Thr Glu Ser Gly Ile His
1               5                   10


<210> SEQ ID NO 1019
<211> LENGTH: 10
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 1019

Gly Phe Asn Ile Thr Ala Tyr Gly Ile His
1 5 10

<210> SEQ ID NO 1020
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1020

Gly Phe Thr Ile Gly Gly Ser Trp Ile His
1 5 10

<210> SEQ ID NO 1021
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1021

Gly Phe Thr Ile Gly Gly Ser Trp Ile His
1 5 10

<210> SEQ ID NO 1022
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1022

Gly Phe Ser Ile Ala Gly Tyr Asp Ile His
1 5 10

<210> SEQ ID NO 1023
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1023

Gly Phe Ser Leu Thr Asn Tyr Gly Val His
1 5 10

<210> SEQ ID NO 1024
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1024

Gly Tyr Thr Phe Thr Ser Tyr Asn Met His
1 5 10

<210> SEQ ID NO 1025
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1025

Gly Phe Thr Phe Thr Asp Phe Tyr Met Asn
1               5                   10

<210> SEQ ID NO 1026
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1026

Gly Tyr Thr Phe Thr Asn Tyr Gly Met Asn
1               5                   10

<210> SEQ ID NO 1027
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1027

Gly Phe Thr Phe Thr Asp Tyr Thr Met Asp
1               5                   10

<210> SEQ ID NO 1028
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1028

Gly Gly Ser Val Ser Ser Gly Asp Tyr Tyr Trp Thr
1               5                   10

<210> SEQ ID NO 1029
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1029

Arg Ile Asp Pro Ala Asn Gly Asn Ser Lys Tyr Val Pro Lys Phe Gln
1               5                   10                  15

Gly

<210> SEQ ID NO 1030
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1030

Arg Ile Asp Pro Ala Asn Gly Asn Ser Lys Tyr Ala Asp Ser Val Lys
1 5 10 15

Gly

<210> SEQ ID NO 1031
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1031

Gln Ile Arg Asn Lys Pro Tyr Asn Tyr Glu Thr Tyr Tyr Ser Asp Ser
1 5 10 15

Val Lys Gly

<210> SEQ ID NO 1032
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1032

Gln Ile Arg Asn Lys Pro Tyr Asn Tyr Glu Thr Tyr Tyr Ala Asp Ser
1 5 10 15

Val Lys Gly

<210> SEQ ID NO 1033
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1033

Trp Ile Ser Pro Tyr Glu Gly Ala Thr Ala Tyr Ala Asp Ser Val Lys
1 5 10 15

Gly

<210> SEQ ID NO 1034
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1034

Val Ile Ser Pro His Asp Gly Thr Thr Tyr Tyr Ala Asp Ser Val Lys
1 5 10 15

Gly

<210> SEQ ID NO 1035
<211> LENGTH: 17
<212> TYPE: PRT
<213> ORGANISM: Artificial Sequence
<220> FEATURE:

<223> OTHER INFORMATION: Description of Artificial Sequence: Synthetic peptide

<400> SEQUENCE: 1035

Leu Ile Asp Pro Ser Ser Gly Tyr Thr Asp Tyr Ala Asp Ser Val Lys
1 5 10 15

Gly

<210> SEQ ID NO 1036
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1036

Val Ile Ala Pro Thr Tyr Gly Tyr Thr Asn Tyr Ala Asp Ser Val Lys
1 5 10 15

Gly

<210> SEQ ID NO 1037
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1037

Tyr Ile Ala Pro Tyr Asp Gly Tyr Thr Tyr Tyr Ala Asp Ser Val Lys
1 5 10 15

Gly

<210> SEQ ID NO 1038
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1038

Val Ile Tyr Pro His Asp Gly Lys Thr Tyr Tyr Ala Asp Ser Val Lys
1 5 10 15

Gly

<210> SEQ ID NO 1039
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1039

Val Ile Thr Pro Tyr Asp Gly Asp Thr Thr Tyr Ala Asp Ser Val Lys
1 5 10 15

Gly

<210> SEQ ID NO 1040
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1040

Val Ile Ser Pro Asp Tyr Gly Tyr Thr Asp Tyr Ala Asp Ser Val Lys
1 5 10 15

Gly

<210> SEQ ID NO 1041
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1041

Val Ile Tyr Pro Thr Tyr Gly Tyr Thr Asp Tyr Ala Asp Ser Val Lys
1 5 10 15

Gly

<210> SEQ ID NO 1042
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1042

Leu Ile Ala Pro Tyr Ala Gly Tyr Thr Asn Tyr Ala Asp Ser Val Lys
1 5 10 15

Gly

<210> SEQ ID NO 1043
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1043

Val Ile Trp Ser Gly Gly Asn Thr Asp Tyr Asn Thr Pro Phe Thr Ser
1 5 10 15

<210> SEQ ID NO 1044
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1044

Ala Ile Tyr Pro Gly Asn Gly Asp Thr Ser Tyr Asn Gln Lys Phe Lys
1 5 10 15

Gly

<210> SEQ ID NO 1045
<211> LENGTH: 19
<212> TYPE: PRT
<213> ORGANISM: Artificial Sequence
<220> FEATURE:

<223> OTHER INFORMATION: Description of Artificial Sequence: Synthetic peptide

<400> SEQUENCE: 1045

Phe Ile Arg Asp Lys Ala Lys Gly Tyr Thr Thr Glu Tyr Asn Pro Ser
1 5 10 15

Val Lys Gly

<210> SEQ ID NO 1046
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1046

Trp Ile Asn Thr Tyr Thr Gly Glu Pro Thr Tyr Ala Ala Asp Phe Lys
1 5 10 15

Arg

<210> SEQ ID NO 1047
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1047

Asp Val Asn Pro Asn Ser Gly Gly Ser Ile Tyr Asn Gln Arg Phe Lys
1 5 10 15

Gly

<210> SEQ ID NO 1048
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1048

His Ile Tyr Tyr Ser Gly Asn Thr Asn Tyr Asn Pro Ser Leu Lys Ser
1 5 10 15

<210> SEQ ID NO 1049
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1049

Phe Gly Tyr Tyr Val Ser Asp Tyr Ala Met Ala Tyr
1 5 10

<210> SEQ ID NO 1050
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1050

Ser Tyr Tyr Gly Met Asp Tyr
1 5

<210> SEQ ID NO 1051
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1051

Thr Ser Trp Ser Lys Pro Tyr Ala Met Asp Tyr
1 5 10

<210> SEQ ID NO 1052
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1052

Trp Gly Trp Glu Thr Asp Gly Ala Met Asp Tyr
1 5 10

<210> SEQ ID NO 1053
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1053

Ser Arg Ala Gly Tyr Thr Tyr Ala Met Asp Tyr
1 5 10

<210> SEQ ID NO 1054
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1054

Trp Gly Ala Lys Gly Thr Trp Ala Met Asp Tyr
1 5 10

<210> SEQ ID NO 1055
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1055

Trp Gly Trp Thr Thr Asn Gly Ala Met Asp Tyr
1 5 10

<210> SEQ ID NO 1056
<211> LENGTH: 11
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 1056

Trp Trp Tyr Ser Trp Asn Trp Ala Met Asp Tyr
1 5 10

<210> SEQ ID NO 1057
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1057

Trp Gly Trp Glu Ala Asn Trp Ala Met Asp Tyr
1 5 10

<210> SEQ ID NO 1058
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1058

Trp Gly Ser Gly Tyr Thr Trp Ala Met Asp Tyr
1 5 10

<210> SEQ ID NO 1059
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1059

Trp Gly Ala Gly Gly Thr Trp Ala Met Asp Tyr
1 5 10

<210> SEQ ID NO 1060
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1060

Ala Ala Ala Trp Ala Ser Tyr Ala Met Asp Tyr
1 5 10

<210> SEQ ID NO 1061
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1061

Ala Leu Thr Tyr Tyr Asp Tyr Glu Phe Ala Tyr
1 5 10

<210> SEQ ID NO 1062
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1062

Ser Thr Tyr Tyr Gly Gly Asp Trp Tyr Phe Asn Val
1 5 10

<210> SEQ ID NO 1063
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1063

Glu Gly His Thr Ala Ala Pro Phe Asp Tyr
1 5 10

<210> SEQ ID NO 1064
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1064

Tyr Pro His Tyr Tyr Gly Ser Ser His Trp Tyr Phe Asp Val
1 5 10

<210> SEQ ID NO 1065
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1065

Asn Leu Gly Pro Ser Phe Tyr Phe Asp Tyr
1 5 10

<210> SEQ ID NO 1066
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1066

Asp Arg Val Thr Gly Ala Phe Asp Ile
1 5

<210> SEQ ID NO 1067
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1067

Arg Ala Ser Gln Asn Val Asn Thr Ala Val Ala
1               5                   10

<210> SEQ ID NO 1068
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1068

Arg Ala Ser Gln Asp Val Ala Thr Ala Val Ala
1               5                   10

<210> SEQ ID NO 1069
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1069

Arg Ala Ser Gln Asp Val Asn Ala Ala Val Ala
1               5                   10

<210> SEQ ID NO 1070
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1070

Arg Ala Ser Gln Asn Val Trp Asp Trp Val Ala
1               5                   10

<210> SEQ ID NO 1071
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1071

Arg Ala Ser Gln Asp Ile Pro Arg Ser Ile Ser Gly Tyr Val Ala
1               5                   10                  15

<210> SEQ ID NO 1072
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1072

Arg Ala Ser Gln Asp Ile Gly Leu Gly Ser Val Ala
1               5                   10

<210> SEQ ID NO 1073
<211> LENGTH: 12

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1073

Arg Ala Ser Gln Asp Ile Arg Ser Gly Ser Val Ala
1 5 10

<210> SEQ ID NO 1074
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1074

Arg Ala Ser Gln Asp Ile Trp Asn Arg Arg Ala Leu Ala
1 5 10

<210> SEQ ID NO 1075
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1075

Arg Ala Ser Gln Asn Val Gly Arg Pro Val Ala
1 5 10

<210> SEQ ID NO 1076
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1076

Arg Ala Ser Gln Asn Val Ser Lys His Val Ala
1 5 10

<210> SEQ ID NO 1077
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1077

Arg Ala Ser Gln Asn Ile Arg Asn Gly Gly Gly Leu Ala
1 5 10

<210> SEQ ID NO 1078
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1078

Arg Ala Ser Gln Ser Val Asp Ile Phe Gly Val Gly Phe Leu His 1 5 10 15

<210> SEQ ID NO 1079
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1079

Arg Ala Ser Gln Ser Val Asp Ile Phe Gly Val Gly Phe Leu His
1 5 10 15

<210> SEQ ID NO 1080
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1080

Arg Ser Ser Gln Ser Leu Val His Ser Gln Gly Asn Thr Tyr Leu Arg
1 5 10 15

<210> SEQ ID NO 1081
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1081

Arg Ala Ser Gln Ser Leu Val His Ser Gln Gly Asn Thr Tyr Leu Arg
1 5 10 15

<210> SEQ ID NO 1082
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1082

Arg Ala Ser Gln Ser Ile Gly Thr Asn Ile His
1 5 10

<210> SEQ ID NO 1083
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1083

Arg Ala Ser Ser Ser Val Ser Tyr Ile His
1 5 10

<210> SEQ ID NO 1084
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1084

Lys Ala Ser Gln Asn Ile Asp Lys Tyr Leu Asn
1 5 10

<210> SEQ ID NO 1085
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1085

Ser Ala Ser Gln Asp Ile Ser Asn Tyr Leu Asn
1 5 10

<210> SEQ ID NO 1086
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1086

Lys Ala Ser Gln Asp Val Ser Ile Gly Val Ala
1 5 10

<210> SEQ ID NO 1087
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1087

Gln Ala Ser Gln Asp Ile Ser Asn Tyr Leu Asn
1 5 10

<210> SEQ ID NO 1088
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1088

Ser Ala Ser Phe Leu Glu Ser
1 5

<210> SEQ ID NO 1089
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1089

Ala Ala Ser Phe Leu Tyr Ser
1 5

<210> SEQ ID NO 1090

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1090

Ser Ala Ala Phe Leu Tyr Ser
1 5

<210> SEQ ID NO 1091
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1091

Ser Ala Ser Asn Leu Tyr Ser
1 5

<210> SEQ ID NO 1092
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1092

Pro Ala Ser Ser Leu Tyr Ser
1 5

<210> SEQ ID NO 1093
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1093

Trp Gly Ser Tyr Leu Tyr Ser
1 5

<210> SEQ ID NO 1094
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1094

Trp Ala Ser Tyr Leu Tyr Ser
1 5

<210> SEQ ID NO 1095
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1095

Trp Gly Ser Tyr Leu Tyr Ser
1 5

<210> SEQ ID NO 1096
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1096

Glu Gly Ser Phe Leu Tyr Ser
1 5

<210> SEQ ID NO 1097
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1097

Gly Gly Ser Phe Leu Tyr Ser
1 5

<210> SEQ ID NO 1098
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1098

Ser Gly Ser Tyr Leu Tyr Ser
1 5

<210> SEQ ID NO 1099
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1099

Ser Ala Ser Phe Leu Tyr Ser
1 5

<210> SEQ ID NO 1100
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1100

Arg Ala Ser Asn Leu Glu Ser
1 5

<210> SEQ ID NO 1101
<211> LENGTH: 7
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 1101

Arg Ala Ser Asn Leu Glu Ser
1 5

<210> SEQ ID NO 1102
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1102

Lys Val Ser Asn Arg Phe Ser
1 5

<210> SEQ ID NO 1103
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1103

Lys Val Ser Asn Arg Phe Ser
1 5

<210> SEQ ID NO 1104
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1104

Tyr Ala Ser Glu Ser Ile Ser
1 5

<210> SEQ ID NO 1105
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1105

Ala Thr Ser Asn Leu Ala Ser
1 5

<210> SEQ ID NO 1106
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1106

Asn Thr Asn Asn Leu Gln Thr
1 5

<210> SEQ ID NO 1107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1107

Phe Thr Ser Ser Leu His Ser
1               5

<210> SEQ ID NO 1108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1108

Ser Ala Ser Tyr Arg Tyr Thr
1               5

<210> SEQ ID NO 1109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1109

Asp Ala Ser Asn Leu Glu Thr
1               5

<210> SEQ ID NO 1110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1110

Gln Gln Ala Tyr Thr Thr Pro Pro Thr
1               5

<210> SEQ ID NO 1111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1111

Gln Gln Phe Tyr Thr Thr Pro Pro Thr
1               5

<210> SEQ ID NO 1112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1112

Gln Gln His Ala Thr Thr Pro Pro Thr
1 5

<210> SEQ ID NO 1113
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1113

Gln Gln His Phe Thr Thr Pro Pro Thr
1 5

<210> SEQ ID NO 1114
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1114

Gln Gln His Tyr Ala Thr Pro Pro Thr
1 5

<210> SEQ ID NO 1115
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1115

Gln Gln His Tyr Thr Ala Pro Pro Thr
1 5

<210> SEQ ID NO 1116
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1116

Gln Gln Gly Trp Tyr Ile Ala Pro Pro Thr
1 5 10

<210> SEQ ID NO 1117
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1117

Gln Gln Gly Gly Ser Tyr Ser Ser Pro Pro Thr
1 5 10

<210> SEQ ID NO 1118
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1118

Gln Gln Tyr Gly Ser Phe Gly Thr Pro Pro Thr
1 5 10

<210> SEQ ID NO 1119
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1119

Gln Gln Ser Tyr Ser Gly Pro Pro Thr
1 5

<210> SEQ ID NO 1120
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1120

Gln Gln Thr Asn Glu Asp Pro Tyr Thr
1 5

<210> SEQ ID NO 1121
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1121

Gln Gln Thr Asn Glu Asp Pro Tyr Thr
1 5

<210> SEQ ID NO 1122
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1122

Ser Gln Ser Thr His Val Pro Trp Thr
1 5

<210> SEQ ID NO 1123
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1123

Gln Gln Ser Thr His Val Pro Trp Thr
1 5

<210> SEQ ID NO 1124
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1124

Gln Gln Asn Asn Asn Trp Pro Thr Thr
1 5

<210> SEQ ID NO 1125
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1125

Gln Gln Trp Thr Ser Asn Pro Pro Thr
1 5

<210> SEQ ID NO 1126
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1126

Leu Gln His Ile Ser Arg Pro Arg Thr
1 5

<210> SEQ ID NO 1127
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1127

Gln Gln Tyr Ser Thr Val Pro Trp Thr
1 5

<210> SEQ ID NO 1128
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1128

Gln Gln Tyr Tyr Ile Tyr Pro Tyr Thr
1 5

<210> SEQ ID NO 1129
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1129

Gln His Phe Asp His Leu Pro Leu Ala
1 5

<210> SEQ ID NO 1130
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1130

Ala Asp Thr Ser Lys Asn Thr Ala Tyr Leu Gln Met Asn Ser Leu Arg
1 5 10 15

Ala Glu Asp Thr Ala Val Tyr Tyr Cys Ser Arg
20 25

<210> SEQ ID NO 1131
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1131

Arg Asp Thr Ser Lys Asn Thr Ala Tyr Leu Gln Met Asn Ser Leu Arg
1 5 10 15

Ala Glu Asp Thr Ala Val Tyr Tyr Cys Ser Arg
20 25

<210> SEQ ID NO 1132
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1132

Ala Asp Thr Ser Lys Asn Thr Ala Tyr Leu Gln Met Asn Thr Leu Arg
1 5 10 15

Ala Glu Asp Thr Ala Val Tyr Tyr Cys Ser Arg
20 25

<210> SEQ ID NO 1133
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1133

Ala Asp Thr Ser Lys Asn Thr Ala Tyr Leu Gln Met Asn Ser Leu Arg
1 5 10 15

Ala Glu Asp Thr Cys Val Tyr Tyr Cys Ser Arg
20 25

<210> SEQ ID NO 1134
<211> LENGTH: 27
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 1134

Arg Asp Asn Ser Lys Asn Thr Leu Tyr Leu Gln Met Asn Ser Leu Arg
1               5                   10                  15

Ala Glu Asp Thr Ala Val Tyr Tyr Cys Ser Arg
            20                  25

<210> SEQ ID NO 1135
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1135

Ala Asp Thr Ser Lys Asn Thr Ala Tyr Leu Gln Met Asn Ser Leu Arg
1               5                   10                  15

Ala Glu Asp Thr Ala Val Tyr Tyr Cys Ala Arg
            20                  25

<210> SEQ ID NO 1136
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1136

Ala Asp Thr Ser Lys Asn Thr Ala Tyr Leu Gln Met Asn Ser Leu Arg
1               5                   10                  15

Ala Glu Asp Thr Ala Thr Tyr Tyr Cys Ser Arg
            20                  25

<210> SEQ ID NO 1137
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1137

Arg Asp Asp Ser Lys Asn Thr Leu Tyr Leu Gln Met Asn Ser Leu Arg
1               5                   10                  15

Ala Glu Asp Thr Ala Val Tyr Tyr Cys Ala Arg
            20                  25

<210> SEQ ID NO 1138
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1138

Ala Asp Asp Ser Lys Asn Thr Leu Tyr Leu Gln Met Asn Ser Leu Arg
1               5                   10                  15

Ala Glu Asp Thr Ala Val Tyr Tyr Cys Ala Arg
            20                  25

<210> SEQ ID NO 1139
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1139

```
Ala Asp Thr Ser Lys Asn Thr Leu Tyr Leu Gln Met Asn Ser Leu Arg
1               5                   10                  15

Ala Glu Asp Thr Ala Val Tyr Tyr Cys Ser Arg
            20                  25
```

<210> SEQ ID NO 1140
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1140

```
Arg Asp Asp Ser Lys Asn Thr Leu Tyr Leu Gln Met Asn Ser Leu Arg
1               5                   10                  15

Ala Glu Asp Thr Ala Val Tyr Tyr Cys Ala Arg
            20                  25
```

<210> SEQ ID NO 1141
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1141

```
Ala Asp Thr Ser Lys Asn Thr Ala Tyr Leu Gln Met Asn Ser Leu Arg
1               5                   10                  15

Ala Glu Asp Thr Ala Val Tyr Tyr Cys Ala Lys
            20                  25
```

<210> SEQ ID NO 1142
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1142

```
Ala Asp Thr Ser Lys Asn Thr Ala Tyr Leu Gln Met Asn Ser Leu Arg
1               5                   10                  15

Ala Glu Asp Thr Ala Val Tyr Tyr Cys Ala Arg
            20                  25
```

<210> SEQ ID NO 1143
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1143

```
Ala Asp Thr Ser Lys Asn Thr Ala Tyr Leu Gln Met Asn Ser Leu Arg
1               5                   10                  15

Ala Glu Asp Thr Ala Val Tyr Tyr Cys Thr Ser
            20                  25


<210> SEQ ID NO 1144
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1144

Ala Asp Thr Ser Lys Asn Thr Ala Tyr Leu Gln Met Asn Ser Leu Arg
1               5                   10                  15

Ala Glu Asp Thr Ala Val Tyr Tyr Cys Gly Leu
            20                  25


<210> SEQ ID NO 1145
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1145

Ala Asp Thr Ser Lys Asn Thr Ala Tyr Leu Gln Met Asn Ser Leu Arg
1               5                   10                  15

Ala Glu Asp Thr Ala Val Tyr Tyr Cys Gly Val
            20                  25


<210> SEQ ID NO 1146
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1146

Ala Asp Thr Ser Lys Asn Thr Ala Tyr Leu Gln Met Asn Ser Leu Arg
1               5                   10                  15

Ala Glu Asp Thr Ala Val Tyr Tyr Cys Arg Thr
            20                  25


<210> SEQ ID NO 1147
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1147

Ala Asp Thr Ser Lys Asn Thr Ala Tyr Leu Gln Met Asn Ser Leu Arg
1               5                   10                  15

Ala Glu Asp Thr Ala Val Tyr Tyr Cys Ser Thr
            20                  25


<210> SEQ ID NO 1148
<211> LENGTH: 27
<212> TYPE: PRT
<213> ORGANISM: Artificial Sequence
```

<220> FEATURE:
<223> OTHER INFORMATION: Description of Artificial Sequence: Synthetic peptide

<400> SEQUENCE: 1148

Ala Asp Thr Ser Lys Asn Thr Ala Tyr Leu Gln Met Asn Ser Leu Arg
1 5 10 15

Ala Glu Asp Thr Ala Val Tyr Tyr Cys Thr Ser
20 25

<210> SEQ ID NO 1149
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1149

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Pro
20 25

<210> SEQ ID NO 1150
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1150

Ala Asp Thr Ser Lys Asn Thr Ala Tyr Leu Gln Met Asn Ser Leu Arg
1 5 10 15

Ala Glu Asp Thr Ala Val Tyr Tyr Cys Ser Thr
20 25

<210> SEQ ID NO 1151
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1151

Ala Asp Thr Ser Lys Asn Thr Ala Tyr Leu Gln Met Asn Ser Leu Arg
1 5 10 15

Ala Glu Asp Thr Ala Val Tyr Tyr Cys Val Thr
20 25

<210> SEQ ID NO 1152
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1152

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Thr
20 25

<210> SEQ ID NO 1153
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1153

Ala Asp Thr Ser Lys Asn Thr Ala Tyr Leu Gln Met Asn Ser Leu Arg
1               5                   10                  15

Ala Glu Asp Thr Ala Val Tyr Tyr Cys Leu Ser
            20                  25

<210> SEQ ID NO 1154
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1154

Ala Asp Thr Ser Lys Asn Thr Ala Tyr Leu Gln Met Asn Ser Leu Arg
1               5                   10                  15

Ala Glu Asp Thr Ala Val Tyr Tyr Cys Ser Ala
            20                  25

<210> SEQ ID NO 1155
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1155

Ala Asp Thr Ser Lys Asn Thr Ala Tyr Leu Gln Met Asn Ser Leu Arg
1               5                   10                  15

Ala Glu Asp Thr Ala Val Tyr Tyr Cys Met Lys
            20                  25

<210> SEQ ID NO 1156
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1156

Ala Asp Thr Ser Lys Asn Thr Ala Tyr Leu Gln Met Asn Ser Leu Arg
1               5                   10                  15

Ala Glu Asp Thr Ala Val Tyr Tyr Cys Thr Ser
            20                  25

<210> SEQ ID NO 1157
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1157

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Ser
20 25

<210> SEQ ID NO 1158
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1158

Ala Asp Thr Ser Lys Asn Thr Ala Tyr Leu Gln Met Asn Ser Leu Arg
1 5 10 15

Ala Glu Asp Thr Ala Val Tyr Tyr Cys Ile Arg
20 25

<210> SEQ ID NO 1159
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1159

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Ser
20 25

<210> SEQ ID NO 1160
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1160

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Gly
20 25

<210> SEQ ID NO 1161
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1161

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Phe
20 25

<210> SEQ ID NO 1162
<211> LENGTH: 27
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 1162

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Thr
20 25

<210> SEQ ID NO 1163
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1163

Ala Asp Thr Ser Lys Asn Thr Ala Tyr Leu Gln Met Asn Ser Leu Arg
1 5 10 15

Ala Glu Asp Thr Ala Val Tyr Tyr Cys Ser Met
20 25

<210> SEQ ID NO 1164
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1164

Ala Asp Thr Ser Lys Asn Thr Ala Tyr Leu Gln Met Asn Ser Leu Arg
1 5 10 15

Ala Glu Asp Thr Ala Val Tyr Ser Cys Gly Ala
20 25

<210> SEQ ID NO 1165
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1165

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Ser
20 25

<210> SEQ ID NO 1166
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1166

Ala Asp Thr Ser Lys Asn Thr Ala Tyr Leu Gln Met Asn Ser Leu Arg
1 5 10 15

Ala Glu Asp Thr Ala Val Tyr Phe Cys Thr Thr 20 25

<210> SEQ ID NO 1167
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1167

Ala Asp Thr Ser Lys Asn Thr Ala Tyr Leu Gln Met Asn Ser Leu Arg
1 5 10 15

Ala Glu Asp Thr Ala Val Tyr Asn Cys Thr Thr
20 25

<210> SEQ ID NO 1168
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1168

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Met
20 25

<210> SEQ ID NO 1169
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1169

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Thr
20 25

<210> SEQ ID NO 1170
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1170

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Pro
20 25

<210> SEQ ID NO 1171
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1171

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Thr
20 25

<210> SEQ ID NO 1172
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1172

Ala Asp Thr Ser Lys Asn Thr Ala Tyr Leu Gln Met Asn Ser Leu Arg
1 5 10 15

Ala Glu Asp Thr Ala Val Tyr Tyr Cys Thr Thr
20 25

<210> SEQ ID NO 1173
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1173

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Met
20 25

<210> SEQ ID NO 1174
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1174

Ala Asp Thr Ser Lys Asn Thr Ala Tyr Leu Gln Met Asn Ser Leu Arg
1 5 10 15

Ala Glu Asp Thr Ala Val Tyr Arg Cys Ile Thr
20 25

<210> SEQ ID NO 1175
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1175

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Ser
20 25

<210> SEQ ID NO 1176
<211> LENGTH: 27

<212> TYPE: PRT
<213> ORGANISM: Artificial Sequence
<220> FEATURE:
<223> OTHER INFORMATION: Description of Artificial Sequence: Synthetic peptide

<400> SEQUENCE: 1176

Ala Asp Thr Ser Lys Asn Thr Ala Tyr Leu Gln Met Asn Ser Leu Arg
1 5 10 15

Ala Glu Asp Thr Ala Val Tyr Val Cys Arg Ala
20 25

<210> SEQ ID NO 1177
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1177

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Met
20 25

<210> SEQ ID NO 1178
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1178

Ala Asp Thr Ser Lys Asn Thr Ala Tyr Leu Gln Met Asn Ser Leu Arg
1 5 10 15

Ala Glu Asp Thr Ala Val Tyr His Cys Val Thr
20 25

<210> SEQ ID NO 1179
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1179

Ala Asp Thr Ser Lys Asn Thr Ala Tyr Leu Gln Met Asn Ser Leu Arg
1 5 10 15

Ala Glu Asp Thr Ala Val Tyr Tyr Cys Thr Arg
20 25

<210> SEQ ID NO 1180
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1180

Ala Asp Thr Ser Lys Asn Thr Ala Tyr Leu Gln Met Asn Ser Leu Arg
1 5 10 15

Ala Glu Asp Thr Ala Val Tyr Tyr Cys Gln Thr
20 25

<210> SEQ ID NO 1181
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1181

Ala Asp Thr Ser Lys Asn Thr Ala Tyr Leu Gln Met Asn Ser Leu Arg
1 5 10 15

Ala Glu Asp Thr Ala Val Tyr Tyr Cys Lys Thr
20 25

<210> SEQ ID NO 1182
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1182

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Ala
20 25

<210> SEQ ID NO 1183
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1183

Ala Asp Thr Ser Lys Asn Thr Ala Tyr Leu Gln Met Asn Ser Leu Arg
1 5 10 15

Ala Glu Asp Thr Ala Val Tyr Tyr Cys Ser Met
20 25

<210> SEQ ID NO 1184
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1184

Ala Asp Thr Ser Lys Asn Thr Ala Tyr Leu Gln Met Asn Ser Leu Arg
1 5 10 15

Ala Glu Asp Thr Ala Val Tyr Tyr Cys Val Ser
20 25

<210> SEQ ID NO 1185
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1185

Ala Asp Thr Ser Lys Asn Thr Ala Tyr Leu Gln Met Asn Ser Leu Arg
1 5 10 15

Ala Glu Asp Thr Ala Val Tyr Arg Cys Gly Met
20 25

<210> SEQ ID NO 1186
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1186

Ala Asp Thr Ser Lys Asn Thr Ala Tyr Leu Gln Met Asn Ser Leu Arg
1 5 10 15

Ala Glu Asp Thr Ala Val Tyr Lys Cys Arg Thr
20 25

<210> SEQ ID NO 1187
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1187

Ala Asp Thr Ser Lys Asn Thr Ala Tyr Leu Gln Met Asn Ser Leu Arg
1 5 10 15

Ala Glu Asp Thr Ala Val Tyr Tyr Cys Lys Thr
20 25

<210> SEQ ID NO 1188
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1188

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Thr
20 25

<210> SEQ ID NO 1189
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1189

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Ser
20 25

<210> SEQ ID NO 1190

<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1190

Ala Asp Thr Ser Lys Asn Thr Ala Tyr Leu Gln Met Asn Ser Leu Arg
1 5 10 15

Ala Glu Asp Thr Ala Val Tyr Phe Cys Ser Thr
20 25

<210> SEQ ID NO 1191
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1191

Ala Asp Thr Ser Lys Asn Thr Ala Tyr Leu Gln Met Asn Ser Leu Arg
1 5 10 15

Ala Glu Asp Thr Ala Val Tyr Tyr Cys Gly Thr
20 25

<210> SEQ ID NO 1192
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1192

Ala Asp Thr Ser Lys Asn Thr Ala Tyr Leu Gln Met Asn Ser Leu Arg
1 5 10 15

Ala Glu Asp Thr Ala Val Tyr Tyr Cys Ser Thr
20 25

<210> SEQ ID NO 1193
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1193

Ala Asp Thr Ser Lys Asn Thr Ala Tyr Leu Gln Met Asn Ser Leu Arg
1 5 10 15

Ala Glu Asp Thr Ala Val Tyr Ser Cys Arg Thr
20 25

<210> SEQ ID NO 1194
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1194

Ala Asp Thr Ser Lys Asn Thr Ala Tyr Leu Gln Met Asn Ser Leu Arg
1 5 10 15

Ala Glu Asp Thr Ala Val Tyr His Cys Ile Thr
20 25

<210> SEQ ID NO 1195
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1195

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Ala
20 25

<210> SEQ ID NO 1196
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1196

Ala Asp Thr Ser Lys Asn Thr Ala Tyr Leu Gln Met Asn Ser Leu Arg
1 5 10 15

Ala Glu Asp Thr Ala Val Tyr Ser Cys Arg Met
20 25

<210> SEQ ID NO 1197
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1197

Ala Asp Thr Ser Lys Asn Thr Ala Tyr Leu Gln Met Asn Ser Leu Arg
1 5 10 15

Ala Glu Asp Thr Ala Val Tyr Phe Cys Arg Thr
20 25

<210> SEQ ID NO 1198
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1198

Ala Asp Thr Ser Lys Asn Thr Ala Tyr Leu Gln Met Asn Ser Leu Arg
1 5 10 15

Ala Glu Asp Thr Ala Val Tyr Tyr Cys Thr Thr
20 25

<210> SEQ ID NO 1199
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1199

Ala Asp Thr Ser Lys Asn Thr Ala Tyr Leu Gln Met Asn Ser Leu Arg
1 5 10 15

Ala Glu Asp Thr Ala Val Tyr Tyr Cys Ser Ile
20 25

<210> SEQ ID NO 1200
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1200

Ala Asp Thr Ser Lys Asn Thr Ala Tyr Leu Gln Met Asn Ser Leu Arg
1 5 10 15

Ala Glu Asp Thr Ala Val Tyr Tyr Cys Ala Thr
20 25

<210> SEQ ID NO 1201
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1201

Ala Asp Thr Ser Lys Asn Thr Ala Tyr Leu Gln Met Asn Ser Leu Arg
1 5 10 15

Ala Glu Asp Thr Ala Val Tyr Tyr Cys Val Thr
20 25

<210> SEQ ID NO 1202
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1202

Ala Asp Thr Ser Lys Asn Thr Ala Tyr Leu Gln Met Asn Ser Leu Arg
1 5 10 15

Ala Glu Asp Thr Ala Val Tyr Tyr Cys Arg Val
20 25

<210> SEQ ID NO 1203
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1203

Ala Asp Thr Ser Lys Asn Thr Ala Tyr Leu Gln Met Asn Ser Leu Arg
1 5 10 15

Ala Glu Asp Thr Ala Val Tyr Tyr Cys Lys Thr
20 25

<210> SEQ ID NO 1204
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1204

```
Ala Asp Thr Ser Lys Asn Thr Ala Tyr Leu Gln Met Asn Ser Leu Arg
1               5                   10                  15

Ala Glu Asp Thr Ala Val Tyr Tyr Cys Gly Arg
            20                  25
```

<210> SEQ ID NO 1205
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1205

```
Ala Asp Thr Ser Lys Asn Thr Ala Tyr Leu Gln Met Asn Ser Leu Arg
1               5                   10                  15

Ala Glu Asp Thr Ala Val Tyr Phe Cys Arg Ala
            20                  25
```

<210> SEQ ID NO 1206
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1206

```
Ala Asp Thr Ser Lys Asn Thr Ala Tyr Leu Gln Met Asn Ser Leu Arg
1               5                   10                  15

Ala Glu Asp Thr Ala Val Tyr Tyr Cys Lys Met
            20                  25
```

<210> SEQ ID NO 1207
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1207

```
Ala Asp Thr Ser Lys Asn Thr Ala Tyr Leu Gln Met Asn Ser Leu Arg
1               5                   10                  15

Ala Glu Asp Thr Ala Val Tyr Ser Cys Lys Thr
            20                  25
```

<210> SEQ ID NO 1208
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1208

```
Ala Asp Thr Ser Lys Asn Thr Ala Tyr Leu Gln Met Asn Ser Leu Arg
```

1 5 10 15

Ala Glu Asp Thr Ala Val Tyr Ser Cys Arg Ser
20 25

<210> SEQ ID NO 1209
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1209

Ala Asp Thr Ser Lys Asn Thr Ala Tyr Leu Gln Met Asn Ser Leu Arg
1 5 10 15

Ala Glu Asp Thr Ala Val Tyr His Cys Arg Ile
20 25

<210> SEQ ID NO 1210
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1210

Ala Asp Thr Ser Lys Asn Thr Ala Tyr Leu Gln Met Asn Ser Leu Arg
1 5 10 15

Ala Glu Asp Thr Ala Val Tyr Gln Cys Ser Thr
20 25

<210> SEQ ID NO 1211
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1211

Ala Asp Asn Thr Gln Asn Met Ala Tyr Leu Gln Met Asn Ser Leu Arg
1 5 10 15

Ala Glu Asp Thr Ala Val Tyr Tyr Cys Ser Arg
20 25

<210> SEQ ID NO 1212
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1212

Ala Asp Thr Ser Ser Asn Thr Ala Tyr Leu Gln Val Ser Arg Leu Thr
1 5 10 15

Ser Glu Asp Thr Ala Val Tyr Tyr Cys Ser Arg
20 25

<210> SEQ ID NO 1213
<211> LENGTH: 27
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 1213

Arg Asp Asn Ser Lys Asn Thr Leu Tyr Leu Gln Met Asn Ser Leu Arg
1               5                   10                  15

Ala Glu Asp Thr Ala Val Tyr Tyr Cys Ser Arg
            20                  25

<210> SEQ ID NO 1214
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1214

Ala Asp Thr Ser Lys Asn Thr Ala Tyr Leu Gln Met Asn Ser Leu Pro
1               5                   10                  15

Ala Glu Asp Thr Ala Val Tyr Tyr Cys Ser Arg
            20                  25

<210> SEQ ID NO 1215
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1215

Val Asp Arg Ser Ser Arg Ile Val Tyr Met Glu Leu Arg Ser Leu Thr
1               5                   10                  15

Phe Glu Asp Thr Ala Val Tyr Tyr Cys Ala Arg
            20                  25

<210> SEQ ID NO 1216
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1216

Val Asp Arg Ser Lys Asn Thr Leu Tyr Leu Gln Met Asn Ser Leu Arg
1               5                   10                  15

Ala Glu Asp Thr Ala Val Tyr Tyr Cys Ala Arg
            20                  25

<210> SEQ ID NO 1217
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1217

Val Asp Thr Ser Lys Asn Thr Ala Tyr Leu Gln Met Asn Ser Leu Arg
1               5                   10                  15

Ala Glu Asp Thr Ala Val Tyr Tyr Cys Ser Arg
            20                  25

<210> SEQ ID NO 1218
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1218

Ala Asp Arg Ser Lys Asn Thr Ala Tyr Leu Gln Met Asn Ser Leu Arg
1               5                   10                  15

Ala Glu Asp Thr Ala Val Tyr Tyr Cys Ser Arg
            20                  25

<210> SEQ ID NO 1219
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1219

Val Asp Arg Ser Lys Asn Thr Ala Tyr Leu Gln Met Asn Ser Leu Arg
1               5                   10                  15

Ala Glu Asp Thr Ala Val Tyr Tyr Cys Ser Arg
            20                  25

<210> SEQ ID NO 1220
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1220

Val Asp Arg Ser Lys Asn Thr Ala Tyr Leu Gln Met Asn Ser Leu Arg
1               5                   10                  15

Ala Glu Asp Thr Ala Val Tyr Tyr Cys Ser Arg
            20                  25

<210> SEQ ID NO 1221
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1221

Val Asp Arg Ser Lys Asn Thr Ala Tyr Leu Gln Met Asn Ser Leu Arg
1               5                   10                  15

Ala Glu Asp Thr Ala Val Tyr Tyr Cys Ser Arg
            20                  25

<210> SEQ ID NO 1222
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1222

Val Asp Arg Ser Lys Asn Thr Val Tyr Leu Gln Met Asn Ser Leu Arg
1               5                   10                  15

Ala Glu Asp Thr Ala Val Tyr Tyr Cys Ser Arg
            20                  25

<210> SEQ ID NO 1223
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1223

Val Asp Arg Ser Lys Asn Thr Ala Tyr Leu Gln Met Asn Ser Leu Arg
1               5                   10                  15

Ala Glu Asp Thr Ala Val Tyr Tyr Cys Ser Arg
            20                  25

<210> SEQ ID NO 1224
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1224

Val Asp Arg Ser Lys Asn Thr Ala Tyr Leu Gln Met Asn Ser Leu Arg
1               5                   10                  15

Ala Glu Asp Thr Ala Val Tyr Tyr Cys Ser Arg
            20                  25

<210> SEQ ID NO 1225
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1225

Thr Cys Arg Ala Ser Gln Asp Val Asn Thr Ala Val Ala Trp Tyr Gln
1               5                   10                  15

Gln Lys Pro Gly Lys Ala
            20

<210> SEQ ID NO 1226
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1226

Asn Cys Lys Ala Ser Gln Asp Val Asn Thr Ala Val Ala Trp Tyr Gln
1               5                   10                  15

Gln Lys Pro Gly Lys Ala
            20

<210> SEQ ID NO 1227
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1227

```
Thr Cys Arg Ala Ser Ser Gln Val Ser Ser Gly Val Ala Trp Tyr Gln
1               5                   10                  15

Gln Lys Pro Gly Lys Ala
            20
```

<210> SEQ ID NO 1228
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1228

```
Thr Cys Arg Ala Ser Arg Gln Val Asn Thr Ala Val Ala Trp Tyr Gln
1               5                   10                  15

Gln Lys Pro Gly Lys Ala
            20
```

<210> SEQ ID NO 1229
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1229

```
Thr Cys Arg Ala Ser Ala Gln Val Ser Ala Gly Val Ala Trp Tyr Gln
1               5                   10                  15

Gln Lys Pro Gly Lys Ala
            20
```

<210> SEQ ID NO 1230
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1230

```
Thr Cys Arg Ala Ser Gln Gly Val Ser Ser Gly Val Ala Trp Tyr Gln
1               5                   10                  15

Gln Lys Pro Gly Lys Ala
            20
```

<210> SEQ ID NO 1231
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1231

```
Thr Cys Arg Ala Ser Gln Gly Val Ser Ser Ala Val Ala Trp Tyr Gln
1               5                   10                  15

Gln Lys Pro Gly Lys Ala
            20
```

-continued

<210> SEQ ID NO 1232
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1232

Thr Cys Arg Ala Ser Gln Arg Val Asn Ser Ala Val Ala Trp Tyr Gln
1               5                   10                  15

Gln Lys Pro Gly Lys Ala
            20

<210> SEQ ID NO 1233
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1233

Thr Cys Arg Ala Ser Gln Gly Val Ser Ser Ala Val Ala Trp Tyr Gln
1               5                   10                  15

Gln Lys Pro Gly Lys Ala
            20

<210> SEQ ID NO 1234
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1234

Thr Cys Arg Ala Ser Asn Pro Val Ser Gln Ala Val Ala Trp Tyr Gln
1               5                   10                  15

Gln Lys Pro Gly Lys Ala
            20

<210> SEQ ID NO 1235
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1235

Thr Cys Arg Ala Ser Ser Gln Val Ser Lys Ala Val Ala Trp Tyr Gln
1               5                   10                  15

Gln Lys Pro Gly Lys Ala
            20

<210> SEQ ID NO 1236
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1236

Thr Cys Arg Ala Ser Phe Asp Val Asn Ala Cys Val Ala Trp Tyr Gln
1 5 10 15

Gln Lys Pro Gly Lys Ala
20

<210> SEQ ID NO 1237
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1237

Thr Cys Arg Ala Ser Gln Ser Val Ser Ser Ala Val Ala Trp Tyr Gln
1 5 10 15

Gln Lys Pro Gly Lys Ala
20

<210> SEQ ID NO 1238
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1238

Thr Cys Arg Ala Ser Gln Asp Val Asn Ser Tyr Leu Ala Trp Tyr Gln
1 5 10 15

Gln Lys Pro Gly Lys Ala
20

<210> SEQ ID NO 1239
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1239

Thr Cys Arg Ala Ser Gln Asn Val Asp Lys Tyr Val Ala Trp Tyr Gln
1 5 10 15

Gln Lys Pro Gly Lys Ala
20

<210> SEQ ID NO 1240
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1240

Pro Lys Leu Leu Ile Tyr Ser Ala Ser Phe Leu Tyr Ser Gly Val Pro
1 5 10 15

Ser Arg Phe Ser Gly Ser Arg
20

<210> SEQ ID NO 1241
<211> LENGTH: 23
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 1241

Pro Lys Leu Leu Ile Tyr Ser Ala Ser Phe Leu Tyr Ser Gly Val Pro
1 5 10 15

Ser Arg Phe Ser Gly Ser Gly
20

<210> SEQ ID NO 1242
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1242

Pro Lys Leu Leu Ile Tyr Ser Ala Ser Phe Leu Tyr Ser Gly Val Pro
1 5 10 15

Ser Arg Phe Ser Gly Ser Arg
20

<210> SEQ ID NO 1243
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1243

Pro Lys Leu Leu Ile Tyr Ser Ala Ser Phe Leu Tyr Ser Gly Val Pro
1 5 10 15

Ser Arg Phe Ser Gly Ser Arg
20

<210> SEQ ID NO 1244
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1244

Pro Lys Leu Leu Ile Tyr Ser Ala Ser Phe Leu Tyr Ser Gly Val Pro
1 5 10 15

Ser Arg Phe Ser Gly Ser Arg
20

<210> SEQ ID NO 1245
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1245

Pro Lys Leu Leu Ile Tyr Ser Ala Ser Phe Leu Tyr Ser Gly Val Pro
1 5 10 15

Ser Arg Phe Ser Gly Ser Ala

20

<210> SEQ ID NO 1246
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1246

Pro Lys Leu Leu Ile Tyr Ser Ala Ser Phe Leu Tyr Ser Gly Val Pro
1 5 10 15

Ser Arg Phe Ser Gly Ser Asn
20

<210> SEQ ID NO 1247
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1247

Pro Lys Leu Leu Ile Tyr Ser Ala Ser Phe Leu Tyr Ser Gly Val Pro
1 5 10 15

Ser Arg Phe Ser Gly Ser Arg
20

<210> SEQ ID NO 1248
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1248

Pro Lys Leu Leu Ile Tyr Ser Ala Ser Phe Leu Tyr Ser Gly Val Pro
1 5 10 15

Ser Arg Phe Ser Gly Ser Met
20

<210> SEQ ID NO 1249
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1249

Pro Lys Leu Leu Ile Tyr Ser Ala Ser Phe Leu Tyr Ser Gly Val Pro
1 5 10 15

Ser Arg Phe Ser Gly Ser Thr
20

<210> SEQ ID NO 1250
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

```
<400> SEQUENCE: 1250

Pro Lys Leu Leu Ile Tyr Ser Ala Ser Phe Leu Tyr Ser Gly Val Pro
1               5                   10                  15

Ser Arg Phe Ser Gly Ser Ser
            20


<210> SEQ ID NO 1251
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1251

Pro Lys Leu Leu Ile Tyr Ser Ala Ser Phe Leu Tyr Ser Gly Val Pro
1               5                   10                  15

Ser Arg Phe Ser Gly Ser Val
            20


<210> SEQ ID NO 1252
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1252

Pro Lys Leu Leu Ile Tyr Ser Ala Ser Phe Leu Tyr Ser Gly Val Pro
1               5                   10                  15

Ser Arg Phe Ser Gly Ser Gly
            20


<210> SEQ ID NO 1253
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1253

Pro Lys Leu Leu Ile Tyr Ser Ala Ser Ser Leu Tyr Ser Gly Val Pro
1               5                   10                  15

Ser Arg Phe Ser Gly Ser Gly
            20


<210> SEQ ID NO 1254
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1254

Pro Lys Leu Leu Ile Tyr Ser Ala Ser Phe Leu Glu Ser Gly Val Pro
1               5                   10                  15

Ser Arg Phe Ser Gly Ser Gly
            20


<210> SEQ ID NO 1255
<211> LENGTH: 23
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1255

Pro Lys Leu Leu Ile Tyr Ser Ala Ser Phe Leu Glu Ser Gly Val Pro
1 5 10 15

Ser Arg Phe Ser Gly Ser Arg
20

<210> SEQ ID NO 1256
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1256

Pro Lys Leu Leu Ile Tyr Ala Ala Ser Ser Leu Tyr Ser Gly Val Pro
1 5 10 15

Ser Arg Phe Ser Gly Ser Gly
20

<210> SEQ ID NO 1257
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1257

Pro Lys Leu Leu Ile Tyr Asn Thr Asn Asn Leu Gln Thr Gly Val Pro
1 5 10 15

Ser Arg Phe Ser Gly Ser Arg
20

<210> SEQ ID NO 1258
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1258

Thr Cys Arg Ala Ser Gln Asn Val Asp Lys Tyr Val Ala Trp Tyr Gln
1 5 10 15

Gln Lys Pro Gly Lys Ala
20

<210> SEQ ID NO 1259
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1259

Thr Cys Arg Ala Ser Gln Asp Val Asn Thr Ala Val Ala Trp Tyr Gln
1 5 10 15

Gln Lys Leu Gly Glu Ser
20

<210> SEQ ID NO 1260
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1260

Thr Cys Arg Ala Ser Gln Asp Val Asn Thr Ala Val Ala Trp Tyr Gln
1 5 10 15

Gln Lys Pro Gly Lys Cys
20

<210> SEQ ID NO 1261
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1261

Thr Cys Arg Ala Ser Gln Asp Val Ser Thr Ala Val Ala Trp Tyr Gln
1 5 10 15

Gln Lys Pro Gly Lys Ala
20

<210> SEQ ID NO 1262
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1262

Pro Lys Leu Leu Ile Tyr Asn Thr Asn Asn Ser Gln Thr Gly Val Pro
1 5 10 15

Ser Arg Phe Ser Gly Ser Arg
20

<210> SEQ ID NO 1263
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1263

Pro Lys Leu Leu Ile Trp Ser Ala Ser Val Ser Ala Ser Gly Val Pro
1 5 10 15

Ser Arg Phe Ser Gly Ser Arg
20

<210> SEQ ID NO 1264
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1264

Pro Lys Leu Leu Ile Trp Ser Ala Ser Phe Ser Ala Ser Gly Val Pro
1 5 10 15

Ser Arg Phe Ser Gly Ser Arg
20

<210> SEQ ID NO 1265
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1265

Pro Lys Leu Leu Ile Leu Ser Ala Ser Phe Ser Ala Ser Gly Val Pro
1 5 10 15

Ser Arg Phe Ser Gly Ser Arg
20

<210> SEQ ID NO 1266
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1266

Pro Lys Leu Leu Ile Phe Ser Ala Ser Phe Ser Ala Ser Gly Val Pro
1 5 10 15

Ser Arg Phe Ser Gly Ser Arg
20

<210> SEQ ID NO 1267
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1267

Pro Lys Leu Leu Ile Trp Ser Ala Ser Val Ser Ala Ser Gly Val Pro
1 5 10 15

Ser Arg Phe Ser Gly Ser Arg
20

<210> SEQ ID NO 1268
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1268

Pro Lys Leu Leu Ile Ser Ser Ala Ser Trp Ser Ala Ser Gly Val Pro
1 5 10 15

Ser Arg Phe Ser Gly Ser Arg
20

<210> SEQ ID NO 1269

<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1269

Pro Lys Leu Leu Ile Lys Ser Ala Ser Phe Ser Ala Ser Gly Val Pro
1 5 10 15

Ser Arg Phe Ser Gly Ser Arg
20

<210> SEQ ID NO 1270
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1270

Pro Lys Leu Leu Ile Tyr Ser Ala Ser Phe Ser Ala Ser Gly Val Pro
1 5 10 15

Ser Arg Phe Ser Gly Ser Arg
20

<210> SEQ ID NO 1271
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1271

Pro Lys Leu Leu Ile Val Ser Ala Ser Trp Leu Tyr Ser Gly Val Pro
1 5 10 15

Ser Arg Phe Ser Gly Ser Arg
20

<210> SEQ ID NO 1272
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1272

Pro Lys Leu Leu Ile Val Ser Ala Ser Phe Leu Tyr Ser Gly Val Pro
1 5 10 15

Ser Arg Phe Ser Gly Ser Arg
20

<210> SEQ ID NO 1273
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1273

Pro Lys Leu Leu Ile Phe Ser Ala Ser Trp Leu Tyr Ser Gly Val Pro
1 5 10 15

Ser Arg Phe Ser Gly Ser Arg
20

<210> SEQ ID NO 1274
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1274

Pro Lys Leu Leu Ile Leu Ser Ala Ser Val Leu Tyr Ser Gly Val Pro
1 5 10 15

Ser Arg Phe Ser Gly Ser Arg
20

<210> SEQ ID NO 1275
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1275

Pro Lys Leu Leu Ile Leu Ser Ala Ser Leu Leu Tyr Ser Gly Val Pro
1 5 10 15

Ser Arg Phe Ser Gly Ser Arg
20

<210> SEQ ID NO 1276
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1276

Pro Lys Leu Leu Ile Trp Ser Ala Ser Trp Leu Tyr Ser Gly Val Pro
1 5 10 15

Ser Arg Phe Ser Gly Ser Arg
20

<210> SEQ ID NO 1277
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1277

Pro Lys Leu Leu Ile Asp Ser Ala Ser Trp Leu Trp Ser Gly Val Pro
1 5 10 15

Ser Arg Phe Ser Gly Ser Arg
20

<210> SEQ ID NO 1278
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1278

Pro Lys Leu Leu Ile Val Ser Ala Ser Thr Leu Trp Ser Gly Val Pro
1 5 10 15

Ser Arg Phe Ser Gly Ser Arg
20

<210> SEQ ID NO 1279
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1279

Pro Lys Leu Leu Ile Tyr Ser Ala Ser Phe Leu Trp Ser Gly Val Pro
1 5 10 15

Ser Arg Phe Ser Gly Ser Arg
20

<210> SEQ ID NO 1280
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1280

Pro Lys Leu Leu Ile Phe Ser Ala Ser His Leu Trp Ser Gly Val Pro
1 5 10 15

Ser Arg Phe Ser Gly Ser Arg
20

<210> SEQ ID NO 1281
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1281

Pro Lys Leu Leu Ile Val Ser Ala Ser Val Leu Trp Ser Gly Val Pro
1 5 10 15

Ser Arg Phe Ser Gly Ser Arg
20

<210> SEQ ID NO 1282
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1282

Pro Lys Leu Leu Ile Ala Ser Ala Ser Val Leu Leu Ser Gly Val Pro
1 5 10 15

Ser Arg Phe Ser Gly Ser Arg
20

<210> SEQ ID NO 1283
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1283

Pro Lys Leu Leu Ile Trp Ser Ala Ser Arg Leu Trp Ser Gly Val Pro
1 5 10 15

Ser Arg Phe Ser Gly Ser Arg
20

<210> SEQ ID NO 1284
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1284

Pro Lys Leu Leu Ile Trp Ser Ala Ser Gln Leu Phe Ser Gly Val Pro
1 5 10 15

Ser Arg Phe Ser Gly Ser Arg
20

<210> SEQ ID NO 1285
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1285

Pro Lys Leu Leu Ile Val Ser Ala Ser Trp Leu Leu Ser Gly Val Pro
1 5 10 15

Ser Arg Phe Ser Gly Ser Arg
20

<210> SEQ ID NO 1286
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1286

Pro Lys Leu Leu Ile Trp Ser Ala Ser Thr Leu Tyr Ser Gly Val Pro
1 5 10 15

Ser Arg Phe Ser Gly Ser Arg
20

<210> SEQ ID NO 1287
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1287

Pro Lys Leu Leu Ile Asp Ser Ala Ser Trp Leu Trp Ser Gly Val Pro 1 5 10 15

Ser Arg Phe Ser Gly Ser Arg
20

<210> SEQ ID NO 1288
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1288

Pro Lys Leu Leu Ile Tyr Ser Ala Ser Phe Leu Trp Ser Gly Val Pro
1 5 10 15

Ser Arg Phe Ser Gly Ser Arg
20

<210> SEQ ID NO 1289
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1289

Thr Cys Arg Ala Ser Gln Asp Val Asn Thr Ala Val Ala Trp Tyr Gln
1 5 10 15

Gln Lys Pro Gly Lys Ala
20

<210> SEQ ID NO 1290
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1290

Thr Cys Lys Ala Ser Gln Asp Val Asn Thr Ala Val Ala Trp Tyr Gln
1 5 10 15

Gln Lys Pro Gly His Ser
20

<210> SEQ ID NO 1291
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1291

Thr Cys Lys Ala Ser Gln Asp Val Ser Ile Gly Val Ala Trp Tyr Gln
1 5 10 15

Gln Arg Pro Gly Gln Ser
20

<210> SEQ ID NO 1292
<211> LENGTH: 22
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 1292

Thr Cys Lys Ala Ser Gln Asp Val Ser Ile Gly Val Ala Trp Tyr Gln
1 5 10 15

Gln Arg Pro Gly Lys Ala
20

<210> SEQ ID NO 1293
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1293

Pro Lys Leu Leu Ile Phe Ser Ala Ser Met Leu Trp Ser Gly Val Pro
1 5 10 15

Ser Arg Phe Ser Gly Ser Arg
20

<210> SEQ ID NO 1294
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1294

Pro Lys Leu Leu Ile Glu Ser Ala Ser Trp Leu Trp Ser Gly Val Pro
1 5 10 15

Ser Arg Phe Ser Gly Ser Arg
20

<210> SEQ ID NO 1295
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1295

Pro Lys Leu Leu Ile Arg Ser Ala Ser Trp Leu Val Ser Gly Val Pro
1 5 10 15

Ser Arg Phe Ser Gly Ser Arg
20

<210> SEQ ID NO 1296
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1296

Pro Lys Leu Leu Ile Thr Ser Ala Ser Lys Leu Trp Ser Gly Val Pro
1 5 10 15

Ser Arg Phe Ser Gly Ser Arg
20

<210> SEQ ID NO 1297
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1297

Pro Lys Leu Leu Ile Arg Ser Ala Ser Ala Leu Trp Ser Gly Val Pro
1               5                   10                  15

Ser Arg Phe Ser Gly Ser Arg
            20

<210> SEQ ID NO 1298
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1298

Pro Lys Leu Leu Ile Thr Ser Ala Ser Arg Leu Val Ser Gly Val Pro
1               5                   10                  15

Ser Arg Phe Ser Gly Ser Arg
            20

<210> SEQ ID NO 1299
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1299

Pro Lys Leu Leu Ile Val Ser Ala Ser Lys Leu Ser Ser Gly Val Pro
1               5                   10                  15

Ser Arg Phe Ser Gly Ser Arg
            20

<210> SEQ ID NO 1300
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1300

Pro Lys Leu Leu Ile Ser Ser Ala Ser Val Leu Trp Ser Gly Val Pro
1               5                   10                  15

Ser Arg Phe Ser Gly Ser Arg
            20

<210> SEQ ID NO 1301
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1301

Pro Lys Leu Leu Ile Tyr Ser Ala Ser Trp Leu Trp Ser Gly Val Pro
1 5 10 15

Ser Arg Phe Ser Gly Ser Arg
20

<210> SEQ ID NO 1302
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1302

Pro Lys Leu Leu Ile Phe Ser Ala Ser Trp Leu Trp Ser Gly Val Pro
1 5 10 15

Ser Arg Phe Ser Gly Ser Arg
20

<210> SEQ ID NO 1303
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1303

Pro Lys Leu Leu Ile Val Ser Ala Ser Ala Leu His Ser Gly Val Pro
1 5 10 15

Ser Arg Phe Ser Gly Ser Arg
20

<210> SEQ ID NO 1304
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1304

Pro Lys Leu Leu Ile Trp Ser Ala Ser Pro Leu His Ser Gly Val Pro
1 5 10 15

Ser Arg Phe Ser Gly Ser Arg
20

<210> SEQ ID NO 1305
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1305

Pro Lys Leu Leu Ile Leu Ser Ala Ser Gly Leu His Ser Gly Val Pro
1 5 10 15

Ser Arg Phe Ser Gly Ser Arg
20

<210> SEQ ID NO 1306
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1306

Pro Lys Leu Leu Ile Tyr Ser Ala Ser Phe Arg Glu Thr Gly Val Pro
1               5                   10                  15

Asp Arg Phe Thr Gly Asn Arg
            20

<210> SEQ ID NO 1307
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1307

Pro Lys Leu Leu Ile Tyr Trp Ala Ser Gly Leu Tyr Ser Gly Val Pro
1               5                   10                  15

Ser Arg Phe Ser Gly Ser Arg
            20

<210> SEQ ID NO 1308
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1308

Pro Lys Leu Leu Ile Tyr Ser Ala Ser Tyr Arg Tyr Thr Gly Val Pro
1               5                   10                  15

Asp Arg Phe Thr Gly Ser Gly
            20

<210> SEQ ID NO 1309
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1309

Pro Lys Leu Leu Ile Tyr Ser Ala Ser Tyr Arg Tyr Thr Gly Val Pro
1               5                   10                  15

Ser Arg Phe Ser Gly Ser Gly
            20

<210> SEQ ID NO 1310
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1310

Arg Ala Ser Gln Pro Val Asn Thr Ala Val Ala
1               5                   10

<210> SEQ ID NO 1311

<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1311

Arg Ala Ser Gln Met Val Asn Thr Ala Val Ala
1 5 10

<210> SEQ ID NO 1312
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1312

Arg Ala Ser Gln Arg Val Asn Thr Ala Val Ala
1 5 10

<210> SEQ ID NO 1313
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1313

Gln Gln His Tyr Asn Thr Pro Pro Thr
1 5

<210> SEQ ID NO 1314
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1314

Gln Gln His Tyr Tyr Thr Pro Pro Thr
1 5

<210> SEQ ID NO 1315
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1315

Arg Ile Tyr Pro Thr Thr Gly Tyr Thr Arg Tyr Ala Asp Ser Val Lys
1 5 10 15

Gly

<210> SEQ ID NO 1316
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1316

Arg Ile Tyr Pro Thr Lys Gly Tyr Thr Arg Tyr Ala Asp Ser Val Lys
1 5 10 15

Gly

<210> SEQ ID NO 1317
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1317

Arg Ile Tyr Pro Thr Pro Gly Tyr Thr Arg Tyr Ala Asp Ser Val Lys
1 5 10 15

Gly

<210> SEQ ID NO 1318
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1318

Arg Ile Tyr Pro Thr Met Gly Tyr Thr Arg Tyr Ala Asp Ser Val Lys
1 5 10 15

Gly

<210> SEQ ID NO 1319
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1319

Arg Ile Tyr Pro Thr Asn Gly Ile Thr Arg Tyr Ala Asp Ser Val Lys
1 5 10 15

Gly

<210> SEQ ID NO 1320
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1320

Arg Ile Tyr Pro Thr Asn Gly Tyr Thr Thr Tyr Ala Asp Ser Val Lys
1 5 10 15

Gly

<210> SEQ ID NO 1321
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1321

Arg Ile Tyr Pro Thr Asn Gly Tyr Thr Lys Tyr Ala Asp Ser Val Lys
1 5 10 15

Gly

<210> SEQ ID NO 1322
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1322

Arg Ile Tyr Pro Thr Asn Gly Tyr Thr Ile Tyr Ala Asp Ser Val Lys
1 5 10 15

Gly

<210> SEQ ID NO 1323
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1323

Trp Gly Gly Thr Gly Phe Tyr Ala Met Asp Tyr
1 5 10

<210> SEQ ID NO 1324
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1324

Trp Gly Gly Tyr Gly Phe Tyr Ala Met Asp Tyr
1 5 10

<210> SEQ ID NO 1325
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1325

Trp Gly Gly Met Gly Phe Tyr Ala Met Asp Tyr
1 5 10

<210> SEQ ID NO 1326
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1326

Trp Gly Gly Lys Gly Phe Tyr Ala Met Asp Tyr
1 5 10

<210> SEQ ID NO 1327
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1327

Ser Leu Arg Ala Glu Asp Thr Ala Val Tyr Tyr Cys Ser Arg Trp
1 5 10 15

<210> SEQ ID NO 1328
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1328

Ser Leu Arg Ala Glu Asp Thr Ala Val Tyr Tyr Cys Asn Arg Trp
1 5 10 15

<210> SEQ ID NO 1329
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1329

Ser Leu Arg Ala Glu Asp Thr Ala Val Tyr Tyr Cys Asp Arg Trp
1 5 10 15

<210> SEQ ID NO 1330
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1330

Ser Leu Arg Ala Glu Asp Thr Ala Val Tyr Tyr Cys Ala Arg Trp
1 5 10 15

<210> SEQ ID NO 1331
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1331

Ser Leu Arg Ala Glu Asp Thr Ala Val Tyr Tyr Cys Val Arg Trp
1 5 10 15

<210> SEQ ID NO 1332
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1332

Ser Leu Arg Ala Glu Asp Thr Ala Val Tyr Tyr Cys Leu Arg Trp
1 5 10 15

<210> SEQ ID NO 1333
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1333

Ser Leu Arg Ala Glu Asp Thr Ala Val Tyr Tyr Cys Ser Arg Tyr
1 5 10 15

<210> SEQ ID NO 1334
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1334

Ser Leu Arg Ala Glu Asp Thr Ala Val Tyr Tyr Cys Asn Arg Tyr
1 5 10 15

<210> SEQ ID NO 1335
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1335

Ser Leu Arg Ala Glu Asp Thr Ala Val Tyr Tyr Cys Asp Arg Tyr
1 5 10 15

<210> SEQ ID NO 1336
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1336

Ser Leu Arg Ala Glu Asp Thr Ala Val Tyr Tyr Cys Ala Arg Tyr
1 5 10 15

<210> SEQ ID NO 1337
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1337

Ser Leu Arg Ala Glu Asp Thr Ala Val Tyr Tyr Cys Val Arg Tyr
1 5 10 15

<210> SEQ ID NO 1338
<211> LENGTH: 15

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1338

Ser Leu Arg Ala Glu Asp Thr Ala Val Tyr Tyr Cys Leu Arg Tyr
1 5 10 15

<210> SEQ ID NO 1339
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1339

Ser Leu Arg Ala Glu Asp Thr Ala Val Tyr Tyr Cys Ser Arg Phe
1 5 10 15

<210> SEQ ID NO 1340
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1340

Ser Leu Arg Ala Glu Asp Thr Ala Val Tyr Tyr Cys Asn Arg Phe
1 5 10 15

<210> SEQ ID NO 1341
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1341

Ser Leu Arg Ala Glu Asp Thr Ala Val Tyr Tyr Cys Asp Arg Phe
1 5 10 15

<210> SEQ ID NO 1342
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1342

Ser Leu Arg Ala Glu Asp Thr Ala Val Tyr Tyr Cys Ala Arg Phe
1 5 10 15

<210> SEQ ID NO 1343
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1343

Ser Leu Arg Ala Glu Asp Thr Ala Val Tyr Tyr Cys Val Arg Phe 1 5 10 15

<210> SEQ ID NO 1344
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1344

Ser Leu Arg Ala Glu Asp Thr Ala Val Tyr Tyr Cys Leu Arg Phe
1 5 10 15

<210> SEQ ID NO 1345
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1345

Ser Gly Arg Ala Glu Asp Thr Ala Val Tyr Tyr Cys Ser Arg Trp
1 5 10 15

<210> SEQ ID NO 1346
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1346

Ser Leu Arg Ala Glu Asp Arg Ala Val Tyr Tyr Cys Ser Arg Trp
1 5 10 15

<210> SEQ ID NO 1347
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1347

Val Leu Arg Ala Glu Asp Thr Ala Val Tyr Tyr Cys Ser Arg Trp
1 5 10 15

<210> SEQ ID NO 1348
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1348

Ser Leu Lys Ala Glu Asp Thr Ala Val Tyr Tyr Cys Ser Arg Trp
1 5 10 15

<210> SEQ ID NO 1349
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1349

Ser Leu Arg Ala Glu Asp Thr Ala Val Tyr Tyr Cys Ser Arg Trp
1 5 10 15

<210> SEQ ID NO 1350
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1350

Thr Cys Arg Ala Ser Gln Asp Val Asn Thr Ala Val Ala Trp Tyr
1 5 10 15

<210> SEQ ID NO 1351
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1351

Thr Cys Arg Ala Ser Gln Gly Val Asn Thr Ala Val Ala Trp Tyr
1 5 10 15

<210> SEQ ID NO 1352
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1352

Thr Cys Arg Ala Ser Gln Ala Val Asn Thr Ala Val Ala Trp Tyr
1 5 10 15

<210> SEQ ID NO 1353
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1353

Thr Cys Arg Ala Ser Gln Asn Val Asn Thr Ala Val Ala Trp Tyr
1 5 10 15

<210> SEQ ID NO 1354
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1354

Thr Cys Arg Ala Ser Gln Leu Val Asn Thr Ala Val Ala Trp Tyr
1 5 10 15

<210> SEQ ID NO 1355

<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1355

Thr Cys Arg Ala Ser Ser Asp Val Asn Thr Ala Val Ala Trp Tyr
1 5 10 15

<210> SEQ ID NO 1356
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1356

Thr Cys Arg Ala Ser Lys Asp Val Asn Thr Ala Val Ala Trp Tyr
1 5 10 15

<210> SEQ ID NO 1357
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1357

Thr Cys Arg Ala Ser Val Asp Val Asn Thr Ala Val Ala Trp Tyr
1 5 10 15

<210> SEQ ID NO 1358
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1358

Thr Cys Arg Ala Ser Leu Asp Val Asn Thr Ala Val Ala Trp Tyr
1 5 10 15

<210> SEQ ID NO 1359
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1359

Thr Cys Arg Ala Ser Phe Asp Val Asn Thr Ala Val Ala Trp Tyr
1 5 10 15

<210> SEQ ID NO 1360
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1360

-continued

Thr Cys Arg Ala Ser Ile Asp Val Asn Thr Ala Val Ala Trp Tyr
1 5 10 15

<210> SEQ ID NO 1361
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1361

Thr Cys Arg Ala Ser Tyr Asp Val Asn Thr Ala Val Ala Trp Tyr
1 5 10 15

<210> SEQ ID NO 1362
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1362

Thr Cys Arg Ala Ser Arg Asp Val Asn Thr Ala Val Ala Trp Tyr
1 5 10 15

<210> SEQ ID NO 1363
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1363

Thr Cys Arg Ala Ser Gln Asp Val Asn Thr Ala Val Gly Trp Tyr
1 5 10 15

<210> SEQ ID NO 1364
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1364

Thr Cys Arg Ala Ser Gln Gly Val Asn Thr Ala Val Gly Trp Tyr
1 5 10 15

<210> SEQ ID NO 1365
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1365

Thr Cys Arg Ala Ser Gln Ala Val Asn Thr Ala Val Gly Trp Tyr
1 5 10 15

<210> SEQ ID NO 1366
<211> LENGTH: 15
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 1366

Thr Cys Arg Ala Ser Gln Asn Val Asn Thr Ala Val Gly Trp Tyr
1 5 10 15

<210> SEQ ID NO 1367
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1367

Thr Cys Arg Ala Ser Gln Leu Val Asn Thr Ala Val Gly Trp Tyr
1 5 10 15

<210> SEQ ID NO 1368
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1368

Thr Cys Arg Ala Ser Ser Asp Val Asn Thr Ala Val Gly Trp Tyr
1 5 10 15

<210> SEQ ID NO 1369
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1369

Thr Cys Arg Ala Ser Lys Asp Val Asn Thr Ala Val Gly Trp Tyr
1 5 10 15

<210> SEQ ID NO 1370
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1370

Thr Cys Arg Ala Ser Val Asp Val Asn Thr Ala Val Gly Trp Tyr
1 5 10 15

<210> SEQ ID NO 1371
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1371

Thr Cys Arg Ala Ser Leu Asp Val Asn Thr Ala Val Gly Trp Tyr
1 5 10 15

<210> SEQ ID NO 1372
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1372

Thr Cys Arg Ala Ser Phe Asp Val Asn Thr Ala Val Gly Trp Tyr
1 5 10 15

<210> SEQ ID NO 1373
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1373

Thr Cys Arg Ala Ser Ile Asp Val Asn Thr Ala Val Gly Trp Tyr
1 5 10 15

<210> SEQ ID NO 1374
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1374

Thr Cys Arg Ala Ser Tyr Asp Val Asn Thr Ala Val Gly Trp Tyr
1 5 10 15

<210> SEQ ID NO 1375
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1375

Thr Cys Arg Ala Ser Arg Asp Val Asn Thr Ala Val Gly Trp Tyr
1 5 10 15

<210> SEQ ID NO 1376
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1376

Thr Cys Arg Ala Ser Gln Asp Val Asn Thr Ala Val Ala Trp Tyr
1 5 10 15

<210> SEQ ID NO 1377
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1377

Thr Cys Arg Ala Ser Gln Asp Val Asn Thr Ala Val Ala Trp Tyr
1 5 10 15

<210> SEQ ID NO 1378
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1378

Thr Cys Arg Ala Ser Gln Asp Val Asn Thr Ala Val Asp Trp Tyr
1 5 10 15

<210> SEQ ID NO 1379
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1379

Thr Cys Arg Ala Ser Gln Gly Val Asn Thr Ala Val Asp Trp Tyr
1 5 10 15

<210> SEQ ID NO 1380
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1380

Thr Cys Arg Ala Ser Gln Ala Val Asn Thr Ala Val Asp Trp Tyr
1 5 10 15

<210> SEQ ID NO 1381
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1381

Thr Cys Arg Ala Ser Gln Asn Val Asn Thr Ala Val Asp Trp Tyr
1 5 10 15

<210> SEQ ID NO 1382
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1382

Thr Cys Arg Ala Ser Gln Leu Val Asn Thr Ala Val Asp Trp Tyr
1 5 10 15

<210> SEQ ID NO 1383
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1383

Thr Cys Arg Ala Ser Ser Asp Val Asn Thr Ala Val Asp Trp Tyr
1 5 10 15

<210> SEQ ID NO 1384
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1384

Thr Cys Arg Ala Ser Lys Asp Val Asn Thr Ala Val Asp Trp Tyr
1 5 10 15

<210> SEQ ID NO 1385
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1385

Thr Cys Arg Ala Ser Val Asp Val Asn Thr Ala Val Asp Trp Tyr
1 5 10 15

<210> SEQ ID NO 1386
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1386

Thr Cys Arg Ala Ser Leu Asp Val Asn Thr Ala Val Asp Trp Tyr
1 5 10 15

<210> SEQ ID NO 1387
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1387

Thr Cys Arg Ala Ser Phe Asp Val Asn Thr Ala Val Asp Trp Tyr
1 5 10 15

<210> SEQ ID NO 1388
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1388

Thr Cys Arg Ala Ser Ile Asp Val Asn Thr Ala Val Asp Trp Tyr
1 5 10 15

<210> SEQ ID NO 1389
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1389

Thr Cys Arg Ala Ser Tyr Asp Val Asn Thr Ala Val Asp Trp Tyr
1 5 10 15

<210> SEQ ID NO 1390
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1390

Thr Cys Arg Ala Ser Arg Asp Val Asn Thr Ala Val Asp Trp Tyr
1 5 10 15

<210> SEQ ID NO 1391
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1391

Thr Cys Arg Ala Ser Gln Asp Val Asn Thr Ala Val Val Trp Tyr
1 5 10 15

<210> SEQ ID NO 1392
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1392

Thr Cys Arg Ala Ser Gln Gly Val Asn Thr Ala Val Val Trp Tyr
1 5 10 15

<210> SEQ ID NO 1393
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1393

Thr Cys Arg Ala Ser Gln Ala Val Asn Thr Ala Val Val Trp Tyr
1 5 10 15

<210> SEQ ID NO 1394
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1394

Thr Cys Arg Ala Ser Gln Asn Val Asn Thr Ala Val Val Trp Tyr
1 5 10 15

<210> SEQ ID NO 1395
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1395

Thr Cys Arg Ala Ser Gln Leu Val Asn Thr Ala Val Val Trp Tyr
1 5 10 15

<210> SEQ ID NO 1396
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1396

Thr Cys Arg Ala Ser Ser Asp Val Asn Thr Ala Val Val Trp Tyr
1 5 10 15

<210> SEQ ID NO 1397
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1397

Thr Cys Arg Ala Ser Lys Asp Val Asn Thr Ala Val Val Trp Tyr
1 5 10 15

<210> SEQ ID NO 1398
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1398

Thr Cys Arg Ala Ser Val Asp Val Asn Thr Ala Val Val Trp Tyr
1 5 10 15

<210> SEQ ID NO 1399
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1399

Thr Cys Arg Ala Ser Leu Asp Val Asn Thr Ala Val Val Trp Tyr
1 5 10 15

<210> SEQ ID NO 1400
<211> LENGTH: 15
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 1400

Thr Cys Arg Ala Ser Phe Asp Val Asn Thr Ala Val Val Trp Tyr
1 5 10 15

<210> SEQ ID NO 1401
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1401

Thr Cys Arg Ala Ser Ile Asp Val Asn Thr Ala Val Val Trp Tyr
1 5 10 15

<210> SEQ ID NO 1402
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1402

Thr Cys Arg Ala Ser Tyr Asp Val Asn Thr Ala Val Val Trp Tyr
1 5 10 15

<210> SEQ ID NO 1403
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1403

Thr Cys Arg Ala Ser Arg Asp Val Asn Thr Ala Val Val Trp Tyr
1 5 10 15

<210> SEQ ID NO 1404
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1404

Thr Cys Arg Ala Ser Gln Asp Val Asn Thr Ala Val Ala Trp Tyr
1 5 10 15

<210> SEQ ID NO 1405
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1405

Ser Leu Lys Ala Glu Asp Thr Ala Val Tyr Tyr Cys Ser Arg Trp
1 5 10 15

<210> SEQ ID NO 1406
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1406

Ser Leu Arg Ala Glu Asp Thr Ala Val Tyr Tyr Cys Ser Arg Phe
1 5 10 15

<210> SEQ ID NO 1407
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1407

Thr Cys Arg Ala Ser Gln Asp Val Asn Thr Ala Val Ala Trp Tyr
1 5 10 15

<210> SEQ ID NO 1408
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1408

Thr Cys Arg Ala Ser Ser Asp Val Asn Thr Ala Val Ala Trp Tyr
1 5 10 15

<210> SEQ ID NO 1409
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1409

Thr Cys Arg Ala Ser Gln Asn Val Asn Thr Ala Val Asp Trp Tyr
1 5 10 15

<210> SEQ ID NO 1410
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1410

Thr Cys Arg Ala Ser Ser Asp Val Asn Thr Ala Val Asp Trp Tyr
1 5 10 15

<210> SEQ ID NO 1411
<211> LENGTH: 15
<212> TYPE: PRT
<213> ORGANISM: Artificial Sequence
<220> FEATURE:
<223> OTHER INFORMATION: Description of Artificial Sequence: Synthetic
peptide -continued

```
<400> SEQUENCE: 1411

Thr Cys Arg Ala Ser Leu Asp Val Asn Thr Ala Val Val Trp Tyr
1               5                   10                  15


<210> SEQ ID NO 1412
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1412

Thr Cys Arg Ala Ser Gln Leu Val Asn Thr Ala Val Asp Trp Tyr
1               5                   10                  15


<210> SEQ ID NO 1413
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1413

Thr Cys Arg Ala Ser Phe Asp Val Asn Thr Ala Val Asp Trp Tyr
1               5                   10                  15


<210> SEQ ID NO 1414
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1414

Thr Cys Arg Ala Ser Gln Asp Val Asn Thr Ala Val Val Trp Tyr
1               5                   10                  15
```

ANTI-HER2 ANTIBODIES AND THEIR USES

1. CROSS-REFERENCE TO RELATED APPLICATIONS

This application claims the benefit under 35 U.S.C. §119 (e) of U.S. Provisional Application No. 61/287,155, filed Dec. 16, 2009, the contents of which are incorporated herein by reference in their entireties.

2. SEQUENCE LISTING

The instant application contains a Sequence Listing which has been submitted in ASCII form via EFS-WEB and is hereby incorporated by reference in its entirety. Said ASCII copy, created on Dec. 13, 2010, is named 381493US.txt and is 394,853 bytes in size.

3. FIELD OF THE INVENTION

The present invention relates to anti-HER2 antibodies, pharmaceutical compositions comprising anti-HER2 antibodies, and therapeutic uses of such antibodies.

4. BACKGROUND

Monoclonal antibody therapy has provided an opportunity to target and destroy tumors using antibodies engineered against tumor-specific antigens. In general, monoclonal antibody therapy stimulates a patient's immune system to attack malignant tumor cells or prevents tumor growth by blocking or inhibiting specific cell receptors. Monoclonal antibodies used in cancer therapy generally target tumor-specific antigens on cell-surface molecules. Representative cell-surface molecules targeted in clinical trials include those originating from various lymphomas/leukemias (such as T-cell and/or B-cell lymphomas/leukemias) and solid tumors (such as epithelial tumors of the breast, colon, and lung).

Promising results have been reported in the treatment of breast cancer with humanized monoclonal antibodies, particularly treatments targeting the HER2 (neu/ErbB2) receptor.

HER2 is a transmembrane surface-bound receptor tyrosine kinase and is normally involved in the signal transduction pathways leading to cell growth and differentiation. HER2, also known as epidermal growth factor receptor 2, belongs to a family of epidermal growth factor receptors (EGFRs) including HER1 (ErbB1), HER3 (ErbB3), and HER4 (ErbB4) (Hudis, 2007, N Engl J Med 357(1):39-51). The ErbB receptors typically dimerize on ligand binding. Although HER2 has no known ligand, it is the preferential dimerization partner of other members of the ErbB family. (Hudis, 2007, N Engl J Med 357(1):39-51). Overexpression of HER2 results in the induction of angiogenesis, a component of cancer growth, and the evocation of an antitumor T-cell response (Ménard et al., 2003, Oncogene 22:6570-6578). HER2 is overexpressed in about one-quarter of breast cancer patients (Bange et al., 2001, Nature Medicine 7:548-552).

The development of a monoclonal antibody therapy based on the discovery of the role of HER2 in breast cancer first involved the development of a murine-based antibody. Researchers discovered that the murine monoclonal antibody 4D5 had a significant and dose dependent efficacy specifically for HER2 overexpressing cancer cells, while having no effect on cells expressing physiological levels of HER2. However, murine antibodies elicit an immunogenic response in human patients. Murine monoclonal antibodies can be humanized (thereby reducing the murine-induced immune response) by identification of a minimum set of amino acid residues in the complementarity determining regions (CDRs) of the murine antibody required for antigen specificity and antigen binding affinity and substituting these regions into the CDRs of a consensus human IgG framework. The framework regions are the non-CDR regions in the variable chains of the antibody. Accordingly, the murine (4D5) monoclonal antibody was humanized, resulting in a recombinant, humanized monoclonal antibody directed against HER2. This drug is commercially known as Herceptin® (trastuzumab), which gained FDA marketing approval in late 1998.

Herceptin® is known to bind with high affinity to the extracellular domain of the HER2 protein, thereby inhibiting the proliferation of human tumor cells that overexpress HER2. Herceptin® is also a mediator of antibody-dependent cellular cytotoxicity (ADCC) which has been shown to be preferentially exerted on HER2 overexpressing cancer cells compared with cancer cells that do not overexpress HER2.

Herceptin® can elicit an immune response when administered to humans. Such an immune response can result in an immune complex-mediated clearance of the antibodies or fragments from the circulation, and make repeated administration unsuitable for therapy, thereby reducing the therapeutic benefit to the patient and limiting the re-administration of the antibody. Further, Herceptin® may be contraindicated in patients with pre-existing heart disease. Herceptin® has been associated with cardiac dysfunction in 2-7% of cases (Borghesi et al., 2006, Immunol Res 36(1-3):27-32). Also, while up to 70% of HER2-positive breast cancers demonstrate a response to Herceptin®-based therapies, resistance almost inevitably arises within a year of the initial response. Finally, additional problems with tumor-specific or tumor-selective monoclonal antibodies such as Herceptin® as therapeutic agents include antigenic variation of the tumor, inefficient killing of cells after binding the monoclonal antibody, inefficient penetration of the antibody into the tumor mass, and soluble target antigens mopping up the antibody.

Accordingly, there is a need to provide improved monoclonal antibodies that interfere with the HER2 receptor that overcome one or more of these problems, for example, by generating variants with higher affinity than Herceptin® that can be administered at reduced dosages, or variants with reduced immunogenicity and other side-effects as compared to Herceptin®. Furthermore, there is a need to provide variants with increased expression in heterologous hosts, with increased solubility, with decreased heterogeneity due to glycosylation and/or with increased stability, e.g., with respect to oxidation, deamidation and/or cyclization of amino acids.

Citation or identification of any reference in Section 4 or in any other section of this application shall not be construed as an admission that such reference is available as prior art to the present disclosure.

5. SUMMARY

The present disclosure relates to improved anti-HER2 antibodies that are related in sequence to the anti-HER2 antibody trastuzumab. In certain aspects, the present disclosure relates to variants of trastuzumab or binding fragments of trastuzumab that are less immunogenic than and/or have binding affinity improvements relative to trastuzumab. Trastuzumab is a humanized version of the antibody produced by the hybridoma 4D5.

The present disclosure provides anti-HER2 antibodies that have heavy and light chain CDRs that have at least one amino acid substitution as compared to the heavy and/or light chain CDRs of trastuzumab. The present disclosure also provides anti-HER2 antibodies that have at least one amino acid substitution as compared to the heavy and/or light chain framework regions of trastuzumab.

Accordingly, the present disclosure provides anti-HER2 antibodies having: (1) light chain CDRs with at least one amino acid substitution as compared to the light chain CDRs of trastuzumab; and/or (2) heavy chain CDRs with at least one amino acid substitution as compared to the heavy chain CDRs of trastuzumab; (3) light chain framework regions with at least one amino acid substitution as compared to the framework regions of trastuzumab; and/or (4) heavy chain framework regions with at least one amino acid substitution as compared to the framework regions of trastuzumab.

Trastuzumab comprises a heavy chain having a sequence corresponding to SEQ ID NO:1 and a light chain having a sequence corresponding to SEQ ID NO:2, and has three heavy chain CDRs, referred to herein (in amino- to carboxy-terminal order) as CDR-H1, CDR-H2 and CDR-H3, and three light chain CDRs referred to herein (in amino- to carboxy-terminal order) as CDR-L1, CDR-L2 and CDR-L3. The sequences of the trastuzumab CDRs are shown in FIGS. 1A and 1B, and their numbering is set forth in Table 1 (for heavy chain CDRs) and Table 2 (for light chain CDRs).

While the disclosure refers to antibodies or antibody fragments with reduced immunogenicity and/or improved affinity relative to trastuzumab, it is intended to encompass anti-HER2 antibodies or anti-HER2 binding fragments with reduced immunogenicity and/or improved affinity as compared to (i) trastuzumab; (ii) an antibody comprising the VH and VL regions of SEQ ID NO:1 and SEQ ID NO:2, respectively; or (iii) an antibody having a VH comprising an amino acid sequence corresponding to positions 1 to 117 of SEQ ID NO:1 and a VL comprising an amino acid sequence corresponding to positions 1 to 103 of SEQ ID NO:2.

As noted above, the present disclosure provides variants of trastuzumab or binding fragments of trastuzumab that are less immunogenic than trastuzumab. For the sake of convenience, such variants are sometimes referred to herein as "deimmunized."

Deimmunized variants of trastuzumab have one or more substitutions in the framework and/or CDR regions. Exemplary positions where one or more substitutions can be made that result in a variant of trastuzumab with reduced immunogenicity relative to trastuzumab include the heavy chain positions R83 and W95 and the light chain positions Q27, D28 and A34.

Exemplary substitutions that can be made at the foregoing positions that result in deimmunized variants of trastuzumab include one or more of the following heavy chain substitutions: R83K or W95F. Exemplary substitutions in the light chain that result in deimmunized variants of trastuzumab include one or more of the following substitutions: Q27S, Q27L, Q27F, D28L, D28N, A34D, and A34V. Combinations of one or more deimmunizing VL chain substitutions and one or more deimmunizing VH chain substitutions can also be made, including, for example, the following VL combinations: D28N+A34D, Q27S+A34D, Q27L+A34V, D28L+A34D or Q27F+A34D.

In one aspect, the anti-HER2 antibody or anti-HER2 binding fragment of an antibody of the disclosure comprises CDRs having overall at least 80% sequence identity to CDRs having amino acid sequences of SEQ ID NO:3 (CDR-H1), SEQ ID NO:4 (CDR-H2), SEQ ID NO:5 (CDR-H3), SEQ ID NO:104 and/or SEQ ID NO:6 (CDR-L1), SEQ ID NO:7 (CDR-L2), and SEQ ID NO:8 (CDR-L3), wherein the anti-HER2 antibody or anti-HER2 binding fragment has reduced immunogenicity as compared to an antibody having a VH of SEQ ID NO:1 and a VL of SEQ ID NO:2.

The anti-HER2 antibody or anti-HER2 binding fragment of an antibody can also comprise a VH and a VL region having amino acid sequences with at least 80% sequence identity to VH and VL regions of trastuzumab, respectively.

In some aspects, the anti-HER2 antibody or anti-HER2 binding fragment of an antibody optionally comprises one or more additional mutations or combinations of mutations as compared to the antibody trastuzumab selected from one or more of Tables 3, 4, 5, 6, 7, 8, 9, 10, 11, 12, 13, 14, 15, 16, 17, 18, 19, 20, 21, 22, and 23, and optionally Table 24.

Deimmunizing substitutions are also provided in FIG. 8. In addition to deimmunizing substitutions, one or more beneficial or neutral substitutions can also be made including one or more substitutions selected from one or more of Tables 3, 4, 5, 6, 7, 8, 9, 10, 11, 12, 13, 14, 15, 16, 17, 18, 19, 20, 21, 22, 23 and/or 24. In further aspects, the six CDRs can altogether have up to 13 amino acid substitutions as compared to CDR sequences of the antibody trastuzumab.

In another aspect, the anti-HER2 antibodies or anti-HER2 binding fragments of the disclosure comprises CDRs having overall at least 80% sequence identity to CDRs having amino acid sequences of SEQ ID NO:3 (CDR-H1), SEQ ID NO:4 (CDR-H2), SEQ ID NO:5 (CDR-H3), SEQ ID NO:104 and/or SEQ ID NO:6 (CDR-L1), SEQ ID NO:7 (CDR-L2), and SEQ ID NO:8 (CDR-L3), wherein said anti-HER2 antibody or anti-HER2 binding fragment has increased affinity to HER2 as compared to an antibody having a VH of SEQ ID NO:1 and a VL of SEQ ID NO:2.

The anti-HER2 antibodies and anti-HER2 binding fragments of the disclosure can optionally comprise one or more additional mutations or combinations of mutations as compared to the antibody trastuzumab selected from one or more of Tables 3, 4, 5, 6, 7, 8, 9, 10, 11, 12, 13, 14, 15, 16, 17, 18, 19, 20, 21, 22, 23, and optionally Table 24. In particular aspects, the six CDRs altogether have up to 13 amino acid substitutions as compared to CDR sequences of the antibody trastuzumab.

In yet further aspects, the anti-HER2 antibody or anti-HER2 binding fragment of an antibody of the disclosure has increased affinity, as measured by BIAcore, FACS (e.g., one-point FACS or FACS competition with a KS-BR3 cell-line) and/or AlphaLISA, to HER2 as compared to an antibody having a VH of SEQ ID NO:1 and a VL of SEQ ID NO:2.

In a particular aspect, the antibody or binding fragment has an affinity that is 1.1-fold or greater than the affinity of trastuzumab to HER-2. Exemplary antibodies or binding fragments include an anti-HER2 antibody or anti-HER2 binding fragment which has (i) at least one VL substitution selected from: T22G and A34V as compared a VL of SEQ ID NO:2;

(ii) at least one VL substitution selected from: T22G, T22S, C23A, R24H, R24C, R24V, A25C, A25G, A25P, Q27V, D28A, V29A, V29S, A34D, A34G, A51S, S52W, S52M, S52Q, S52H, S52G, S52R, L54I, L54G, L54V, S56A, S56P, S56G, S56H, S56Y, S56F, S56N, S56M, R66K, Y92M, T93L, T93M, T93V, and P96G as compared a VL of SEQ ID NO:2 and/or at least one VH substitution selected from D31H, Y52K, T53R, K64S, A88E, V89Y, S93D, D98L, D98M and D98V as compared a VH of SEQ ID NO:1;

(iii) at least one VL substitution selected from: T22G, L54I, and S56Y as compared a VL of SEQ ID NO:2; and/or at least one VH substitution selected from D31H, D31T, Y52K, D98M, and D98W, as compared to SEQ ID NO:1;

(iv) at least one VL substitution selected from: T22G, L54I, and S56Y as compared a VL of SEQ ID NO:2; and/or at least one VH substitution selected from D31H, D31T, Y52K, and D98M, as compared to SEQ ID NO:1; or (v) at least one VL substitution selected from: T22G, T22S, C23A, R24H, R24C, R24V, A25C, A25G, A25P, Q27V, D28A, V29A, V29S, A34D, A34G, A51S, S52W, S52M, S52Q, S52H, S52G, S52R, L541, L54G, L54V, S56A, S56P, S56G, S56H, S56Y, S56F, S56N, S56M, R66K, Y92M, T93L, T93M, T93V, and P96G as compared a VL of SEQ ID NO:2 and/or at least one VH substitution selected from D31H, Y52K, T53R, K64S, A88E, V89Y, S93D, D98L and D98V as compared a VH of SEQ ID NO:1.

In another particular aspect, the antibody or binding fragment has an affinity that is 1.2-fold or greater than the affinity of trastuzumab to HER-2. Exemplary antibodies or binding fragments include an anti-HER2 antibody or anti-HER2 binding fragment which has (i) the VL substitution A34V as compared a VL of SEQ ID NO:2;

(ii) at least one VL substitution selected from: T22G, T22S, R24H, R24C, A25G, D28A, V29A, V29S, A34D, A51S, S52W, S52M, S52H, S52G, S52R, L54I, L54G, L54V, S56A, S56P, S56G, S56H, S56Y, S56F, S56N, T93L, T93M, T93V, and P96G as compared a VL of SEQ ID NO:2 and/or at least one VH substitution selected from D31H, T53R, and D98V as compared a VH of SEQ ID NO:1;

(iii) at least one VL substitution selected from: T22G, L54I, and S56Y as compared a VL of SEQ ID NO:2; and/or at least one VH substitution selected from D31T, Y52K, D98M, and D98W, as compared to SEQ ID NO:1; or (iv) at least one VL substitution selected from: T22G, L541, and S56Y as compared a VL of SEQ ID NO:2; and/or at least one VH substitution selected from D31T and Y52K, as compared to SEQ ID NO:1.

In still further aspects, the antibody or binding fragment has an affinity that is 1.3-fold or greater than the affinity of trastuzumab to HER-2. Exemplary antibodies or binding fragments include an anti-HER2 antibody or anti-HER2 binding fragment which has (i) at least the VL substitution A34V as compared a VL of SEQ ID NO:2;

(ii) at least one VL substitution selected from: T22G, D28A, V29S, A34D, A51S, S52G, S52R, L54G, L54V, S56A, S56P, S56Y, S56F, S56N, T93M, T93V, and P96G as compared a VL of SEQ ID NO:2 and/or at the VH substitution D98M as compared a VL of SEQ ID NO:1; or (iii) at least one VL substitution selected from: T22G and S56Y as compared a VL of SEQ ID NO:2; and/or at least one VH substitution selected from D31T and D98M, as compared to SEQ ID NO:1.

In another aspect, the antibody or binding fragment has an affinity that is 1.4-fold or greater than the affinity of trastuzumab to HER-2. Exemplary antibodies or binding fragments include an anti-HER2 antibody or anti-HER2 binding fragment which has (i) at least the VL substitution A34V as compared to a VL of SEQ ID NO:2;

(ii) at least one VL substitution selected from: T22G, A34D, A51S, S52R, L54V and S56Y, as compared a VL of SEQ ID NO:2 and/or at least the VH substitution D98M as compared a VL of SEQ ID NO:1; or (iii) at least the VL substitution T22G as compared a VL of SEQ ID NO:2.

The anti-HER2 antibodies or binding fragments of the disclosure can also contain one or more mutations from any one or more of FIG. 2, 3 or 9.

In still other aspects, antibody or binding fragments with increased affinity have at least at least one of the following combinations of substitutions as compared to the corresponding residues of trastuzumab: A34V as compared to a VL of SEQ ID NO:2 and R83K as compared to a VH of SEQ ID NO:1; Q27L and A34V, as compared to a VL of SEQ ID NO:2; T22G as compared to a VL of SEQ ID NO:2 and D31T as compared to a VH of SEQ ID NO:1; T22G as compared to a VL of SEQ ID NO:2 and D31H as compared to a VH of SEQ ID NO:1; D28L and A34D, as compared to a VL of SEQ ID NO:2; D28N and A34D, as compared to a VL of SEQ ID NO:2; Q27L as compared to a VL of SEQ ID NO:2, A34V as compared to a VL of SEQ ID NO:2 and R83K as compared to a VH of SEQ ID NO:1; Q27L as compared to a VL of SEQ ID NO:2, A34V as compared to a VL of SEQ ID NO:2 and W95F as compared to a VH of SEQ ID NO:1; D28N as compared to a VL of SEQ ID NO:2, A34D as compared to a VL of SEQ ID NO:2 and R83K as compared to a VH of SEQ ID NO:1; or D28N as compared to a VL of SEQ ID NO:2, A34D as compared to a VL of SEQ ID NO:2 and W95F as compared to a VH of SEQ ID NO:1.

In certain aspects, the antibodies of the disclosure have $V_H$ and $V_L$ sequences having at least 80% sequence identity (and in certain embodiments, at least 85%, at least 90%, at least 95%, at least 98%, or at least 99% sequence identity) to the $V_H$ and $V_L$ sequences of trastuzumab, and include at least one amino acid substitution in at least one CDR as compared to trastuzumab. In other aspects, the antibodies of the disclosure have $V_H$ and $V_L$ sequences having at least 80% sequence identity (and in certain embodiments, at least 85%, at least 90%, at least 95%, at least 98%, or at least 99% sequence identity) to the $V_H$ and $V_L$ sequences of trastuzumab, and include at least one amino acid substitution in at least one framework region as compared to trastuzumab. In specific embodiments, the percentage sequence identity for the heavy chain and the light chain compared to the $V_H$ and $V_L$ sequences of trastuzumab is independently selected from at least 80%, at least 85%, at least 90%, at least 95% sequence identity, or at least 99% sequence identity. In certain aspects, the antibodies of the disclosure have $V_H$ and/or $V_L$ sequences having at least 95%, at least 98% or at least 99% sequence identity to the $V_H$ and/or $V_L$ sequences of trastuzumab.

In other aspects, the CDR regions of antibodies of the disclosure have at least 80% sequence identity overall (and in certain embodiments, at least 85%, at least 90%, at least 95%, at least 98%, or at least 99% sequence identity overall) to the CDR sequences of trastuzumab. In specific embodiments, the percentage sequence identity for the CDRs compared to the CDR sequences of trastuzumab is independently selected from at least 70%, at least 75%, at least 80%, at least 85%, at least 90%, at least 95% sequence identity, or at least 99% sequence identity overall. In certain aspects, the antibodies of the disclosure have CDR sequences having at least 95%, at least 98% or at least 99% sequence identity overall to the CDR sequences of trastuzumab.

The antibodies of the disclosure can have up to 17 amino acid substitutions in their CDRs as compared to trastuzumab. In some aspects, the antibodies of the disclosure have up to 13 amino acid substitutions in their CDRs as compared to trastuzumab. In specific embodiments, the antibodies of the disclosure have up to 2, up to 3, up to 4, up to 5, up to 6, up to 7, up to 8, up to 9, up to 10, up to 11, up to 12, up to 13, up to 14, up to 15, up to 16, or up to 17 amino acid substitutions in their CDRs as compared to trastuzumab.

The antibodies of the disclosure can have up to 10 amino acid substitutions in their framework regions as compared to trastuzumab. In specific embodiments, the antibodies of the disclosure have up to 1, up to 2, up to 3, up to 4, up to 5, up to 6, up to 7, up to 8, up to 9 or up to 10 amino acid substitutions in their CDRs as compared to trastuzumab.

In one or more embodiments, the antibodies or binding fragments of the disclosure do not comprise and/or consist of one or more the variants disclosed in Tables 15, 16, 17, 18, 19, 20, 21, 22, 23, and/or 24. In some embodiments, the anti-HER2 antibodies or binding fragments of the disclosure comprise the VH substitution D98W, as compared to trastuzumab. In other embodiments, the anti-HER2 antibodies or binding fragments of the disclosure exclude the VH substitution D98W, as compared to trastuzumab.

The anti-HER2 antibodies of the disclosure differs in sequence from trastuzumab and can also differ in certain characteristics (e.g., stability, ease of expression or production), but retains similar functional characteristics to trastuzumab (e.g., binding to HER2) so as to be suitable for use as a "biosimilar" or "bioequivalent" protein.

Variants of trastuzumab with improved affinity to HER2 as compared to trastuzumab can include one or more substitutions in the framework and/or CDR regions of trastuzumab. Exemplary light chain CDR substitutions are disclosed in Tables 4, 6, 8 and 14. Exemplary heavy chain CDR substitutions are disclosed in Tables 3, 5 and 7. Exemplary framework region substitutions are disclosed in Tables 9, 10, 11, 12 and 13. Table 13 recites heavy chain combination mutations comprising a framework mutation and a CDR mutation.

In some aspects, the anti-HER2 antibodies and binding fragments of the disclosure have:

- heavy chain CDRs with at least one amino acid substitution in at least one heavy chain CDR as compared to trastuzumab; and/or
- light chain CDRs with at least one amino acid substitution in at least one light chain CDR as compared to trastuzumab; and/or
- framework regions with at least one amino acid substitution in at least one framework region of a $V_H$ region as compared to trastuzumab; and/or
- framework regions with at least one amino acid substitution in at least one framework region of a $V_L$ region as compared to trastuzumab.

Additional exemplary embodiments of the disclosure are listed hereinbelow.

In certain aspects, the anti-HER2 antibodies include at least one substitution as compared to trastuzumab selected from D31L, D31R, D31V, T32K, T32R, and I34D in CDR-H1 (SEQ ID NO:3). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 15, 16, 17, 18, 19, 20, 21, 22, 23, and, optionally, Table 24.

In certain aspects, the anti-HER2 antibodies include at least one substitution as compared to trastuzumab selected from T53L, T53R, K64R, and K64S in CDR-H2 (SEQ ID NO:4). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In various aspects, the anti-HER2 antibodies include at least one substitution as compared to trastuzumab selected from G26C, N28G, K30R, K30V, D31H, D31Q, D31T and T32V in CDR-H1 (SEQ ID NO:3). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In other aspects, the anti-HER2 antibodies include at least one substitution as compared to trastuzumab selected from Y52K, Y52Q, T57G, T57V, A60K, D61S, D61E, S62E, S62G, S62A, V63A, K64A, G65V, G65E, and G65I in CDR-H2 (SEQ ID NO:4). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In still other aspects, the anti-HER2 antibodies include at least one substitution as compared to trastuzumab selected from D98V, D98M, D101L and Y102R in CDR-H3 (SEQ ID NO:5). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In some aspects, the anti-HER2 antibodies include at least one substitution as compared to trastuzumab selected from N28S, N28W, K30W, D31W, D31G and D31S in CDR-H1 (SEQ ID NO:3), wherein CDR-H1 in the HER2 antibodies does not consist of a CDR-H1 sequence set forth in Tables 17 or Table 20. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 18, 19, 21, 22, 23, and, optionally, Table 24.

In other embodiments, the anti-HER2 antibodies include at least one substitution selected from Y52R, Y52S, T53S, T53K, T53G, N54S, T57S, S62R and K64Q in CDR-H2 (SEQ ID NO:4), wherein CDR-H2 in the HER2 antibodies does not consist of a CDR-H2 sequence set forth in Tables 17 or Table 20. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 18, 19, 21, 22, 23, and, optionally, Table 24.

In still other embodiments, the anti-HER2 antibodies include at least one substitution selected from W95Y, W95F, G97R, G97T, D98G, D98T, D98R, D98Q, D98E, D98S, D98Y, D98F, D98L, D98P, D98H, A100bV, A100bS, A100bE, M100cF, Y102G, Y102S, Y102K and Y102H in CDR-H3 (SEQ ID NO:5), wherein CDR-H3 in the HER2 antibodies does not consist of a CDR-H3 sequence set forth in Tables 15, 17, or 20. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 16, 18, 19, 21, 22, 23, and, optionally, Table 24.

In certain aspects, the anti-HER2 antibodies include at least one substitution as compared to trastuzumab selected from Q27L, Q27V, Q271, Q27Y, D28L, D28A, D28M, D28W, A34V, A34G, A34D, A34S and A34E in CDR-L1 (SEQ ID NO:6). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In other aspects, the anti-HER2 antibodies include at least one substitution as compared to trastuzumab selected from R24H, R24E, R24C, R24V, A25C, A25G, A25P, V29A and V29S in CDR-L1 (SEQ ID NO:6). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In still other aspects, the anti-HER2 antibodies include at least one substitution as compared to trastuzumab selected from A51S, S52W, S52M, S52Q, S52H, S52G, S52R, L54I, L54G, L54V, S56A, S56P, S56G, S56H, S56Y, S56F, S56N and S56M in CDR-L2 (SEQ ID NO:7). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In certain aspects, the anti-HER2 antibodies include at least one substitution as compared to trastuzumab selected from Y92M, T93L, T93M, T93G, T93V, P96G and T97D in CDR-L3 (SEQ ID NO:8). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In various aspects, the anti-HER2 antibodies include at least one substitution as compared to trastuzumab selected from A25S, Q27R, Q27S, Q27F, D28G, D28N, D28R, D28P, D28S, V29I, T31S, and A34N in CDR-L1 (SEQ ID NO:6), wherein CDR-L1 in the HER2 antibodies does not consist of a CDR-L1 sequence set forth in Tables 18, 19 or 21. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 20, 22, 23, and, optionally, Table 24.

In other aspects, the anti-HER2 antibodies include at least one substitution as compared to trastuzumab selected from A51G, F53W, F53Y, L54S, Y55L and Y55A in CDR-L2 (SEQ ID NO:7), wherein CDR-L2 in the HER2 antibodies does not consist of a CDR-L2 sequence set forth in Tables 16, 18, 19 or 21. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 17, 20, 22, 23, and, optionally, Table 24.

In yet other aspects, the anti-HER2 antibodies include at least one substitution as compared to trastuzumab selected from H91W, H91Y, T93S, T94S and P96S in CDR-L3 (SEQ ID NO:8), wherein CDR-L3 in the HER2 antibodies does not consist of a CDR-L3 sequence set forth in Tables 16, 18, 19 or 21. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 17, 20, 22, 23, and, optionally, Table 24.

In certain aspects, the anti-HER2 antibodies include at least one substitution as compared to trastuzumab selected from A88Q, A88W, A88E, V89R, V89Y, S93N, S93Y, S93P and S93D in framework region 3 of the heavy chain (FR-H3) (SEQ ID NO:79). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In various aspects, the anti-HER2 antibodies include at least one substitution as compared to trastuzumab selected from A78C, A78W, A78Q, S82bV, S82bL, L82cV, L82cA, L82cE, L82cG, R83V, R83L, R83G, R83K, A84M, A84W, A84K, A84G, A84Q, A84R, E85L, E85G, E85A, E85S, E85N, E85H, D86S, D86G, T87W, T87E, T87L, T87F, T87H, T87D, A88G, A88R, A88K, A88V, V89K, V89S, V89W, V89G, Y90V, Y90L, Y90I, Y91L, Y91W and C92G in FR-H3 (SEQ ID NO:79). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In various aspects, the anti-HER2 antibodies include at least one substitution as compared to trastuzumab selected from T22G, T22S, C23A and C23N in FR-L1 (SEQ ID NO:81). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In other aspects, the anti-HER2 antibodies include at least one substitution as compared to trastuzumab selected from W35H and W35F in FR-L2 (SEQ ID NO:82). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In yet other aspects, the anti-HER2 antibodies include the substitution R66K in FR-L3 (SEQ ID NO:83). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In some aspects, the anti-HER2 antibodies include at least one substitution as compared to trastuzumab selected from A78V, Y91F, S93V, S93L, S93Q and S93T in FR-H3 (SEQ ID NO:79), wherein FR-H3 in the HER2 antibodies does not consist of a FR-H3 sequence set forth in Tables 22. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 23, and, optionally, Table 24.

In some aspects, the anti-HER2 antibodies include a combination of substitutions as compared to trastuzumab selected from S93N in FR-H3 (SEQ ID NO:79) and W95Y in CDR-H3 (SEQ ID NO:5); S93D in FR-H3 and W95Y in CDR-H3; S93A in FR-H3 and W95Y in CDR-H3; S93L in FR-H3 and W95Y in CDR-H3; S93N in FR-H3 and W95F in CDR-H3; S93D in FR-H3 and W95F in CDR-H3; and S93L in FR-H3 and W95F in CDR-H3. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In other aspects, the anti-HER2 antibodies include a combination of substitutions as compared to trastuzumab selected from S93V in FR-H3 (SEQ ID NO:79) and W95Y in CDR-H3 (SEQ ID NO:5); S93A in FR-H3 and W95F in CDR-H3; and S93V in FR-H3 and W95F in CDR-H3, wherein position 94 in FR-H3 of said HER2 antibodies is not serine or threonine. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In other aspects, the anti-HER2 antibodies include a combination of substitutions as compared to trastuzumab selected from Q27K and A34G; Q27V and A34G; Q27L and A34G; Q27F and A34G; Q27I and A34G; Q27Y and A34G; Q27R and A34G; Q27S and A34D; Q27K and A34D; Q27V and A34D; Q27L and A34D; Q27F and A34D; Q27I and A34D; Q27Y and A34D; Q27R and A34D; Q27S and A34V; Q27K and A34V; Q27V and A34V; Q27L and A34V; Q27F and A34V; Q27I and A34V; Q27Y and A34V; Q27R and A34V; D28A and A34G; D28N and A34G; D28L and A34G; D28G and A34D; D28A and A34D; D28N and A34D; D28L and A34D; D28G and A34V; D28A and A34V; D28N and A34V; and D28L and A34V in CDR-L1 (SEQ ID NO:6). Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In still other aspects, the anti-HER2 antibodies include a combination of substitutions as compared to trastuzumab selected from Q27S in CDR-L1 and A34G in CDR-L1 (SEQ ID NO:6); and D28G in CDR-L1 and A34G in CDR-L1, wherein position 9 in CDR-L1 of said anti-HER2 antibodies is not serine. Additional mutations that can be incorporated into the variant antibodies can be mutations that do not destroy the ability of the antibodies to bind to HER2, including but not limited to the mutations described in Tables 3, 4, 7, 8, 9, 10, 11, 13 and 14, or known mutations such as the mutations described in Tables 5, 6, 15, 16, 17, 18, 19, 20, 21, 22, 23, and, optionally, Table 24.

In certain aspects, the present disclosure provides anti-HER2 antibodies that result in a greater adaptive immune response than trastuzumab. Accordingly, the present disclosure provides anti-HER2 antibodies having single or multiple amino acid substitutions in their CDRs and/or framework regions as compared to the CDRs and/or framework regions of trastuzumab, wherein at least one substitution results in an increased adaptive immune response induced by the antibody as compared to trastuzumab.

The present disclosure provides pharmaceutical compositions comprising modified anti-HER2 antibodies.

Nucleic acids comprising nucleotide sequences encoding the anti-HER2 antibodies of the disclosure are provided herein, as are vectors comprising nucleic acids. Additionally, prokaryotic and eukaryotic host cells transformed with a vector comprising a nucleotide sequence encoding an anti-HER2 antibody are provided herein, as well as eukaryotic (such as mammalian) host cells engineered to express the nucleotide sequences. Methods of producing anti-HER2 antibodies by culturing host cells are also provided.

The anti-HER2 antibodies of the disclosure are useful in the treatment of cancers (e.g., breast cancer, ovarian cancer, gastric tumors, colon cancer, non-small cell lung cancer, oral cancer, cervical cancer, osteosarcoma, pancreatic cancer, salivary gland cancer, prostate cancer, endometrial cancer, and bladder cancer), and mammary and extra-mammary Paget's disease.

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art base or were common general knowledge in the field relevant to the present disclosure as it existed anywhere before the priority date of this application.

The features and advantages of the disclosure will become further apparent from the following detailed description of embodiments thereof.

6. BRIEF DESCRIPTION OF THE TABLES AND FIGURES

Table 1 shows the numbering of the amino acids in the heavy chain CDRs of trastuzumab.

Table 2 shows the numbering of the amino acids in the light chain CDRs of trastuzumab.

Table 3 shows mutations in the trastuzumab heavy chain CDRs that do not substantially negatively impact HER2 binding, i.e., result in comparable or improved affinity relative to trastuzumab, and can be incorporated into the antibodies of the disclosure.

Table 4 shows mutations in the trastuzumab light chain CDRs that do not substantially negatively impact HER2 binding, i.e., result in comparable or improved affinity relative to trastuzumab, and can be incorporated into the antibodies of the disclosure.

Table 5 shows known mutations in the trastuzumab heavy chain CDRs that can be incorporated into the antibodies of the disclosure.

Table 6 shows known mutations in the trastuzumab light chain CDRs that can be incorporated into the antibodies of the disclosure.

Table 7 shows additional mutations in the trastuzumab heavy chain CDRs that do not substantially negatively impact HER2 binding, i.e., result in comparable or improved affinity relative to trastuzumab, and can be incorporated into the antibodies of the disclosure.

Table 8 shows additional mutations in the trastuzumab light chain CDRs that do not substantially negatively impact HER2 binding, i.e., result in comparable or improved affinity relative to trastuzumab, and can be incorporated into the antibodies of the disclosure.

Table 9 shows mutations in the trastuzumab heavy chain framework regions that do not substantially negatively impact HER2 binding, i.e., result in comparable or improved affinity relative to trastuzumab, and can be incorporated into the antibodies of the disclosure.

Table 10 shows additional mutations in the trastuzumab heavy chain framework regions that do not substantially negatively impact HER2 binding, i.e., result in comparable or improved affinity relative to trastuzumab, and can be incorporated into the antibodies of the disclosure.

Table 11 shows additional mutations in the trastuzumab light chain framework regions that do not substantially negatively impact HER2 binding, i.e., result in comparable or improved affinity relative to trastuzumab, and can be incorporated into the antibodies of the disclosure.

Table 12 shows known mutations in the trastuzumab heavy chain framework regions that can be incorporated into the antibodies of the disclosure.

Table 13 shows combinations of mutations that do not substantially negatively impact HER2 binding, i.e., result in comparable or improved affinity relative to trastuzumab, and can be incorporated into the antibodies of the disclosure.

Table 14 shows combinations of mutations that do not substantially negatively impact HER2 binding, i.e., result in comparable or improved affinity relative to trastuzumab, and can be incorporated into the antibodies of the disclosure.

Table 15 (15.1 to 15.3) shows known mutations in the trastuzumab heavy chain CDRs that can be incorporated into the antibodies of the disclosure.

Table 16 (16.1 to 16.2) shows known mutations in the trastuzumab light chain CDRs that can be incorporated into the antibodies of the disclosure.

Table 17 (17-1.1 to 17-12) show known mutations in the trastuzumab heavy chain CDRs found in phage binding libraries that can be incorporated into the antibodies of the disclosure.

Table 18 (18-1 to 18-13.2) show known mutations in the trastuzumab light chain CDRs found in phage binding libraries that can be incorporated into the antibodies of the disclosure.

Table 19 (19-1 to 19-5) show known mutations in the trastuzumab light chain CDRs found in bispecific antibody phage binding libraries that can be incorporated into the antibodies of the disclosure.

Table 20 (20-1.1 to 20-2.2) shows known mutations in the trastuzumab heavy chain CDRs that can be incorporated into the antibodies of the disclosure.

Table 21 (21.1 to 21.2) shows known mutations in the trastuzumab light chain CDRs that can be incorporated into the antibodies of the disclosure.

Table 22 (22-1 to 22-6) shows known mutations in the framework regions of the trastuzumab heavy chain that can be incorporated into the antibodies of the disclosure.

Table 23 (23-1.1 to 23-4.2) shows known mutations in the framework and CDR regions of the trastuzumab light chain that can be incorporated into the antibodies of the disclosure.

Table 24 (24-1 and 24-2) shows mutations disclosed in Li et al., 2009, Journal of Biological Chemistry 285(6):3865-3871.

FIG. 1A-1C. FIG. 1A shows the amino acid sequences and numbering of the trastuzumab heavy and light chain variable regions, SEQ ID NO:1 and SEQ ID NO:2, respectively, with CDR regions shaded. FIG. 1B shows the CDR sequences and corresponding sequence identifiers of trastuzumab. FIG. 1C shows the framework sequences and corresponding sequence identifiers of trastuzumab.

FIGS. 2A-2G show the binding affinities of trastuzumab variants for HER2 relative to trastuzumab (binding affinity=100) as measured in FACS binding assays with labeled HER2 ECD-Cλ. Experiments were repeated 2-3 times and mean value relative to that of parental trastuzumab were shown as tables (FIGS. 2A and 2B) and bar graphs of heavy and light chain variants (FIGS. 2C-2G).

FIG. 3 shows the FACS competition on KS-BR3, a hormone-independent cell line derived from a breast adenocarcinoma expressing high level of HER2 (Koyama et al., Neoplasia 9: 1021-1029 (2007)). Trastuzumab produced in 293c18 competes with Herceptin® while irrelevant IgG1 showed no competition (FIG. 3A). Comparison of binding among selected beneficial mutations, deimmunizing mutation and combinatorial mutation are shown in FIGS. 3B, 3C and 3D, respectively. Bar graph representations of beneficial mutations, deimmunizing mutations and combinatorial mutations are shown in FIGS. 3E, 3F and 3G, respectively.

FIGS. 4A-4B respectively show the amino acid sequences, respectively, of all $V_L$ and $V_H$ peptides of trastuzumab tested as potential $CD4^+$ epitopes.

FIGS. 5A-5D show trastuzumab $V_L$ and $V_H$ peptide responses. FIG. 5A and FIG. 5B respectively show percent of donor responses to each $V_L$ and $V_H$ peptide with a stimulation index of 2.95 or greater. N=100 donors. FIG. 5C and FIG. 5D respectively show the average stimulation index for all 100 donors for each $V_L$ and $V_H$ peptide plus or minus standard error.

FIGS. 6A-6C show a series of variant peptides based on the identified $CD4^+$ T cell epitope regions, the peptide at position 29 that encompasses $V_H$ framework 3 and 3 amino acids of CDR3 and the peptide at position 8 that encompasses $V_L$ CDR1 and portions of Framework 1 and 2. FIG. 6A shows specific amino acid changes in the $V_H$ framework 3 and CDR3 (shaded amino acids). FIGS. 6B and 6C show specific amino acid changes in $V_L$ CDR2 and portions of frameworks 1 and 2 (shaded amino acids). The specific amino acid changes shown were confirmed to have no impact on the affinity of antigen binding. All peptides were tested for their ability to induce proliferative responses in human $CD4^+$ T cells by the methods detailed in Example 1.

FIG. 7 shows in vitro CD4+ T cell proliferation responses of 83 donor samples to trastuzumab variant peptides. FIG. 7A. VH epitope peptide variants. FIG. 7B. VL epitope variants. (Open diamonds: parent peptides. Closed diamonds: variant peptides as per FIGS. 6A-6C. Open circles: selected deimmunized variants).

FIG. 8 shows exemplary trastuzumab VH and VL epitope variant peptides, wherein "SI" is the stimulation index averaged for all 83 tested donors and "Percent responders" is the percentage of donors with an SI>2.95.

FIG. 9 shows the binding of trastuzumab variants to HER2 as measured by competition AlphaLISA®. Representative results of binding competition are shown in FIG. 9A (beneficial single mutations), 9B (deimmunizing mutations) and 9C (combinatorial mutations). Relative binding activities of variants that showed equivalent binding to trastuzumab are shown in FIG. 9D (single chain variants) and 9E (combination of heavy and light chain variants). Data are normalized with an $IC_{50}$ value obtained from wild-type trastuzumab from three independent sets of experiments. Each data point of the dilution curve was duplicated in the assay plate.

FIG. 10 shows the binding kinetics of trastuzumab variants as measured by BIAcore. Association ($k_{on}$) and dissociation ($k_{off}$) rate constant of trastuzumab binding against HER2 ECD were determined using surface plasmon resonance in a BIAcore. The dissociation constant ($K_D$) was calculated from $k_{on}/k_{off}$.

7. DETAILED DESCRIPTION

7.1. Anti-HER2 Antibodies

The present disclosure provides anti-HER2 antibodies. Unless indicated otherwise, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including e.g., Fab', $F(ab')_2$, Fab, Fv, rIgG, and scFv fragments. Moreover, unless otherwise indicated, the term "monoclonal antibody" (mAb) is meant to include both intact molecules, as well as, antibody fragments (such as, for example, Fab and $F(ab')_2$ fragments) which are capable of specifically binding to a protein. Fab and $F(ab')_2$ fragments lack the Fc fragment of intact antibody, clear more rapidly from the circulation of the animal, and may have less non-specific tissue binding than an intact antibody (Wahl et al., 1983, J. Nucl. Med. 24:316).

The term "scFv" refers to a single chain Fv antibody in which the variable domains of the heavy chain and the light chain from a traditional antibody have been joined to form one chain.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at the amino terminus a variable domain ($V_H$) followed by a number of constant domains. Each light chain has a variable domain at the amino terminus ($V_L$) and a constant domain at the carboxy terminus.

The anti-HER2 antibodies of the disclosure bind to human HER2 and inhibit its activity in a cell.

The anti-HER2 antibodies of the disclosure contain complementarity determining regions (CDRs) that are related in sequence to the CDRs of the antibody trastuzumab (also known as Herceptin®).

CDRs are also known as hypervariable regions both in the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions in the order FR1-CDR1-FR2-CDR2-FR3-CDR3-FR4 and, with the CDRs from the other chain, contribute to the formation of the target binding site of antibodies (see Kabat et al., Sequences of Proteins of Immunological Interest (National Institute of Health, Bethesda, Md. 1987)). As used herein, numbering of immunoglobulin amino acid residues is done according to the immunoglobulin amino acid residue numbering system of Kabat et al., unless otherwise indicated.

The sequences of the heavy and light chain variable regions of trastuzumab are represented by SEQ ID NO:1 and SEQ ID NO:2, respectively. The sequences of the heavy and light chain variable regions are also depicted in FIG. 1A. The sequences of the CDRs of trastuzumab, and their corresponding identifiers, are presented in FIG. 1B. Any nucleotide sequences encoding SEQ ID NO:1 or SEQ ID NO:2 can be used in the compositions and methods of the present disclosure.

The present disclosure further provides anti-HER2 antibody fragments comprising CDR sequences that are related to the CDR sequences of trastuzumab. The term "antibody fragment" refers to a portion of a full-length antibody, generally the target binding or variable region. Examples of antibody fragments include Fab, Fab', $F(ab')_2$ and Fv fragments. An "Fv" fragment is the minimum antibody fragment which contains a complete target recognition and binding site. This region consists of a dimer of one heavy and one light chain variable domain in a tight, noncovalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target. "Single chain Fv" or "scFv" antibody fragments comprise the $V_H$ and $V_L$ domains of an antibody in a single polypeptide chain. Generally, the Fv polypeptide further comprises a polypeptide linker between the $V_H$ and $V_L$ domains which enables the scFv to form the desired structure for target binding. "Single domain antibodies" are composed of a single $V_H$ or $V_L$ domain which exhibit sufficient affinity to the target. In a specific embodiment, the single domain antibody is a camelid antibody (see, e.g., Riechmann, 1999, Journal of Immunological Methods 231: 25-38).

The Fab fragment contains the constant domain of the light chain and the first constant domain ($CH_1$) of the heavy chain. Fab' fragments differ from Fab fragments by the addition of a few residues at the carboxyl terminus of the heavy chain $CH_1$ domain including one or more cysteines from the antibody hinge region. F(ab') fragments are produced by cleavage of the disulfide bond at the hinge cysteines of the $F(ab')_2$ pepsin digestion product. Additional chemical couplings of antibody fragments are known to those of ordinary skill in the art.

In certain embodiments, the anti-HER2 antibodies of the disclosure are monoclonal antibodies. The term “monoclonal antibody” as used herein is not limited to antibodies produced through hybridoma technology. The term “monoclonal antibody” refers to an antibody that is derived from a single clone, including any eukaryotic, prokaryotic, or phage clone, and not the method by which it is produced. Monoclonal antibodies useful in connection with the present disclosure can be prepared using a wide variety of techniques known in the art including the use of hybridoma, recombinant, and phage display technologies, or a combination thereof. The anti-HER2 antibodies of the disclosure include chimeric, primatized, humanized, or human antibodies.

The anti-HER2 antibodies of the disclosure can be chimeric antibodies. The term “chimeric” antibody as used herein refers to an antibody having variable sequences derived from a non-human immunoglobulin, such as rat or mouse antibody, and human immunoglobulin constant regions, typically chosen from a human immunoglobulin template. Methods for producing chimeric antibodies are known in the art. See, e.g., Morrison, 1985, Science 229 (4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816397, which are incorporated herein by reference in their entireties.

The anti-HER2 antibodies of the disclosure can be humanized. “Humanized” forms of non-human (e.g., murine) antibodies are chimeric immunoglobulins, immunoglobulin chains or fragments thereof (such as Fv, Fab, Fab', $F(ab')_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

The anti-HER2 antibodies of the disclosure can be human antibodies. Completely “human” anti-HER2 antibodies can be desirable for therapeutic treatment of human patients. As used herein, “human antibodies” include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Completely human antibodies that recognize a selected epitope can be generated using a technique referred to as “guided selection.” In this approach a selected non-human monoclonal antibody, e.g., a mouse antibody, is used to guide the selection of a completely human antibody recognizing the same epitope (Jespers et al., 1988, Biotechnology 12:899-903).

The anti-HER2 antibodies of the disclosure can be primatized. The term “primatized antibody” refers to an antibody comprising monkey variable regions and human constant regions. Methods for producing primatized antibodies are known in the art. See e.g., U.S. Pat. Nos. 5,658,570; 5,681,722; and 5,693,780, which are incorporated herein by reference in their entireties.

The anti-HER2 antibodies of the disclosure can be bispecific antibodies. Bispecific antibodies are monoclonal, often human or humanized, antibodies that have binding specificities for at least two different antigens. In the present disclosure, one of the binding specificities can be directed towards HER2, the other can be for any other antigen, e.g., for a cell-surface protein, receptor, receptor subunit, tissue-specific antigen, virally derived protein, virally encoded envelope protein, bacterially derived protein, or bacterial surface protein, etc.

The anti-HER2 antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein (see Section 7.9 for a discussion of antibody conjugates), etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (see, e.g., Wolfson, 2006, Chem. Biol. 13(10):1011-2).

In yet another embodiment of the disclosure, the anti-HER2 antibodies or fragments thereof can be antibodies or antibody fragments whose sequence has been modified to alter at least one constant region-mediated biological effector function relative to the corresponding wild type sequence.

For example, in some embodiments, an anti-HER2 antibody of the disclosure can be modified to reduce at least one constant region-mediated biological effector function relative to an unmodified antibody, e.g., reduced binding to the Fc receptor (FcγR). FcγR binding can be reduced by mutating the immunoglobulin constant region segment of the antibody at particular regions necessary for FcγR interactions (see e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

In other embodiments, an anti-HER2 antibody of the disclosure can be modified to acquire or improve at least one constant region-mediated biological effector function relative to an unmodified antibody, e.g., to enhance FcγR interactions (see, e.g., US 2006/0134709). For example, an anti-HER2 antibody of the disclosure can have a constant region that binds FcγRIIA, FcγRIIB and/or FcγRIIIA with greater affinity than the corresponding wild type constant region.

Thus, antibodies of the disclosure can have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" shown in FIG. 4 of U.S. Pat. No. 5,834,597, in which residue 236 is deleted and residues 234, 235 and 237 (using EU numbering) are substituted with alanines.

In some embodiments, the anti-HER2 antibodies of the disclosure have low levels of or lack fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

In yet another aspect, the anti-HER2 antibodies or fragments thereof can be antibodies or antibody fragments that have been modified to increase or reduce their binding affinities to the fetal Fc receptor, FcRn, for example by mutating the immunoglobulin constant region segment at particular regions involved in FcRn interactions (see e.g., WO 2005/123780). In particular embodiments, an anti-HER2 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which table is incorporated by reference herein in its entirety. Such mutations increase the antibody's binding to FcRn, which protects the antibody from degradation and increases its half-life.

In yet other aspects, an anti-HER2 antibody has one or more amino acids inserted into one or more of its hypervariable regions, for example as described in S. Jung and A. Plückthun (1997) Improving in vivo folding and stability of a single-chain Fv antibody fragment by loop grafting. Protein Engineering 10:9, 959-966; Yazaki, et al. (2004) Humanization of the anti-CEA T84.66 antibody based on crystal structure data. Protein Eng Des Sel. 17(5):481-9. Epub 2004 Aug. 17.

In various embodiments, the anti-HER2 antibodies or fragments thereof can be antibodies or antibody fragments that have been modified for increased expression in heterologous hosts. In certain embodiments, the anti-HER2 antibodies or fragments thereof can be antibodies or antibody fragments that have been modified for increased expression in and/or secretion from heterologous host cells. In some embodiments, the anti-HER2 antibodies or fragments thereof are modified for increased expression in bacteria, such as *E. coli*. In other embodiments, the anti-HER2 antibodies or fragments thereof are modified for increased expression in yeast. (Kieke et al., 1999, Proc. Nat'l Acad. Sci. USA 96:5651-5656). In still other embodiments, the anti-HER2 antibodies or fragments thereof are modified for increased expression in insect cells. In additional embodiments, the anti-HER2 antibodies or fragments thereof are modified for increased expression in mammalian cells, such as CHO cells.

In certain embodiments, the anti-HER2 antibodies or fragments thereof can be antibodies or antibody fragments that have been modified to increase stability of the antibodies during production. In some embodiments, the antibodies or fragments thereof can be modified to replace one or more amino acids such as asparagine or glutamine that are susceptible to nonenzymatic deamidation with amino acids that do not undergo deamidation. (Huang et al., 2005, Anal. Chem. 77:1432-1439). In other embodiments, the antibodies or fragments thereof can be modified to replace one or more amino acids that is susceptible to oxidation, such as methionine, cysteine or tryptophan, with an amino acid that does not readily undergo oxidation. In still other embodiments, the antibodies or fragments thereof can be modified to replace one or more amino acids that is susceptible to cyclization, such as asparagine or glutamic acid, with an amino acid that does not readily undergo cyclization.

7.2. Nucleic Acids and Expression Systems

The present disclosure encompasses nucleic acid molecules and host cells encoding the anti-HER2 antibodies of the disclosure.

An anti-HER2 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

In one embodiment, the anti-HER2 antibodies are similar to trastuzumab but for changes in one or more CDRs (referred to herein as having "trastuzumab-related" sequences). In another embodiment, the anti-HER2 antibodies are similar to trastuzumab but for changes in one or more framework regions. In yet another embodiment, the anti-HER2 antibodies are similar to trastuzumab but for changes in one or more CDRs and in one or more framework regions. To generate nucleic acids encoding such anti-HER2 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (see e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference). A DNA fragment encoding the heavy or light chain variable region of trastuzumab can be synthesized and used as a template for mutagenesis to generate a variant as described herein using routine mutagenesis techniques; alternatively, a DNA fragment encoding the variant can be directly synthesized.

Once DNA fragments encoding trastuzumab or trastuzumab-related VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($CH_1$, $CH_2$, $CH_3$ and, optionally, $CH_4$). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ constant region. For a Fab fragment heavy chain gene, the $V_H$-encoding DNA can be operatively linked to another DNA molecule encoding only the heavy chain $CH_1$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al., 1991, Sequences of Proteins of Immunological Interest, Fifth Edition (U.S. Department of Health and Human Services, NIH Publication No. 91-3242)) and DNA fragments encompassing these regions can be obtained by standard PCR amplification. The light chain constant region can be a kappa or lambda constant region, but in certain embodiments is a kappa constant region.

To create a scFv gene, the $V_H$ and $V_L$-encoding DNA fragments are operatively linked to another fragment encoding a flexible linker, e.g., encoding the amino acid sequence $(Gly_4{\sim}Ser)_3$, such that the $V_H$ and $V_L$ sequences can be expressed as a contiguous single-chain protein, with the $V_L$ and $V_H$ regions joined by the flexible linker (see e.g., Bird et al., 1988, Science 242:423-426; Huston et al., 1988, Proc. Natl. Acad. Sci. USA 85:5879-5883; McCafferty et al., 1990, Nature 348:552-554).

To express the anti-HER2 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the trastuzumab or trastuzumab-related light or heavy chain sequences, the expression vector can already carry antibody constant region sequences. For example, one approach to converting the trastuzumab or trastuzumab-related $V_H$ and $V_L$ sequences to full-length antibody genes is to insert them into expression vectors already encoding heavy chain constant and light chain constant regions, respectively, such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in $DHFR^-$ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies of the disclosure include Chinese Hamster Ovary (CHO cells) (including $DHFR^-$ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-HER2 antibody of this disclosure.

Recombinant DNA technology can also be used to remove some or all of the DNA encoding either or both of the light and heavy chains that is not necessary for binding to HER2. The molecules expressed from such truncated DNA molecules are also encompassed by the antibodies of the disclosure.

In addition, bifunctional antibodies can be produced in which one heavy and one light chain are an antibody of the disclosure and the other heavy and light chain are specific for an antigen other than HER2 by crosslinking an antibody of the disclosure to a second antibody by standard chemical crosslinking methods. Bifunctional antibodies can also be made by expressing a nucleic acid engineered to encode a bifunctional antibody.

In certain embodiments, dual specific antibodies, i.e., antibodies that bind HER2 and an unrelated antigen using the same binding site, can be produced by mutating amino acid residues in the light chain and/or heavy chain CDRs. In various embodiments, dual specific antibodies that bind two antigens, such as HER2 and VEGF, can be produced by mutating amino acid residues in the periphery of the antigen binding site. (Bostrom et al., 2009, Science 323:1610-1614). Dual functional antibodies can be made by expressing a nucleic acid engineered to encode a dual specific antibody.

For recombinant expression of an anti-HER2 antibody of the disclosure, the host cell can be co-transfected with two expression vectors of the disclosure, the first vector encoding a heavy chain derived polypeptide and the second vector encoding a light chain derived polypeptide. Typically, the two vectors each contain a separate selectable marker. Alternatively, a single vector can be used which encodes both heavy and light chain polypeptides.

Once a nucleic acid encoding one or more portions of trastuzumab or of an anti-HER2 antibody with CDR sequences related to the CDR sequences of trastuzumab is generated, further alterations or mutations can be introduced into the coding sequence, for example to generate nucleic acids encoding antibodies with different CDR sequences, antibodies with reduced affinity to the Fc receptor, or antibodies of different subclasses.

The anti-HER2 antibodies of the disclosure can also be produced by chemical synthesis (e.g., by the methods described in Solid Phase Peptide Synthesis, 2nd ed., 1984 The Pierce Chemical Co., Rockford, Ill.). Variant antibodies can also be generated using a cell-free platform (see, e.g., Chu et al., Biochemia No. 2, 2001 (Roche Molecular Biologicals)).

Once an anti-HER2 antibody of the disclosure has been produced by recombinant expression, it can be purified by any method known in the art for purification of an immunoglobulin molecule, for example, by chromatography (e.g., ion exchange, affinity, particularly by affinity for HER2 after Protein A or Protein G selection, and sizing column chromatography), centrifugation, differential solubility, or by any other standard technique for the purification of proteins. Further, the anti-HER2 antibodies of the present disclosure or fragments thereof can be fused to heterologous polypeptide sequences described herein or otherwise known in the art to facilitate purification.

Once isolated, an anti-HER2 antibody can, if desired, be further purified, e.g., by high performance liquid chromatography (See, e.g., Fisher, Laboratory Techniques In Biochemistry And Molecular Biology (Work and Burdon, eds., Elsevier, 1980)), or by gel filtration chromatography on a Superdex™ 75 column (Pharmacia Biotech AB, Uppsala, Sweden).

7.3. Biological Activities of Anti-HER2 Antibodies

In certain embodiments, the anti-HER2 antibodies of the disclosure have certain biological activities, such as competing with trastuzumab for binding to HER2 or neutralizing HER2 activity.

Accordingly, in certain embodiments, anti-HER2 antibodies of the disclosure compete with trastuzumab for binding to HER2. The ability to compete for binding to HER2 can be tested using a competition assay. Anti-HER2 antibodies of the disclosure can be titered in PBS-BSA and tested for the ability to block the binding of a particular concentration of biotinylated trastuzumab (e.g., 40 nM) to HER2 extracellular domain ("HER2-ECD") immobilized on microtiter plates (e.g., by incubating 5 μg/ml HER2-ECD in 50 mM ammonium bicarbonate, pH 9.3 overnight at 4° C.). Following a 1 h incubation with antibody, the plate is washed with PBS-Tween and Strepavidin/HRP conjugate (Streptavidin-POD, Roche Molecular Biochemicals) is added for 30 min. Plates are washed again with PBS-Tween and the bound HRP is assayed using ABTS/$H_2O_2$ substrate (Kirkegaard & Perry Laboratories) and the absorbance at 405 nm is monitored. The absorbance at 405 nm is plotted versus the concentration of anti-HER2 antibody originally added to the well. Sigmoidal curves are fit to a four parameter equation by nonlinear regression analysis (Marquardt, J. Soc. Indust. Appl. Math. 11:431-441 (1963)); the concentration of anti-HER2 antibody required to give a half-maximal signal in the assay ($IC_{50}$) can be calculated from the curves. Variations on this competition assay can also be used to test competition between an anti-HER2 antibody of the disclosure and trastuzumab. For example, in certain aspects, the anti-HER2 antibody is used as a reference antibody and trastuzumab is used as a test antibody.

Additionally, instead of soluble HER2, membrane-bound HER2 expressed on the surfaces of cell (for example mammalian cells) in culture can be used.

Other formats for competition assays are known in the art and can be employed, such as, for example, Amplified Luminescence Proximity Homogeneous Assay ("Alpha"), for example the AlphaLISA assay.

AlphaLISA is an analogous screening process to ELISA, which involves the attachment of a capture antibody to a solid phase support, whereupon samples containing antigen are then added in a matrix or buffer adapted to minimize attachment to the solid phase. In AlphaLISA, an analyte is captured by a biotinylated antibody bound to streptavidin-coated donor beads and a second antibody conjugated to AlphaLISA acceptor beads. The binding of the two antibodies to the analyte brings donor and acceptor beads into proximity. Laser irradiation of donor beads at 680 nm generates a flow of singlet oxygen, triggering a cascade of chemical events in nearby acceptor beads, which results in a chemiluminescent emission at 615 nm. In competitive AlphaLISA immunoassays, a biotinylated analyte bound to streptavidin donor beads is used with an antibody conjugated to AlphaLISA acceptor beads. AlphaLISA can also be used to determine the binding affinity of individual variants, e.g., anti-HER2 antibodies or antibody binding fragments of the disclosure, to HER2. See, for example, Ullman et al., Clinical Chemistry 42, no. 9:1518-1526, 1996.

In other aspects, an anti-HER2 antibody of the disclosure inhibits (or neutralizes) HER2 activity in a range of in vitro assays, such as cell proliferation, tyrosine phosphorylation, inhibition of heregulin binding and apoptosis. For example, in one embodiment, the anti-HER2 antibody is assayed for the ability to inhibit growth of SK-BR-3 human breast cancer tumor cells. (See U.S. Pat. No. 6,577,171). In particular, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish) and 0.5 to 30 μg/ml of the anti-HER2 antibody is added per dish. After six days, the number of cells in the wells is counted using an electronic COULTER™ counter and compared to the number of cells in untreated wells. The antibodies that inhibit the growth of SK-BR-3 cells by about 20-100%, and preferably by about 50-100% may be selected as growth inhibitory antibodies.

In various embodiments, an anti-HER2 antibody of the disclosure reduces the binding of labeled trastuzumab by at least 30%, by at least 40%, by at least 50%, by at least 60%, by at least 70%, by at least 80%, by at least 90%, by at least 95%, by at least 99%, or by a percentage ranging between any of the foregoing values (e.g., an anti-HER2 antibody of the disclosure reduces the binding of labeled trastuzumab by 50% to 70%) when the anti-HER2 antibody is used at a concentration of 0.08 μg/ml, 0.4 μg/ml, 2 μg/ml, 10 μg/ml, 50 μg/ml, 100 μg/ml or at a concentration ranging between any of the foregoing values (e.g., at a concentration ranging from 2 μg/ml to 10 μg/ml).

In certain embodiments, the activity assayed is phosphorylation of the HER2 receptor tyrosine kinase. In particular embodiments, the assay screens anti-HER2 antibodies for inhibition of heregulin stimulation of p180 tyrosine phosphorylation in MCF7 cells. Specifically, MCF7 cells are plated in 24-well plates and an antibody to be tested is added to each well and incubated with the cells for 30 minutes at room temperature. Subsequent to the incubation step, rHRGβ$1_{177-244}$ is added to each well to a final concentration of 0.2 nM and the incubation is continued for 8 minutes. Media is then aspirated from each well and reactions are stopped by the addition of 100 μl of SDS sample buffer (5% SDS, 25 mM DTT, and 25 mM Tris-HCl, pH 6.8). Each sample is then electrophoreses on a 4-12% gradient gel (Novex) and then electrophoretically transferred to polyvinylidene difluoride membrane. Antiphosphotyrosine (1 μg/ml) immunoblots are developed and the intensity of the predominant reactive band a $M_r$~180,000 quantified by reflectance densitometry.

In various embodiments, the anti-HER2 antibody activity is assayed by inhibition of heregulin binding to MCF7 breast tumor cells. MCF7 cells are cultured in 24-well-plates and then put on ice. An anti-HER2 antibody is added to each well and incubated for 30 minutes. $^{125}$I-labeled rHRGβ$1_{177-224}$ (25 pm) are then added and the incubation continued for 4 to 16 hours. Dose response curves are prepared and an $IC_{50}$ value is calculated for the anti-HER2 antibody. In certain embodiments, the antibody that blocks ligand activation of a EGF receptor will have an $IC_{50}$ for inhibiting heregulin binding to MCF7 cells in the assay of about 100 nM or less, such as about 75 nM or less, such as about 50 nM or less, such as about 25 nM or less, such as about 10 nM or less, or such as about 1 nM or less.

In other embodiments, the anti-HER2 antibody activity is assayed by induction of apoptosis. In certain embodiments, an assay for propidium iodide uptake using BT474 cells is used to identify antibodies that induce apoptosis. BT474 cells (from the American Type Culture Collection (Rockville, Md.)) are cultured in Dulbecco's Modified Eagle Medium: Ham's F12 (50:50) supplemented with 10% heat-inactivated FBS (Hyclone) and 2 mM L-glutamine. BT474 cells are seeded at a density of $3\times10^6$ per dish in 100×20 mm dishes and allowed to attach overnight. Medium is then removed and replaced with fresh medium alone or medium containing 10 μg/ml of antibody. After a 3-day incubation, monolayers are washed with PBS and detached by trypsinization. Cells are centrifuged at 1200 rpm for 5 minutes at 4° C., and the pellet is resuspended in 3 ml ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 ml per tube, 3 tubes per treatment group) to remove cell clumps. Tubes then receive 10 μg/ml propidium iodide and samples are analyzed by flow cytometry. Antibodies that induce statistically significant levels of cell death as determined by propidium iodide uptake relative to control are apoptosis-inducing antibodies.

Alternatively, an annexin binding assay using BT474 cells is used to identify apoptosis inducing antibodies. In this assay, cells are grown and treated as detailed in the previous paragraph. Tubes then received labeled annexin (e.g., annexin V-FTIC) (1 μg/ml) and are then assayed by flow cytometry. In other embodiments, a DNA staining assay using BT474 cells is used to identify anti-HER2 antibodies that induce apoptosis. BT474 cells that have been grown and treated as detained in the previous paragraph are incubated with 9 μg/ml HOECHST 33342™ for 2 hours at 37° C., and then analyzed by flow cytometry. Antibodies that induce a greater than 2-fold change in the percentage of apoptotic cells as compared to untreated cells are apoptosis-inducing antibodies.

Other formats for HER2 neutralization assays are known in the art and can be employed.

In various embodiments, an anti-HER2 antibody of the disclosure neutralizes HER2 by at least 30%, by at least 40%, by at least 50%, by at least 60%, by at least 70%, by at least 80%, by at least 90%, or by a percentage ranging between any of the foregoing values (e.g., an anti-HER2 antibody of the disclosure neutralizes HER2 activity by 50% to 70%) when the anti-HER2 antibody is used at a concentration of 2 ng/ml, 5 ng/ml, 10 ng/ml, 20 ng/ml, 0.1 μg/ml, 0.2 μg/ml, 1 μg/ml, 2 μg/ml, 5 μg/ml, 10 μg/ml, 20 μg/ml, or at a concentration ranging between any of the foregoing values (e.g., at a concentration ranging from 1 μg/ml to 5 μg/ml).

In some embodiments, an anti-HER2 antibody of the disclosure is at least 0.7-fold as effective, 0.8-fold as effective, at least 0.9-fold as effective, at least 1-fold as effective, at least 1.1-fold as effective, at least 1.25-fold as effective, at least 1.5-fold as effective, at least 2-fold as effective, at least 5-fold as effective, at least 10-fold as effective, at least 20-fold as effective, at least 50-fold as effective, at least 100-fold as effective, at least 200-fold as effective, at least 500-fold as effective, at least 1000-fold as effective as trastuzumab at neutralizing HER2, or having an effectiveness at neutralizing HER2 relative to trastuzumab ranging between any pair of the foregoing values (e.g., 0.9-fold to 5-fold as effective as trastuzumab or 2-fold to 50-fold as effective as trastuzumab in neutralizing HER2).

7.4. Kinetic Properties of Anti-HER2 Antibodies

In certain embodiments, the anti-HER2 antibodies of the disclosure have a high binding affinity for HER2. In specific embodiments, the anti-HER2 antibodies of the present disclosure have specific association rate constants ($k_{on}$ or $k_a$ values), dissociation rate constants ($k_{off}$ or $k_d$ values), affinity constants ($K_A$ values), dissociation constants ($K_D$ values) and/or $IC_{50}$ values. In various embodiments, binding constants for the interaction of the anti-HER2 antibodies with HER2 receptor extracellular domain ($p185^{HER2-ECD}$) can be determined using surface plasmon resonance according to the method disclosed in Karlsson et al. (1991) J. Immunol. Methods 145:229-240. In certain aspects, such values are selected from the following embodiments.

In some embodiments, an anti-HER2 antibody of the disclosure binds to HER2 with a $K_A$ ($k_{on}/k_{off}$) of at least $10^8$ $M^{-1}$, at least $4\times10^8$ $M^{-1}$, at least $10^9$ $M^{-1}$ at least $4\times10^9$ $M^{-1}$ at least $10^{10}$ $M^{-1}$, at least $4\times10^{11}$ $M^{-1}$, at least $10^{11}$ $M^{-1}$, at least $4\times10^{12}$ $M^{-1}$, at least $10^{12}$ $M^{-1}$, at least $4\times10^{13}$ $M^{-1}$, at least $10^{13}$ $M^{-1}$, at least $4\times10^{14}$ $M^{-1}$, at least $10^{14}$ $M^{-1}$, at least $4\times10^{15}$ $M^{-1}$, at least $10^{15}$ $M^{-1}$, or with a $K_A$ of any range between any pair of the foregoing values (e.g., $4\times10^8$ $M^{-1}$ to $4\times10^{13}$ $M^{-1}$ or $4\times10^{12}$ $M^{-1}$ to $4\times10^{15}$ $M^{-1}$).

In certain embodiments, an anti-HER2 antibody of the disclosure binds to HER2 with a $K_D$ ($k_{off}/k_{on}$) of $5\times10^{-8}$ M or less, of $10^{-8}$ M or less, of $5\times10^{-9}$ M or less, of $10^{-9}$ M or less, of $5\times10^{-10}$ M or less, $10^{-10}$ M or less, $5\times10^{-11}$ M or less, $10^{-11}$ M or less, $4\times10^{-12}$ M or less, $10^{-12}$ M or less, $5\times10^{-13}$ M or less, $10^{-13}$ M or less, $5\times10^{-14}$ M or less, $10^{-14}$ M or less, $5\times10^{-15}$ M or less, $10^{-15}$ M or less, or with a $K_D$ of any range between any pair of the foregoing values (e.g., $5\times10^{-11}$ M to $5\times10^{-13}$ M or $5\times10^{-12}$ M to $10^{-15}$ M).

In specific embodiments, the $K_D$ ($k_{off}/k_{on}$) value is determined by assays well known in the art, e.g., ELISA, isothermal titration calorimetry (ITC), fluorescent polarization assay or any other biosensors such as BIAcore.

In some embodiments, an anti-HER2 antibody of the disclosure binds to HER2 and inhibits cell growth at an $IC_{50}$ less than 3 nM, less than 2 nM, less than 1 nM, less than 0.5 nM, less than 0.2 nM, less than 0.1 nM, less than 0.05 nM, less than 0.02 nM, less than 0.01 nM, less than 0.005 nM, less than 0.002 nM, less than 0.001 nM, less than $5\times10^{-4}$ nM, less than $2\times10^{-4}$ nM, less than $1\times10^{-4}$ nM, less than $5\times10^{-5}$ nM, less than $2\times10^{-5}$ nM, less than $1\times10^{-5}$ nM, less than $5\times10^{-6}$ nM, less than $2\times10^{-6}$ nM, less than $1\times10^{-6}$ nM, less than $5\times10^{-7}$ nM, less than $2\times10^{-7}$ nM, less than $1\times10^{-7}$ nM, or with an $IC_{50}$ of any range between any pair of the foregoing values (e.g., 0.02 nM to $2\times10^{-5}$ nM, or $5\times10^{-5}$ nM to $1\times10^{-7}$ nM). $IC_{50}$ can be measured according to methods well known in the art, e.g., ELISA.

In certain embodiments, an anti-HER2 antibody of the disclosure binds to HER2 at a minimum effective concentration ($EC_{50}$) less than 10 nM, less than 9 nM, less than 8 nM, less than 7 nM, less than 6 nM, less than 5 nM, less than 4 nM, less than 3 nM, less than 2 nM, less than 1 nM, less than 0.5 nM, less than 0.2 nM, less than 0.1 nM, less than 0.05 nM, less than 0.02 nM, less than 0.01 nM, less than 0.005 nM, less than 0.002 nM, less than 0.001 nM, less than $5\times10^{-4}$ nM, less than $2\times10^{-4}$ nM, less than $1\times10^{-4}$ nM, less than $5\times10^{-5}$ nM, less than $2\times10^{-5}$ nM, less than $1\times10^{-5}$ nM, less than $5\times10^{-6}$ nM, less than $2\times10^{-6}$ nM, less than $1\times10^{-6}$ nM, less than $5\times10^{-7}$ nM, less than $2\times10^{-7}$ nM, less than $1\times10^{-7}$ nM, or with an $EC_{50}$ of any range between any pair of the foregoing values (e.g., 5 nM to $5\times10^{-2}$ nM, or $1\times10^{-4}$ nM to $1\times10^{-7}$ nM). $EC_{50}$ can be measured according to methods well known in the art, e.g., FACS competition binding assay.

In certain embodiments, the kinetic properties of an antibody of the disclosure are comparable to, or improved relative to, trastuzumab in a comparable assay. For example, in certain embodiments, an anti-HER2 antibody of the disclosure binds to HER2 with a $k_{on}$ rate ranging from approximately 0.5× to 1000× of the $k_{on}$ of trastuzumab, for example a $k_{on}$ of 0.75 of the $k_{on}$ of trastuzumab, a $k_{on}$ of 1× of the $k_{on}$ of trastuzumab, a $k_{on}$ of 1.1× of the $k_{on}$ of trastuzumab, a $k_{on}$ of 1.2× of the $k_{on}$ of trastuzumab, a $k_{on}$ of 1.3× of the $k_{on}$ of trastuzumab, a $k_{on}$ of 1.4× of the $k_{on}$ of trastuzumab, a $k_{on}$ of 1.5× of the $k_{on}$ of trastuzumab, a $k_{on}$ of 1.6× of the $k_{on}$ of trastuzumab, a $k_{on}$ of 1.6× of the $k_{on}$ of trastuzumab, a $k_{on}$ of 1.7× of the $k_{on}$ of trastuzumab, a $k_{on}$ of 1.8× of the $k_{on}$ of trastuzumab, a $k_{on}$ of 1.9× of the $k_{on}$ of trastuzumab, a $k_{on}$ of 2× of the $k_{on}$ of trastuzumab, a $k_{on}$ of 2.25× of the $k_{on}$ of trastuzumab, a $k_{on}$ of 2.5× of the $k_{on}$ of trastuzumab, a $IC_{on}$ of 2.75× of the $k_{on}$ of trastuzumab, a $k_{on}$ of 3× of the $k_{on}$ of trastuzumab, a $k_{on}$ of 4× of the $k_{on}$ of trastuzumab, a $k_{on}$ of 5× of the $k_{on}$ of trastuzumab, a $k_{on}$ of 6× of the $k_{on}$ of trastuzumab, a $k_{on}$ of 7× of the $k_{on}$ of trastuzumab, a $k_{on}$ of 8× of the $k_{on}$ of trastuzumab, a $k_{on}$ of 9× of the $k_{on}$ of trastuzumab, a $k_{on}$ of 10× of the $k_{on}$ of trastuzumab, a $k_{on}$ of 15× of the $k_{on}$ of trastuzumab, a $k_{on}$ of 20× of the $k_{on}$ of trastuzumab, a $k_{on}$ of 50× of the $k_{on}$ of trastuzumab, a $k_{on}$ of 75× of the $k_{on}$ of trastuzumab, a $k_{on}$ of 100× of the $k_{on}$ of trastuzumab, a $k_{on}$ of 150× of the $k_{on}$ of trastuzumab, a $k_{on}$ of 200× of the $k_{on}$ of trastuzumab, or a $k_{on}$ ranging between any pair of the foregoing values, e.g., a $k_{on}$ of 2×-75× of the $k_{on}$ of trastuzumab, a $k_{on}$ of 5×-100× of the $k_{on}$ of trastuzumab, a $k_{on}$ of 0.05×-1000× of the $k_{on}$ of trastuzumab, a $k_{on}$ of 0.75×-250× of the $k_{on}$ of trastuzumab, etc.

In various embodiments, an anti-HER2 antibody of the disclosure binds to HER2 with a $k_{off}$ rate ranging from about 0.001× to about 3× of the $k_{off}$ of trastuzumab, for example a $k_{off}$ of 0.002× of the $k_{off}$ of trastuzumab, a $k_{off}$ of 0.003× of the $k_{off}$ of trastuzumab, a $k_{off}$ of 0.004× of the $k_{off}$ of trastuzumab, a $k_{off}$ of 0.005× of the $k_{off}$ of trastuzumab, a $k_{off}$ of 0.006× of the $k_{off}$ of trastuzumab, a $k_{off}$ of 0.0075× of the $k_{off}$ of trastuzumab, a $k_{off}$ of 0.01× of the $k_{off}$ of trastuzumab, a $k_{off}$ of 0.025× of the $k_{off}$ of trastuzumab, a $k_{off}$ of 0.05× of the $k_{off}$ of trastuzumab, a $k_{off}$ of 0.075× of the $k_{off}$ of trastuzumab, a $k_{off}$ of 0.1× of the $k_{off}$ of trastuzumab, a $k_{off}$ of 0.25× of the $k_{off}$ of trastuzumab, a $k_{off}$ of 0.5× of the $k_{off}$ of trastuzumab, a $k_{off}$ of 0.75× of the $k_{off}$ of trastuzumab, a $k_{off}$ of 1× of the $k_{off}$ of trastuzumab, a $k_{off}$ of 1.25× of the $k_{off}$ of trastuzumab, a $k_{off}$ of 1.5× of the $k_{off}$ of trastuzumab, a $k_{off}$ of 1.75× of the $k_{off}$ of trastuzumab, a $k_{off}$ of 2× of the $k_{off}$ of trastuzumab, a $k_{off}$ of 2.25× of the $k_{off}$ of trastuzumab, a $k_{off}$ of 2.5× of the $k_{off}$ of trastuzumab, a $k_{off}$ of 3× of the $k_{off}$ of trastuzumab, or a $k_{off}$ ranging between any pair of the foregoing values, e.g., a $k_{off}$ of 0.01× to 1.25× of the $k_{off}$ of trastuzumab, a $k_{off}$ of 0.05× to 2.5× of the $k_{off}$ of trastuzumab, or a $k_{off}$ of 0.006× to 0.1× of the $k_{off}$ of trastuzumab, etc.

In other embodiments, an anti-HER2 antibody of the disclosure binds to HER2 with a $K_A$ ($k_{on}/k_{off}$) ranging from about 0.25× to about 1000× of the $K_A$ of trastuzumab, for example a $K_A$ of 0.5× of the $K_A$ of trastuzumab, a $K_A$ of 0.75 of the $K_A$ of trastuzumab, a $K_A$ of 1× of the $K_A$ of trastuzumab, a $K_A$ of 2× of the $K_A$ of trastuzumab, a $K_A$ of 3× of the $K_A$ of trastuzumab, a $K_A$ of 4× of the $K_A$ of trastuzumab, a $K_A$ of 5× of the $K_A$ of trastuzumab, a $K_A$ of 10× of the $K_A$ of trastuzumab, a $K_A$ of 15× of the $K_A$ of trastuzumab, a $K_A$ of 20× of the $K_A$ of trastuzumab, a $K_A$ of 30× of the $K_A$ of trastuzumab, a $K_A$ of 40× of the $K_A$ of trastuzumab, a $K_A$ of 50× of the $K_A$ of trastuzumab, a $K_A$ of 75× of the $K_A$ of trastuzumab, a $K_A$ of 100× of the $K_A$ of trastuzumab, a $K_A$ of 200× of the $K_A$ of trastuzumab, a $K_A$ of 250× of the $K_A$ of trastuzumab, a $K_A$ of 300× of the $K_A$ of trastuzumab, a $K_A$ of 350× of the $K_A$ of trastuzumab, a $K_A$ of 400× of the $K_A$ of trastuzumab, a $K_A$ of 500× of the $K_A$ of trastuzumab, a $K_A$ of 750× of the $K_A$ of trastuzumab, a $K_A$ of 100× of the $K_A$ of trastuzumab, or a $K_A$ ranging between any pair of the foregoing values, e.g., a $K_A$ of 0.75× to 100× of the $K_A$ of trastuzumab, a $K_A$ of 10× to 50× of the $K_A$ of trastuzumab, or a $K_A$ of 5× to 50× of the $K_A$ of trastuzumab, etc.

In still other embodiments, an anti-Her2 antibody of the disclosure binds to HER2 with a $K_D$ ($k_{off}/k_{on}$) ranging from about 0.001× to 10× of the $K_D$ of trastuzumab, or example a $K_D$ of 0.001× of the $K_D$ of trastuzumab, a $K_D$ of 0.002× of the $K_D$ of trastuzumab, a $K_D$ of 0.003× of the $K_D$ of trastuzumab, a $K_D$ of 0.004× of the $K_D$ of trastuzumab, a $K_D$ of 0.005× of the $K_D$ of trastuzumab, a $K_D$ of 0.0075× of the $K_D$ of trastuzumab, a $K_D$ of 0.01× of the $K_D$ of trastuzumab, a $K_D$ of 0.025× of the $K_D$ of trastuzumab, a $K_D$ of 0.05× of the $K_D$ of trastuzumab, a $K_D$ of 0.075× of the $K_D$ of trastuzumab, a $K_D$ of 0.1× of the $K_D$ of trastuzumab, a $K_D$ of 0.2× of the $K_D$ of trastuzumab, a $K_D$ of 0.3× of the $K_D$ of trastuzumab, a $K_D$ of 0.4× of the $K_D$ of trastuzumab, a $K_D$ of 0.5× of the $K_D$ of trastuzumab, a $K_D$ of 0.75× of the $K_D$ of trastuzumab, a $K_D$ of 1× of the $K_D$ of trastuzumab, a $K_D$ of 1.5× of the $K_D$ of trastuzumab, a $K_D$ of 2× of the $K_D$ of trastuzumab, a $K_D$ of 3× of the $K_D$ of trastuzumab, a $K_D$ of 4× of the $K_D$ of trastuzumab, a $K_D$ of 5× of the $K_D$ of trastuzumab, a $K_D$ of 7.5× of the $K_D$ of trastuzumab, a $K_D$ of 10× of the $K_D$ of trastuzumab, or a $K_D$ ranging between any pair of the foregoing values, e.g., a $K_D$ of 0.001× to 0.5× of the $K_D$ of trastuzumab, a $K_D$ of 0.1× to 4× of the $K_D$ of trastuzumab, a $K_D$ of 0.05 to 1× of the $K_D$ of trastuzumab, etc.

In certain embodiments, an anti-HER2 antibody of the disclosure binds to HER2 and inhibits cell growth or neutralizes the activity of HER2 at a $IC_{50}$ value ranging from about 0.001× to 10× of the $IC_{50}$ of trastuzumab, for example at an $IC_{50}$ value of 0.01× of the $IC_{50}$ of trastuzumab, at an $IC_{50}$ of 0.05× of the $IC_{50}$ of trastuzumab, at an $IC_{50}$ of 0.1× of the $IC_{50}$ of trastuzumab, at an $IC_{50}$ of 0.2× of the $IC_{50}$ of trastuzumab, at an $IC_{50}$ of 0.3× of the $IC_{50}$ of trastuzumab, at an $IC_{50}$ of 0.4× of the $IC_{50}$ of trastuzumab, at an $IC_{50}$ of 0.5× of the $IC_{50}$ of trastuzumab, at an $IC_{50}$ of 0.6× of the $IC_{50}$ of trastuzumab, at an $IC_{50}$ of 0.7× of the $IC_{50}$ of trastuzumab, at an $IC_{50}$ of 0.8× of the $IC_{50}$ of trastuzumab, at an $IC_{50}$ of 0.9× of the $IC_{50}$ of trastuzumab, at an $IC_{50}$ of 1× of the $IC_{50}$ of trastuzumab, at an $IC_{50}$ of 1.5× of the $IC_{50}$ of trastuzumab, at an $IC_{50}$ of 2× of the $IC_{50}$ of trastuzumab, at an $IC_{50}$ of 3× of the $IC_{50}$ of trastuzumab, at an $IC_{50}$ of 4× of the $IC_{50}$ of trastuzumab, at an $IC_{50}$ of 5× of the $IC_{50}$ of trastuzumab, at an $IC_{50}$ of 7.5× of the $IC_{50}$ of trastuzumab, at an $IC_{50}$ of 10× of the $IC_{50}$ of trastuzumab, or an $IC_{50}$ ranging between any pair of the foregoing values, e.g., an $IC_{50}$ of 0.01 to 0.2 of the $IC_{50}$ of trastuzumab, an $IC_{50}$ of 0.1× to 1.5× of the $IC_{50}$ of trastuzumab, an $IC_{50}$ of 0.2× to 2× of the $IC_{50}$ of trastuzumab, etc. In certain embodiments, a single CDR substitution can result in the foregoing differences in $IC_{50}$ as compared to trastuzumab, whereas an anti-HER2 antibody of the disclosure can comprise such substitution and up to 16 additional CDR substitutions as compared to trastuzumab.

7.5. Improved Expression of Anti-HER2 Antibodies

In certain aspects, the present disclosure provides anti-HER2 antibodies having improved expression as compared to trastuzumab. The present disclosure provides anti-HER2 antibodies having single or multiple amino acid substitutions in their CDRs and/or framework regions as compared to the CDRs and/or framework regions of trastuzumab, wherein at least one substitution improves the expression of the antibody as compared to trastuzumab. In certain embodiments, the improved expression is an increase in overall expression levels. In other embodiments, the improved expression results in a more homogenous population of antibodies with respect to molecular weight, glycosylation, or other property of the molecule. Without being bound by any theory, the improvement in expression levels can result from improved folding, reduced glycosylation (e.g., due elimination of a glycosylation site) and/or reduced proteolysis (e.g., due to elimination of a protease recognition motif) as compared to trastuzumab.

In certain embodiments, the expression of an anti-HER2 antibody of the disclosure can be at least 10% greater, at least 20% greater, at least 30% greater, at least 40% greater, at least 50% greater, at least 75% greater, at least 100% greater, at least 125% greater, at least 150% greater or at least 200% greater than the expression of trastuzumab in any given prokaryotic or eukaryotic (e.g., yeast, insect or mammalian) host cell as described in Section 7.2 above. In certain embodiments, the expression of an anti-HER2 antibody of the disclosure can be increased relative to trastuzumab in any given prokaryotic or eukaryotic (e.g., yeast, insect or mammalian) host cell in a range between any of the foregoing values, e.g., 20%-75% greater, 50%-100% greater, 30%-125% greater, or the like. In various specific embodiment, the host cell is *E. coli*, Sf9, *S. cereviseae*, or CHO cells.

In other embodiments, the homogeneity of an anti-HER2 antibody of the disclosure upon expression in a given prokaryotic or eukaryotic (e.g., yeast, insect or mammalian) host cell (as described in Section 7.2 above) and, optionally isolation and/or purification (e.g., by passage on an affinity column) can be at least 10% greater, at least 20% greater, at least 30% greater, at least 40% greater, at least 50% greater, at least 60% greater, at least 70% greater, at least 80% greater, at least 90% greater, at least 100% greater, at least 125% greater, at least 150% greater or at least 200% greater than the homogeneity of trastuzumab when expressed in the same host cell given host cell an subjected to the same treatment (e.g., isolation and/or purification). In certain embodiments, the homogeneity of an anti-HER2 antibody of the disclosure can be increased relative to trastuzumab in a range between any of the foregoing values, e.g., 20%-80% greater, 50%-100% greater, 30%-125% greater, or the like. In various specific embodiment, the host cell is *E. coli*, Sf9, *S. cereviseae*, or CHO, and the homogeneity is assayed in a composition after the anti-HER2 antibody is purified such that various anti-HER2 antibody species in the composition represent at least 70%, at least 80%, at least 90%, or at least 95% of proteins in the composition.

The present disclosure further provides methods for screening anti-HER2 antibodies for improved expression relative to trastuzumab. In specific embodiments, the methods comprise the steps of (a) determining an amount of the anti-HER2 antibody or anti-HER2 antibody binding fragment expressed in the host cell; and (b) comparing the amount of anti-HER2 antibody or anti-HER2 binding fragment produced in the host cell to an amount of trastuzumab produced in the host cell.

Methods of assaying for improved antibody expression are known in the art. In certain embodiments, an improvement in antibody expression is tested according to the methods referenced in Section 7.1 above.

7.6. Increased Adaptive Immune Response of Anti-HER2 Antibodies

As described in Section 4, anti-HER2 antibody therapy has been shown to induce tumor regression of HER-2 expressing tumors. The mechanisms of tumor regression by anti-HER2 therapy include induction of the adaptive immune response, i.e., an increase in the innate immune response against HER-2 tumor cells. See Park et al., 2010, Cancer Cell 18:160-170.

In certain aspects, the present disclosure provides anti-HER2 antibodies that result in a greater adaptive immune response than trastuzumab. Accordingly, the present disclosure provides anti-HER2 antibodies having single or multiple amino acid substitutions in their CDRs and/or framework regions as compared to the CDRs and/or framework regions of trastuzumab, wherein at least one substitution results in an increased adaptive immune response induced by the antibody as compared to trastuzumab.

In certain embodiments, anti-HER2 antibodies of the disclosure induce an adaptive immune response that is at least 10% greater, at least 20% greater, at least 30% greater, at least 40% greater, at least 50% greater, at least 75% greater, at least 100% greater, at least 125% greater, at least 150% greater or at least 200% greater than the adaptive immune response induced by trastuzumab. In certain embodiments, the adaptive immune response induced by an anti-HER2 antibody of the disclosure is greater than the adaptive immune response induced by trastuzumab in an amount ranging between any of the foregoing values, e.g., 20%-75% greater, 50%-100% greater, 30%-125% greater, or the like.

7.7. Increased Stability of Anti-HER2 Antibodies

In certain aspects, the present disclosure provides anti-HER2 antibodies having increased protein stability as compared to trastuzumab. The present disclosure provides anti-HER2 antibodies having single or multiple amino acid substitutions in their CDRs and/or framework regions as compared to the CDRs and/or framework regions of trastuzumab, wherein at least one substitution results in increased stability of the antibody as compared to trastuzumab. In certain embodiments, the increased stability is upon storage of the antibody. In other embodiments, the increased stability is due to resistance to degradation by proteases and the like.

In certain embodiments, the stability of an anti-HER2 antibody of the disclosure can be at least 10% greater, at least 20% greater, at least 30% greater, at least 40% greater, at least 50% greater, at least 75% greater, at least 100% greater, at least 125% greater, at least 150% greater or at least 200% greater than the stability of trastuzumab. In certain embodiments, the stability of an anti-HER2 antibody of the disclosure is increased relative to the stability of trastuzumab in a range between any of the foregoing values, e.g., 20%-75% greater, 50%-100% greater, 30%-125% greater, or the like. In certain aspects, the stability of an anti-HER2 antibody of the disclosure in a sample is greater than the stability of trastuzumab in a sample where the samples are substantially identical (e.g., are both in pharmaceutical compositions containing the same ingredients) and/or are processed or handled in substantially the same way (e.g., are stored under the same conditions of temperature and humidity for the same period of time).

In certain aspects, the increased stability of an anti-HER2 antibody of the disclosure is an increase in shelf-life. An increased shelf life can result from a decrease in amino acid oxidation (for example because an amino acid residue susceptible to oxidation, such as methionine, cysteine or tryptophan, in a CDR or FR has been substituted relative to trastuzumab). An increased shelf life can also result from a decrease in amino acid cyclization (for example because an amino acid residue susceptible to cyclization, such as asparagines or glutamic acid) in a CDR or FR has been substituted relative to trastuzumab. An increased shelf life can also result from the elimination of an amino acid motif that is recognized by proteases that may be in antibody purifications at residual levels. The increase in shelf life or decrease in oxidation, cyclization or proteolysis levels relative to trastuzumab can be at least 10%, at least 20%, at least 30%, at least 40%, at least 50%, at least 75%, at least 100%, at least 125%, at least 150% or at least 200%. In certain embodiments, increase in shelf life or decrease in oxidation, cyclization or proteolysis levels relative to trastuzumab is in a range between any of the foregoing values, e.g., 20%-75% greater, 50%-100% greater, 30%-125% greater, or the like.

The present disclosure further provides methods for screening anti-HER2 antibodies for increased stability relative to trastuzumab. In specific embodiments, the methods comprise the steps of: (a) determining the amount of full-length anti-HER2 antibody or anti-HER2 binding fragment in a first sample; and (b) comparing the amount of full-length anti-HER2 antibody or anti-HER2 binding fragment in the first sample with an amount of full-length trastuzumab in a second sample.

Methods of assaying for antibody stability are known in the art. In certain embodiments, an increase in antibody stability is tested according to the methods referenced in Section 7.1 above.

7.8. Reduced Immunogenicity of Anti-HER2 Antibodies

In certain aspects, the present disclosure provides anti-HER2 antibodies having reduced immunogenicity as compared to trastuzumab. The present disclosure provides anti-HER2 antibodies having single or multiple amino acid substitutions in their CDRs and/or framework regions as compared to the CDRs and/or framework regions of trastuzumab, wherein at least one substitution reduces the immunogenicity of the antibody as compared to trastuzumab. In certain embodiments, the reduced immunogenicity results from one or more amino acid substitutions that result in eliminating or mitigating one or more T cell epitopes.

In certain aspects, the anti-HER2 antibodies of the disclosure having reduced immunogenicity have comparable or improved biological activity as compared to trastuzumab, e.g., affinity towards HER2 or neutralization of HER2 activity. Such properties can be tested, for example, by the methods described in Section 7.3 above.

In certain embodiments, the immunogenicity of an anti-HER2 antibody of the disclosure is reduced relative to trastuzumab. Such antibodies generally have variant sequences relative to the heavy and/or light chain variable region in regions corresponding to SEQ ID NOS:16, 27, 31, 49 and/or 69. The antibodies will generally have one, two or three amino acid substitutions in one or more of the sequences corresponding to SEQ ID NOS:16, 27, 31, 49 and/or 69, although up to four or five substitutions in one or more of the regions are contemplated herein.

As used in the present disclosure, a variant with "reduced immunogenicity" refers to an anti-HER2 antibody with a variant sequence in a region corresponding to SEQ ID NOS: 16, 27, 31, 49 or 69, and wherein a peptide having the variant sequence as compared to SEQ ID NOS:16, 27, 31, 49 or 69 elicits a reduced proliferative response in peripheral blood mononuclear cells as compared to a peptide of SEQ ID NOS: 16, 27, 31, 49 or 69, respectively. An exemplary proliferation assay that can be used to evaluate the proliferative response is set forth in Section 9 below. The reduced proliferative response can be reflected in terms of the percentage of responders, the stimulation index, or both.

In other embodiments, as compared to a peptide having the sequence of SEQ ID NOS:16, 27, 31, 49 or 69, the variant sequence results in at least 25% fewer responders, in at least 30% fewer responders, in at least 35% fewer responders, in at least 40% fewer responders, in at least 45% fewer responders, in at least 50% fewer responders, in at least 60% fewer responders, in at least 65% fewer responders, in at least 70% fewer responders, in at least 75% fewer responders, in at least 80% fewer responders, in at least 85% fewer responders, in at least 90% fewer responders, in at least 95% fewer responders, in at least 100% fewer responders, or a reduction in responders in a range between any of the foregoing values, e.g., 25%-75% fewer responders, 50%-90% fewer responders, 60%-100% fewer responders, 70%-90% fewer responders, or the like.

In other embodiments, the variant sequence results in a stimulation index that is at least 5% less, at least 10% less, at least 15% less, at least 20% less, at least 25% less, at least 30% less, at least 35% less, or at least 40% less than the stimulation index elicited by a peptide of SEQ ID NOS:16, 27, 31, 49 or 69, respectively, or results in a stimulation reduced by a range between any of the foregoing values as compared to a peptide of SEQ ID NOS:16, 27, 31, 49 or 69, e.g., 5%-20% less, 10%-30% less, 30%-40% less, or the like.

Exemplary embodiments of anti-HER2 antibodies with reduced immunogenicity as compared to trastuzumab comprise one or more of the CDR and/or framework substitutions or combination of substitutions set forth in Tables 4, 6, 8, 9, 10, 11, 12, 13 and 14. Optionally, anti-HER2 antibodies with reduced immunogenicity as compared to trastuzumab comprise one or more additional substitutions, such as the CDR mutations in any of Tables 3, 5 and 7, singly or in combination.

7.9. Antibody Conjugates

The anti-HER2 antibodies of the disclosure include antibody conjugates that are modified, e.g., by the covalent attachment of any type of molecule to the antibody, such that covalent attachment does not interfere with binding to HER2.

In certain aspects, an anti-HER2 antibody of the disclosure can be conjugated to an effector moiety or a label. The term "effector moiety" as used herein includes, for example, antineoplastic agents, drugs, toxins, biologically active proteins, for example enzymes, other antibody or antibody fragments, synthetic or naturally occurring polymers, nucleic acids (e.g., DNA and RNA), radionuclides, particularly radioiodide, radioisotopes, chelated metals, nanoparticles and reporter groups such as fluorescent compounds or compounds which can be detected by NMR or ESR spectroscopy.

In one example, anti-HER2 antibodies can be conjugated to an effector moiety, such as a cytotoxic agent, a radionuclide or drug moiety to modify a given biological response. The effector moiety can be a protein or polypeptide, such as, for example and without limitation, a toxin (such as abrin, ricin A, *Pseudomonas* exotoxin, or Diphtheria toxin), a signaling molecule (such as α-interferon, β-interferon, nerve growth factor, platelet derived growth factor or tissue plasminogen activator), a thrombotic agent or an anti-angiogenic agent (e.g., angiostatin or endostatin) or a biological response modifier such as a cytokine or growth factor (e.g., interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In another example the effector moieties can be cytotoxins or cytotoxic agents. Examples of cytotoxins and cytotoxic agents include taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector moieties also include, but are not limited to, antimetabolites (e.g. methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C5 and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and anti-mitotic agents (e.g., vincristine and vinblastine).

Other effector moieties can include radionuclides such as, but not limited to, $^{111}$In and $^{90}$Y, Lu$^{177}$, Bismuth$^{213}$, Californium$^{252}$, Iridium$^{192}$ and Tungsten$^{18s}$/Rhenium$^{188}$ and drugs such as, but not limited to, alkylphosphocholines, topoisomerase I inhibitors, taxoids and suramin.

Techniques for conjugating such effector moieties to antibodies are well known in the art (see, e.g., Hellstrom et al., Controlled Drug Delivery, 2nd Ed., at pp. 623-53 (Robinson et al., eds., 1987)); Thorpe et al., 1982, Immunol. Rev. 62:119-58 and Dubowchik et al., 1999, Pharmacology and Therapeutics 83:67-123).

In one example, the anti-HER2 antibody or fragment thereof is fused via a covalent bond (e.g., a peptide bond), through the antibody's N-terminus or C-terminus or internally, to an amino acid sequence of another protein (or portion thereof; for example at least a 10, 20 or 50 amino acid portion of the protein). The antibody, or fragment thereof, can linked to the other protein at the N-terminus of the constant domain of the antibody. Recombinant DNA procedures can be used to create such fusions, for example as described in WO 86/01533 and EP0392745. In another example the effector molecule can increase half-life in vivo, and/or enhance the delivery of an antibody across an epithelial barrier to the immune system. Examples of suitable effector molecules of this type include polymers, albumin, albumin binding proteins or albumin binding compounds such as those described in WO 2005/117984.

In certain aspects, an anti-HER2 antibody is conjugated to a small molecule toxin. In certain exemplary embodiments, an anti-HER2 antibody of the disclosure is conjugated to a dolastatin or a dolostatin peptidic analogs or derivatives, e.g., an auristatin (U.S. Pat. Nos. 5,635,483 and 5,780,588). The dolastatin or auristatin drug moiety may be attached to the antibody through its N (amino) terminus, C (carboxyl) terminus or internally (WO 02/088172). Exemplary auristatin embodiments include the N-terminus linked monomethylauristatin drug moieties DE and DF, as disclosed in U.S. Pat. No. 7,498,298, which is hereby incorporated by reference in its entirety (disclosing, e.g., linkers and methods of preparing monomethylvaline compounds such as MMAE and MMAF conjugated to linkers).

In other exemplary embodiments, small molecule toxins include but are not limited to calicheamicin, maytansine (U.S. Pat. No. 5,208,020), trichothene, and CC1065. In one embodiment of the disclosure, the antibody is conjugated to one or more maytansine molecules (e.g., about 1 to about 10 maytansine molecules per antibody molecule). Maytansine may, for example, be converted to May-SS-Me which may be reduced to May-SH3 and reacted with an antibody (Chari et al., 1992, Cancer Research 52: 127-131) to generate a maytansinoid-antibody or maytansinoid-Fc fusion conjugate. Structural analogues of calicheamicin that can also be used include but are not limited to $\gamma_1^1$, $\gamma_3^1$, $\gamma_3^1$, N-acetyl-$\gamma_1^1$, PSAG, and $\theta_1^1$, (Hinman et al., 1993, Cancer Research 53:3336-3342; Lode et al., 1998, Cancer Research 58:2925-2928; U.S. Pat. Nos. 5,714,586; 5,712,374; 5,264,586; 5,773,001).

Antibodies of the disclosure can also be conjugated to liposomes for targeted delivery (See, e.g., Park et al., 1997, Adv. Pharmacol. 40:399-435; Marty & Schwendener, 2004, Methods in Molecular Medicine 109:389-401).

In one example antibodies of the present disclosure can be attached to poly(ethyleneglycol) (PEG) moieties. In one particular example the antibody is an antibody fragment and the PEG moieties can be attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See for example U.S. Pat. No. 5,219,996. Multiple sites can be used to attach two or more PEG molecules. PEG moieties can be covalently linked through a thiol group of at least one cysteine residue located in the antibody fragment. Where a thiol group is used as the point of attachment, appropriately activated effector moieties, for example thiol selective derivatives such as maleimides and cysteine derivatives, can be used.

In a specific example, an anti-HER2 antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545. PEG can be attached to a cysteine in the hinge region. In one example, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can therefore be approximately 40,000 Da.

The word "label" when used herein refers to a detectable compound or composition which can be conjugated directly or indirectly to an anti-HER2 antibody of the disclosure. The label can itself be detectable (e.g., radioisotope labels or fluorescent labels) or, in the case of an enzymatic label, can catalyze chemical alteration of a substrate compound or composition which is detectable. Useful fluorescent moieties include, but are not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase and the like.

Additional anti-HER2 antibody conjugates that are useful for, inter alia, diagnostic purposes, are described in Section 7.10 below.

7.10. Diagnostic Uses of Anti-HER2 Antibodies

The anti-HER2 antibodies of the disclosure, including those antibodies that have been modified, e.g., by biotinylation, horseradish peroxidase, or any other detectable moiety (including those described in Section 7.9), can be advantageously used for diagnostic purposes.

In particular, the anti-HER2 antibodies can be used, for example, but not limited to, to purify or detect HER2, including both in vitro and in vivo diagnostic methods. For example, the antibodies have use in immunoassays for qualitatively and quantitatively measuring levels of HER2 in biological samples. See, e.g., Harlow et al., Antibodies: A Laboratory Manual, Second Edition (Cold Spring Harbor Laboratory Press, 1988), which is incorporated by reference herein in its entirety. In a specific embodiment, the anti-HER2 antibodies can be used for detecting and quantitating levels of HER2 in the serum, i.e., levels of HER2 extracellular domain that has been shed from the surface of cells.

The present disclosure further encompasses antibodies or fragments thereof conjugated to a diagnostic agent. The antibodies can be used diagnostically, for example, to detect expression of a target of interest in specific cells, tissues, or serum; or to monitor the development or progression of an immunologic response as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. Examples of enzymatic labels include luciferases (e.g., firefly luciferase and bacterial luciferase; U.S. Pat. No.

4,737,456), luciferin, 2,3-dihydrophthalazinediones, malate dehydrogenase, urease, peroxidase such as horseradish peroxidase (HRPO), alkaline phosphatase, β-galactosidase, acetylcholinesterase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

The disclosure provides for the detection of expression of HER2 comprising contacting a biological sample (cells, tissue, or body fluid of an individual) using one or more anti-HER2 antibodies of the disclosure (optionally conjugated to detectable moiety), and detecting whether or not the sample is positive for HER2 expression, or whether the sample has altered (e.g., reduced or increased) expression as compared to a control sample.

The overexpression of HER2 can be determined by routine clinical laboratory testing, usually immunohistochemistry (IHC) and silver, chromogenic or fluorescent in situ hybridization (SISH/CISH/FISH). FISH testing is considered the gold-standard technique for identifying patients who would benefit from Herceptin® treatment but its use is limited by its cost. Other techniques include virtual karyotyping of formalin-fixed paraffin embedded tumors.

Diseases that can be diagnosed using the present methods include, but are not limited to, the diseases described herein. In certain embodiments, the tissue or body fluid is peripheral blood, peripheral blood leukocytes, biopsy tissues such as breast or lymph node biopsies, and tissue.

7.11. Therapeutic Methods Using Anti-HER2 Antibodies 7.11.1. Clinical Benefits

The anti-HER2 antibodies of the disclosure can be used to treat various neoplasms.

The antibodies of the disclosure are useful in the treatment of tumors, including cancers and benign tumors. Examples of cancer to be treated herein include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

More particularly, cancers that are amenable to treatment by the antibodies of the disclosure include those that overexpress HER2. In certain embodiments, cancers that are amenable to treatment by the antibodies disclosed herein include breast cancer, ovarian cancer, gastric cancer, colon cancer, non-small cell lung cancer, oral cancer, cervical cancer, osteosarcoma, pancreatic cancer, salivary gland cancer, prostate cancer, endometrial cancer, and bladder cancer. In some embodiments, the anti-HER2 antibodies of the disclosure are used to treat breast cancer in a human patient. In other embodiments, the anti-HER2 antibodies of the disclosure are used to treat mammary and extra-mammary Paget's disease.

In certain embodiments, the present disclosure encompasses anti-angiogenic therapy, a cancer treatment strategy aimed at inhibiting the development of tumor blood vessels required for providing nutrients to support tumor growth. Because angiogenesis is involved in both primary tumor growth and metastasis, the antiangiogenic treatment provided by the disclosure is capable of inhibiting the neoplastic growth of tumor at the primary site as well as preventing metastasis of tumors at the secondary sites.

Accordingly, the present disclosure provides methods of treating any of the foregoing diseases in a patient in need thereof, comprising: administering to the patient an anti-HER2 antibody of the disclosure. Optionally, said administration is repeated, e.g., after one day, two days, three days, five days, one week, two weeks, three weeks, one month, five weeks, six weeks, seven weeks, eight weeks, two months or three months. The repeated administration can be at the same dose or at a different dose. The administration can be repeated once, twice, three times, four times, five times, six times, seven times, eight times, nine times, ten times, or more. For example, according to certain dosage regimens a patient receives anti-HER2 therapy for a prolonged period of time, e.g., 6 months, 1 year or more. The amount of anti-HER2 antibody administered to the patient is in certain embodiments a therapeutically effective amount. As used herein, a "therapeutically effective" amount of HER2 antibody can be administered as a single dose or over the course of a therapeutic regimen, e.g., over the course of a week, two weeks, three weeks, one month, three months, six months, one year, or longer. Exemplary therapeutic regimens are described in Section 7.14 below.

In certain aspects, the methods include before the step of administering to the patient an anti-HER2 antibody of the disclosure, a step of detecting HER2 overexpression. Said detecting step can be accomplished by any method known in the art, including, but not limited to, an immunohistochemistry assay to measure HER2 protein levels (such as HercepTest™ or Pathway®), and a fluorescence in situ hybridization (FISH) assay to measure HER2 gene amplification (such as PathVysion® and pharmDx™). In certain embodiments, immunohistochemistry assays can be performed using a labeled antibody of the disclosure, such as those described in Section 7.9, above.

According to the present disclosure, treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom the anti-HER2 antibody of the disclosure is administered is preferably a mammal such as a non-primate (e.g., cow, pig, horse, cat, dog, rat, etc.) or a primate (e.g., monkey or human). In certain embodiments, the subject or patient is a human. In certain aspects, the human is an adult patient. In other aspects, the human is a pediatric patient.

7.12. Pharmaceutical Compositions and Routes of Administration

Compositions comprising an anti-HER2 antibody of the disclosure and, optionally one or more additional therapeutic agents, such as the combination therapeutic agents described in Section 7.13 below, are provided herein. The compositions will usually be supplied as part of a sterile, pharmaceutical composition that will normally include a pharmaceutically acceptable carrier. This composition can be in any suitable form (depending upon the desired method of administering it to a patient).

The anti-HER2 antibodies of the disclosure can be administered to a patient by a variety of routes such as orally, transdermally, subcutaneously, intranasally, intravenously, intramuscularly, intraocularly, topically, intrathecally and intracerebroventricularly. The most suitable route for administration in any given case will depend on the particular antibody, the subject, and the nature and severity of the disease and the physical condition of the subject.

For treatment of indications described herein, the effective dose of an anti-HER2 antibody of the disclosure can range from about 0.1 to about 75 mg/kg per single (e.g., bolus) administration, multiple administrations or continuous administration, or to achieve a serum concentration of 0.01-5000 μg/ml serum concentration per single (e.g., bolus) administration, multiple administrations or continuous administration, or any effective range or value therein depending on the condition being treated, the route of administration and the age, weight and condition of the subject. In certain embodiments, e.g. for the treatment of cancer, each dose can range from about 0.2 mg to about 50 mg per kilogram of body weight, for example from about 0.5 mg to about 20 mg per kilogram body weight. The antibody can be formulated as an aqueous solution and administered by subcutaneous injection.

Pharmaceutical compositions can be conveniently presented in unit dose forms containing a predetermined amount of an anti-HER2 antibody of the disclosure per dose. Such a unit can contain for example but without limitation 0.1 mg to 5 g, for example 1 mg to 1 g, or 10 to 50 mg. Pharmaceutically acceptable carriers for use in the disclosure can take a wide variety of forms depending, e.g., on the condition to be treated or route of administration.

Therapeutic formulations of the anti-HER2 antibodies of the disclosure can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid monosodium succinate mixture, succinic acid-sodium hydroxide mixture, succinic acid disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Nonionic surfactants can be present in a range of about 0.05 mg/ml to about 1.0 mg/ml, for example about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a combination therapeutic agent in addition to the anti-HER2 antibody of the disclosure. Examples of suitable combination therapeutic agents are provided in Section 7.13 below.

The dosing schedule for subcutaneous administration can vary from once every six months to daily depending on a number of clinical factors, including the type of disease, severity of disease, and the patient's sensitivity to the anti-HER2 antibody.

The dosage of an anti-HER2 antibody of the disclosure to be administered will vary according to the particular antibody, the type of cancer, the subject, and the severity of the disease, the physical condition of the subject, the therapeutic regimen (e.g., whether a combination therapeutic agent is used), and the selected route of administration; the appropriate dosage can be readily determined by a person skilled in the art.

It will be recognized by one of skill in the art that the optimal quantity and spacing of individual dosages of an anti-HER2 antibody of the disclosure will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop, the amount and/or frequency of the dosage can be altered or reduced, in accordance with normal clinical practice.

7.13. Combination Therapy

Described below are combinatorial methods in which the anti-HER2 antibodies of the disclosure can be utilized. The combinatorial methods of the disclosure involve the administration of at least two agents to a patient, the first of which is an anti-HER2 antibody of the disclosure, and the second of which is a combination therapeutic agent. The anti-HER2 antibody and the combination therapeutic agent can be administered simultaneously, sequentially or separately.

The combinatorial therapy methods of the present disclosure can result in a greater than additive effect, providing therapeutic benefits where neither the anti-HER2 antibody or combination therapeutic agent administered in an amount that is alone therapeutically effective.

In the present methods, the anti-HER2 antibody of the disclosure and the combination therapeutic agent can be administered concurrently, either simultaneously or successively. As used herein, the anti HER2 antibody of the disclosure and the combination therapeutic agent are said to be administered successively if they are administered to the patient on the same day, for example during the same patient visit. Successive administration can occur 1, 2, 3, 4, 5, 6, 7 or 8 hours apart. In contrast, the anti-HER2 antibody of the disclosure and the combination therapeutic agent are said to be administered separately if they are administered to the patient on the different days, for example, the anti-HER2 antibody of the disclosure and the combination therapeutic agent can be administered at a 1-day, 2-day or 3-day, one-week, 2-week or monthly intervals. In the methods of the present disclosure, administration of the anti-HER2 antibody of the disclosure can precede or follow administration of the combination therapeutic agent.

As a non-limiting example, the anti-HER2 antibody of the disclosure and combination therapeutic agent can be administered concurrently for a period of time, followed by a second period of time in which the administration of the anti-HER2 antibody of the disclosure and the combination therapeutic agent is alternated.

Because of the potentially synergistic effects of administering an anti-HER2 antibody of the disclosure and a combination therapeutic agent, such agents can be administered in amounts that, if one or both of the agents is administered alone, is/are not therapeutically effective.

In certain aspects, the combination therapeutic agent is a chemotherapeutic agent, an anti-angiogenic agent, an anti-inflammatory agent, a radiotherapeutic, an immunosuppressive agent, or a cytotoxic drug.

It is contemplated that when used to treat various diseases, the anti-HER2 antibodies of the disclosure can be combined with other therapeutic agents suitable for the same or similar diseases. When used for treating cancer, antibodies of the present disclosure may be used in combination with conventional cancer therapies, such as surgery, radiotherapy, chemotherapy or combinations thereof.

In some other aspects, other therapeutic agents useful for combination tumor therapy with the antibody of the disclosure include antagonists, e.g., antibodies, of other factors that are involved in tumor growth, such as EGFR, HER3, HER4, VEGF, or α5β1 integrin.

Sometimes, for treatment of cancers it may be beneficial to also administer one or more cytokines to the patient. In a preferred embodiment, the HER2 antibody is co-administered with a growth inhibitory agent.

Suitable dosages for the growth inhibitory agent are those presently used and may be lowered due to the combined action (synergy) of the growth inhibitory agent and anti-HER2 antibody.

For treatment of cancers, anti-inflammatory agents can suitably be used in combination with the anti-HER2 antibodies of the disclosure. Anti-inflammatory agents include, but are not limited to, acetaminophen, diphenhydramine, meperidine, dexamethasone, pentasa, mesalazine, asacol, codeine phosphate, benorylate, fenbufen, naprosyn, diclofenac, etodolac and indomethacin, aspirin and ibuprofen.

For treatment of cancers, chemotherapeutic agents can suitably be used in combination with the anti-HER2 antibodies of the disclosure. Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, an anti-α5β1 integrin antibody, alkylating agents, allopurinol sodium, altretamine, amifostine, anastrozole, anthramycin (AMC)), anti-mitotic agents, cisdichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, eolociximab, emetine, epoetin-α, *Erwinia* Lasparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, tretinoin, valrubicin, vinblastine sulfate, vincristine sulfate, and vinorelbine tartrate.

Any anti-angiogenic agent can be used in conjunction with the anti-HER2 antibodies of the disclosure, including those listed by Carmeliet and Jain, 2000, Nature 407:249-257. In certain embodiments, the anti-angiogenic agent is a VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, an anti-VEGF antibody may be co-administered to the patient.

In certain embodiments, hormone therapy can be used in conjunction with anti-HER2 antibodies of the disclosure. In some embodiments, the hormone therapy includes one or more agents that inhibit estrogen and/or progesterone from promoting cancer cell growth, e.g., a selective estrogen-receptor modulator such as tamoxifen, an aromatase inhibitor such as anastrozole (Arimidex®) or letrozole (Femara), an aromatase inactivator such as exemestane (Aromasin®), or an agent that inhibits estrogen production such as goserelin (Zoladex). In other embodiments, the hormone therapy is one or more agents that inhibit production of hormones from the ovaries.

In some aspects, an anti-HER2 antibody can be used in conjunction with a small molecule protein tyrosine kinase (PTK) inhibitor. In some embodiments, the PTK inhibitor is specific for the HER3 tyrosine kinase. In other embodiments, the PTK inhibitor binds to more than one of the HER family of tyrosine kinases (e.g., EGFR, HER3 and/or HER4). In still other embodiments, the PTK inhibitors bind to and inhibit the tyrosine kinases of one or more proteins that interact with or are regulated by one or more HER family members, e.g., proteins involved in one or more signaling cascades that originate with one or more HER family members. In other embodiments, protein tyrosine kinase inhibitors useful in the compositions and methods of the invention include PTK inhibitors that do not bind selectively to the HER family of receptor tyrosine kinases, but also bind to the tyrosine kinase domains of other families of proteins such as VEGFR, PDGFR, and/or Raf.

In some embodiments, the tyrosine kinase is a receptor tyrosine kinase, i.e., is an intra-cellular domain of a larger protein that has an extra-cellular ligand binding domain and is activated by the binding of one or more ligands. In certain embodiments, the protein tyrosine kinase is a non-receptor tyrosine kinase. PTK inhibitors for use in the methods of the present disclosure include, but are not limited to, gefitinib (ZD-1839, Iressa®), erlotinib (OSI-1774, Tarceva™), canertinib (CI-1033), vandetanib (ZD6474, Zactima®), tyrphostin AG-825 (CAS149092-50-2), lapatinib (GW-572016), sorafenib (BAY43-9006), AG-494 (CAS 133550-35-3), RG-13022 (CAS149286-90-8), RG-14620 (CAS136831-49-7), BIBW 2992 (Tovok), tyrphostin 9 (CAS 136831-49-7), tyrphostin 23 (CAS 118409-57-7), tyrphostin 25 (CAS 118409-58-8), tyrphostin 46 (CAS 122520-85-8), tyrphostin 47 (CAS 122520-86-9), tyrphostin 53 (CAS 122520-90-5), butein (1-(2,4-dihydroxyphenyl)-3-(3,4-dihydroxyphenyl)-2-propen-1-one 2',3,4,4'-Tetrahydroxychalcone; CAS 487-52-5), curcumin ((E,E)-1,7-bis(4-Hydroxy-3-methoxyphenyl)-1,6-heptadiene-3,5-dione; CAS 458-37-7), N4-(1-Benzyl-1H-indazol-5-yl)-N6,N6-dimethyl-pyrido-[3,4-d] pyrimidine-4,6-diamine (202272-68-2), AG-1478, AG-879, Cyclopropanecarboxylic acid-(3-(6-(3-trifluoromethyl-phenylamino)-pyrimidin-4-ylamino)-phenyl)-amide (CAS 879127-07-8), N8-(3-Chloro-4-fluorophenyl)-N2-(1-methylpiperidin-4-yl)-pyrimido[5,4-d]pyrimidine-2,8-diamine, 2HCl (CAS 196612-93-8), 4-(4-Benzyloxyanilino)-6,7-dimethoxyquinazoline (CAS 179248-61-4), N-(4-((3-Chloro-4-fluorophenyl)amino)pyrido[3,4-d]pyrimidin-6-yl) 2-butynamide (CAS 881001-19-0), EKB-569, HKI-272, and HKI-357.

In a specific embodiment, an anti-HER2 antibody of the disclosure is used as part of a treatment regimen consisting of doxorubicin, cyclophosphamide and either paclitaxel or docetaxel. This combination is suitable for, inter alia, adjuvant treatment of patients with HER2-overexpressing node positive or node negative breast cancer.

In another specific embodiment, an anti-HER2 antibody of the disclosure is used in combination with docetaxel and carboplatin. This combination is suitable for, inter alia, adjuvant treatment of patients with HER2-overexpressing node positive or node negative breast cancer.

In yet another specific embodiment, an anti-HER2 antibody of the disclosure is used as a single agent following multi-modality anthracycline based therapy. This combination is suitable for, inter alia, adjuvant treatment of patients with HER2-overexpressing node positive or node negative breast cancer.

In another specific embodiment, the anti-HER2 antibody of the disclosure is used in combination with paclitaxel. This combination is suitable for, inter alia, first-line treatment of HER2-overexpressing metastatic breast cancer.

In another specific embodiment, an anti-HER2 antibody of the disclosure is used as a single agent for treatment of HER2-overexpressing breast cancer in patients who have received one or more chemotherapy regimens for metastatic disease.

7.14. Therapeutic Regimens

The present disclosure provides therapeutic regimens involving the administration of the anti-HER2 antibodies of the disclosure. The therapeutic regimen will vary depending on the patient's age, weight, and disease condition. The therapeutic regimen can continue for 2 weeks to indefinitely. In specific embodiments, the therapeutic regimen is continued for 2 weeks to 6 months, from 3 months to 5 years, from 6 months to 1 or 2 years, from 8 months to 18 months, or the like. The therapeutic regimen can be a non-variable dose regimen or a multiple-variable dose regimen.

For the dosage exemplary regimens described below, the anti-HER2 antibody can be administered as a sterile, preservative-free solution for subcutaneous administration.

For adjuvant breast cancer treatment during and/or following treatment with paclitaxel, docetaxel or with a combination of docetaxel and carboplatin, an anti-HER2 antibody of the disclosure is administered intravenously at an initial dose of 0.1 to 10 mg/kg. In specific embodiments, the initial dose is 0.2-8 mg/kg, 0.5-8 mg/kg, 1-6 mg/kg, 1.5-5 mg/kg, 2-5 mg/kg, or 1-4.5 mg/kg. Following the initial dose, an anti-HER2 antibody of the disclosure is administered intravenously for the first 12 weeks of chemotherapy (treatment with paclitaxel or docetaxel) or for the first 18 weeks of chemotherapy (treatment with a combination of docetaxel and carboplatin) at a dose of 0.05 to 10 mg/kg, such as 0.1-10 mg/kg, such as 0.3-8 mg/kg, such as 0.5-6 mg/kg, such as 0.8-6.5 mg/kg, such as 1-5 mg/kg, such as 1.5-3.5 mg/kg. One week after the last weekly dose of an anti-HER2 antibody of the present disclosure, an anti-HER2 antibody of the present disclosure is administered intravenously every three weeks at a dose of 0.1-12 mg/kg. In specific embodiments, the dose is 0.1-10 mg/kg, 0.5-8 mg/kg, 1-6.5 mg/kg, 1.5-6 mg/kg, 2-6 mg/kg, 0.1-5.5 mg/kg, or 1-4 mg/kg.

For adjuvant breast cancer treatment within three weeks following completion of a multi-modality, anthracycline-base chemotherapy regimen, an anti-HER2 antibody of the disclosure is administered intravenously as a single agent at an initial dose of 0.1 to 15 mg/kg. In specific embodiments, the initial dose is 0.2-12.5 mg/kg, 0.5-12 mg/kg, 1-10.5 mg/kg, 2-10 mg/kg, 3-9 mg/kg, or 4-8.5 mg/kg. Subsequent doses of an anti-HER2 antibody of the present disclosure are administered intravenously every three weeks and are from 0.1-12 mg/kg. In specific embodiments, each subsequent dose is 0.1-10 mg/kg, 0.5-8 mg/kg, 1-6.5 mg/kg, 1.5-6 mg/kg, 2-6 mg/kg, 0.1-5.5 mg/kg, or 1-4 mg/kg.

For treatment of metastatic breast cancer treatment, an anti-HER2 antibody of the disclosure is administered intravenously either alone or in combination with paclitaxel at an initial dose of 0.1 to 10 mg/kg. In specific embodiments, the initial dose is 0.2-8 mg/kg, 0.5-8 mg/kg, 1-6 mg/kg, 1.5-5 mg/kg, 2-5 mg/kg, or 1-4.5 mg/kg. Following the initial dose, an anti-HER2 antibody of the disclosure is administered intravenously once weekly at a dose of 0.05 to 10 mg/kg, such as 0.1-10 mg/kg, such as 0.3-8 mg/kg, such as 0.5-6 mg/kg, such as 0.8-6.5 mg/kg, such as 1-5 mg/kg, such as 1.5-3.5 mg/kg.

7.15. Diagnostic and Pharmaceutical Kits

Encompassed by the present disclosure are pharmaceutical kits containing the anti-HER2 antibodies (including antibody conjugates) of the disclosure. The pharmaceutical kit is a package comprising the anti-HER2 antibody of the disclosure (e.g., either in lyophilized form or as an aqueous solution) and one or more of the following:

- A combination therapeutic agent, for example as described in Section 7.13 above;
- A device for administering the anti-HER2 antibody, for example a pen, needle and/or syringe; and
- Pharmaceutical grade water or buffer to resuspend the antibody if the antibody is in lyophilized form.

In certain aspects, each unit dose of the anti-HER2 antibody is packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen.

Diagnostic kits containing the anti-HER2 antibodies (including antibody conjugates) of the disclosure are also encompassed herein. The diagnostic kit is a package comprising the anti-HER2 antibody of the disclosure (e.g., either in lyophilized form or as an aqueous solution) and one or more reagents useful for performing a diagnostic assay. Where the anti-HER2 antibody is labeled with an enzyme, the kit can include substrates and cofactors required by the enzyme (e.g., a substrate precursor which provides the detectable chromophore or fluorophore). In addition, other additives can be included, such as stabilizers, buffers (e.g., a block buffer or lysis buffer), and the like. In certain embodiments, the anti-HER2 antibody included in a diagnostic kit is immobilized on a solid surface, or a solid surface (e.g., a slide) on which the antibody can be immobilized is included in the kit. The relative amounts of the various reagents can be varied widely to provide for concentrations in solution of the reagents which substantially optimize the sensitivity of the assay. In a specific embodiment, the antibody and one or more reagents can be provided (individually or combined) as dry powders, usually lyophilized, including excipients which on dissolution will provide a reagent solution having the appropriate concentration.

8. EXAMPLE 1

Identification of Variants of Trastuzumab with Affinity to HER2

Trastuzumab was subjected to comprehensive mutational analysis to identify mutants that had affinity to HER2 as compared to wild-type trastuzumab. Mutants were analyzed by FACS to confirm their binding affinity to HER2 as compared to trastuzumab.

8.1. Materials and Methods

To determine binding of individual variants to HER2, cell surface displayed trastuzumab immunoglobulin variants were incubated with soluble HER2 at sub-saturating conditions (below $K_D$), and the degree of binding was quantitated by FACS. Individual trastuzumab variants were constructed in the mammalian cell surface display vector (Akamatsu et al., 2007, J. Immunol. Methods 327(1-2):40-52), and transfected into a human cell line. 400 ng of plasmid DNA in 50 μl Hybridoma-Serum Free Medium (SFM) were mixed with 1 μl of Lipofectamine 2000 in 50 μl Hybridoma-SFM and incubated for 20 minutes at room temperature. This mixture was then added to one well of a 24-well plate, previously seeded 24 hours earlier with $2\times10^5$ cells of the human embryonic kidney-derived cell line 293c18 in 0.5 ml of DME medium supplemented with 10% Fetal Bovine Serum and 0.25 mg/ml G418. After 48 hours, the cells were harvested and ready for FACS staining.

For FACS staining, approximately $5\times10^5$ cells were incubated with 1 nM HER2-C Lambda-AF647 (HER2 extracellular domain fused to C Lambda and directly conjugated with Alexa Fluor 647 dye) and 1/500 dilution of Goat anti-Human Kappa-PE (Southern Biotech #2060-09) in 1 ml of Phosphate Buffered Saline (PBS) plus 0.5% Bovine Serum Albumin (BSA), and incubated at room temperature for 1 hour. Cells were washed 3 times with 1 ml of cold PBS+0.5% BSA, resuspended in 200 μl of PBS+1% Formaldehyde, and analyzed on a BD FACS Calibur. Cells were gated to only include the IgG expressing population, and the mean fluorescence intensity (MFI) of the binding (Alexa Fluor 647) channel was determined. The MFI for binding of each variant was compared to wild-type trastuzumab for each sample set to normalize for experiment-to-experiment variability.

8.2. Results

FIGS. 2A-2D show exemplary data for the binding affinity of trastuzumab variants to labeled HER2 extracellular domain as compared to wild-type trastuzumab (binding affinity=100). The $EC_{50}$ of wild-type trastuzumab was determined by a FACS competition binding assay to be 2.638 μg/ml (FIG.

3). All variants were found to have a binding affinity to HER2 extracellular domain that is comparable to the binding affinity of wild-type trastuzumab.

9. EXAMPLE 2

Testing for CD4+ T Cell Epitope Regions in Trastuzumab 9.1. Methods

The testing for T cell epitopes detailed below was performed in accordance with U.S. Pat. No. 6,838,269.

Peptides. Peptides were synthesized using a multi-pin format by Mimotopes (Adelaide, Australia). The sequences of the trastuzumab light and heavy chain variable regions were synthesized as 15-mer peptides overlapping by 12 amino acids for a total of 68 peptides. (FIGS. 4A and 4B; SEQ ID NOs: 9-76) Peptides arrived lyophilized and were resuspended in DMSO (Sigma-Aldrich) at approximately 1-2 mg/ml. Stock peptides were kept frozen at −20° C.

Peripheral blood mononuclear cells. Community donor buffy coat products were purchased from the Stanford Blood Center, Palo Alto, Calif. Buffy coat material was diluted 1:1 v:v with DPBS containing no calcium or magnesium. Diluted buffy coat material (25-35 mls) was underlayed in 50 ml conical centrifuge tubes (Sarsted or Costar) with 12.5 mls of FicollPaque-PLUS (GE Healthcare). The samples were centrifuged at 900 g for 30 minutes at room temperature. Peripheral blood mononuclear cells (PBMC) were collected from the interface. DPBS was added to bring the final volume to 50 mls and the cells were centrifuged at 350 g for 5 minutes. Pelleted cells were resuspended in DPBS and counted.

Dendritic cells. For isolation of dendritic cells, T75 culture flasks (Costar) were seeded with $10^8$ freshly isolated PBMC in a total volume of 30 mls AIM V media (Invitrogen). Excess PBMC were frozen at −80° C. in 90% fetal calf serum (FCS), 10% DMSO at $5\times10^7$ cells/ml. T75 flasks were incubated at 37° C. in 5% $CO_2$ for 2 hours. Nonadherent cells were removed, and the adherent monolayer was washed with DPBS. To differentiate dendritic cells from monocytes, 30 mls of AIM V media containing 800 units/ml of GM-CSF (R and D Systems) and 500 units/ml IL-4 (R and D Systems) were added. Flasks were incubated for 5 days. On day 5 IL-1α (Endogen) and TNFα (Endogen) were added to 50 μg/ml and 0.2 ng/ml, respectively. Flasks were incubated for two more days. On day 7, dendritic cells were collected by the addition of 3 mls of 100 mM EDTA containing 0.5 to 1.0 mg Mitomycin C (Sigma-Aldrich) for a final concentration of 10 mM EDTA and 16.5 to 33 μg/ml Mitomycin C. Flasks were incubated an additional hour at 37° C. and 5% $CO_2$. Dendritic cells were collected, and washed in AIM V media 2-3 times.

Cell culture. On day 7, previously frozen autologous PBMC were thawed quickly in a 37° C. water bath. Cells were immediately diluted into DPBS or AIM V media and centrifuged at 350 g for 5 minutes. $CD4^+$ cells were enriched by negative selection using magnetic beads (Easy-Sep $CD4^+$ kit, Stem Cell Technologies). Autologous $CD4^+$ T cells and dendritic cells were cocultured at $2\times10^5$ $CD4^+$ T cells per $2\times10^4$ dendritic cells per well in 96 well round bottomed plates (Costar 9077). Peptides were added at approximately 5 μg/ml. Control wells contained the DMSO (Sigma) vehicle alone at 0.25% v:v. Positive control wells contained DMSO at 0.25% and tetanus toxoid (List Biologicals or CalBioChem) at 1 μg/ml. Cultures were incubated for 5 days. On day 5, 0.25 μCi per well of tritiated thymidine (Amersham or GE Healthcare) was added. Cultures were harvested on day 6 to filtermats using a Packard Filtermate Cell harvester. Scintillation counting was performed using a Wallac MicroBeta 1450 scintillation counter (Perkin Elmer).

Data analyses. Average background CPM values were calculated by averaging individual results from 6 to 12 replicates. The CPM values of the four positive control wells were averaged. Replicate or triplicate wells for each peptide were averaged. Stimulation index values for the positive control and the peptide wells were calculated by dividing the average experimental CPM values by the average control values. In order to be included in the dataset, a stimulation index of greater than 3.0 in the tetanus toxoid positive control wells was required. A response was noted for any peptide resulting in a stimulation index of 2.95 or greater. Peptides were tested using peripheral blood samples from a group of 100 donors. Responses to all peptides were compiled. For each peptide tested, the percentage of the donor set that responded with a stimulation index of 2.95 or greater was calculated. In addition, the average stimulation index for all donors was calculated.

9.2. Results

Identification of a $CD4^+$ T cell epitopes in the trastuzumab $V_H$ and $V_L$ regions. $CD4^+$ T cell epitope peptides were identified by an analysis of the percent responses to the peptides within the set of 100 donors. The average percent response and standard deviation were calculated for all peptides tested describing the trastuzumab heavy chain and light chain variable regions. A response rate greater than or equal to the average background response plus three standard deviations was considered a potential $CD4^+$ T cell epitope. For the trastuzumab light chain variable region, 32 peptides were tested (FIG. 4A) which resulted in an average background percent response of 2.63±2.67%. Three standard deviations above background was determined to be 10.6%. One light chain peptide at position 8 (T22-Y36; SEQ ID NO:16) displayed this level of response in the trastuzumab light chain peptide dataset, with a response rate of 15.0% (FIG. 5A). For the trastuzumab heavy chain variable region, 36 peptides were tested (FIG. 4B). The average background percent response was 3.28±2.14%. Three standard deviations above background was 9.7%. No peptides within the trastuzumab heavy chain dataset achieved epitope status. (FIG. 5B) However, the peptide at position 29 (S85-W99; SEQ ID NO:69) in the heavy chain dataset achieved a response rate of 9.0%, and was considered an epitope due to an increase stimulation index (see below).

The average stimulation index was calculated for all peptides in the dataset (light chain and heavy change stimulation indices are set forth respectively in FIGS. 5C and 5D). The light chain peptide at position 8 (SEQ ID NO:16) had a high average stimulation index of 1.73. The heavy chain peptide at position 29 (SEQ ID NO:69) returned an average stimulation index of 2.51. Due to an elevated average stimulation index and an above average response rate, the heavy chain peptide at position 29 was included when determining $CD4^+$ T cell epitope content of this antibody variable region. All of these stimulation index values are significantly higher than the average stimulation index for all peptides in the two datasets (1.17±0.03 for all 68 heavy chain and light chain peptides).

Two $CD4^+$ T cell epitope regions are present in the trastuzumab variable regions (FIG. 1A). In the $V_L$ region, an epitope was found in the peptide at position 8 that encompasses CDR1 and portions of framework 1 and 2. The CDR-derived amino acids are in bold underlined type in FIG. 1A. In the heavy chain, an epitope peptide region was identified in the peptide at position 29 that encompasses $V_H$ framework 3 and 3 amino acids of CDR3. This epitope peptide also encompasses a back-mutation at S97 that was incorporated during humanization.

A series of variant peptides were selected for additional testing based on the PxP analysis of trastuzumab CDR regions. (FIGS. 6A, 6B and 6C) The specific amino acid changes selected for incorporation into the variant peptides were confirmed to have no impact on the affinity of antigen binding. Variant peptides were designed to have a single amino acid modification, or to have two amino acid substitutions. All peptides were synthesized via pin synthesis, and will be tested for their ability to induce proliferative responses in human $CD4^+$ T cells by the methods detailed above.

10. EXAMPLE 3

Production and Purification of HER2 Protein

HER2 protein was expressed as monomeric secreted fusion proteins. The extracellular domain (ECD) of HER2 was fused with human lambda constant region (Cλ) containing a Cys to Ser mutation to disrupt the intermolecular disulfide bond (Akamatsu et al., 2007, J. Immunol. Methods 327: 40). The HER2 ECD-Cλ fusion protein was expressed in the culture supernatant of 293S stable transfectant. The fusion protein was purified over an affinity column with Herceptin® linked to sepharose beads. After binding at neutral pH, the protein was eluted with 20 mM sodium acetate pH 2.5. Eluted protein was dialyzed into PBS (pH 7.4).

11. EXAMPLE 4

Production and Purification of Trastuzumab and its Variants

To produce the soluble trastuzumab and its variants, 293c18 in DME medium containing 2% ultra low Ig FBS was transfected with Lipofectamine 2000 (Invitrogen). After 7 days, culture supernatants containing soluble antibodies were harvested. Transiently expressed antibody variants were purified using protein G (GE Healthcare, Uppsala, Sweden). Antibodies were eluted with 20 mM sodium citrate (pH 2.5), neutralized with 1M Tris (pH 8.0), and buffer exchanged into PBS (pH 7.4) by centrifugal filter (Vivaspin 50 kDa MWCO, GE Healthcare). Purity was evaluated by SDS-PAGE.

12. EXAMPLE 5

Binding of Trastuzumab Variants with Purified HER2 Protein

HER2 ECD fused with a Cλ tag was bound to AlphaLISA® acceptor beads conjugated with goat anti-human a antibody and biotinylated Herceptin® was bound to AlphaScreen® streptavidin-coated donor beads (Perkin Elmer, Waltham, Mass.). Herceptin® was biotinylated with Sulfo-NHS-Biotin using standard methods and dialyzed in PBS. Conjugation of AlphaLISA® acceptor beads was performed by following the manufacturer's instructions ("AlphaLISA® Assay Development Guide", Perkin Elmer). The binding assay was performed in a 96-well AlphaPlate (Perkin Elmer) in assay buffer (0.5% BSA, 0.01% Tween20 in PBS (pH 7.1)). Each well contained 1.25 nM biotinylated Herceptin®, 1:4 serially diluted unlabeled trastuzumab variant protein starting from 200 nM, 1.25 μg/mL HER2 ECD-Cλ, and 5 μg/ml goat anti-human Cλ-conjugated acceptor beads. The plate was incubated in the dark for 1 h at room temperature. Streptavidin donor beads were subsequently added to each well at 5 μg/mL. The plate was incubated in the dark at room temperature for an additional 30 min, after which it was read on an EnVision reader (Perkin Elmer). Data were fit using nonlinear regression with the software GRAPHPAD PRISM (GraphPad, San Diego, Calif.).

13. EXAMPLE 6

FACS Competition of Trastuzumab Variants with HER2 Expressed on Cells

The relative binding affinities of Herceptin® and trastuzumab to native HER2 expressed on breast cancer cell line were determined by a competition assay using FACS. KS-BR3 cells were washed with FACS buffer containing 0.5% FBS in PBS. Biotinylated Herceptin® diluted to a final concentration of 1.0 μg/mL was mixed with competitor antibodies at 1:3 serial dilution starting with 50 μg/ml (at final concentration) and the mixture were transferred to the 96-well plates containing the cells at $1\times10^5$ per well. The plate were incubated at 4° C. for 1 hour, and then washed twice with FACS buffer. 100 μL of Streptavidin-RPE conjugate (Invitrogen, Carlsbad, Calif.) diluted to 2.5 μg/mL in FACS buffer were added to the wells, and the plates were incubated 4° C. for another 30 minutes in the dark. Cells were washed twice with FACS buffer and resuspended with 200 μL of fixing buffer (1% paraformaldehyde in PBS). Samples were analyzed on a FACS Calibur (BD, Franklin Lakes, N.J.)

14. EXAMPLE 7

Binding Kinetics of Trastuzumab Variants with Purified HER2 Protein

Binding kinetics of trastuzumab variants were measured by using a BIAcore T100 system (GE Healthcare Life Sciences, Piscataway, N.J.). Approx. 5000 RU of polyclonal goat anti-human Fc antibody (Thermo Fisher Scientific, Rockford, Ill.) was immobilized on a CM5 chip according to the manufacturer's instructions. Binding assays to study the binding of trastuzumab and HER2 were run at a flow rate of 50 μL/min at room temperature. HER2 ECD-Cλ in 5 different concentrations between 6.25-100 nM were injected over surfaces where trastuzumab and its variants were captured, with a 5 min association phase followed by 15 min dissociation phase. Binding data were fit to the 1:1 Langmuir model to extract binding constants from the BIAevaluation T100 software.

15. EXAMPLE 8

Deimmunization Study

A series of variant peptides were selected for additional testing based on the PxP analysis of trastuzumab CDR regions. See FIGS. 6A to 6C. The specific amino acid changes incorporated into the variant peptides were selected for minimal impact on antigen binding. Variant peptides were designed to have a single amino acid modification, or to have two amino acid substitutions. All peptides were synthesized via pin synthesis, and were tested for this ability to induce a CD4+ T cell proliferative response. A total of 76 peptides, including two replicates of each parent peptide, were tested using cells from 83 community donors. The results are shown in FIG. 7. The epitope peptide identified in trastuzumab VH (peptide #29) was tested twice in this replicate of donors FIG.

7A (open triangles), and the percent responses were 10.8% and 4.8%. The first value is consistent with the response rate seen in the initial screening (9.0%), and the second value is low. Within the set of 21 VH epitope variant peptides, there were two variants with response rates of 1.20% (FIG. 7). One of these peptides (SEQ ID NO:1405) contained an amino acid modification within the framework region. The epitope peptides identified in trastuzumab VL (peptide # 8) was also tested twice in this replicate of donors (FIG. 7B open triangles), and the percent responses were 8.4% and 6.0%. These results compare unfavorably to the initial screening, where 15% of the tested donors responded to the peptide. However, within this dataset of 51 variant peptides, two variants did not induce responses in any of the tested donors, and 5 peptides induced proliferative responses in 1.2% of the donors (FIG. 8). The variant peptides selected for further characterization are shown in FIG. 8.

16. SPECIFIC EMBODIMENTS, CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An anti-HER2 antibody or an anti-HER2 binding fragment of an antibody which comprises a VH having positions 1 to 117 of SEQ ID NO:1 and a VL having positions 1 to 103 of SEQ ID NO:2 that have one or more amino acid substitutions or combinations of amino acid substitutions as compared to an antibody having a VH comprising an amino acid sequence corresponding to positions 1 to 117 of SEQ ID NO:1 and a VL comprising an amino acid sequence corresponding to positions 1 to 103 of SEQ ID NO:2, wherein said one or more amino acid substitutions or combinations of amino acid substitutions are selected from:

(i) the third framework of the VH chain (FR-H3) substitution R83K as compared to a VH of SEQ ID NO: 1;

(ii) the first CDR of the VL chain (CDR-L1) substitution D28L as compared to a VL of SEQ ID NO:2;

(iii) the first CDR of the VL chain (CDR-L1) substitution A34D as compared to a VL of SEQ ID NO:2;

(iv) the first CDR of the VL chain (CDR-L 1) substitution A34V as compared to a VL of SEQ ID NO:2;

(v) the first CDR of the VH chain (CDR-H 1) substitution D31T as compared to a VH of SEQ ID NO: 1;

(vi) the first CDR of the VH chain (CDR-H 1) substitution D31H as compared to a VH of SEQ ID NO: 1;

(vii) the second CDR of the VH chain (CDR-H2) substitution Y52K as compared to a VH of SEQ ID NO: 1; and (viii) the third CDR of the VH chain (CDR-H3) substitution W95F as compared to a VH of SEQ ID NO: 1.

2. The anti-HER2 antibody or anti-HER2 binding fragment of an antibody of claim 1, wherein FR-H3 includes the substitution R83K as compared to a VH of SEQ ID NO:1.

3. The anti-HER2 antibody or anti-HER2 binding fragment of an antibody of claim 1, wherein CDR-H3 includes the substitution W95F as compared to CDR-H3 of a VH of SEQ ID NO:1.

4. The anti-HER2 antibody or anti-HER2 binding fragment of an antibody of claim 1, wherein CDR-L1 includes the substitution Q27S as compared to CDR-L1 of a VL of SEQ ID NO:2.

5. The anti-HER2 antibody or anti-HER2 binding fragment of an antibody of claim 1, wherein CDR-L1 includes the substitution A34V as compared to CDR-L1 of a VL of SEQ ID NO:2.

6. The anti-HER2 antibody or anti-HER2 binding fragment of an antibody of claim 1, wherein CDR-L1 includes at least one of the combination of substitutions selected from D28N +A34D and D28L +A34D as compared to CDR-L1 of a VL of SEQ ID NO:2.

7. The anti-HER2 antibody or anti-HER2 binding fragment of an antibody of claim 1, wherein CDR-L1 includes at least one of the combination of substitutions selected from Q27S +A34D , Q27L +A34V, and Q27F +A34D as compared to CDR-L1 of a VL of SEQ ID NO:2.

8. The anti-HER2 antibody or anti-HER2 binding fragment of an antibody of claim 1 which has increased affinity to HER2 as compared to an antibody having a VH comprising an amino acid sequence corresponding to positions 1 to 117 of SEQ ID NO:1 and a VL comprising an amino acid sequence corresponding to positions 1 to 103 of SEQ ID NO:2.

9. The anti-HER2 antibody or anti-HER2 binding fragment of claim 8 which has an affinity to HER-2 that is at least 1.1-fold that of an antibody having a VH comprising an amino acid sequence corresponding to positions 1 to 117 of SEQ ID NO:1 and a VL comprising an amino acid sequence corresponding to positions 1 to 103 of SEQ ID NO:2, as assayed by BIAcore, AlphaLISA or by FACS.

10. The anti-HER2 antibody or anti-HER2 binding fragment of claim 9 which has (i) at least one VL substitution selected from: T22G and A34V as compared a VL of SEQ ID NO:2;

(ii) at least one VL substitution selected from: T22G, T22S, C23A, R24H, R24C, R24V, A25C, A25G, A25P, Q27V, D28A, V29A, V29S, A34D, A34G, A51S, S52W, S52M, S52Q, S52H, S52G, S52R, L54I, L54G, L54V, S56A, S56P, S56G, S56H, S56Y, S56F, S56N, S56M, R66K, Y92M, T93L, T93M, T93V, and P96G as compared a VL of SEQ ID NO:2 and/or at least one VH substitution selected from D31H, Y52K, T53R, K64S, A88E, V89Y, S93D, D98L, D98M and D98V as compared a VH of SEQ ID NO:1;

(iii) at least one VL substitution selected from: T22G, L54I, and S56Y as compared a VL of SEQ ID NO:2; and/or at least one VH substitution selected from D31H, D31T, Y52K, D98M and D98W, as compared to SEQ ID NO:1;

(iv) at least one VL substitution selected from: T22G, L54I, and S56Y as compared a VL of SEQ ID NO:2; and/or at least one VH substitution selected from D31H, D31T, Y52K and D98M, as compared to SEQ ID NO:1; or (v) at least one VL substitution selected from: T22G, T22S, C23A, R24H, R24C, R24V, A25C, A25G, A25P, Q27V, D28A, V29A, V29S, A34D, A34G, A51S, S52W, S52M, S52Q , S52H, S52G, S52R, L54I, L54G, L54V, S56A, S56P, S56G, S56H, S56Y, S56F, S56N, S56M, R66K, Y92M, T93L, T93M, T93V, and P96G as compared a VL of SEQ ID NO:2 and/or at least one VH substitution selected from D31H, Y52K, T53R, K64S, A88E, V89Y, S93D, D98L and D98V as compared a VH of SEQ ID NO:1.

11. The anti-HER2 antibody or anti-HER2 binding fragment of claim 1 which is a monoclonal antibody or anti-HER2 binding fragment of a monoclonal antibody, respectively.

12. The anti-HER2 antibody or anti-HER2 binding fragment of claim 1 which is a human or humanized antibody, or anti-HER2 binding fragment of a human or humanized antibody, respectively.

13. An antibody-drug conjugate comprising an anti-HER2 antibody or anti-HER2 binding fragment according to claim 1.

14. A pharmaceutical composition comprising an anti-HER2 antibody or anti-HER2 binding fragment according to claim 1 and a pharmaceutically acceptable carrier.

15. An anti-HER2 antibody or an anti-HER2 binding fragment of an antibody which comprises six CDRs having amino acid sequences of SEQ ID NO: 3 (CDR-H1), SEQ ID NO:4 (CDR-H2), SEQ ID NO: 5 (CDR-H3), SEQ ID NO:104 (CDR-L1), SEQ ID NO:7 (CDR-L2), and SEQ ID NO:8 (CDR-L3) that have one or more amino acid substitutions or combinations of substitutions as compared to an antibody comprising CDRs having amino acid sequences of SEQ ID NO:3 (CDR-H1), SEQ ID NO:4 (CDR-H2), SEQ ID NO:5 (CDR-H3), SEQ ID NO:104 (CDR-L1), SEQ ID NO:7 (CDR-L2), and SEQ ID NO:8 (CDR-L3), wherein said one or more amino acid substitutions or combinations of amino acid substitutions are selected from:

(i) the CDR-L1 substitution D28L;

(ii) the CDR-L1 substitution A34D;

(iii) the CDR-L1 substitution A34V;

(iv) the CDR-H1 substitution D31T;

(v) the CDR-H1 substitution D31H;

(vi) the CDR-H2 substitution Y52K; and (vi) the CDR-H3 substitution W95F.

16. The anti-HER2 antibody or anti-HER2 binding fragment of an antibody of claim 15, wherein the antibody or anti-HER2 binding fragment further comprises a VH that has the amino acid substitution R83K as compared to the VH of SEQ ID NO:1.

* * * * *

UNITED STATES PATENT AND TRADEMARK OFFICE

CERTIFICATE OF CORRECTION

PATENT NO. : 8,937,159 B2
APPLICATION NO. : 12/969375
DATED : January 20, 2015
INVENTOR(S) : Harding et al.

It is certified that error appears in the above-identified patent and that said Letters Patent is hereby corrected as shown below:

In the Claims

In column 581, line 59, claim 1, "D28L" should read --D28L + A34D--.

In column 582, line 44, claim 1, "SEQ ID NO:1; and" should read --SEQ ID NO:1;--.

In column 582, line 46, claim 1, "SEQ ID NO:1." should read --SEQ ID NO:1;

(ix) the first CDR of the VL chain (CDR-L1) substitutions Q27S + A34D as compared to a VL of SEQ ID NO:2;

(x) the first CDR of the VL chain (CDR-L1) substitutions Q27L + A34D as compared to a VL of SEQ ID NO:2; and (xi) the first CDR of the VL chain (CDR-L1) substitutions Q27F + A34D as compared to a VL of SEQ ID NO:2.--.

In column 584, line 33, claim 15, "D28L;" should read --D28L + A34D;--.

In column 584, line 37, claim 15, "Y52K; and" should read --Y52K;--.

In column 584, line 38, claim 15, "(vi)" should read --(vii)--.

In column 584, line 38, claim 15, "W95F." should read --W95F;

(viii) the CDR-L1 substitutions Q27S + A34D;

(ix) the CDR-L1 substitutions Q27L + A34D; and (x) the CDR-L1 substitutions Q27F + A34D.--.

Signed and Sealed this
Eleventh Day of August, 2015

Michelle K. Lee

Michelle K. Lee
*Director of the United States Patent and Trademark Office*